United States Patent
Overstreet

(10) Patent No.: US 12,097,260 B2
(45) Date of Patent: *Sep. 24, 2024

(54) TEMPERATURE-RESPONSIVE DEGRADABLE HYDROGELS

(71) Applicant: Sonoran Biosciences, Inc., Tempe, AZ (US)

(72) Inventor: Derek J. Overstreet, Tempe, AZ (US)

(73) Assignee: Sonoran Biosciences, Inc., Tempe, AZ (US)

( * ) Notice: Subject to any disclaimer, the term of this patent is extended or adjusted under 35 U.S.C. 154(b) by 120 days.

This patent is subject to a terminal disclaimer.

(21) Appl. No.: 17/528,111

(22) Filed: Nov. 16, 2021

(65) Prior Publication Data

US 2022/0072134 A1 Mar. 10, 2022

Related U.S. Application Data

(63) Continuation of application No. 16/858,479, filed on Apr. 24, 2020, now Pat. No. 11,173,210, which is a continuation of application No. PCT/US2018/057398, filed on Oct. 24, 2018.

(60) Provisional application No. 62/838,176, filed on Apr. 24, 2019, provisional application No. 62/576,269, filed on Oct. 24, 2017.

(51) Int. Cl.
| | |
|---|---|
| *A61K 47/32* | (2006.01) |
| *A61J 1/20* | (2006.01) |
| *A61K 9/06* | (2006.01) |
| *A61K 31/435* | (2006.01) |
| *A61K 31/702* | (2006.01) |
| *A61K 31/7036* | (2006.01) |
| *A61M 5/19* | (2006.01) |
| *C08F 220/58* | (2006.01) |

(52) U.S. Cl.
CPC ............. *A61K 47/32* (2013.01); *A61J 1/2096* (2013.01); *A61K 9/06* (2013.01); *A61K 31/435* (2013.01); *A61K 31/702* (2013.01); *A61K 31/7036* (2013.01); *A61M 5/19* (2013.01); *C08F 220/58* (2013.01); *C08F 2800/10* (2013.01)

(58) Field of Classification Search
None
See application file for complete search history.

(56) References Cited

U.S. PATENT DOCUMENTS

| | | | |
|---|---|---|---|
| 6,956,077 B1 | 10/2005 | Akiyama et al. | |
| 2005/0177103 A1 | 8/2005 | Hunter et al. | |
| 2018/0228903 A1* | 8/2018 | Kohane | A61K 47/22 |

FOREIGN PATENT DOCUMENTS

| | | |
|---|---|---|
| WO | 0044800 A1 | 8/2000 |
| WO | 2013056170 A1 | 4/2013 |

OTHER PUBLICATIONS

Prosperi-Porta, G., Muirhead, B., & Sheardown, H. (2017). Tunable release of ophthalmic therapeutics from injectable, resorbable, thermoresponsive copolymer scaffolds. Journal of Biomedical Materials Research Part B: Applied Biomaterials, 105(1), 53-62. (Year: 2017).*
Turturica, Gabriel et al.; "ABA triblock copolymers of poly(N-isopropylarcrylamide-co-5,6-benzo-2-methylene-1,3-dioxepane) (A) and poly (ethylene glycol) (B): synthesis and thermogelation and degradation properties in aqueous solutions." Colloid Polym Sci; Springer; (2016) vol. 294; pp. 743-753.
PCT Application No. PCT/US2018/057398 Filing date Oct. 24, 2018, Derek J. Overstreet International Search Report, Mailing date Mar. 1, 2019, 12 Pages.
Kuckling, D. et al.; "Temperature and pH dependent solubility of novel poly(N-isopropylacrylamide)-copolymers." Macromolecular Chemistry and Physics 201 (2000); pp. 273-280.
Overstreet, D.J., et al.; "In situ forming, resorbable graft copolymer hydrogels providing controlled drug release." J. Biomed Mater Res Part A, 101(5); (Year 2012); pp. 1437-1446.
Prosperi-Porta G, et al.; :"Tunable release of ophthalmic therapeutics from injectable, resorbable, thermoresponsive copolymer scaffolds," J Biomed Mater Res B Appl Biomater. Jan. 2017;105(1):53-62.

* cited by examiner

*Primary Examiner* — Dale R Miller
(74) *Attorney, Agent, or Firm* — Thorpe North & Western, LLP; David W. Osborne

(57) ABSTRACT

A polymer composition can include an aqueous vehicle and a temperature-responsive degradable polymer having a polymer including a LCST-imparting unit and a lactone-bearing unit including a pendent lactone group. The number of LCST-imparting units is greater than the number of lactone-bearing units. The temperature-responsive degradable polymer has an initial lower critical solution temperature (LCST) of 37° C. or below. The polymer composition can have a pH lower than 7.

20 Claims, 35 Drawing Sheets

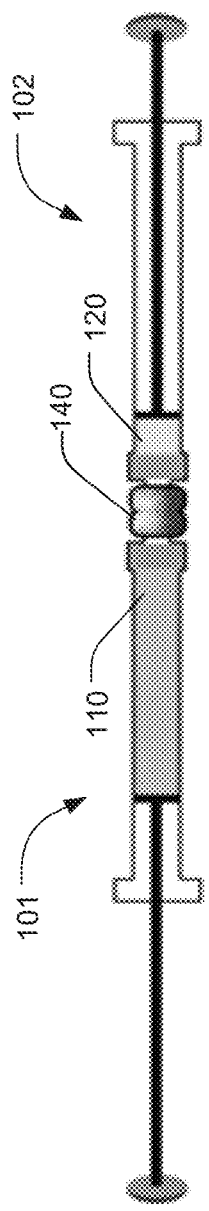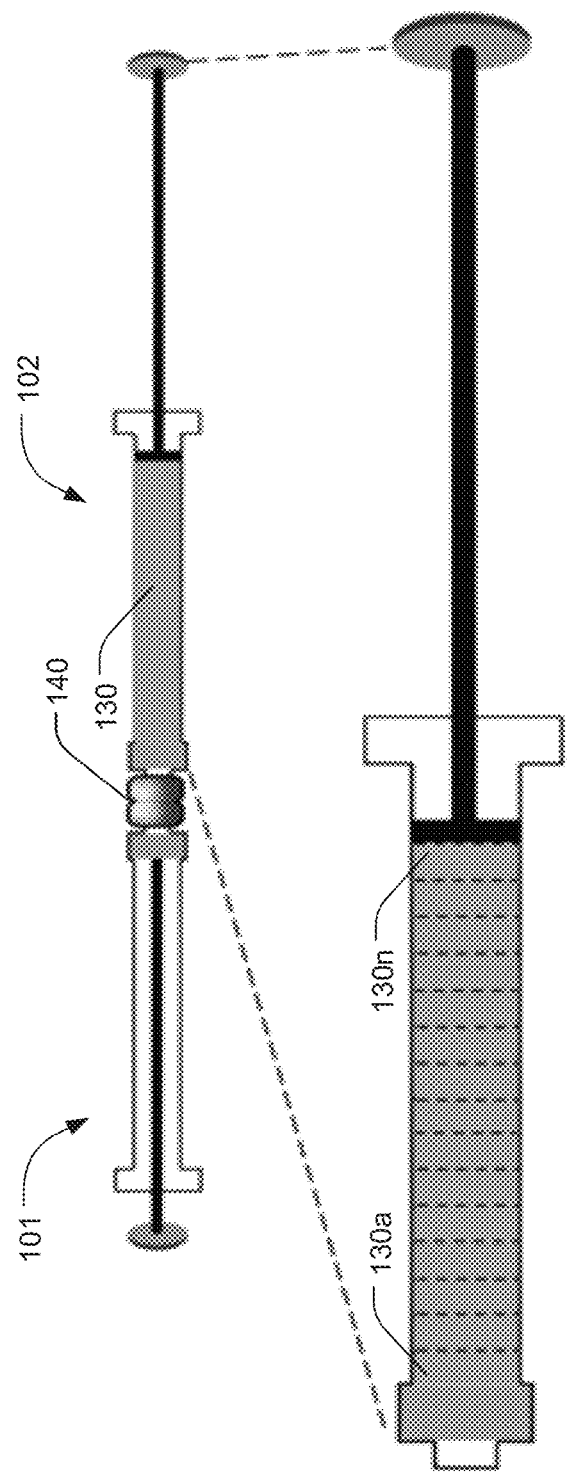
FIG. 1A
FIG. 1B

TEMPERATURE-RESPONSIVE DEGRADABLE HYDROGELS

PRIORITY DATA

This application is a continuation of U.S. patent application Ser. No. 16/858,479, filed Apr. 24, 2020, now issued as U.S. Pat. No. 11,173,210, which claims the benefit of U.S. Provisional Patent Application Ser. No. 62/838,176 filed on Apr. 24, 2020 and is additionally a continuation of Patent Cooperation Treaty Application Serial No. PCT/US18/57398, filed on Oct. 24, 2018, which claims the benefit of U.S. Provisional Patent Application Ser. No. 62/576,269, filed Oct. 24, 2017, each of which is incorporated herein by reference.

GOVERNMENT INTEREST

This invention was made with government support under grant numbers 1R41AR064080, 1R41AR065917, and 5R44AR070685 awarded by the National Institutes of Health. The government has certain rights in the invention.

BACKGROUND

Hydrogels are utilized in a wide variety of biomedical applications due to their high water content, good biocompatibility, mechanical similarity to natural tissues, and tunable material properties. Among hydrogels, "in situ forming" hydrogels or injectable hydrogels which form in vivo from a liquid precursor solution are particularly promising. As compared to conventional pre-formed hydrogels, in situ forming hydrogels can conform to their application site (maintaining thorough contact with surrounding tissues) and also can be applied into the body in a less invasive manner.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Features and advantages of invention embodiments will be apparent from the detailed description which follows, and further with reference to the accompanying drawings, wherein:

FIG. 1A illustrates an example of a mixing apparatus prior to end-to-end mixing of two components, in accordance with an example embodiment.

FIG. 1B illustrates the example of FIG. 1A after end-to-end mixing of the two components, in accordance with an example embodiment.

Figure 1C:
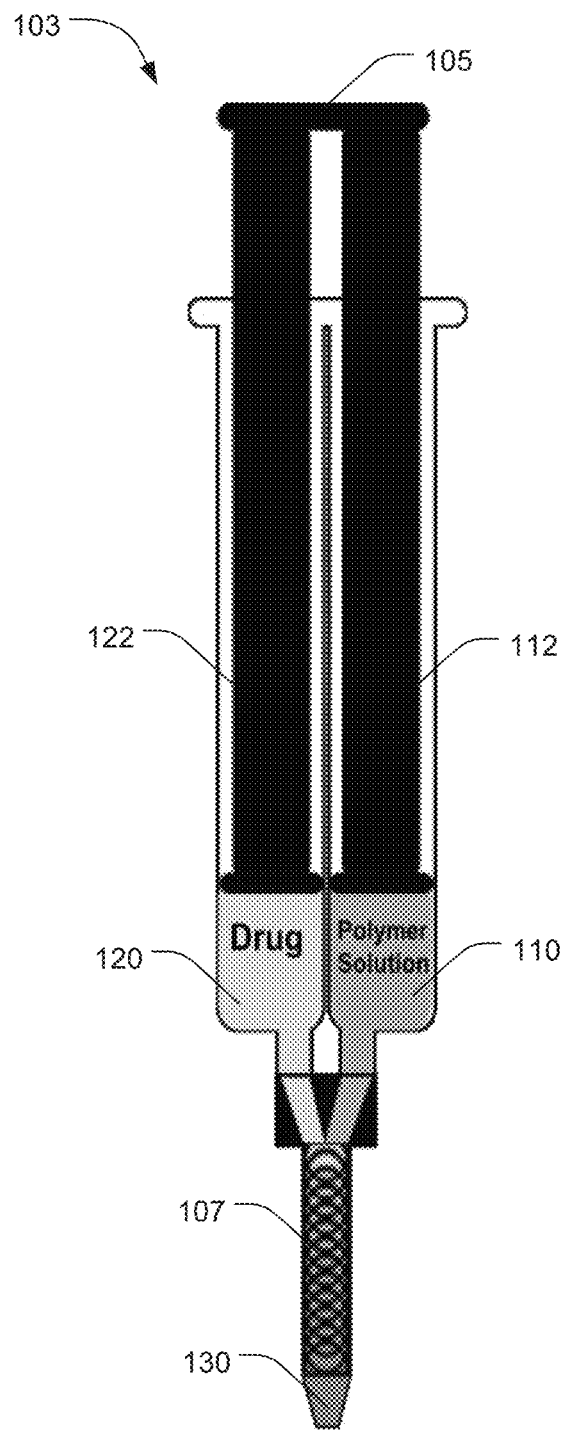
FIG. 1C illustrates another example of a mixing apparatus for mixing two components, in accordance with an example embodiment.

Reference will now be made to the exemplary embodiments illustrated, and specific language will be used herein to describe the same. It will nevertheless be understood that no limitation on technology scope is thereby intended.

DESCRIPTION OF EMBODIMENTS

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this written description, the singular forms "a," "an" and "the" include express support for plural referents unless the context clearly dictates otherwise. Thus, for example, reference to "a polymer" can include a plurality of such polymers.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The term "coupled," as used herein, is defined as directly or indirectly connected. "Directly coupled" structures or elements are in physical contact with one another and are attached. Objects described herein as being "adjacent to" each other may be in physical contact with each other, in close proximity to each other, or in the same general region or area as each other, as appropriate for the context in which the phrase is used.

As used herein, "equilibrium" or "steady state" can be used interchangeably and refer to a state in which both forward and reverse reactions between two species are occurring, resulting in relative amounts of the reactant and product that will remain approximately constant in the same conditions over time. For example, the "forward" reaction of lactone hydrolysis and the "reverse" reaction of lactone formation can be said to reach an equilibrium or steady state in which the number of lactones being formed is approximately equal to the number of lactones being hydrolyzed, resulting in no net change in the proportion of lactones versus hydroxyacids. "Equilibrium composition" or "steady state composition" refers to the proportion of the two species, e.g. lactones and hydroxyacids, present when the aforementioned reactions are in equilibrium.

As used herein, the term "subject" refers to a mammal that can benefit from application of the present technology. Examples of subjects include humans, and other animals such as horses, pigs, cattle, dogs, cats, rabbits, rats, mice, and aquatic mammals.

The term "dosage unit" or "dose" are understood to mean an amount of an active agent that is suitable for administration to a subject in order achieve or otherwise contribute to a therapeutic effect. In some embodiments, a dosage unit can refer to a single dose which is capable of being administered to a subject or patient, and that may be readily handled and packed, remaining as a physically and chemically stable unit dose.

The phrase "effective amount," "therapeutically effective amount," or "therapeutically effective rate(s)" of an active ingredient refers to a non-toxic, but sufficient amount or delivery rates of the active ingredient, to achieve therapeutic results in treating a disease or condition for which the drug is being delivered. It is understood that various biological factors may affect the ability of a substance to perform its intended task. Therefore, an "effective amount," "therapeutically effective amount," or "therapeutically effective rate(s)" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

The terms "treat," "treating," or "treatment" as used herein and as well understood in the art, mean an approach for obtaining beneficial or desired results, including without limitation clinical results in a subject being treated. Beneficial or desired results can include, but are not limited to, alleviation or amelioration of one or more signs or symptoms of a condition, diminishment of extent of disease, stabilizing (i.e. not worsening) the state of a disease or condition, delaying or slowing of disease progression, amelioration or palliation of the disease state, diminishment of the reoccurrence of disease, and remission (whether partial or total), whether detectable or undetectable. "Treat," "treating" and "treatment" can also mean prolonging survival as compared to expected survival if not receiving treatment and can be prophylactic. Such prophylactic treatment can also be referred to as prevention or prophylaxis of a disease or condition. The prophylaxis may be partial or complete. Partial prophylaxis may result in the delayed onset of a physiological condition.

An "active agent" or "therapeutic agent" or "medicament" or "drug" can be used interchangeably and refer to any element, compound, mixture of compounds, or molecule having pharmacological activity. Generally, these terms refer to any organic or inorganic compound or substance having bioactivity and adapted or used for therapeutic purposes. As used herein, specific reference to a chemical compound includes express support for the compound per se, as well as any of its pharmaceutically acceptable forms, including isomers such as diastereomers and enantiomers, salts, solvates, and polymorphs, particular crystalline forms, as well as racemic mixtures and pure isomers of the compounds described herein, where applicable. Active agents are distinguishable from such components as vehicles, carriers, depots, diluents, lubricants, binders, and other encapsulating or otherwise protective components. Another term for an inactive component is "excipient". Examples of active agents are pharmaceutical agents. Suitable pharmaceutical agents can include locally or systemically acting pharmaceutically active agents which may be administered to a subject, including a human, by topical or intralesional application (including for example to a surgical site or wound) or by injection, such as subcutaneous, intramuscular, intra-articular, or intra-ocular injection. Suitable pharmaceutical agents include antimicrobials (including antibacterials, antivirals, and antifungals), antiseptics (including chlorhexidine gluconate), opioids (such as morphine, buprenorphine, oxymorphone, and the like), anti-inflammatory agents (meloxicam, aspirin, ibuprofen, ketorolac, COX-1 inhibitors, COX-2 inhibitors, and the like), local anesthetics (such as bupivacaine, levobupivacaine, dibucaine, mepivacaine, procaine, lidocaine, tetracaine, ropivacaine, and the like), polysaccharides, polynucleotides, antigens, antibodies, vaccines, vitamins, enzymes, proteins, and other pharmaceutically active agents.

"Antimicrobial" denotes an active agent that kills microorganisms or inhibits their growth. Subgroups of antimicrobials include antibacterials, antivirals, antifungals, antiparasitics, and antiseptics. Examples of antibacterials include but are not limited to the following: tobramycin, vancomycin, gentamicin, cefazolin, penicillin, amoxicillin, doxycycline, cephalexin, ciprofloxacin, metronidazole, azithromycin, sulamethoxaole/trimethoprim, bacitracin, levofloxacin, ceftaroline, dalbavancin, oritavancin, amikacin, rifampin, and teixobactin.

"Buffering agent" refers to a water-soluble species that, when added to water, forms a buffer solution, which reduces the pH change of the solution in response to the generation of other acids or bases. Buffering agent refers also to multiple agents when two species in water are known to be used in tandem in a buffer solution. For example, sodium acetate and acetic acid form buffers in the pH range between about 3.7 and about 5.6. Examples of buffering agents include monobasic sodium phosphate, dibasic sodium phosphate, citric acid, sodium citrate, acetic acid, sodium acetate, imidazole, sodium carbonate, sodium bicarbonate, and biological buffering agents including 4-Morpholineethanesulfonic acid, 2,2-Bis(hydroxymethyl)-2,2',2''-nitrilotriethanol, N-(2-Acetamido)iminodiacetic acid, N-(2-Acetamido)-2-aminoethanesulfonic acid, 1,4-Piperazinediethanesulfonic acid, β-Hydroxy-4-morpholinepropanesulfonic acid, 1,3-Bis[tris(hydroxymethyl)methylamino]propane, N,N-Bis(2-hydroxyethyl)-2-aminoethanesulfonic acid, 3-(N-Morpholino) propanesulfonic acid, 2-[(2-Hydroxy-1,1-bis(hydroxymethyl)ethyl)amino]ethanesulfonic acid, 4-(2-Hydroxyethyl)piperazine-1-ethanesulfonic acid, 3-(N,N-Bis[2-hydroxyethyl]amino)-2-hydroxypropanesulfonic acid, 4-(N-Morpholino)butanesulfonic acid, 2-Hydroxy-3-[tris(hydroxymethyl)methylamino]-1-propanesulfonic acid, 2-Amino-2-(hydroxymethyl)-1,3-propanediol, 4-(2-Hydroxyethyl)piperazine-1-(2-hydroxypropanesulfonic acid), Piperazine-1,4-bis(2-hydroxypropanesulfonic acid), 4-(2-Hydroxyethyl)-1-piperazinepropanesulfonic acid, EPPS, N-[Tris(hydroxymethyl)methyl]glycine, glycine, diglycine, N,N-Bis(2-hydroxyethyl)glycine, N-(2-Hydroxyethyl)piperazine-N'-(4-butanesulfonic acid), N-[Tris(hydroxymethyl)methyl]-3-aminopropanesulfonic acid, 2-Amino-2-methyl-1,3-propanediol, N-tris(Hydroxymethyl)methyl-4-aminobutanesulfonic acid, N-(1,1-Dimethyl-2-hydroxyethyl)-3-amino-2-hydroxypropanesulfonic acid, 2-(Cyclohexylamino)ethanesulfonic acid, 3-(Cyclohexylamino)-2-hydroxy-1-propanesulfonic acid, β-Aminoisobutyl alcohol, 3-(Cyclohexylamino)-1-propanesulfonic acid, and 4-(Cyclohexylamino)-1-butanesulfonic acid.

"Pharmaceutically acceptable acids" refers to acids that are compatible with the preparation of pharmaceutical formulations, such as those listed in Handbook of Pharmaceutical Salts: Properties, Selection and Use or acids that are included in publicly available databases such as the United States Food and Drug Administration's list of inactive ingredients for approved drug products. Examples of non-polymeric pharmaceutically acceptable acids are: 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, boric acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dehydroacetic acid, deoxycholic acid, diatrozoic acid, dodecylsulfuric acid, edetic acid, erythorbic acid, ethane-1,2-disulfonic acid, ethanesulfonic acid, fatty acid mixtures, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid. Polymeric examples include hyaluronic acid and alginic acid.

"Synergistic" generally refers to a combination of two or more active agents which shows a more than additive benefit than the expected sum of the individual agents, or as compared to an equivalent amount of a single active agent. With respect to postoperative pain, synergy refers to a combination of two or more active agents wherein the use of one active agent lowers the amount of another agent that is required to manage pain. For example, a synergistic combination of an amide-type local anesthetic and an NSAID allows for a lower amount of the amide-type local anesthetic and the NSAID to be administered in a single dose to provide a given level of pain relief than if the amide-type local anesthetic or NSAID were administered alone thereby providing a greater than additive analgesic effect in combination. When referring to antimicrobials, the term "synergistic" describes two drugs against a particular microorganism if the total concentration of the two antimicrobials required to kill or inhibit growth of the microorganism is less than the concentration of either agent alone to achieve the same goal. For example, tobramycin and vancomycin have synergy against a fraction of MRSA strains. Synergy may be determined on the basis of in vitro testing, for example measurement of the minimum inhibitory concentration (MIC). Synergy is said to occur for a given pair of antimicrobials against a microorganism when the MIC of the combination is lower than the MIC of either agent alone against the same microorganism. Synergy may also be said to occur on the basis of other tests including other in vitro tests (including biofilm killing tests) and in vivo animal or human clinical tests.

"Complementary" when used to describe antimicrobials is intended to refer to a combination of two or more agents which have different spectra of activity, such that when the agents are applied simultaneously, the spectrum of activity of the combination is broader than either single agent alone. Spectrum of activity refers to the set of micro-organism species and strains against which the antimicrobial is effective in killing or inhibiting growth.

"Optional" or "optionally" means that the subsequently described circumstance may or may not occur, so that the description includes instances where the circumstance occurs and instances where it does not.

"Water-soluble," unless otherwise clarified, indicates species which are soluble in water at a concentration of no less than about 1 wt %. Unless otherwise clarified, the species referred to is not a salt form but only the molecule itself. For example bupivacaine (base) is not water-soluble, but bupivacaine hydrochloride is water-soluble. "Highly water-soluble" indicates species have solubility in water at some pH that is no less than about 8 wt %. Solubility in water is generally available from manufacturers or in reference information for many commercially available materials. Solubility in water of a chemical species may vary depending on the context, specifically whether the solubility of the species is in a dosage form versus in physiological conditions. Unless otherwise clarified, the solubility in water is intended to indicate solubility of the species in deionized water.

As used herein, the term "lower critical solution temperature (LCST) imparting unit" refers to any repeat unit in a temperature responsive degradable polymer where a homopolymer of that repeat unit can have an LCST in aqueous solution that is between 0° C. and 100° C. Exemplary LCST-imparting units include without limitation, units derived from radical polymerization of N-substituted acrylamides, also called N-substituted acrylamide units.

As used herein, the term "lactone-bearing unit" refers to any repeat unit in a temperature-responsive degradable polymer that includes a lactone which when structurally changed, provides or otherwise contributes to a change in the polymer's existing LCST, established, for example, by an LCST imparting unit. Exemplary lactone-bearing units include repeat units having pendent lactones. Such repeat units may be connected to the polymer backbone via a variety of linkage groups, including without limitation, amides.

As used herein, the term "water content modifying unit" refers to a repeat unit in a temperature responsive degradable polymer that includes a pendent water soluble polymer having at least six repeat units and a weight average molecular weight of at least 500 g/mol.

As used herein, comparative terms such as "increased," "decreased," "better," "worse," "higher," "lower," "enhanced," "maximized," "minimized," "improved," and the like refer to a property of a device, component, or activity that is measurably different from other comparable devices, components, or activities, or from different iterations or embodiments of the same device, properties lacking the same features or characteristics. For example, a reservoir with properties that provide "improved" drug release would achieve a result that is measurably different than a reservoir with different properties.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 milligrams to about 80 milligrams" should also be understood to provide support for the range of "50 milligrams to 80 milligrams." Furthermore, it is to be understood that in this written description support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Example Embodiments

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

In-situ forming hydrogels often include the problems of (1) slow dissolution of temperature-responsive degradable polymers, (2) undesirable degradation of temperature-responsive degradable polymer solutions during storage, and (3) the difficulty of uniformly distributing certain drugs within temperature-responsive degradable polymer hydrogels. Accordingly, the present disclosure describes temperature-responsive degradable polymers, polymer compositions, therapeutic systems, and associated methods that address these problems. For example, the temperature-responsive degradable polymers can be stored as part of a polymer solution or composition in which the net lactone degradation of the polymer is slowed or halted (by approaching an equilibrium extent of lactone degradation). Further, in compositions containing one or more active agents, a precursor therapeutic composition can be employed having an appropriate composition to provide compatibility of a greater number of active agents with the hydrogel. For example, active agents that are not compatible with the storage conditions of the hydrogel or those that are not suspended uniformly within the hydrogel can be stored in a precursor therapeutic composition for subsequent combination with the polymer composition to form a therapeutic hydrogel composition. The resulting therapeutic hydrogel composition can be applied as a medical device or controlled release pharmaceutical formulation that is more convenient to prepare, has improved shelf-life, and facilitates adequate mixing with a wide variety of active agents. A method for hydrolyzing degradable lactone-bearing units in the polymer to reach an equilibrium composition prior to packaging is also disclosed, which can allow for long-term storage of the polymer with minimal net change in the hydrophilicity of the polymer, resulting in consistent properties such as the lower critical solution temperature (LCST), over subsequent storage.

It is noted that when discussing temperature-responsive degradable polymers, polymer compositions, therapeutic systems, and associated methods, each of these discussions can be considered applicable to each of these examples, whether or not they are explicitly discussed in the context of that example. Thus, for example, in discussing details about the temperature-responsive degradable polymers per se, such discussion also refers to the polymer compositions, therapeutic systems, and methods described herein, and vice versa.

Hydrogels based on polymers of N-substituted acrylamides can have viscoelastic rheological properties, degrade at a rate that is predictably and repeatably controlled independently of gel shape and fluid flow near the hydrogel, and provide rates of release of entrapped drugs which are predictably and reproducibly controlled with minimal initial burst release. Degradable polymers based on N-substituted acrylamides undergo a change in LCST over time as the side groups of certain repeat units in the polymer are hydrolyzed, leading to an increase in the LCST. For example, repeat units that have a lactone attached to the backbone by a linkage are hydrolyzed in physiological conditions to hydroxyacids which are more hydrophilic than the corresponding lactone structure due to additional presence of polar and charged moieties. When the LCST increases to above physiological temperature in physiological conditions, the polymer spontaneously dissolves. Degradation of hydrogels into soluble byproducts is considered desirable for a variety of biomedical applications. In particular, soluble byproducts are more likely to be cleared from the body safely. For example, soluble linear polymers are predominantly expected to be cleared from the body by renal excretion. In contrast, temperature-responsive polymers that dissolve or erode over time without hydrolysis, such as gels based on Poloxamer 407, which dissolve as a result of partial solubility in the surrounding aqueous media, are not suitable for the hydrogels described herein.

When the LCST is below physiological temperature, the hydrogel is a viscoelastic semi-solid material that remains at the site of administration and releases any entrapped drugs. As the LCST increases to above the physiological temperature, the hydrogel dissolves and the constituent polymer molecules dilute in the surrounding aqueous fluid and are cleared from the body. Generally, the temperature-responsive degradable polymers contain a first plurality of repeat units of an N-substituted polyacrylamide (e.g. N-isopropylacrylamide or N,N-diethylacrylamide). Temperature-responsive degradable polymers further contain a second plurality of lactone-bearing units containing a lactone having a five-membered or six-membered lactone ring connected to the polymer backbone by a linkage. In some further examples, a pendent water-soluble polymer graft is attached to the polymer backbone via a linkage.

A variety of linkage groups can be used to connect the polymer backbone to a lactone ring, to a water-soluble polymer graft, etc. Non-limiting examples can include an ester, an amide, a thioester, urea, thiourea, a $C_1$-$C_{12}$ alkyl, the like, or a combination thereof. In some specific examples, the linkage group can be an amide. It is noted that amide linkages can, in some cases, provide temperature-responsive degradable polymers having improved stability in storage conditions compared to previously disclosed temperature-responsive degradable polymers. For example, the degradation of temperature-responsive degradable polymers employing amide linkage groups can result in fewer low molecular weight byproducts following in vivo hydrolysis. Further, in some cases, temperature-responsive degradable polymers incorporating amide linkage groups can have improved stability over a larger pH range, such as from about 2 to about 11, from about 2 to about 10, from about 2 to about 9, from about 2 to about 8, or less than 8 (e.g., as compared to an ester linkage). For example, as described above, both in acidic storage conditions as well as in physiological conditions, it can be desirable to minimize the generation of low molecular weight degradation byproducts. Polymers with linkages susceptible to hydrolysis, such as esters, between the polymer backbone and lactones can lead to greater and essentially irreversible loss of lactones from the polymer in both storage conditions and physiological conditions. In some examples, this secondary mechanism of degradation can be avoided using an amide linkage.

With this in mind, compositions with acidic pH, for example between about 2 and 6, can be desirable because they afford increased stability in long-term storage at refrigerated or ambient temperatures. However, the advantages of temperature-responsive degradable polymers containing an amide linkage between the polymer backbone and lactone also are realized when the pH of the polymer solution is in the physiological range (between about 6 and about 8) because of the reduction in low molecular weight degradation byproducts compared to previously disclosed temperature-responsive degradable polymers of similar design that include an ester linkage rather than an amide linkage. In such situations, the polymer solution can be prepared including an aqueous solvent with a neutral pH (for example, between about 6 and about 8) and then stored at a lower temperature, for example at a temperature below about 0° C. or below about −20° C., to mitigate instability in storage until immediately prior to use.

In further detail, temperature-responsive degradable polymers as described herein can generally include a LCST-imparting unit and a lactone-bearing unit. In some embodiments, the number of LCST-imparting units can be greater than the number of lactone-bearing units. Further, the temperature-responsive degradable polymer can have a lower critical solution temperature (LCST) of 37° C. or below.

A variety of LCST-imparting units can be employed in the temperature-responsive degradable polymer. Generally, suitable LCST-imparting units are those that form polymers with an LCST in aqueous solution that is in a practical range, namely near or below physiological temperature. Both N-isopropylacrylamide and N,N-diethylacrylamide can result in homopolymers having an LCST at or below 37° C. (e.g. about 32° C., for example). Thus, in some examples, the LCST-imparting unit can include, or otherwise be, a unit derived from polymerization of an N-substituted acrylamide that results in a homopolymer having an LCST at or below 37° C., 35° C., 34° C., 32° C., or 30° C. In other examples, the LCST-imparting unit can be or include a unit derived from the polymerization of an N-substituted acrylamide that results in a homopolymer having an LCST at or below 100° C., but where the temperature-responsive degradable polymer can be adjusted with other repeat units to have an LCST at or below 37° C., 35° C., 34° C., 32° C., or 30° C. The LCST of a polymer based on N-substituted acrylamides can be measured by a number of measurement techniques including rheometry, cloud point determination, and differential scanning calorimetry (DSC).

Depending on the polymer concentration, molecular weight, solvent, and method of measurement, slightly different values may be obtained, as the LCST is a single number reflecting a distribution of polymer chains that are known to have slightly variable compositions even within polymer from a single batch. For clarity, unless specified otherwise, LCST generally refers to the temperature at which a low-concentration (e.g. 0.1-0.3 wt %) solution of polymer in a physiological buffer reaches half of the maximum absorbance level as determined by cloud point determination. The variety of LCST measurement methods and sensitivity to the factors listed above will produce slightly different determinations of LCST, but do not change the fact that the LCST is a predictable and controllable property of temperature-responsive polymers that can be adjusted by controlling a number of parameters including the polymer molecular weight, composition including the number and hydrophilicity of comonomers, and properties of the solvent including pH and the type and concentration of salts.

In some specific examples, the LCST-imparting units can have a structure:

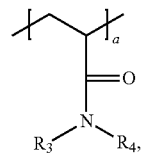

where R3 and R4 are independently selected from H, methyl, ethyl, propyl, and isopropyl, with the proviso that at least one of R3 and R4 is not H, and a is an integer from 15 to 20,000. In some specific examples, R3 is H and R4 is isopropyl, or the LCST-imparting unit is N-isopropylacrylamide. In some additional examples, R3 is ethyl and R4 is ethyl.

Generally, the proportion of LCST-imparting units in the polymer is from about 50 mol % to about 99 mol %. In other examples, the proportion of LCST-imparting units in the polymer is from about 60 mol % to about 95 mol %, or from about 70 mol % to about 95 mol %. In some specific examples, the proportion of LCST-imparting units in the polymer is at least 50 mol %, at least 60 mol %, or at least 70 mol %. In other specific examples, the proportion of LCST-imparting units in the polymer is from about 73.5 mol % to about 84.2 mol %. In still other specific examples, the proportion of LCST-imparting units in the polymer is from about 88.5 mol % to about 94.2 mol %.

In addition to the LCST-imparting units that are derived from N-substituted acrylamides, the temperature-responsive degradable polymer can also include lactone-bearing units. However, it is noted that functional groups other than lactones are susceptible to hydrolysis at rates that are generally greater than the majority or many other moieties and thus are suitable for imparting the capability of undergoing structural change over a reasonable time in physiological conditions. Examples of such functional groups include esters, anhydrides, carbamates, and sulfonyl ureas. When incorporated into a repeat unit side group, such moieties can thus contribute to the LCST change of the material in a similar fashion to a lactone in the lactone-bearing units. As such, in some examples, the temperature-responsive degradable polymer can include an ester-bearing unit, an anhydride-bearing unit, a carbamate-bearing unit, and/or a sulfonyl urea-bearing unit in addition to, or instead of, the lactone-bearing unit. Generally, the lactone-bearing units can include a pendent lactone having a five-membered or six-membered lactone ring bound to the polymer backbone by a first linkage group. The role of the lactone-bearing units is to provide an increase in the LCST of the polymer over time in physiological conditions.

The LCST of temperature-responsive degradable polymers can be adjustable in a predictable fashion by altering the polymer structure. Specifically, the LCST of temperature-responsive polymers based on N-substituted acrylamides can be affected by the hydrophilicity of any included comonomers. Hydrophilic comonomers can increase the LCST and hydrophobic comonomers can decrease the LCST. Lactones are generally susceptible to hydrolysis in aqueous solution during which the intact lactone ester is broken, forming a hydroxyacid that is more hydrophilic than the lactone due to the presence of a polar hydroxyl group and a highly polar charged carboxylic acid group. This hydrolysis reaction can occur in aqueous solution regardless of pH, but can proceed irreversibly in physiological conditions, namely at a neutral pH, more specifically near pH 7.4.

Conversion of a lactone to a hydroxyacid by hydrolysis leads to an increase in hydrophilicity and thus an increase in LCST of these polymers.

The LCST, degradation time in physiological conditions, release rate of entrapped drugs, and other properties of the hydrogel depend upon the structure and amount of hydrolyzable repeat units in the temperature-responsive degradable polymer. The LCST may be predicted according to the equation:

$$LCST = m*x + LCST0$$

where LCST0 is the LCST of the homopolymer of the N-substituted acrylamide, x is the mol % content of the co-monomer and m is a coefficient with units of (° C./mol %) that is specific to the comonomer, being positive for hydrophilic or water-soluble units and being negative for hydrophobic units.

Regardless of whether a given repeat unit structure causes an increase or decrease in the LCST, a reaction that causes a repeat unit to become more hydrophilic relative to its initial structure (or, put another way, to become less hydrophobic) will cause an increase in the LCST. A general relative order for the hydrophilicity of groups is as follows (from most hydrophilic to least): carboxylic acid, hydroxyl, ketone/aldehyde, amine, ester, ether, alkane). Thus, conversion of a lactone from an ester to a hydroxyacid (a hydroxyl plus a carboxylic acid) results in an increase in hydrophilicity and thus this reaction will lead to an increase in LCST regardless of the structure of the specific lactone.

As alternative examples, hydrophobic comonomers, for example HEMA-monolactate, HEMA-oligolactate, and dimethyl-butyrolactone acrylate, can be incorporated with N-isopropylacrylamide (NIPAAm) to lower the LCST initially, and then undergo hydrolysis to form a more hydrophilic structure, resulting in an increased LCST after degradation. This mechanism is predictable based on the hydrolysis products of esters or anhydrides being more hydrophilic than the original structure. So, for example, the hydroxyacid formed after degradation of dimethyl-butyrolactone has a positive effect on LCST (i.e., its presence in the polymer increases the LCST) whereas intact dimethyl butyrolactone has a negative effect on LCST. In order to include a lactone-bearing repeat unit in a temperature-responsive degradable polymer having the design described herein, a first linkage group can be used to connect the polymer backbone and the lactone. A suitable first linkage group can be a low molecular weight structure joining the lactone and polymer backbone. Examples of first linkage groups can include, but are not limited to, the following: amide, ester, urea, thiourea, thioester, and alkyl, more specifically $C_1$-$C_{10}$ alkyl. Examples of lactones include butyrolactone, valerolactone, substituted butyrolactones, and substituted valerolactones. The word "substituted" is intended to convey that other chemical moieties may be present, for example alkyl groups, hydroxyl groups, amine groups, the like, or a combination thereof. The hydrophilicity of specific additional groups on the lactone of the lactone-bearing units can alter the LCST effect of the repeat unit. However, the increase in LCST as a result of lactone hydrolysis can be preserved, regardless of the identity of the other chemical moieties in a substituted lactone. In some specific examples, substituted lactones can be lactones that are substituted with alkyl groups having no more than 2 carbons. For example, substituted butyrolactones can include dimethyl butyrolactone, or other suitable substituted butyrolactone.

In some specific examples, the lactone-bearing units can have the structure:

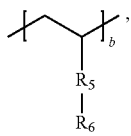

where $R_5$ is the first linkage group and is selected from an ester, an amide, a thioester, urea, thiourea, and a $C_1$-$C_{12}$ alkyl, $R_6$ is a lactone, such as a butyrolactone or a valerolactone, and b is an integer from 1 to 20,000. In some specific examples, $R_5$ is an ester or an amide. In some additional examples, $R_6$ is a butyrolactone. In some further examples, $R_6$ is dimethyl butyrolactone (e.g., the lactone bearing unit can be derived from dimethyl-butyrolactone acrylamide). In some other examples, $R_6$ is a valerolactone. In some specific examples, the lactone-bearing unit can have the structure:

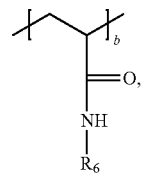

where $R_6$ can include those moieties described above or elsewhere herein.

The proportion of lactone-bearing units in the polymer is generally from about 1 mol % to about 50 mol %. In other examples, the proportion of lactone-bearing units in the polymer is from about 5 mol % to about 45 mol %, from about 5 mol % to about 40 mol %, from about 5 mol % to about 30 mol %, from about 5 mol % to about 25 mol %, from about 10 mol % to about 40 mol %, from about 10 mol % to about 30 mol %, from about 10 mol % to about 25 mol %, or from about 15 mol % to about 25 mol %. In some specific examples, the proportion of lactone-bearing units in the polymer is from about 5 mol % to about 10 mol %.

In some examples, the combined proportion of LCST-imparting units and lactone-bearing units is greater than 80%. In other examples, the combined proportion of LCST-imparting units and lactone-bearing units is greater than 85%. In still other examples, the combined proportion of LCST-imparting units and lactone-bearing units is greater than 90%. In yet other examples, the combined proportion of LCST-imparting units and lactone-bearing units is greater than 95%. In further examples, the combined proportion of LCST-imparting units and lactone-bearing units is greater than 98%.

In some additional examples, the temperature-responsive degradable polymer can further include a water content-modifying unit in addition to the LCST-imparting units and the lactone-bearing units. The water content-modifying unit can include a water-soluble polymer covalently bound to the polymer backbone via a second linkage group. The role of the water content-modifying unit is to control the water content in the resulting hydrogel, which can allow for control of a variety of properties of the gel. "Water-soluble polymer" generally refers to water-soluble polymers having greater than 6 repeat units and a weight average molecular weight of at least 500 g/mol.

The water content-modifying units can allow for control of a variety of hydrogel properties that are valuable in medical applications. For example, incorporation of water content-modifying units into the polymer can increase the accessibility of the temperature-responsive degradable polymer to water in the gelled state and therefore can increases the rate of hydrolysis, leading to faster degradation and dissolution in physiological conditions. The release rate of active agents contained within the gel can also be controlled by adjusting the proportion of water content-modifying units in the polymer. In general, adding more water content-modifying units including a water-soluble polymer can generally increase the rate of drug release by retaining more water within the gel. In some cases, adding a threshold minimum amount of water content-modifying units can provide slower release compared to materials with no water content-modifying units including pendent water-soluble polymers by retaining water within the gel and limiting the initial burst release. In general, adding water content-modifying units to the polymer can reduce high initial burst release but can also increase the rate of release after the period of initial burst release. Polymers with a greater number of water content-modifying units will generally result in weaker, softer hydrogels.

The water solubility and polymeric nature of the water content-modifying units can be valuable features for certain applications of the temperature-responsive degradable polymers that entail the controlled release of one or more active agents and in applications where control of gel volume is important. The water-soluble nature of the pendent polymer is important for the reasons described previously, namely that controlled water content can be used to predictably and reliably control important properties of the resulting hydrogel including drug release, degradation rate, volume, and rheological properties. The polymeric nature of the water content-modifying units is important because a low molecular weight unit [such as acrylic acid or other charged units like (diethylamino)ethyl methacrylate (DEAEMA)] can have an undesirably large effect on LCST when in the polymer backbone with an N-substituted acrylamide. For example, LCST can be largely controlled by the average chain length between hydrophilic moieties in a poly(N-substituted acrylamide) backbone, whereas distribution of hydrophilic moieties in a chain that are not part of the poly(N-substituted acrylamide) backbone can have a minimal effect on LCST. Put more simply, LCST can be said to be a function of mol % of a given comonomer while swelling is a function of wt % [more weight of a water-soluble (wettable) material will retain more water, independently of the number of repeat units that weight of water-soluble material is in]. The weight fraction of a water-soluble polymer grafted onto a poly(N-substituted acrylamide) backbone determines equilibrium swelling rather than the molar fraction. A pendent water-soluble polymer, having higher molecular weight than the N-substituted acrylamide first repeat unit, therefore constitutes a higher wt % than mol % of the overall polymer, leading to a relatively higher effect on hydrogel swelling with a relatively lower effect on LCST compared to conventional hydrophilic comonomers used in these materials, such as acrylic acid.

In some embodiments, the water-soluble polymer is a polymer of the water content-modifying units can include one or more of the following repeat units: ethylene oxide, propylene oxide, vinyl alcohol, acrylic acid, methacrylic acid, 2-hydroxyethyl methacrylate, N-2-hydroxypropylmethacrylamide, vinylpyrrolidone, amino acid, a monosaccharide, the like, or a combination thereof. In one specific examples, the water content-modifying units can contain Jeffamine M-1000, which is a copolymer of ethylene oxide and propylene oxide in about a 19:3 ratio by mole % as the water-soluble polymer having a methoxy terminus at one end and a primary amine at the other. Thus, the water-soluble nature of the polymer can be exploited to control the water content within the resulting hydrogel and thus the amount and type of water content-modifying units can be used to control the rate of degradation of the polymer as well as the release rate of any active agents contained within the hydrogel. In some additional examples, other water-soluble polymers can be inserted in place of Jeffamine M-1000 to achieve similar effects on the properties of the hydrogel. The amounts of different water content-modifying units to achieve an equivalent effect will differ from pendent polymer to pendent polymer, but arriving at a comparable formulation can be achieved by adjusting the amount of water content-modifying units included in the polymer. The particular species of water content-modifying units that has an amide linkage and a copolymer of ethylene oxide and propylene oxide with a methoxy terminus as the water-soluble polymer is convenient for incorporation in this polymer due to the ease of functionalizing the Jeffamine M-1000 into the macromer Jeffamine M-1000 acrylamide. Nevertheless, any suitable water-soluble pendent polymer can be employed with the water content-modifying units. The solubility in water of commercially available materials is typically available. If the solubility in water is not available, then it is intended that a polymer will be considered to be a water-soluble polymer for the purposes of the scope of the present disclosure if it is a polymer that is essentially a polymer of one or more of the following repeat units: ethylene oxide, propylene oxide, vinyl alcohol, acrylic acid, methacrylic acid, 2-hydroxyethyl methacrylate, N-2 hydroxypropylmethacrylamide, vinylpyrrolidone, amino acid, or a monosaccharide.

In some specific examples, the water content-modifying units can have the structure:

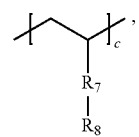

where $R_7$ is a second linking group selected from an ester, an amide, a thioester, urea, thiourea, and a $C_1$-$C_{12}$ alkyl, $R_8$ is a water soluble polymer or pendent polymer including at least six repeat units selected from ethylene oxide, propylene oxide, vinyl alcohol, acrylic acid, methacrylic acid, 2-hydroxyethyl methacrylate, N-2-hydroxypropylmethacrylamide, vinylpyrrolidone, an amino acid, a monosaccharide, and combinations thereof, and c is an integer from 1 to 5000.

The proportion of the weight of the water content-modifying units (i.e., the units containing a pendent water-soluble polymer) as a fraction of the total temperature-responsive degradable polymer weight is generally less than 25 wt %. In some specific examples, the proportion of the weight of the water content-modifying units is from about 5 wt % to about 25 wt %, from about 5 wt % to about 20 wt %, from about 5 wt % to about 15 wt %, or from about 7 wt % to about 12 wt %.

Further, the proportion of water content-modifying units in the temperature-responsive degradable polymer is generally less than 10 mol %. In some specific examples, the proportion of the water content-modifying units in the temperature-responsive degradable polymers is from about 0.1 mol % to about 5 mol %, from about 0.2 mol % to about 4 mol %, from about 0.5 mol % to about 3 mol %, from about 0.8 mol % to about 2 mol %, or from about 0.8 mol % to about 1.5 mol %.

The various repeat units of the temperature-responsive degradable polymer can be arranged in a variety of ways. For example, in some cases, the LCST-imparting units, the lactone-bearing units, and optionally the water content-modifying units can be arranged randomly. In other examples, the LCST-imparting units, the lactone-bearing units, and optionally the water content-modifying units can be arranged in blocks. Other suitable repeat unit arrangements can also be employed.

In further detail, the temperature-responsive degradable polymer compositions can be prepared by a variety of radical polymerization techniques, including conventional free radical polymerization, reversible addition-fragmentation chain transfer (RAFT) polymerization, atom transfer radical polymerization (ATRP), or the like. Examples of initiators for conventional free radical polymerization include azo compounds [for example 4,4'-azobis(4-cyanovaleric acid) (ACVA), 1,1'-azobis(cyclohexanecarbonitrile), azobisisobutyronitrile (AIBN), 2,2'-azobis(2-methylpropionitrile), and 2,2'-azobis(2-methylpropionamidine) dihydrochloride], inorganic peroxides [for example ammonium persulfate, potassium persulfate, sodium persulfate, and hydroxymethanesulfinic acid], organic peroxides [for example benzoyl peroxide, tert-butyl peroxide, and dicumyl peroxide], and photoinitiators [for example (2-hydroxy-1-[4-(2-hydroxyethoxy) phenyl]-2-methyl-1-propanone)].

RAFT polymerization can be performed by adding a quantity of a RAFT agent (thiocarbonylthio compounds) to a conventional free radical polymerization. Usually the same monomers, initiators, solvents, and temperatures can be used. Because of the low concentration of the RAFT agent in the system, the concentration of the initiator is usually lower than in conventional free radical polymerization. Radical initiators such as AIBN and ACVA are widely used as the initiator in RAFT. RAFT polymerization is known for its compatibility with a wide range of monomers, including for example acrylates and acrylamides. ATRP can be effected using ethyl 2-chloropropionate (ECP) as an initiator and CuCl/tris(2-dimethylaminoethyl)amine (Me6TREN) as a catalytic system. The living character of the polymerization allows preparation of block copolymers.

In some specific examples, the temperature-responsive degradable polymers can have the structure:

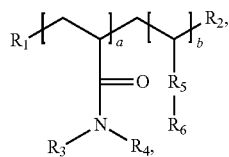

where $R_1$ and $R_2$ are independently selected from H, alkyl, phenyl, benzyl, 2-cyanoprop-2-yl, and ethyl-2-propionate sulfate, $R_3$ and $R_4$ are independently selected from H, methyl, ethyl, propyl, and isopropyl, with the proviso that at least one of $R_3$ and $R_4$ is not H, $R_5$ is a first linking group selected from an ester, an amide, a thioester, urea, thiourea, and a $C_1$-$C_{12}$ alkyl, $R_6$ is a lactone, such as a butyrolactone or a valerolactone, a is an integer from 15 to 20,000, and b is an integer from 1 to 20,000.

In some specific examples, $R_1$ and $R_2$ are 2-cyanoprop-2-yl. In some additional examples, $R_3$ is H and $R_4$ is isopropyl. In still other examples, $R_3$ is ethyl and $R_4$ is ethyl. In other examples, $R_5$ is an amide. In yet other examples, $R_6$ is a butyrolactone. In some specific examples, $R_6$ is β,β-dimethyl-γ-butyrolactone. As described previously, the LCST-imparting units can be a majority of the repeat units in the temperature-responsive degradable polymer. The temperature-responsive degradable polymer is not crosslinked. By "not crosslinked," it is to be understood that the temperature-responsive degradable polymer is substantially uncrosslinked, or uncrosslinked (i.e. does not include any crosslinks). This limitation excludes the incorporation of bifunctional units that incorporate into two polymer backbones, such as bisacrylamide, and also any units that have water-soluble polymers that also serve as crosslinkers, for example polyethylene glycol diacrylate (PEGDA). Chemically crosslinked temperature-responsive degradable polymers, i.e. those in which multiple polymer backbones are covalently bound, are not soluble regardless of temperature, having a volume phase transition temperature (VPTT).

In some specific examples, the temperature-responsive degradable polymer can have the structure:

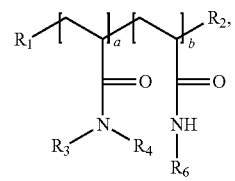

where $R_1$, $R_2$, $R_3$, $R_4$, and $R_6$ can be the same as described elsewhere herein.

In some additional examples, the temperature-responsive degradable polymer can have the structure:

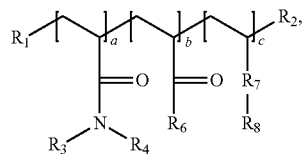

where $R_1$, $R_2$, $R_3$, $R_4$, $R_5$, and $R_6$ can each independently be selected from the options provided herein, wherein $R_7$ is a second linking group selected from the following: ester, amide, thioester, thioamide, urea, thiourea, and $C_1$-$C_{12}$ alkyl, $R_8$ is a water-soluble polymer, and c is and integer from about 1 to about 5,000. The water-soluble polymer does not crosslink between two different polymer backbones.

In some specific examples, $R_7$ is an amide. In other examples, $R_5$ is a copolymer of ethylene oxide and propylene oxide having a weight average molecular weight ($M_W$) of from about 700 g/mol to about 3000 g/mol. In some further examples, $R_5$ includes a majority of ethylene oxide units.

The proportion of water content-modifying units is typically less than 25% of the total number of repeat units in the polymer. The proportion of any units in the polymer other than the LCST-imparting units, the lactone-bearing units, and water content-modifying units that contain carboxylic acids is typically less than 1 mol %. The LCST of temperature-responsive polymers containing carboxylic acid moieties can be pH-dependent, having a lower LCST in acidic pH compared to neutral pH due to the presence of a charge on the carboxy moieties at neutral pH. For example, protonated methacrylic acid or propylacrylic acid repeat units can have a negative effect on LCST at pH 4.0 and a high, positive effect on LCST at pH values approximating physiological pH. As with any comonomer, the effect on LCST can be modeled as being proportional to the content of the comonomer. The LCST of such polymers can be controlled according to the theory described in this specification, for example by including comonomers which are hydrophobic to offset the increase in LCST due to the carboxylic acid-bearing group, or by limiting the content of such groups, for example to below 1 mol %, which has a low effect on LCST.

The LCST-imparting units may be in blocks or randomly located with respect to the lactone-bearing units and/or water content-modifying units, the lactone-bearing units may be in blocks or randomly located with respect to the LCST-imparting units and/or water content-modifying units, and the water content-modifying units may be in blocks or randomly located with respect to the LCST-imparting units and lactone-bearing units.

In some specific examples, the temperature responsive degradable polymers can have the structure:

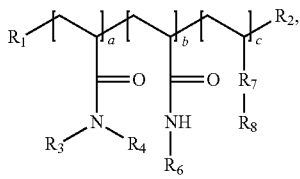

where $R_1$, $R_2$, $R_3$, $R_4$, $R_6$, $R_7$, and $R_8$ can include those substituents described elsewhere herein.

The temperature-responsive degradable polymers generally have a weight-average molecular weight ($M_w$) of from about 3,000 g/mol to about 2,000,000 g/mol. In some specific examples, the temperature-responsive degradable polymers can have an $M_w$ of from about 3,000 g/mol to about 1,000,000 g/mol, from about 3,000 g/mol to about 75,000 g/mol, from about 5,000 g/mol to about 70,000 g/mol, from about 10,000 g/mol to about 50,000 g/mol, from about 20,000 g/mol to about 50,000 g/mol, or from about 25,000 g/mol to about 50,000 g/mol. In some further examples, the temperature-responsive degradable polymers can have an $M_w$ of from about 15,000 g/mol to about 100,000 g/mol, or from about 30,000 g/mol to about 50,000 g/mol. It is noted that molecular weights below about 50,000 g/mol are generally considered desirable for polymers that are expected to be cleared from the body by renal excretion as soluble intact polymer molecules, i.e. without degradation of the polymer backbone. Thus, many of the examples disclosed describe temperature-responsive degradable polymers within this range. However, it has been determined that hydrogels based on temperature-responsive degradable polymers having a weight-average molecular weight of about 80,000 g/mol did not cause renal toxicity in rats at large doses when applied locally. The relationship between molecular weight, polymer amount, and toxicity has not been fully characterized. For applications in which the amount of polymer is low or where material strength is particularly important, material with a high $M_w$ in excess of 50,000 g/mol may be desirable despite increased risk of toxicity arising from polymer metabolism and clearance.

Thus, there is a trade-off between material strength and toxicity, and optimal molecular weight will differ depending on the intended use.

In some specific examples, the temperature-responsive degradable polymer has a weight-average molecular weight ($M_w$) of from about 25,000 g/mol to about 50,000 g/mol, $R_1$ and $R_2$ are 2-cyanoprop-2-yl, $R_3$ is H and $R_4$ is isopropyl, $R_5$ is an amide, $R_6$ is β,β-dimethyl-γ-butyrolactone, $R_7$ is an amide, $R_8$ is a copolymer of ethylene oxide and propylene oxide having a ratio of about 19 ethylene oxide units to about 3 propylene oxide units with a methoxy terminus, the proportion of LCST-imparting units is from about 73.5 mol % to about 84.2 mol %, the proportion of lactone-bearing units is from about 15 mol % to about 25 mol %, the proportion of water content-modifying units is from about 0.8 mol % to about 1.5 mol %, and the temperature-responsive degradable polymer does not contain substantial amounts of other repeat units.

In another specific example, the temperature-responsive degradable polymer has a $M_w$ of from about 25,000 g/mol to about 50,000 g/mol, $R_1$ and $R_2$ are 2-cyanoprop-2-yl, $R_3$ is H and $R_4$ is isopropyl, $R_5$ is an ester, $R_6$ is β,β-dimethyl-γ-butyrolactone, $R_7$ is an amide, $R_8$ is a copolymer of ethylene oxide and propylene oxide having a ratio of about 19 ethylene oxide units to about 3 propylene oxide units with a methoxy terminus, the proportion of LCST-imparting units is from about 88.5 mol % to about 94.2 mol %, the proportion of lactone-bearing units is from about 5 mol % to about 10 mol %, the proportion of water content-modifying units is from about 0.8 mol % to about 1.5 mol %, and the temperature-responsive degradable polymer does not contain substantial amounts of other repeat units.

Temperature-responsive degradable polymers based on polymers of N-substituted acrylamides pose a particular challenge for successful commercial development because of their slow dissolution time and instability in physiological conditions. For example, temperature-responsive degradable polymers as described herein can require several hours to dissolve at concentrations useful for the formation of hydrogels. In a laboratory environment, common methods can include combining a lyophilized polymer powder and the aqueous solvent followed by a combination of cooling and agitating the mixture until a reasonably clear solution is obtained. Dissolution times can be longer and require more agitation where polymers are not available in a physical state with high surface area and low density, such as a lyophilized powder. Further, such polymers can act as surfactants, such that even after dissolution, a layer of air bubbles can remain on top of the solution for a period of 24 hours or longer. Air bubbles in temperature-responsive polymer formulations are of concern because they lead to inconsistency in the content and properties of the resulting hydrogel. Over time, air bubbles can disrupt the structure of certain hydrogels as air bubbles exit the material. Thus, the slow dissolution of the temperature-responsive degradable polymers disclosed herein has the potential to add significant complexity to any pharmaceutical or medical device preparation where the temperature-responsive degradable polymer is part of a commercial product requiring reconstitution within 1-2 days prior to use. Typically, it can be challenging to reconstitute a product involving these polymers in a commercially feasible fashion in less than 3 hours.

At useful concentrations, the temperature-responsive degradable polymers described herein dissolve slowly, and can require several hours or even days to achieve complete full and even dissolution in aqueous solvents, regardless of the method of polymer preparation or the specific aspects of the dissolution method. Incomplete dissolution is undesirable because it can lead to inconsistent and poorly controlled properties. Vigorous mixing, for example stirring, shaking, or using a vortex mixer, aids in dissolution of the temperature-responsive degradable polymers, but dissolution is still unacceptably slow for many commercial applications. Dissolution remains slow even for temperature-responsive degradable polymers that are lyophilized and that seem to be ideal for reconstitution. For example, it can be inconvenient for a hospital pharmacy to repeatedly mix the sample or to obtain equipment to maintain the stirring and cold temperature necessary to dissolve such a temperature-responsive degradable polymer. Additionally, even when vigorous mixing is done to dissolve the temperature-responsive degradable polymers as rapidly as possible, air bubbles can remain trapped in the polymer composition for several hours or days. Entrapment of air bubbles can lead to inconsistency in the properties of a hydrogel. Thus, by allowing for long-term storage of the temperature-responsive degradable polymers in solution, a sufficient amount of time for the polymer to be dissolved and for air bubbles to release can be achieved, rather than dissolving such polymers relatively soon, for example within 1 week or within 1 month, before its intended end use.

Moreover, dissolving a polymer in a neutral pH buffer well in advance and providing it in a solution also is undesirable due to the risk of hydrolysis of the degradable moieties on the polymer during storage. Polymers of the structures described herein have been determined to degrade over a period of about 1 week to 6 months, depending on the particular structure employed. However, it is generally desirable for a pharmaceutical formulation or medical device to have a shelf life of at least 18-24 months in ambient (about 25° C.) or refrigerated (about 5° C.) conditions. A product that must be stored at lower temperatures, especially at −20° C. or below, is associated with greater costs of storage and transportation. Thus, a composition that has long-term stability in storage conditions, but also retains the desirable properties of temperature-responsive degradable polymers is advantageous and commercially useful.

In further detail, temperature-responsive degradable polymers with pendent lactones are configured to undergo hydrolysis of the lactones in physiological conditions, forming hydroxyacids that are more hydrophilic than the corresponding lactone structure, which causes an increase in the LCST of the temperature-responsive degradable polymer. In the context of a pharmaceutical or medical device formulation, when the LCST increases to above the physiological temperature, the temperature-responsive degradable polymer will dissolve and then the soluble temperature-responsive degradable polymer will be excreted from the body.

The conventional method of preparation of such temperature-responsive degradable polymer solutions involves buffer solutions that are intended to approximate the osmolarity and pH in the body, for example phosphate buffered saline with a total osmolarity of about 300 mOsm/L and pH of about 7.4. However, storage in a neutral pH or slightly alkaline buffer can lead to hydrolysis of lactones by the same hydrolysis mechanism that is intended to occur in the body. Thus, storing a temperature-responsive lactone-bearing polymer in a buffer approximating physiological pH leads to instability of the lactone rings due to conversion to form hydroxyacids.

However, it has been discovered that temperature-responsive degradable polymers with pendent lactone rings have substantially altered degradation properties when dissolved in an aqueous acidic solution having a pH less than 7. Specifically, the pendent lactone rings can reach an equilibrium in which the proportion of lactone rings that may be described as "closed" or "intact" as opposed to the "open" hydroxyacid is relatively high (between about 80 and about 98%). The equilibrium arises from a reverse reaction in which the pendent hydroxyacid structure undergoes intramolecular esterification to form the lactone. For example, lactones having five or six atoms in the ring containing the ester, also called five-membered and six-membered rings, respectively, can undergo intramolecular esterification under appropriate conditions. In aqueous acidic solutions, both the hydrolysis of lactone esters and the reverse reaction, lactone formation by intramolecular esterification, occur. When the number of esters being formed is about equal to the number of esters being hydrolyzed, an equilibrium composition is approached.

This discovery was surprising and advantageous because it allows for the temperature-responsive degradable polymers described herein to have greatly improved stability in solution. Pharmaceutically acceptable acids can be used to control the pH in a polymer composition, resulting in a greater number of polymer-bound lactone rings lasting for longer and more stable polymer properties over time. Although other structures including other ester structures (for example, an ester linkage between the polymer backbone and lactone ring, or an ester linkage between the polymer backbone and some other structure) or amide structures are in principle hydrolyzable and are a potential cause of instability, reducing the effect of lactone hydrolysis functions to stabilize the polymer. For example, the ester linkage between the polymer backbone and dimethyl butyrolactone is more stable than the lactone itself. Likewise, ester linkages in butyl acrylate and tert-butyl acrylate described in the examples below undergo relatively slow degradation. Slowing the loss of lactones can increase the useful shelf life of temperature-responsive degradable polymers even with other groups that are hydrolyzable to some extent.

Hydrolysis of esters and anhydrides is a widely used chemical reaction to impart degradability into materials in physiological conditions. For example, polymers of lactic acid and glycolic acid (polyesters) are commonly used in medicine for sustained release pharmaceutical formulations including microparticles and nanoparticles and also for medical devices such as resorbable sutures. The rate of hydrolysis of esters and anhydrides depends on the structure of adjacent chemical groups, the pH of the solution, and the accessibility of the bonds to water. For example, the same type of bond on a solid material will usually degrade more slowly than the same bond in a hydrogel. An estimate is that an ester on a solid material such as polyglycolic acid or polylactic acid will require approximately 3-24 months to degrade, whereas degradation times are on the order of days to weeks for esters in soluble materials. For polymers described herein, water accessibility is intermediate between a totally soluble material and a non-hydrated insoluble material. Water accessibility depends at least upon temperature and the presence and quantity of any hydrophilic units in the temperature-responsive degradable polymer, such as water content-modifying units containing a water-soluble polymer, which serve to increase the water accessibility of the hydrolyzable moieties, increasing the hydrolysis rate. The pH of a solution also affects hydrolysis rate of esters and anhydrides. Both strong alkaline and strong acidic conditions can promote hydrolysis. At pH values near the physiologic range which is about 7.4, increasing pH generally leads to an increase in hydrolysis rate of esters or anhydrides.

In the polymers described herein, hydrolysis of the lactones of the lactone-bearing units occurs, resulting in a hydroxyacid. In acidic conditions, intramolecular esterification occurs, which results in the reverse reaction of the hydroxyacid to form the lactone. Thus, although hydrolysis of the lactone is unavoidable at any pH, lactones can be re-formed at a rate approximately equal to their rate of hydrolysis in acidic conditions. As such, the LCST of the polymer in acidic conditions can be controlled and stabilized, including for long-term storage.

As such, in some examples the polymer compositions described herein can be acidic. In one embodiment, the polymer solution can include an aqueous acidic solvent. In one embodiment, the acidic pH of the solvent is primarily attributable to the acid groups on the temperature-responsive degradable polymer as a result of partial hydrolysis of the lactones on the lactone-bearing units of the polymer such that a weakly buffered or unbuffered solution regardless of its initial pH can become acidic during storage of the polymer. In one embodiment, the polymer solution contains acidic species that are one or more of the group including pharmaceutically acceptable acids and acidic active agents. A variety of pharmaceutically acceptable acids are known, for example in the textbook Handbook of Pharmaceutical-Salts: Properties, Selection and Use. Thus, the pH of the polymer composition can be controlled in a variety of ways, such as by using a buffering agent, a pharmaceutically acceptable acid, acidic moieties on the temperature-responsive degradable polymer, or a combination thereof. In selected embodiments, the aqueous acidic solvent is a buffering agent. In selected embodiments the aqueous acidic solvent contains sodium acetate and acetic acid. In selected embodiments, the aqueous acidic solvent contains 2-(N-morpholino)ethanesulfonic acid. In selected embodiments, the aqueous acidic solvent contains citric acid. In selected embodiments, the aqueous acidic solvent contains citric acid and sodium citrate. In selected embodiments, the aqueous acidic solvent contains citric acid and dibasic sodium phosphate. In selected embodiments, the aqueous acidic solvent contains dibasic sodium phosphate and monobasic sodium phosphate. In selected embodiments, the aqueous acidic solvent contains hydrochloric acid. A variety of other buffering agents, pharmaceutically acceptable acids, or the like can also be used. For example, molecules with pKa values in the acidic range of a particular pH are suitable for buffering solutions in that pH range. Thus, while the present written description only names a few buffering agents, pharmaceutically acceptable acids, etc. (e.g. acetic acid, acetic acid and sodium acetate, hydrochloric acid, or monobasic sodium phosphate and dibasic sodium phosphate) for the sake of brevity, the function of stabilizing the temperature-responsive degradable polymer is not dependent on any specific molecule, but rather is determined by the pH of the aqueous acidic solvent or the resulting polymer composition. In some examples, the aqueous acidic solvent contains less than 10 millimoles of acids, bases, or other buffering agents per liter.

In other examples, the polymer compositions described herein can be neutral. In one embodiment, the polymer solution can include an aqueous neutral solvent (e.g. from about pH 6 to about pH 8). In still other examples, the polymer compositions described herein can be alkaline. In one embodiment, the polymer solution can include an aqueous alkaline solvent (e.g. from about pH 8 to about pH 11).

As noted previously, pH can be adjusted using a variety of buffering agents (e.g., phosphate buffers, bicarbonate buffers, etc.), pH adjusters (e.g., sodium hydroxide, hydrochloric acid, phosphoric acid, etc.).

In further detail, the temperature-responsive degradable polymers can be dissolved in an aqueous vehicle to prepare a polymer solution or polymer composition. The concentration of the temperature-responsive degradable polymers in the polymer composition can be sufficient for formation of a hydrogel. The minimum concentration required for formation of a hydrogel decreases with increasing molecular weight of the polymer. As reported below in the Examples, the minimum gelation concentration (in wt %) can be estimated as:

$$-0.494*M_w+23.68,$$

where $M_w$ is in kDa for $M_w \leq 43$ kDa, 3 wt % for 183 kDa $\geq M_w > 43$ kDa, 2 wt % for 1,510 kDa $\geq M_w > 183$ kDa, and about 1 wt % for $M_w > 1,510$ kDa.

In embodiments where the hydrogel is prepared from the combination of the polymer solution and a second composition, the polymer solution can generally have a viscosity low enough to allow for mixing with the second composition. Studies described below in the Examples indicate that polymer solutions with a viscosity of less than 2 Pa*s at a shear rate of 100 sec$^{-1}$ can be mixed evenly with a second composition. Because viscosity of the polymer solution increases as a function of the molecular weight and concentration of the polymer, the concentration of the polymer can be kept below a certain threshold value, described here as the maximum mixing concentration. As reported below in the Examples, the maximum mixing concentration (in wt %) can be estimated as:

$$-6.872*\ln(x)+64.76,$$

where x is the weight-average molecular weight of the polymer in kDa.

Commercial products including pharmaceutical and medical device formulations generally have consistent and reliable properties throughout their intended shelf life. As such, the present disclosure provides a method for manufacturing a temperature-responsive degradable polymer by subjecting the polymer to a hydrolysis reaction and then packaging the polymer in solution following the reaction once the composition of lactones reaches about an equilibrium composition. In one embodiment, the temperature-responsive degradable polymer is packaged with a composition other than its equilibrium composition and then the lactone-bearing units approach an equilibrium composition over time in storage prior to use. In one embodiment, the temperature-responsive degradable polymer of the polymer solution favors an equilibrium in which degradable lactone moieties on the temperature-responsive degradable polymer are largely intact, where the ratio of the number of intact lactones to the number of corresponding hydroxyacids is greater than 1 to 1, greater than 3 to 1, greater than 5 to 1, greater than 10 to 1, or greater than 20 to 1.

In further detail, the temperature-responsive degradable polymers can be either dissolved far in advance of use (for example, during manufacturing) and then stored as a solution until use or dissolved shortly before the time of use. Complete dissolution of temperature-responsive polymers at useful concentrations can require several hours (for example, over 24 hours) which is inconvenient for many medical applications. A readily available "off-the-shelf" formulation or "ready-to-use" formulation is generally desirable.

An alternative strategy can be to dissolve the temperature-responsive degradable polymers prior to use. However, temperature-responsive degradable polymers are inherently unstable in aqueous solution. Storage of the polymer solution (for example at −20° C.) prior to use reduces the rate of hydrolysis, but is expensive to maintain and potentially complicated for the user of the product, requiring the product to be thawed in a controlled environment prior to use. Such a procedure is inconvenient or unacceptable for a variety of medical procedures. In contrast, the polymer solution described herein can provide a pre-dissolved composition sufficiently stable to allow application of a temperature-responsive degradable hydrogel within a short time after storage (for example, less than 15 minutes). The polymer solution can allow storage of a temperature-responsive degradable polymer in solution for an appropriate shelf life either entirely or in part at refrigerated (2-8° C.) or ambient temperature (20-25° C.). In some examples, the polymer solutions can be stable for a period of at least about 180 days at 4° C. or ambient temperature, at least about 365 days at 4° C. or ambient temperature, at least about 730 days at 4° C. or ambient temperature. In some specific examples, the polymer solutions can be stable for a period of at least about 730 days at 25° C.

The polymer solution can include a temperature-responsive degradable polymer as described herein and an aqueous vehicle (e.g. an aqueous acidic solvent). The polymer can be soluble in the aqueous acidic solvent at temperatures below the lower critical solution temperature (LCST). Generally, the LCST can be below 37° C., or in some examples below 30° C. In some specific examples, the LCST can be from about 5° C. to about 30° C., or from about 15° C. to about 30° C. The polymer solution can have a smooth and flowable texture at temperatures below the LCST. In some specific examples, polymer solution can have a pH less than 7, or from about 2 to about 6.5, from about 2.5 to about 6, or from about 3 to about 5. In some examples, the temperature-responsive degradable polymer can be present in the polymer solution in an amount from about 5 wt % to about 55 wt %, from about 20 wt % to about 50 wt %, from about 25 wt % to about 45 wt %, from about 30 wt % to about 42 wt %, from about 33 wt % to about 40 wt %, or from about 30 wt % to about 40 wt % based on total weight of the polymer solution. In some specific examples, the temperature-responsive degradable polymer concentration in the polymer solution can be from about 35 wt % to about 40 wt % and the aqueous acidic solvent has a pH between 2 and 6. In one embodiment, the polymer composition can be a sustained-release delivery vehicle. In one embodiment, the polymer composition can be injectable. In another embodiment, the polymer composition can be suitable for administration as an intramuscular injection, transdermally, topically, as a subcutaneous injection, as a perineural injection, as an intra-articular injection, or to a surgical site. In one embodiment, the polymer composition can have a complex modulus of less than 100 Pa*s at 1 Hz frequency at a temperature below the lower critical solution temperature when measured on a rheometer.

In some specific examples, the aqueous vehicle can include one or more of a pH adjuster, a buffering agent, and a tonicity agent. Non-limiting examples of pH adjusters or buffering agents can include a number of acids, bases, and combinations thereof, such as hydrochloric acid, phosphoric acid, citric acid, sodium hydroxide, potassium hydroxide, calcium hydroxide, acetate buffers, citrate buffers, tartrate buffers, phosphate buffers, triethanolamine (TRIS) buffers, the like, or combinations thereof. Non-limiting examples of tonicity agents can include sodium chloride, potassium chloride, calcium chloride, magnesium chloride, mannitol, sorbitol, dextrose, glycerin, propylene glycol, ethanol, trehalose, phosphate-buffered saline (PBS), Dulbecco's PBS, Alsever's solution, Tris-buffered saline (TBS), water, balanced salt solutions (BSS), such as Hank's BSS, Earle's BSS, Grey's BSS, Puck's BSS, Simm's BSS, Tyrode's BSS, and BSS Plus, the like, or combinations thereof.

The present disclosure also describes therapeutic systems including a polymer solution or composition as described herein and a precursor therapeutic composition. The precursor therapeutic composition can include a therapeutic agent and can be formulated for combination with the polymer solutions described herein. In some examples, the precursor therapeutic composition can be a lyophilized product. In other examples, the precursor therapeutic composition can be a liquid composition where the therapeutic agent is a liquid. In some further examples, where the therapeutic agent is a lyophilized product or a liquid, the precursor therapeutic composition can consist of or consist essentially of the therapeutic agent. In other examples, the precursor therapeutic composition can include a variety of excipients. In still other examples, the precursor therapeutic composition can include a liquid or semi-solid carrier. The precursor therapeutic composition can generally have a liquid or semi-solid texture suitable for mixing with the polymer solution. In some embodiments, the precursor therapeutic composition further contains one or more excipients. In some embodiments, the excipients can include an aqueous acidic solution. In some embodiments, the excipients can include a copolymer of one of more of ethylene oxide units and propylene oxide units having a molecular weight of less than about 1,000 g/mol. Other suitable excipients can also be used, such as those described elsewhere herein. In some embodiments, the precursor therapeutic composition can be a solution of one or more active agents. In some embodiments, the precursor therapeutic composition can be a suspension of one or more active agents. In some embodiments, the precursor therapeutic composition can be a colloid. In some embodiments, the precursor therapeutic composition can be prepared immediately (within 1 hour) prior to mixing with the polymer solution. In some embodiments, the precursor therapeutic composition can be prepared in advance (for example, during manufacturing) and stored for a period of time prior to mixing with the polymer solution.

In some embodiments, the precursor therapeutic composition contains between about 10-25 wt % of the active agent(s) and the balance is a liquid or semi-solid carrier. In some embodiments, the precursor therapeutic composition can be an aqueous solution of tobramycin and vancomycin with a total drug concentration of from about 18 wt % to about 24 wt %. In some embodiments, the precursor therapeutic composition can be a suspension of a local anesthetic in a biocompatible organic excipient carrier. In some embodiments, the precursor therapeutic composition can be a suspension of bupivacaine at a concentration of from about 9 wt % to about 33 wt % and the balance is a biocompatible organic excipient as the carrier.

One purpose of the precursor therapeutic composition is to facilitate mixing of one or more active agents into the hydrogel. Thus, the precursor therapeutic composition does not include a crosslinker. A crosslinker is a molecule or set of molecules that undergo a reaction with two or more polymer backbones. For example, in embodiments where the temperature-responsive degradable polymer includes a thiol-bearing group, a molecule in the precursor therapeutic composition containing two or more acrylates is a crosslinker. A variety of pairs of lactone-bearing groups can be used to crosslink hydrogels, including primary amide and aldehyde, hydrazide and aldehyde, primary amine and acrylate, and azide and alkyne, for example.

In some examples, the polymer solution and the precursor therapeutic composition can be contained in separate containers. In other examples, the polymer solution and the precursor therapeutic composition can be contained in different compartments of a common container. In some specific examples, the common container can be a double-barrel syringe. In some examples, the double-barrel syringe can include a metered mixing dispenser or other suitable dispenser configured to mix the polymer solution and the precursor therapeutic composition as they are dispensed from the common container.

Substantial uniformity is a general requirement for pharmaceutical dosage forms including hydrogels. If not substantially uniformly distributed, non-dissolved therapeutic agent can either settle to the bottom of polymer solutions or accumulate on the top, if stored along with the gel. Further, non-uniform distribution of insoluble therapeutic agents can lead to instability of the hydrogel itself and poorly controlled properties of interest, including the rate of drug release.

It can be difficult to obtain an even distribution of an insoluble therapeutic agent in the hydrogel because of the viscosity of the polymer solution. Vigorous mixing leads to the formation of air bubbles, while gentle mixing or shaking often does not distribute the therapeutic agent homogeneously. In some further examples, some therapeutic agents can form aqueous biphasic systems when combined with temperature-responsive degradable polymer solutions at concentrations that are estimated to be useful. Thus, in addition to the challenges with shelf life recited above, certain drugs can be challenging to distribute uniformly within hydrogels without some new technology or additive that can add cost and complexity. Further a wide variety of therapeutic agents are conventionally stored as dry powders for reconstitution immediately before dosing. These therapeutic agents, in many cases, are strongly recommended to be used within a short time, for example 1-2 days, following reconstitution. Longer term storage of such drugs in solution can lead to instability by a number of mechanisms including chemical reaction, recrystallization, degradation, inactivation, and the like. Concentrations in sustained release dosage forms are often even higher than in conventional pharmaceutical formulations, and thus the aforementioned mechanisms of instability can be exacerbated if active agents are required to be dissolved in a temperature-responsive polymer solution for long-term storage.

However, the present disclosure describes compositions and methods by which one or more active agents may be stored under conditions that are suitable for those active agents and then combined to obtain a hydrogel containing a reasonably uniform distribution of the active agents. For example, in some embodiments, a precursor therapeutic composition can be prepared within a short time (less than one day) prior to use by reconstitution of the active agent. In some embodiments, the precursor therapeutic composition may be formed during manufacturing but without water. These methods can address the general challenges related to the formation of an aqueous biphasic system or poor solubility in water. These methods also address the general challenge related to the stability and storage of a wide variety of active agents followed by reconstitution within a short time before use. Appropriate practices for stability and reconstitution of drug products are provided in commercial labeling and developed by conducting appropriate stability tests according to standardized methods, for example the methods provided in ICH guideline Q1A(R2).

By storing temperature-responsive degradable polymers in acidic solution and mixing with separately prepared precursor therapeutic compositions at the time of use, improved stability and uniformity of hydrogels can be achieved. Additionally, improved consistency, ease, and speed of incorporating active agents into the hydrogels can also be achieved. Further, the resulting therapeutic hydrogel composition can have improved and consistent sustained release of active agents in vitro. Further, the resulting therapeutic hydrogel composition can provide sustained drug release in vivo and can be effective in animal models of postoperative pain and deep infection.

The precursor therapeutic compositions can include a variety of therapeutic agents. Non-limiting examples can include an antimicrobial agent, an anesthetic agent, an opioid, an anti-inflammatory agent, a polysaccharide, a polynucleotide, an antigen, an antibody, a vaccine, a vitamin, an enzyme, a protein, the like, or a combination thereof. The precursor therapeutic compositions can also include additional inactive substances, including excipients, preservatives, buffering salts, the like, or a combination thereof.

In some embodiments, a precursor therapeutic composition can be mixed with the polymer solution to form a hydrogel. The hydrogel is a physical gel, meaning that the polymer responsible for gelation is not covalently cross-linked. Because the gel-forming polymer is not crosslinked, it can be isolated from low molecular weight impurities and reagents typical of cross-linking reactions prior to dissolution and mixing with any therapeutic agent. The mixing with therapeutic agent(s) can be accomplished after a solution of the polymer (which is already manufactured and purified) is prepared.

Further, the hydrogel can be applied as an injectable liquid rather than a solid material. The hydrogel has a first LCST, such as a first LCST below 37° C. in physiological conditions. This allows for the material to be applied or injected into an animal, including a human, as a liquid and to thicken via precipitation and entanglement of the polymer molecules to form a soft solid or semi-solid at body temperature. The hydrogel is configured to be converted in vivo into a modified hydrogel having a second lower critical solution temperature greater than the first lower critical solution temperature, which, in some examples, can be greater than the body temperature. When the LCST increases above body temperature, the hydrogel dissolves, leaves the site of administration, and is excreted from the body. In embodiments where the hydrogel does not contain a drug, the hydrogel can be a medical device. In some embodiments, the hydrogel results from the combination of the polymer solution and the precursor therapeutic composition that contains one or more therapeutic agents. In these embodiments, the hydrogel can be a temperature-responsive controlled release pharmaceutical formulation for controlled delivery of the therapeutic agent.

In one embodiment, the weight ratio of the polymer solution to the precursor therapeutic composition can be from about 1:1 to about 99:1. In some embodiments, the weight ratio of the polymer solution to the precursor therapeutic composition can be from about 2:1 to about 19:1, from about 3:1 to about 15:1, from about 3:1 to about 11:1, from about 4:1 to about 7:1, or from about 4:1 to about 5:1.

In some embodiments, the total concentration of the therapeutic agent(s) in the therapeutic hydrogel composition can be an amount from about 0.1 wt % to about 10 wt %, about 1 wt % to about 8 wt %, about 1 wt % to about 6 wt %, about 1 wt % to about 5 wt %, about 2 wt % to about 5 wt %, or about 3 wt % to about 5 wt % based on the total weight of the therapeutic hydrogel composition.

Another embodiment provides a hydrogel for the controlled delivery of therapeutic agents acting locally at the administration site, in particular one or more of: local anesthetics, steroids, anti-inflammatory drugs, opioids, cannabinoids, antibacterials, antifungals, antiseptics, and agents used for prevention, weakening, disruption, or killing of biofilms. In another embodiment the hydrogel contains one or more therapeutic agents that are dissolved within the hydrogel following combination of the polymer solution and precursor therapeutic composition. In another embodiment, the hydrogel contains one or more therapeutic agents that are distributed throughout the hydrogel but are not fully dissolved within the hydrogel following combination or mixing of the polymer solution and precursor therapeutic composition. In one embodiment the hydrogel forms an implant or depot in situ.

In one embodiment, the hydrogel contains an amide-type local anesthetic. In one embodiment, the therapeutic agent is bupivacaine or ropivacaine. In one embodiment, the hydrogel contains an amide-type local anesthetic and a non-steroidal anti-inflammatory drug. In one embodiment, the hydrogel contains bupivacaine and meloxicam. In one embodiment, the hydrogel contains one or more antimicrobials.

In one embodiment the hydrogel contains an aminoglycoside antimicrobial and one or two additional antimicrobials. In a further embodiment the aminoglycoside is tobramycin. In another embodiment the aminoglycoside is gentamicin. In a specific embodiment, the therapeutic agents are tobramycin and vancomycin. In a specific embodiment the therapeutic agents are tobramycin and an agent used for the prevention, weakening, disruption, or killing of biofilms. In another embodiment the therapeutic agents include an agent targeted toward the killing of bacterial persister cells. In another embodiment the therapeutic agent is an antiseptic.

In a specific embodiment the therapeutic agent is chlorhexidine.

The temperature-responsive degradable polymer concentration in the hydrogel is less than or equal to the polymer concentration in the polymer solution. In one embodiment, the temperature-responsive degradable polymer concentration in the hydrogel exceeds the minimum gelation concentration, which is the minimum polymer concentration required to form a hydrogel rather than a suspension of insoluble polymer molecules. The minimum concentration of temperature-responsive polymer required to form a hydrogel may be estimated by the line on FIG. 13. In one embodiment, the polymer concentration in the hydrogel can be greater than the minimum gelation concentration, which is a function of polymer molecular weight as described above. In another embodiment, the polymer concentration in the hydrogel can be at least about 1 wt % for $M_w$ >1,510 kDa, at least about 2 wt % for 1,510 kDa≥$M_w$ >183 kDa, at least about 3 wt % for 183 kDa≥$M_w$ >43 kDa, at least 12 wt % for 43 kDa≥$M_w$ >18 kDa, at least 20 wt % for 18 kDa≥$M_w$ >10 kDa, and at least [-0.494*$M_w$+23.68] wt % for $M_w$<10 kDa, where $M_w$ is in kDa. In selected embodiments the temperature-responsive degradable polymer concentration in the hydrogel is from about 4.5 wt % to about 45 wt %, from about 20 wt % to about 40 wt %, from about 25 wt % to about 35 wt %, or from about 27 wt % to about 35 wt % based on the total weight of the hydrogel. In selected embodiments, the temperature-responsive degradable polymer concentration in the hydrogel is no greater than about 55 wt % based on the total weight of the hydrogel. In some specific examples, the concentration of temperature-responsive degradable polymer in the hydrogel can be from about 15 wt % to about 40 wt %, from about 20 wt % to about 30 wt %, or from about 25 wt % to about 35 wt % based on the total weight of the hydrogel.

In further detail, the precursor therapeutic compositions can be suitable for dispersing the one or more therapeutic agents evenly throughout the hydrogel, and can have a liquid or paste-like texture at a temperature suitable for mixing with the hydrogel, such as between about 0° C. and physiological temperature (37° C.). The one or more therapeutic agents can distribute evenly within the hydrogel as a result of nonlaminar flow or the formation of an emulsion during mixing. It is noted that the function of the precursor therapeutic composition, which is to facilitate even distribution of the one or more therapeutic agents within the hydrogel, may be achieved with a wide variety of specific compositions. For example, in embodiments where the active agent is a liquid, the precursor therapeutic composition may be the therapeutic agent itself. In embodiments where the active agent is water-soluble, the precursor therapeutic compositions can include the therapeutic agent and an aqueous solvent (e.g. an aqueous acidic solvent, for example) suitable for dissolving the therapeutic agent. In some specific examples, the therapeutic agent can be present in the precursor therapeutic compositions in an amount of from about 20 wt % to about 24 wt % based on total weight of the precursor therapeutic compositions. In some embodiments, in particular in those embodiments in which one or more of the therapeutic agents is not highly water-soluble, the precursor therapeutic compositions can include the therapeutic agent and a biocompatible organic excipient (e.g. a solvent or a dispersing agent, for example). Non-limiting examples of biocompatible organic excipients can include one of more of the following: polyethylene glycol having a weight average molecular weight less than 1000 g/mol, polypropylene glycol having a weight average molecular weight less than 1000 g/mol, copolymers of ethylene oxide and propylene oxide having a weight average molecular weight less than 1000 g/mol, poly(ethylene glycol) ether derivatives having a weight average molecular weight of between 200 g/mol and 4,000 g/mol, such as poly(ethylene glycol) mono- or di-alkyl ethers, poly(ethylene glycol) copolymers having a weight average molecular weight of between 200 g/mol and 10,000 g/mol such as poly(ethylene glycol-co-polypropylene glycol); propylene glycol mono- or di-esters of a $C_2$-$C_{19}$ aliphatic carboxylic acid or a mixture of such acids, such as propylene glycol dicaprylate or dicaprate; mono-, di- or tri-glycerides of a $C_2$-$C_{19}$ aliphatic carboxylic acid or a mixture of such acids, such as glyceryl caprylate, glyceryl caprate, glyceryl caprylate/caprate, glyceryl caprylate/caprate/laurate, glycofurol and similar ethoxylated tetrahydrofurfuryl alcohols and their $C_1$-$C_4$ alkyl ethers and $C_2$-$C_{19}$ aliphatic carboxylic acid esters, water-soluble organic solvents (ethanol, propylene glycol, glycerin, N-methyl-2-pyrrolidone, dimethylacetamide, and dimethylsulfoxide), non-ionic surfactants (Cremophor EL, Cremophor RH 40, Cremophor RH 60, d-α-tocopherol, polyethylene glycol 1000 succinate, polysorbate 20, polysorbate 80, Solutol HS 15, sorbitan monooleate, poloxamer 407, Labrafil M-1944CS, Labrafil M-2125CS, Labrasol, Gellucire 44/14, Softigen 767, and mono- and di-fatty acid esters of PEG 300, 400, or 1750), water-insoluble lipids (castor oil, corn oil, cottonseed oil, olive oil, peanut oil, peppermint oil, safflower oil, sesame oil, soybean oil, sunflower oil, other non- or partially hydrogenated vegetable oils, hydrogenated vegetable oils, hydrogenated soybean oil, and medium-chain triglycerides of coconut oil and palm seed oil), organic liquids/semi-solids (beeswax, d-α-tocopherol, oleic acid, medium-chain mono- and diglycerides),various cyclodextrins (α-cyclodextrin, β-cyclodextrin, hydroxypropyl-β-cyclodextrin, and sulfobutylether-β-cyclodextrin), and phospholipids (for example, hydrogenated soy phosphatidylcholine, distearoylphosphatidylglycerol, L-α-dimyristoylphosphatidylcholine, L-α dimyristoylphosphatidylglycerol). In some specific examples, the concentration of therapeutic agent in the precursor therapeutic compositions can be from about 9 wt % to about 33 wt %, or from about 20 wt % to about 26 wt % based on total weight of the precursor therapeutic compositions.

In some embodiments, the precursor therapeutic compositions can further contain a preservative. Examples of preservatives include acids (benzoic acid, sorbic acid, boric acid), esters (methylparaben, ethylparaben, propylparaben, butylparaben, sodium benzoate, sodium propionate, potassium sorbate), alcohols (chlorobutanol, benzyl alcohol, phenyl ethyl alcohol), phenols (phenol, chlorocresol, o-phenyl phenol), mercurial compounds (thiomersal, nitromersol, phenylmercuric nitrate, phenylmercuric acetate), and quaternary ammonium compounds (benzalkonium chloride, cetyl pyridinium chloride). In some embodiments, the amount of preservative in the precursor therapeutic compositions can be less than 10 wt %, less than 5 wt %, or less than 2 wt %.

The polymer compositions and the precursor therapeutic compositions can be combined or mixed to prepare a therapeutic hydrogel composition. The concentration of the one or more therapeutic agents in the hydrogel can vary depending on the specific therapeutic agent and other factors including its release from the hydrogel and its mechanism of action. Although the most suitable concentration of therapeutic agent in a hydrogel will vary based on the application, generally the concentration can be between about 0.1 wt % and 10 wt % based on the total weight of the hydrogel. In specific examples in which the therapeutic agent in the hydrogel is approved for use in an unencapsulated or immediate-release dosage form and the intended use (also called an "indication") is the same as for the immediate-release form, the concentration in the hydrogel can be greater than the concentration in the corresponding immediate-release form. For example, bupivacaine is approved for use at a concentration of 0.5 wt % in an immediate-release form. As such, a sustained release hydrogel formulation of bupivacaine can include a concentration greater than 0.5 wt % bupivacaine, because the drug can be released over a longer period of time rather than immediately. An appropriate active agent concentration can be determined through appropriate studies of in vitro properties as well as safety, pharmacokinetics, and effectiveness studies in animals and humans.

In embodiments where the hydrogel is prepared solely from the polymer solution and does not contain a therapeutic agent, mixing is not required as the polymer solution is homogeneous. Where this is the case, the present disclosure provides a method of preserving a material for improved shelf life as a medical device for the prevention of postoperative scar formation, treatment of joint pain, or other beneficial uses. In a specific aspect, the present disclosure provides a method of preserving a material for improved shelf life as a medical device for the prevention of peridural adhesions. In a specific aspect, the present disclosure provides a method of preserving a material for improved shelf life as a medical device for treatment of joint pain.

In embodiments where the hydrogel is prepared from the combination of the polymer solution and a precursor therapeutic composition, the polymer solution can be mixed with the precursor therapeutic composition at room temperature to result in a homogeneous hydrogel composition. In another variation of the process, the polymer solution can be homogeneously mixed with the precursor therapeutic composition at a temperature between about 0° C. and 37° C., between about 2° C. and 30° C., or between about 10° C. and 25° C. In one variation, the polymer solution can be at one temperature, for example between about 4° C. and 25° C. and the precursor therapeutic composition can be at a different temperature, for example between about 20° C. and 28° C., and the two components are mixed. Specific temperatures for each of the two components are based on the composition of the polymer used in the polymer solution and the composition of the precursor therapeutic composition. The resulting hydrogel can have a useful texture and viscosity, and the release rate of the therapeutic agent from the hydrogel can be conveniently and reliably adjusted to accommodate the desired therapeutic effect.

In another embodiment, the polymer solution can be mixed with the precursor therapeutic composition to form a heterogeneous mixture such as a suspension, colloid, or emulsion. The resulting hydrogel can have a useful texture and viscosity, and the release rate of the active agent from the hydrogel can be conveniently and reliably adjusted to accommodate the desired therapeutic effect.

As described above, the polymer solution containing a temperature-responsive polymer can be mixed with a precursor therapeutic composition that contains a therapeutic agent to form a hydrogel with uniform composition. In some examples, the manner of mixing can avoid the formation of air bubbles while causing nonlaminar flow or otherwise minimizing laminar flow. One example of a suitable method of mixing is end-to-end syringe mixing as depicted in FIGS. 1A-1B. More specifically, as illustrated in FIG. 1A, a first syringe 101 can be coupled to a second syringe 102 via a coupling device 140. The first syringe 101 can include the polymer solution 110 and the second syringe can include the precursor therapeutic composition 120. As illustrated in FIG. 1A, the polymer solution 110 can be transferred to the second syringe 102 to mix with the precursor therapeutic composition 120, or vice versa. This process can be repeated in an end-to-end mixing process to prepare therapeutic hydrogel composition 130. Individual fractions 130a, ..., 130n of the therapeutic hydrogel composition 130 are also represented, and will be referred to in greater detail in the Examples section.

Another example of a suitable method of mixing is to have the syringes joined to a common apparatus and expelled via a tip that allows the polymer solution and precursor therapeutic composition to mix, as shown in FIG. 1C. More specifically, a double-barrel syringe 103 can include a first compartment 112 and a second compartment 122. The polymer solution 110 can be loaded into the first compartment 112 and the precursor therapeutic composition 120 can be loaded into the second compartment 122. The first compartment 112 and the second compartment 122 can be the same size or different sizes, depending on the mixing ratio for the precursor compositions 110, 120. A common plunger or dual plunger 105 can be used to dispense the polymer solution 110 and the precursor therapeutic composition 120 through a metered mixing dispenser 107 to form therapeutic hydrogel composition 130 prior to dispensing from the double barrel syringe 103.

Described another way, a common apparatus can include a mixing compartment with two inlets (one for each precursor composition) and one outlet for the hydrogel. The mixing compartment contains obstructions to flow, for example, spirals, rods, or some other shape to allow for mixing of the two phases from the inlets. A dual syringe can include a joined dual plunger wherein a single piece of material is the plunger on both syringes allowing for simultaneous expulsion of the material in a fixed volume ratio from each syringe barrel. Alternatively, syringes of the same size or syringes of different sizes may be loaded into a common apparatus and depressed. The syringes may be affixed to a separate clip or placed in a housing, allowing the plungers to be pressed into the two syringe barrels to the same distance. Thus, where the volumes of the two syringes are different, the volume ratio of the two precursor phases can be equal to the ratio of the cross-sectional areas of the two syringes. In some examples, the syringes containing each phase can be secured onto the common apparatus, for example by a Luer lock fitting.

In one embodiment, the polymer solution can be mixed with the precursor therapeutic composition aseptically. In another embodiment, the polymer solution and precursor therapeutic composition are contained in separate syringes prior to mixing. In another embodiment, the mixing method is performed by joining a syringe containing the polymer solution with a syringe containing the precursor therapeutic composition and then mixing the separate compositions end-to-end. In a specific embodiment, the end-to-end mixing occurs via a Luer-lock female-to-female coupler. In another embodiment, the syringe containing the polymer solution and the syringe containing the precursor therapeutic composition are both loaded onto a common apparatus that facilitates simultaneous ejection of the polymer solution and the precursor therapeutic composition in a fixed volume ratio. In another embodiment, the polymer solution and precursor therapeutic composition are contained in a double-barreled syringe prior to mixing and the contents are mixed during expulsion of the compositions from the double-barreled syringe.

In another aspect, a method of delivering one or more therapeutic agents in vivo for a disease state treatable by controlled release administration of said therapeutic agent(s) is described. The therapeutic hydrogel composition can release the therapeutic agent(s) over time and dissolve over time in vivo via an increase in its lower critical solution temperature. In a specific aspect, one or more therapeutic agents can be delivered in vivo for treatment of a biofilm-based infection. In a specific aspect, one or more therapeutic agents can be delivered in vivo for treatment of prosthetic joint infection. In a specific aspect, one or more therapeutic agents can be delivered in vivo for treatment of osteomyelitis. In a specific aspect, one or more therapeutic agents can be delivered in vivo for treatment of septic arthritis. In a specific aspect, one or more therapeutic agents can be delivered in vivo for treatment of surgical site infection. In a specific aspect, one or more therapeutic agents can be delivered in vivo for treatment of otitis. In a specific aspect, one or more therapeutic agents can be delivered in vivo for treatment of postoperative pain. In a specific aspect, one or more therapeutic agents can be delivered in vivo for prevention of surgical site infection, including in cardiac surgery, colorectal surgery, or orthopaedic surgery.

In another aspect, one or more therapeutic agents can be delivered in vivo for a disease state treatable by localized controlled release to a specific site within the body that is performed by mixing of a polymer solution and a therapeutic precursor composition to form a hydrogel that is applied at or near the desired site of action. In some embodiments, the desired site of action can be a surgical site. The resulting hydrogel releases the therapeutic agent(s) over time and dissolves over time in vivo via an increase in its lower critical solution temperature.

Thus, the resulting therapeutic hydrogel compositions can be used to treat a variety of adverse health conditions in a subject. In one specific example, the therapeutic hydrogel compositions can be used in managing infection in a subject. Accordingly, methods of treating infection by providing local delivery of antimicrobials are provided. In another embodiment, a method for the prophylactic treatment of infection is provided, such as in the situation of a surgical procedure at risk for infection. In other embodiments, a method is provided for providing multiple agents that act synergistically or in a complementary fashion against known or suspected micro-organisms that cause infection. In particular, examples are disclosed demonstrating sustained release over a period of about 1 day to about 3 days following administration. Appropriate antimicrobial combinations generally have different mechanisms of action, for example inhibition of cell wall synthesis and inhibition of protein synthesis are different mechanisms of action.

In a particular embodiment, the composition can be effective to release a significant portion of the antimicrobial such that at least 90% by weight or more of the antimicrobials are released over a period of about 3 days in vivo. In a particular embodiment, local antimicrobial concentrations in the range of from about 100 µg/mL to about 10,000 µg/mL are present in nearby tissue 24 hours following administration. Although multiple active agents may be released in approximately the same amount and over approximately the same time frame as a single active agent or a different ratio of active agents can be released, the incorporation and release of two antimicrobials in approximately equal amounts (for example, where each active agent represents at least 25% of the total mass of all active agents initially contained within the hydrogel) is expected based on microbiological data of biofilm susceptibility to provide complementary coverage against pathogens found in surgical site infections, with synergy against some selected pathogens.

In another aspect, a method is provided for storage and preparation of a hydrogel providing sustained local delivery of one or more antimicrobials. In a particular embodiment, the antimicrobials can be tobramycin and vancomycin. In another embodiment, the antimicrobials can be tobramycin and an agent used for the prevention, weakening, disruption, or killing of biofilms. In another embodiment, the antimicrobials can be tobramycin and an antimicrobial agent used for the killing of gram-positive bacteria found in surgical site infections. In a particular embodiment, the hydrogel releases the one or more antimicrobials for a period of about 8 hours to about 3 days, about 1 day to about 3 days, about 1 day to about 5 days, about 3 days to about 5 days, about 3 days to about 7 days, or about 5 days to about 10 days. In one embodiment the plasma concentration of the released active agent(s) may be measured by LC/MS/MS.

In another aspect, the hydrogel contains a synergistic combination of antimicrobial active agents to treat an infection. In another aspect, the hydrogel contains a combination of antimicrobial active agents with complementary spectra of activity (for example, one agent covering gram-negative bacteria and one covering gram-positive bacteria) against some of the pathogens commonly found in the infection to be treated.

In a particular embodiment the composition releases a significant portion of the one or more antimicrobials, such that about 80% by weight of the antimicrobials are released over a period of up to about 1 day, or up to about 3 days, or up to about 5 days, or up to about 10 days following administration in vivo.

In one embodiment, the hydrogel is provided to a subject suffering from an infection. In another embodiment, the subject can be in need of prophylactic treatment for infection. In one embodiment, the hydrogel is provided to prevent recurrence of an infection that has been removed surgically. In a further embodiment, the hydrogel is provided following debridement and irrigation in the treatment of a surgical site infection. In a further embodiment, the surgical site infection is a prosthetic joint infection.

The therapeutic hydrogel compositions provided can also be used in managing pain in a subject by providing local delivery of a local anesthetic. In another embodiment, a method for prophylactic treatment of pain is provided, such as in the situation of a painful medical procedure. In other embodiments, a method is provided for delivery of multiple agents that act synergistically to provide effective pain relief. In particular, examples are disclosed that indicate sustained release of local anesthetics over a period of about 5 days to about 7 days in vitro. In one embodiment, the composition is effective in providing measurable plasma concentrations of bupivacaine for at least 7 days following administration.

In another aspect, a method is provided for storage and preparation of a hydrogel providing sustained local delivery of an amide-type local anesthetic. In a particular embodiment, the hydrogel releases the local anesthetic to provide reduction of pain at the administration site for a period of up to 2 days or up to about 3 days or up to about 5 days or up to about 7 days or up to about 10 days, or for a period of about 1 day to about 3 days, about 1 day to about 5 days, about 3 days to about 5 days, about 3 days to about 7 days, or about 5 days to about 10 days. In related embodiments the hydrogel releases the local anesthetic to provide measurable plasma concentrations of the local anesthetic over a period of up to 2 days, or up to about 3 days, or up to about 5 days, or up to about 7 days, or up to about 10 days, or for a period of about 1 days to about 3 days, about 1 days to about 5 days, about 3 days to about 5 days, about 3 days to about 7 days, or about 5 days to about 10 days. In one embodiment the plasma concentration of the released concentration can be measured by LC/MS/MS (liquid chromatography/tandem mass spectrometry).

In another aspect, a method is provided for storage and preparation of a hydrogel providing sustained local delivery of an amide-type local anesthetic and an NSAID. In a particular embodiment, the hydrogel releases the local anesthetic and NSAID to provide reduction of pain. The hydrogel releases the therapeutic agents that produce measurable plasma concentrations of the agents at the administration site for a period of up to about 2 days, or up to about 3 days, or up to about 5 days, or up to about 7 days, or up to about 10 days, or for a period of about 1 days to about 3 days, about 1 days to about 5 days, about 3 days to about 5 days, about 3 days to about 7 days, or about 5 days to about 10 days.

In one embodiment, the hydrogel is provided to a subject suffering from acute or chronic pain. In another embodiment, the subject can be in need of prophylactic treatment for pain.

For administration of the compositions described herein, the compositions can be injected, instilled, or otherwise applied with standard syringes, needles, and applicators (for example, between about 14 and 22 gauge). The compositions can be injected subcutaneously, intradermally, intramuscularly, intraarticularly, or into a surgical site after closure. The compositions can be applied to a wound topically or percutaneously. The compositions can be applied in a bone or on the surface of an implanted medical device. The compositions can also be applied near the intended site of action, such as for example in the ear canal for treatment of otitis media, in a debrided surgical wound for the treatment of orthopedic infection, or perineurally for nerve block in the treatment of pain. The compositions can be applied using various methods known in the art, including by syringe.

The following represent non-limiting examples of the temperature-responsive degradable polymers, polymer compositions, therapeutic systems, and associated methods described herein:

In one example, there is provided a temperature-responsive degradable polymer, said temperature-responsive degradable polymer comprising a LCST-imparting unit having the structure:

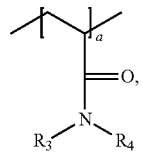

a lactone-bearing unit having the structure:

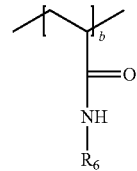

where $R_3$ and $R_4$ are independently selected from hydrogen (H), methyl, ethyl, propyl, and isopropyl, with the proviso that at least one of $R_3$ and $R_4$ is not H, $R_6$ is a butyrolactone or a valerolactone, a is an integer from 15 to 20,000, and b is an integer from 1 to 20,000, wherein a is greater than b, and wherein the polymer has a lower critical solution temperature (LCST) of 37° C. or below.

In one example of the temperature-responsive degradable polymer, $R_3$ is H and $R_4$ is isopropyl.

In one example of the temperature-responsive degradable polymer, $R_6$ is a butyrolactone.

In one example of the temperature-responsive degradable polymer, the butyrolactone is dimethyl butyrolactone.

In one example of the temperature-responsive degradable polymer, the LCST-imparting unit and the lactone-bearing unit are arranged randomly.

In one example of the temperature-responsive degradable polymer, the LCST-imparting unit and the lactone-bearing unit are arranged in blocks.

In one example of the temperature-responsive degradable polymer, the LCST-imparting unit is present in the polymer in an amount of at least 70 mol %.

In one example of the temperature-responsive degradable polymer, the lactone-bearing unit is present in the polymer in an amount of from about 5 mol % to about 25 mol %.

In one example of the temperature-responsive degradable polymer, the polymer is not crosslinked In one example of the temperature-responsive degradable polymer, the weight-average molecular weight ($M_w$) of the temperature-responsive degradable polymer is from about 5,000 g/mol to about 70,000 g/mol.

In one example of the temperature-responsive degradable polymer, the polymer has a structure:

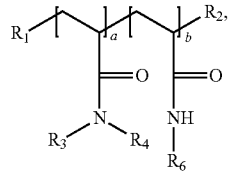

where $R_1$ and $R_2$ are independently selected from H, alkyl, phenyl, benzyl, 2-cyanoprop-2-yl, and ethyl-2-propionate sulfate.

In one example of the temperature-responsive degradable polymer, the polymer further comprises a water content-modifying unit having the structure:

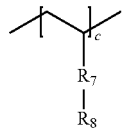

where $R_7$ is selected from an ester, an amide, a thioester, urea, thiourea, and a $C_1$-$C_{12}$ alkyl, $R_8$ is a polymer including at least six repeat units selected from ethylene oxide, propylene oxide, vinyl alcohol, acrylic acid, methacrylic acid, 2-hydroxyethyl methacrylate, N-2-hydroxypropylmethacrylamide, vinylpyrrolidone, an amino acid, a monosaccharide, and combinations thereof, and c is an integer from 1 to 5000.

In one example of the temperature-responsive degradable polymer, $R_7$ is an amide.

In one example of the temperature-responsive degradable polymer, $R_5$ includes ethylene oxide, propylene oxide, or a combination thereof.

In one example of the temperature-responsive degradable polymer, ethylene oxide and propylene oxide are present in a molar ratio of from 15:3 to 25:3.

In one example of the temperature-responsive degradable polymer, the water content-modifying unit comprises from about 5 wt % to about 15 wt % of the temperature-responsive degradable polymer.

In one example of the temperature-responsive degradable polymer, the water content-modifying unit is present in the polymer in an amount of from about 0.8 mol % to about 2 mol %.

In one example of the temperature-responsive degradable polymer, the water content-modifying unit is randomly distributed along the polymer.

In one example of the temperature-responsive degradable polymer, the water content-modifying unit is arranged in blocks along the polymer.

In one example of the temperature-responsive degradable polymer, the polymer has a structure:

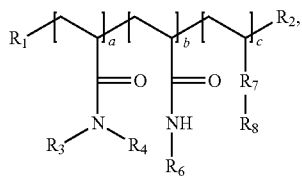

where $R_1$ and $R_2$ are independently selected from H, alkyl, phenyl, benzyl, 2-cyanoprop-2-yl, and ethyl-2-propionate sulfate.

In one example, there is provided a polymer composition, comprising a temperature-responsive degradable polymer comprising LCST-imparting units and one or more lactone-bearing units including a pendent lactone group, wherein the number of LCST-imparting units is greater than the number of lactone-bearing units, and wherein the temperature-responsive degradable polymer has a lower critical solution temperature (LCST) of 37° C. or below, and an aqueous vehicle, wherein the polymer composition has a pH of from 2 to 6.5.

In one example of the polymer composition, the temperature-responsive degradable polymer is present in the composition in an amount of from about 20 wt % to about 50 wt %.

In one example of the polymer composition, the temperature-responsive degradable polymer has a $M_w$ of from about 3,000 g/mol to about 2,000,000 g/mol.

In one example of the polymer composition, the LCST-imparting unit has the structure:

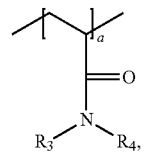

where $R_3$ and $R_4$ are independently selected from H, methyl, ethyl, propyl, and isopropyl, with the proviso that at least one of $R_3$ and $R_4$ is not H, and a is an integer from 15 to 20,000.

In one example of the polymer composition, the LCST-imparting unit is an N-isopropylacrylamide unit.

In one example of the polymer composition, the LCST-imparting unit is present in the polymer in an amount of at least 70 mol %.

In one example of the polymer composition, the lactone-bearing unit has the structure:

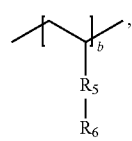

where $R_5$ is selected from an ester, an amide, a thioester, urea, thiourea, and a $C_1$-$C_{12}$ alkyl, $R_6$ is a butyrolactone or a valerolactone, and b is an integer from 1 to 20,000.

In one example of the polymer composition, $R_5$ is an ester.

In one example of the polymer composition, $R_5$ is an amide.

In one example of the polymer composition, $R_6$ is a butyrolactone.

In one example of the polymer composition, the butyrolactone is dimethyl butyrolactone.

In one example of the polymer composition, the lactone-bearing unit is present in the polymer in an amount of from about 5 mol % to about 25 mol %.

In one example of the polymer composition, the LCST-imparting unit and the lactone-bearing unit are arranged randomly.

In one example of the polymer composition, the LCST-imparting unit and the lactone-bearing unit are arranged in blocks.

In one example of the polymer composition, the temperature-responsive degradable polymer has the structure:

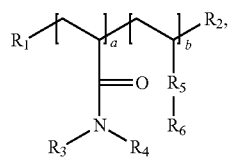

where $R_1$ and $R_2$ are independently selected from H, alkyl, phenyl, benzyl, 2-cyanoprop-2-yl, and ethyl-2-propionate sulfate, $R_3$ and $R_4$ are independently selected from H, methyl, ethyl, propyl, and isopropyl, with the proviso that at least one of $R_3$ and $R_4$ is not H, $R_5$ is selected from an ester, an amide, a thioester, urea, thiourea, and a $C_1$-$C_{12}$ alkyl, $R_6$ is selected from a butyrolactone or a valerolactone, a is an integer from 15 to 20,000, and b is an integer from 1 to 20,000.

In one example of the polymer composition, the temperature-responsive degradable polymer further comprises one or more water content-modifying units having a pendent polymer.

In one example of the polymer composition, the water content-modifying unit has the structure:

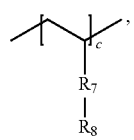

where $R_7$ is selected from an ester, an amide, a thioester, urea, thiourea, and a $C_1$-$C_{12}$ alkyl, $R_8$ is a polymer including at least six repeat units selected from ethylene oxide, propylene oxide, vinyl alcohol, acrylic acid, methacrylic acid, 2-hydroxyethyl methacrylate, N-2-hydroxypropylmethacrylamide, vinylpyrrolidone, an amino acid, a monosaccharide, and combinations thereof, and c is an integer from 1 to 5000.

In one example of the polymer composition, $R_7$ is an amide.

In one example of the polymer composition, $R_5$ includes ethylene oxide, propylene oxide, or a combination thereof.

In one example of the polymer composition, ethylene oxide and propylene oxide are present in a molar ratio of from 15:3 to 25:3.

In one example of the polymer composition, the water content-modifying unit comprises from about 5 wt % to about 15 wt % of the temperature-responsive degradable polymer.

In one example of the polymer composition, the water content-modifying unit is present in the polymer in an amount of from about 0.8 mol % to about 2 mol %.

In one example of the polymer composition, the water content-modifying unit is randomly distributed along the polymer.

In one example of the polymer composition, the water content-modifying unit is arranged in blocks along the polymer.

In one example of the polymer composition, the temperature-responsive degradable polymer has the structure:

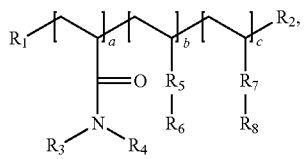

where $R_1$ and $R_2$ are independently selected from H, alkyl, phenyl, benzyl, 2-cyanoprop-2-yl, and ethyl-2-propionate sulfate, $R_3$ and $R_4$ are independently selected from H, methyl, ethyl, propyl, and isopropyl, with the proviso that at least one of $R_3$ and $R_4$ is not H, $R_5$ is selected from an ester, an amide, a thioester, urea, thiourea, and a $C_1$-$C_{12}$ alkyl, $R_6$ is selected from a butyrolactone or a valerolactone, $R_7$ is selected from an ester, an amide, a thioester, urea, thiourea, and a $C_1$-$C_{12}$ alkyl, $R_8$ is a polymer including at least six repeat units selected from ethylene oxide, propylene oxide, vinyl alcohol, acrylic acid, methacrylic acid, 2-hydroxyethyl methacrylate, N-2-hydroxypropylmethacrylamide, vinylpyrrolidone, an amino acid, a monosaccharide, and combinations thereof, and a is an integer from 15 to 20,000, b is an integer from 1 to 20,000, and c is an integer from 1 to 5000.

In one example of the polymer composition, the aqueous vehicle comprises one or more of a pH adjuster, a buffering agent, and a tonicity agent.

In one example of the polymer composition, the polymer composition has a pH of from about 3 to about 5.

In one example, there is provided a therapeutic system, comprising a polymer composition as described herein, and a precursor therapeutic composition comprising a therapeutic agent.

In one example of the therapeutic system, the therapeutic agent comprises an antimicrobial agent, an anesthetic agent, an opioid, an anti-inflammatory agent, a polysaccharide, a polynucleotide, an antigen, an antibody, a vaccine, a vitamin, an enzyme, a protein, or a combination thereof.

In one example of the therapeutic system, the therapeutic agent is present in the precursor therapeutic composition in an amount of from about 5 wt % to about 40 wt %.

In one example of the therapeutic system, the therapeutic agent comprises bupivacaine.

In one example of the therapeutic system, the therapeutic agent comprises vancomycin, tobramycin, or a combination thereof.

In one example of the therapeutic system, the therapeutic agent is a liquid and the precursor therapeutic composition consists essentially of the therapeutic agent.

In one example of the therapeutic system, the therapeutic agent comprises a hydrophilic therapeutic agent.

In one example of the therapeutic system, the therapeutic agent comprises a lipophilic therapeutic agent.

In one example of the therapeutic system, the precursor therapeutic composition further comprises a liquid or semi-solid carrier.

In one example of the therapeutic system, the carrier comprises d-α-tocopherol, sesame oil, peanut oil, safflower oil, walnut oil, polyethylene glycol methyl ether, polyethylene glycol, polypropylene glycol, or a combination thereof.

In one example of the therapeutic system, the carrier comprises water.

In one example of the therapeutic system, the carrier is a liquid.

In one example of the therapeutic system, the carrier is a semi-solid.

In one example of the therapeutic system, the polymer composition is contained in a first container and the precursor therapeutic composition is contained in a second container.

In one example of the therapeutic system, the first container and the second container are syringes.

In one example of the therapeutic system, the polymer composition is contained in a first compartment of a container and the precursor therapeutic composition is disposed in a second compartment of the container, wherein the first compartment and the second compartment are substantially isolated from one another.

In one example of the therapeutic system, the container is a double-barrel syringe.

In one example of the therapeutic system, the double-barrel syringe comprises a metered mixing dispenser configured to mix the polymer composition and the precursor therapeutic composition during dispensing.

In one example, there is provided a method of making a therapeutic hydrogel composition, comprising obtaining a polymer composition as described herein, obtaining a precursor therapeutic composition, said precursor therapeutic composition comprising a therapeutic agent, and mixing the polymer composition and the precursor therapeutic composition to prepare the therapeutic hydrogel composition.

In one example of the method of making a therapeutic hydrogel composition, the precursor therapeutic composition can include a lyophilized component.

In one example of the method of making a therapeutic hydrogel composition, the therapeutic agent comprises an antimicrobial agent, an anesthetic agent, an opioid, an anti-inflammatory agent, a polysaccharide, a polynucleotide, an antigen, an antibody, a vaccine, a vitamin, an enzyme, a protein, or a combination thereof.

In one example of the method of making a therapeutic hydrogel composition, the therapeutic agent is present in the precursor therapeutic composition in an amount of from about 5 wt % to about 40 wt %.

In one example of the method of making a therapeutic hydrogel composition, the therapeutic agent comprises bupivacaine.

In one example of the method of making a therapeutic hydrogel composition, the therapeutic agent comprises vancomycin, tobramycin, or a combination thereof.

In one example of the method of making a therapeutic hydrogel composition, the therapeutic agent is a liquid and the precursor therapeutic composition consists essentially of the therapeutic agent.

In one example of the method of making a therapeutic hydrogel composition, the therapeutic agent comprises a hydrophilic therapeutic agent.

In one example of the method of making a therapeutic hydrogel composition, the therapeutic agent comprises a lipophilic therapeutic agent.

In one example of the method of making a therapeutic hydrogel composition, the precursor therapeutic composition further comprises a liquid or semi-solid carrier.

In one example of the method of making a therapeutic hydrogel composition, the carrier comprises d-α-tocopherol, sesame oil, peanut oil, safflower oil, walnut oil, polyethylene glycol methyl ether, polyethylene glycol, polypropylene glycol, or a combination thereof.

In one example of the method of making a therapeutic hydrogel composition, the carrier comprises water.

In one example of the method of making a therapeutic hydrogel composition, the carrier is a liquid.

In one example of the method of making a therapeutic hydrogel composition, the carrier is a semi-solid.

In one example of the method of making a therapeutic hydrogel composition, mixing minimizes laminar flow.

In one example of the method of making a therapeutic hydrogel composition, mixing is performed using end-to-end mixing.

In one example of the method of making a therapeutic hydrogel composition, mixing is performed in a metered mixing dispenser.

In one example of the method of making a therapeutic hydrogel composition, the therapeutic agent is present in the therapeutic hydrogel composition in an amount of from about 0.1 wt % to about 10 wt %.

In one example of the method of making a therapeutic hydrogel composition, the polymer composition and the precursor therapeutic composition are mixed at a weight ratio of from about 2:1 to 19:1 to prepare the therapeutic hydrogel composition.

In one example, there is provided a method of treating a subject with an adverse health condition responsive to said treatment, comprising mixing a polymer composition as described herein with a precursor therapeutic composition to prepare a therapeutic hydrogel composition, said precursor therapeutic composition including a therapeutic agent and administering the therapeutic hydrogel composition to the subject.

In one example of a method of treating a subject with an adverse health condition, the adverse health condition comprises microbial infection, postoperative pain, or a combination thereof.

In one example of a method of treating a subject with an adverse health condition, mixing is performed within 90 minutes of administering.

In one example of a method of treating a subject with an adverse health condition, the therapeutic composition can include a lyophilized component.

In one example of a method of treating a subject with an adverse health condition, the therapeutic agent comprises an antimicrobial agent, an anesthetic agent, an opioid, an anti-inflammatory agent, a polysaccharide, a polynucleotide, an antigen, an antibody, a vaccine, a vitamin, an enzyme, a protein, or a combination thereof.

In one example of a method of treating a subject with an adverse health condition, the therapeutic agent is present in the precursor therapeutic composition in an amount of from about 5 wt % to about 40 wt %.

In one example of a method of treating a subject with an adverse health condition, the therapeutic agent comprises bupivacaine.

In one example of a method of treating a subject with an adverse health condition, the therapeutic agent comprises vancomycin, tobramycin, or a combination thereof.

In one example of a method of treating a subject with an adverse health condition, the therapeutic agent is a liquid and the precursor therapeutic composition consists essentially of the therapeutic agent.

In one example of a method of treating a subject with an adverse health condition, the therapeutic agent comprises a hydrophilic therapeutic agent.

In one example of a method of treating a subject with an adverse health condition, the therapeutic agent comprises a lipophilic therapeutic agent.

In one example of a method of treating a subject with an adverse health condition, the precursor therapeutic composition further comprises a liquid or semi-solid carrier.

In one example of a method of treating a subject with an adverse health condition, the carrier comprises d-α-tocopherol, sesame oil, peanut oil, safflower oil, walnut oil, polyethylene glycol methyl ether, polyethylene glycol, polypropylene glycol, or a combination thereof.

In one example of a method of treating a subject with an adverse health condition, the carrier comprises water.

In one example of a method of treating a subject with an adverse health condition, the carrier is a liquid.

In one example of a method of treating a subject with an adverse health condition, the carrier is a semi-solid.

In one example of a method of treating a subject with an adverse health condition, the therapeutic hydrogel composition is configured to provide sustained release of the therapeutic agent.

In one example of a method of treating a subject with an adverse health condition, the therapeutic hydrogel composition is administered to a surgical site.

In one example of a method of treating a subject with an adverse health condition, the therapeutic agent is released from the therapeutic hydrogel composition over a period of up to about 10 days.

EXAMPLES

Example 1—Polymer Synthesis

Temperature-responsive polymers were synthesized by free radical polymerization as follows: The monomers were dissolved in THF/dioxane, but other appropriate solvents can also be used, such as THF, 1,4-dioxane, benzene, the like, or a mixture of solvents (e.g.

THF/dioxane, dioxane/benzene, etc.). The solvent blend can be used to control polymer molecular weight.

Monomers were dissolved in anhydrous solvent at a total monomer concentration of 10 (w/v) %. In the examples provided, a mixture of dioxane/THF at either an 80/20 or 50/50 ratio by volume was used. The monomer feed ratios were adjusted to control the content of the polymer and were based on previous batch records of monomer feeds and polymer compositions determined by NMR spectroscopy. Using a 50:50 volume ratio of THF:dioxane resulted in weight-average molecular weights of 30-45 kDa for polymers containing a majority of N-isopropylacrylamide units. The monomer solution was stirred and nitrogen bubbles were introduced into the solution for at least 15 minutes to remove dissolved oxygen from the reaction. The reaction mixture was heated to 65° C. Then the free radical polymerization initiator azobisisobutyronitrile (AIBN) was added to the polymerization and the reaction proceeded under stirring for 18 hr under nitrogen atmosphere in an amount of approximately 0.007 mol AIBN per mol of total monomer. The reaction solution was then poured into an excess of ethyl ether (5-10 fold over the polymerization solvent by volume) which caused the polymer to precipitate. Other antisolvents such as MTBE may also be used. The precipitated polymer was collected by filtration and vacuum dried overnight. At laboratory scale, polymers were then dissolved at 10 wt % in deionized water and purified by dialysis using a low molecular weight cutoff dialysis membrane (for example 10000 MWCO or less, most often about 3500 MWCO) against an excess of deionized water, with multiple exchanges of the water to remove low molecular weight residuals (monomers and solvents). At a greater scale, this step can be replaced during scale-up by ultradialysis, for example, by using a tangential flow filtration unit. The resulting solution was then filtered and lyophilized to obtain a white to light yellow powder.

Multiple batches were made with varying amounts of N-isopropylacrylamide (NIPAAm) as the temperature-responsive repeat unit, Jeffamine M-1000 acrylamide (JAAm, a random copolymer of ethylene oxide units and propylene oxide units in a 19:3 ratio with a methoxy terminal group) as the pendent polymer for regulating gel water content, and either dimethyl butyrolactone acrylate (DBLA) or dimethyl butyrolactone acrylamide (DBLAAm) as the repeat unit imparting degradability by hydrolysis. See Tables 1 and 2 for specific examples of polymer batches.

TABLE 1

Content (in mol %) of selected batches of poly(NIPAAm-co-DBLA-co-JAAm) temperature-responsive degradable polymers

| Batch ID | NIPAAm | DBLA | JAAm |
| --- | --- | --- | --- |
| 1A | 91.67% | 6.95% | 1.37% |
| 1B | 91.07% | 7.06% | 1.86% |
| 1C | 91.26% | 7.07% | 1.67% |
| 1D | 91.36% | 7.29% | 1.35% |
| 1E | 92.11% | 7.03% | 0.86% |
| 1F | 91.01% | 8.02% | 0.97% |
| 1G | 92.20% | 6.78% | 1.02% |
| 1H | 93.56% | 5.41% | 1.03% |
| 1I | 90.40% | 8.34% | 1.25% |
| 1J | 91.31% | 7.40% | 1.30% |
| 1K | 93.23% | 5.46% | 1.30% |
| 1L | 90.39% | 8.03% | 1.58% |
| 1M | 91.94% | 6.54% | 1.53% |
| 1N | 93.07% | 5.43% | 1.50% |
| 1O | 90.61% | 8.02% | 1.38% |
| 1P | 93.07% | 5.48% | 1.45% |
| 1Q | 94.43% | 4.12% | 1.45% |
| 1R | 91.79% | 7.02% | 1.19% |
| 1S | 92.44% | 6.42% | 1.13% |
| 1T | 93.92% | 4.76% | 1.32% |
| 1U | 91.86% | 6.63% | 1.50% |
| 1V | 91.88% | 6.71% | 1.42% |
| 1W | 91.29% | 7.40% | 1.31% |
| 1X | 91.95% | 6.69% | 1.36% |
| 1Y | 92.29% | 6.62% | 1.09% |

TABLE 2

Content (in mol %) of selected batches of poly(NIPAAm-co-DBLAAm-co-JAAm) temperature-responsive degradable polymers

| Batch ID | NIPAAm | DBLAAm | JAAm |
| --- | --- | --- | --- |
| 2A | 98.52% | 0.00% | 1.48% |
| 2B | 87.78% | 10.91% | 1.31% |
| 2C | 92.59% | 6.02% | 1.40% |
| 2D | 79.01% | 19.08% | 1.90% |
| 2E | 72.98% | 25.19% | 1.83% |

TABLE 2-continued

Content (in mol %) of selected batches of poly(NIPAAm-co-DBLAAm-co-JAAm) temperature-responsive degradable polymers

| Batch ID | NIPAAm | DBLAAm | JAAm |
|---|---|---|---|
| 2F | 81.91% | 16.26% | 1.83% |
| 2G | 77.69% | 20.36% | 1.95% |
| 2H | 78.94% | 19.90% | 1.16% |
| 2I | 79.03% | 20.14% | 0.83% |
| 2J | 78.62% | 19.82% | 1.56% |
| 2K | 78.94% | 19.89% | 1.18% |
| 2L | 79.33% | 19.10% | 1.57% |
| 2M | 79.45% | 19.68% | 0.87% |
| 2N | 74.27% | 24.64% | 1.08% |
| 2O | 74.02% | 24.38% | 1.60% |
| 2P | 79.07% | 20.02% | 0.90% |
| 2Q | 79.28% | 19.45% | 1.27% |
| 2R | 79.71% | 19.38% | 0.91% |
| 2S | 79.46% | 19.25% | 1.29% |
| 2T | 79.52% | 19.35% | 1.13% |

Additionally, in some polymers, a fourth monomer selected from butyl methacrylate (BMA), butyl acrylate (BA), tert-butyl acrylate (tBA), and tert-butyl acrylamide (tBAm) were included. These monomers are hydrophobic and thus can be used to decrease the lower critical solution temperature (LCST). Materials with BA, tBA, and tBAm did not include alactone but lactone-bearing units such as DBLA and DBLAAm are easily and conveniently incorporated in polymers containing these fourth monomers. It is noted that other comonomers in small amounts can be incorporated in the polymer and the LCST predictably and conveniently adjusted based on the amount and hydrophilicity of the monomer added. The materials prepared with NIPAAm, JAAm, and various 4th units were prepared using 6 or 12 mol % of the 4th unit and 1.5 mol % JAAm in the feed. See Table 3 for some specific examples.

TABLE 3

Content (in mol %) of selected batches of temperature-responsive degradable polymers containing hydrophobic fourth units

| Batch ID | NIPAAm | DBLAAm | JAAm | BMA | BA | tBA | tBAm |
|---|---|---|---|---|---|---|---|
| 3A | 79.61% | 16.88% | 1.37% | 2.14% | — | — | — |
| 3B | 79.27% | 16.60% | 1.54% | 2.58% | — | — | — |
| 3C | 79.57% | 10.17% | 0.62% | 9.64% | — | — | — |
| 3D | 77.66% | 10.55% | 1.13% | 10.66% | — | — | — |
| 3E | 78.17% | 10.90% | 0.90% | 10.02% | — | — | — |
| 3F | 87.61% | — | 1.21% | — | 11.18% | — | — |
| 3G | 91.72% | — | 1.32% | — | 6.96% | — | — |
| 3H | 87.45% | — | 1.44% | — | — | — | 11.11% |
| 3I | 92.94% | — | 1.36% | — | — | — | 5.70% |
| 3J | 88.06% | — | 1.23% | — | — | 10.71% | — |
| 3K | 92.63% | — | 1.43% | — | — | 5.94% | — |
| 3L | 84.85% | — | 1.13% | 14.02% | — | — | — |
| 3M | 91.02% | — | 1.32% | 7.66% | — | — | — |

TABLE 2-continued

Content (in mol %) of selected batches of poly(NIPAAm-co-DBLAAm-co-JAAm) temperature-responsive degradable polymers

| Batch ID | NIPAAm | DBLAAm | JAAm |
|---|---|---|---|
| 2U | 79.67% | 19.50% | 0.83% |
| 2V | 79.31% | 19.41% | 1.27% |
| 2W | 74.70% | 24.20% | 1.10% |
| 2X | 84.42% | 14.48% | 1.10% |
| 2Y | 74.98% | 23.84% | 1.18% |
| 2Z | 83.79% | 15.46% | 0.75% |
| 2AA | 75.11% | 24.06% | 0.83% |
| 2AB | 83.91% | 14.82% | 1.26% |
| 2AC | 74.59% | 24.11% | 1.30% |
| 2AD | 84.45% | 14.71% | 0.84% |
| 2AE | 83.82% | 14.95% | 1.23% |
| 2AF | 79.68% | 19.18% | 1.14% |
| 2AG | 74.57% | 24.35% | 1.07% |
| 2AH | 74.76% | 24.07% | 1.17% |
| 2AI | 74.52% | 24.32% | 1.16% |
| 2AJ | 79.62% | 19.56% | 0.81% |
| 2AK | 84.26% | 15.04% | 0.69% |
| 2AL | 84.06% | 14.73% | 1.21% |
| 2AM | 79.80% | 19.10% | 1.10% |
| 2AN | 84.68% | 14.31% | 1.02% |
| 2AO | 78.88% | 19.82% | 1.30% |
| 2AP | 75.45% | 23.74% | 0.81% |
| 2AQ | 75.49% | 23.71% | 0.80% |
| 2AR | 84.43% | 14.88% | 0.68% |

Batch compositions are specified in various examples, but selected recipes are disclosed below. The recipes vary in JAAm content. Increased JAAm content results in weaker and less durable gels, faster drug release in vitro, higher-LCST, and shorter degradation time. All batches contained no free monomer within the limits of detection by $^1$H NMR. Table 4 presents properties of selected preparations of temperature-responsive polymers.

TABLE 4

Composition and properties of selected preparations of temperature-responsive polymers

| Polymer | Composition (mol %) | | Molecular Weight (g/mol) | | Initial LCST (° C.) | In Vitro Degradation Time (37° C., pH 7.4, PBS) |
|---|---|---|---|---|---|---|
| | DBLA | JAAm | $M_w$ | $M_n$ | | |
| PNJ22-DBLA | 6.2-6.8 | 1.85-1.98 | ~60,000 | ~30,000 | 27 | 14-21 days |
| PNJ18-DBLA | 6.0-6.8 | 1.55-1.67 | ~60,000 | ~30,000 | 26 | 21-28 days |
| PNJ15-DBLA | 6.0-7.3 | 1.27-1.37 | ~60,000 | ~30,000 | 25 | 42-56 days |

The effect on LCST of a comonomer can be determined by preparing polymers with varying content and evaluating the slope of a line of best fit for the plot of LCST vs. mol % X, where X is the comonomer. A partial list of comonomer effects on LCST is given in Table 5.

TABLE 5

Effect of various comonomers on the LCST of
NIPAAm-based temperature-responsive polymers

| Comonomer | Effect on LCST (° C./mol %) |
|---|---|
| DBLA | −1.8 |
| Tert-butyl acrylate | −0.69 |
| BMA | −0.62 |
| DBLAAm | −0.51 |
| Butyl acrylate | −0.44 |
| Tert-butyl acrylamide | −0.41 |
| Acrylamide | +0.4 |
| JAAm | +1.8 |
| Acrylic acid | +2.6 |

For polymers of N-isopropylacrylamide having a molecular weight of about 30-45 kDa, the LCST of a polymer in PBS may be predicted according to the equation $LCST=34.5+\sum m_i*x_i$ where for each ith comonomer, $m_i$ is the effect of the comonomer on the LCST (in ° C./mol %) and $x_i$ is the content of the ith comonomer (in mol %). For pharmaceutical applications, it can be desirable for formulations to have an LCST between about 20-30° C., which is about ambient temperature while being below the physiological temperature. Thus, most of the example batches have been prepared to have an LCST in this range. Notably the content of DBLA as the degradable unit was selected to be in the range of about 4-9 mol %, while the content of DBLAAm as the degradable unit was higher, in the range of about 15-25 mol % in most batches. This difference is because the effect of DBLA lowering the LCST is a stronger effect per mol % incorporation, and thus less DBLA is required to obtain a convenient LCST. Otherwise the properties of the hydrogel relevant to pharmaceutical applications (for example, drug release rates, viscosity, injectability, and LCST) are similar between polymers formulated with DBLA and those with DBLAAm as two examples of suitable repeat unit structures. Similar properties can also be achieved with other lactone structures in addition to those where dimethylbutyrolactone is the lactone. JAAm content was adjusted between about 0.8 and 2.0 mol % based on prior knowledge of the effect of JAAm content in these polymers on water content in the resulting hydrogels and the effect on drug release and gel degradation time. Specifically, JAAm increases water retention in these hydrogels, and greater JAAm content is generally associated with faster sustained drug release, and also faster gel degradation. However, gels without JAAm provide high burst release of water-soluble drugs (for example, antimicrobials) which is reduced when JAAm is included.

Example 2—Dissolution of Temperature-Responsive Polymers

Dissolution of temperature-responsive polymers, such as those based on N-isopropylacrylamide, is slow, which poses a major obstacle to the commercial feasibility of these polymers. Pharmaceutical formulations requiring preparation are typically able to be prepared (for example, by reconstitution of a lyophilized powder drug) by a pharmacy technician, nurse, or physician within a short time such as less than 1 minute. Unfortunately, temperature responsive degradable polymers require several hours to dissolve.

In this study, the dissolution of a representative temperature-responsive degradable polymer was observed over time. A polymer containing 90.40% NIPAAm, 8.34% DBLA, and 1.25% JAAm and having a weight-average molecular weight of about 45 kDa was dissolved in phosphate buffered saline (PBS), a common solution used in medical research to approximate physiologic pH and osmolarity. Polymer powder (300 mg) was added to 8 mL glass vials and then 700 mg of refrigerated PBS was added to result in a 30 wt % solution of polymer. Samples were mixed by a vortex mixer for either 1, 3, or 10 minutes and maintained at 4° C. in a refrigerator after mixing to facilitate dissolution of the polymer. A control sample, which was not mixed, was also prepared. The vials were photographed immediately after mixing and then at 1, 3, 24, 50, and 71 hours thereafter. In the unmixed control sample, solid material stuck to the outside of the vial was scraped down into the solution at 25 hours after initial mixing. Vortex mixing is commonly available in research laboratories but is not commonly available in medical settings such as surgical operating rooms and hospital pharmacies. Thus, the mixing performed in this study is more thorough than what would be performed in most end-use settings.

Figure 2:
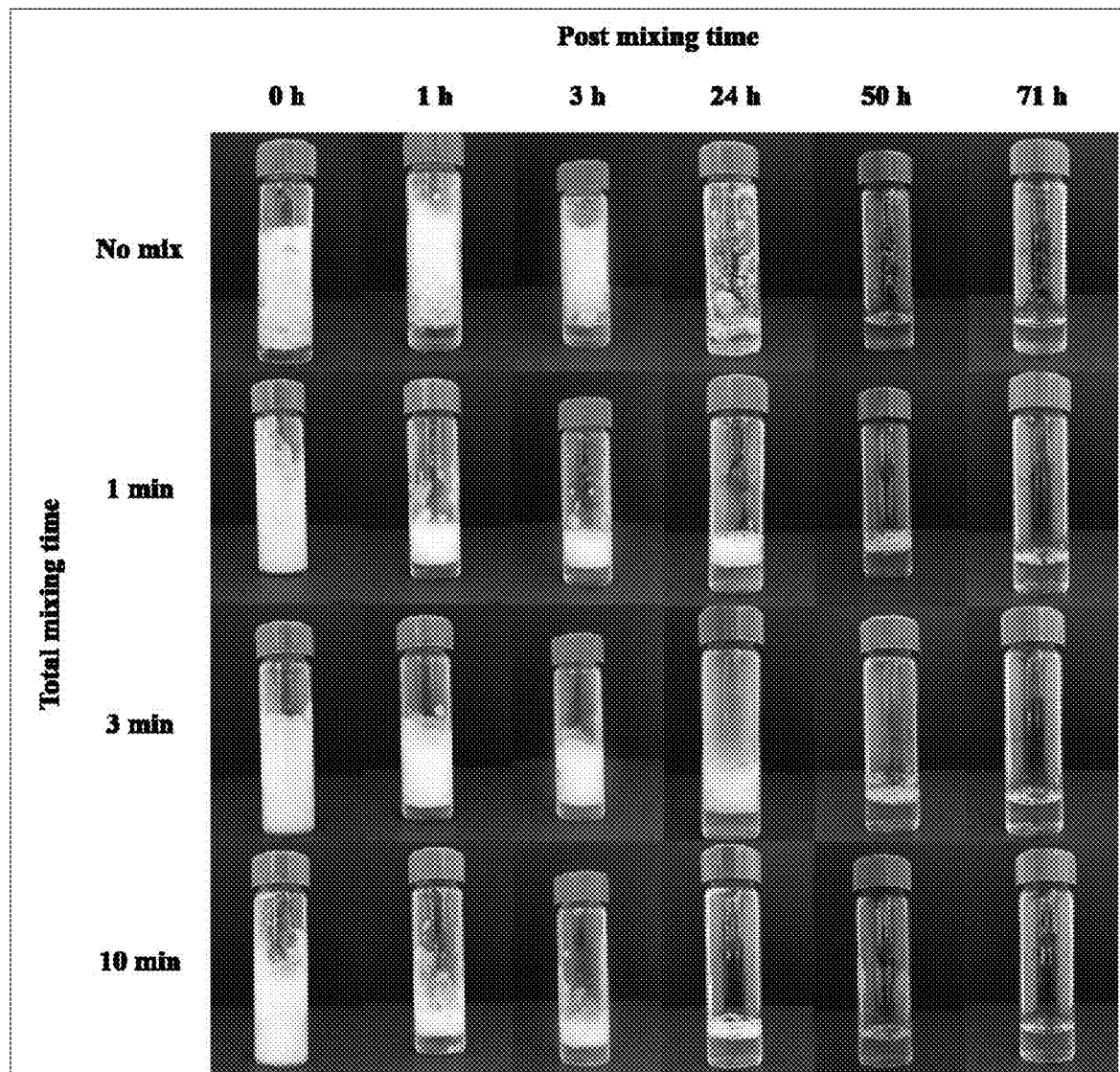
FIG. 2 presents images of dissolution of temperature-responsive degradable polymer after addition of aqueous solvent to vial containing polymer powder.

Pictures of the polymer solutions are shown in FIG. 2 Immediately after mixing, polymer dissolution was incomplete, even after 10 minutes of mixing. All of the mixed samples contained a large space of air bubbles on top of the polymer solution after mixing. The unmixed control sample had a large mass of white, solid polymer that remained undissolved. After 3 hours of refrigeration after mixing, the unmixed control remained nearly the same with a large fraction of the polymer remaining above the clear liquid solution in the bottom of the vial. The samples that were mixed for 1 or 3 minutes had a large volume of air bubbles on top of the solution, about twice the volume of the polymer solution itself. Air bubbles can pose a significant problem for preparation of a pharmaceutical formulation due to lack of homogeneity. The sample mixed for 10 minutes had a smaller volume of air bubbles on top, but the volume was still approximately the same size as the solution. After 24 hours, the unmixed sample still had a substantial amount of polymer stuck to the walls of the glass vial as indicated by white streaks and patterns on the vial walls. Once more, the sample mixed most thoroughly had the fewest air bubbles, but all were still potentially unacceptable for use in a pharmaceutical formulation. After 50 hours, the unmixed sample and the solution mixed for 10 minutes formed a clear solution with few air bubbles, but the bubbles did not yet resolve in the samples mixed for 1 or 3 minutes. The samples mixed for 1 or 3 minutes only resolved by 71 hours. The study indicates that, even with very thorough mixing, such polymers require about 2 to 3 days to form a suitably homogeneous solution without air bubbles.

Figure 3A:
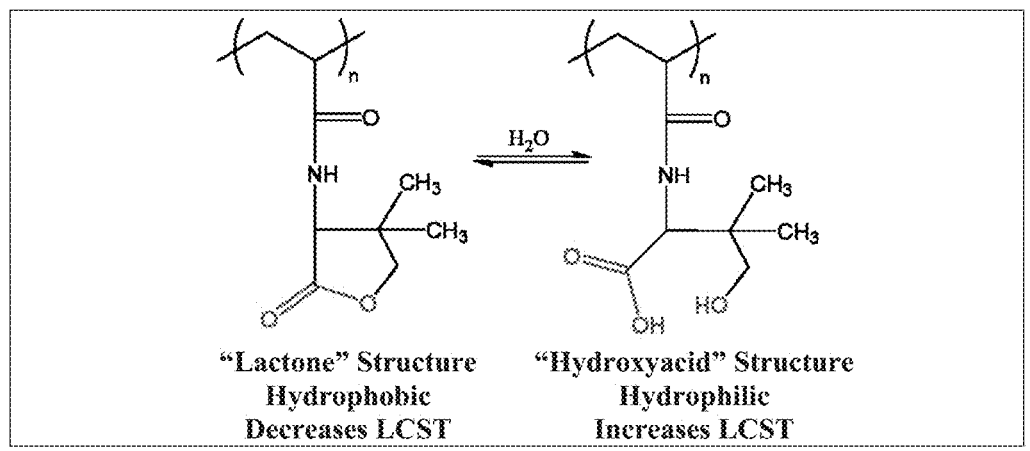
FIG. 3A depicts a reaction scheme of the ring-opening hydrolysis of DBLAAm repeat units. The polymer initially contains intact lactone rings which are hydrolyzed in vivo to form hydroxyacids. In acidic solution, an equilibrium is reached with ~97% lactones. At physiological pH near 7.4, the reaction proceeds to form hydroxyacids, causing polymer dissolution over time.

Example 3—Demonstration of Time-Temperature Relationship for Accelerated Storage Testing For brevity, polymers of NIPAAm, DBLAAm, and JAAm are abbreviated as PNJ-DBLAAm. Polymers of NIPAAm, DBLA, and JAAm are abbreviated PNJ-DBLA. Both example polymers are configured to undergo hydrolysis in physiological conditions, opening the lactone ring and forming a hydroxyacid as shown in FIG. 3A. The hydroxyacid species is more hydrophilic than the intact lactone species. As a result, the LCST will increase in proportion to the number of "open rings" or hydroxyacid groups on the polymer. In PNJ-DBLA, a second ester hydrolysis reaction is also possible in which the lactone ring detaches.

This example summarizes development of an accelerated stability testing method for temperature-responsive degradable polymers. Accelerated stability testing at elevated temperatures is a common approach to testing the stability of pharmaceutical formulations (also referred to as "drug products" rather than "drug substance"). While the temperature-dependent reaction kinetics of soluble compounds are well-understood, NIPAAm-based copolymers have temperature-dependent solubility. Specifically, the polymers are insoluble at high temperatures above the LCST.

It was previously believed that hydrolysis of polymer-bound lactones at temperatures above the LCST is initially slow due to limited accessibility of the lactones to water. DBLA has two esters which are susceptible to hydrolysis, but the hydrolysis of the ester in the lactone is faster. As hydrolysis proceeds, the hydrophilicity of the polymer increases incrementally, leading to increased accessibility to water and an increase in the rate of hydrolysis, causing further increased accessibility to water, further increase in hydrolysis rate, and so on until a maximal hydrolysis rate is reached. Thus, a typical degradation profile would begin with an initial "lag phase" of relatively little LCST change over time followed by a period of more rapid increase over time. In NIPAAm-JAAm-DBLA polymers (PNJ-DBLA), JAAm incorporation increases the water content of the polymer, which results in a shorter initial lag phase of degradation. In the study described here, the relationship between degradation time and temperature over a range of temperatures both above and below the LCST was evaluated.

Material from a single batch of PNJ18-DBLA was used. 0.2 M phosphate buffer (pH 7.4) was used to control the pH in the samples throughout the study. A high concentration of phosphate ions is known to decrease the LCST, an effect known as "salting-out." Thus, the LCST values measured in this study are lower than for the same polymer in PBS.

The polymer was dissolved at 3 mg/mL in 0.2 M phosphate buffer (pH 7.4). Samples of polymer solution (500 μL) were transferred to microcentrifuge tubes and incubated at a range of temperatures (80, 60, 40, 22, or 4° C.) for time points covering the course of degradation until the LCST increased by at least 15° C. The buffer was not replaced. This was done to maintain a controlled experiment between temperatures because the samples at low temperatures contained polymer solution, preventing exchange of the buffer. Tubes contained transparent solution at 4° C. and slightly turbid solution at 22° C. Samples incubated at 40-80° C. formed opaque, milky solutions immediately upon heating. After overnight storage, samples incubated at 40-80° C. contained a separated solid precipitate phase at the bottom of the tube, and transparent overlying buffer. The solid precipitate phase at 60° C. and 80° C. turned clear and firm over time. Collected samples were stored at −20° C. until analysis.

The LCST of each sample was determined using a cloud point method. Briefly, each sample was diluted with 2.5 mL of additional 0.2 M phosphate buffer (pH 7.4), dissolved by agitation and cooling in ice water bath, and the solution was placed in a cuvette. Cuvettes were heated at PC intervals starting at 15° C. The cuvettes were allowed to equilibrate for at least 2 minutes at each temperature. At each temperature, the absorbance of the solution was measured using a spectrophotometer (450 nm). The temperature at which the absorbance was half of the maximum value was recorded as the LCST.

The time required for the LCST to reach 30° C. at each incubation temperature was compared. For temperatures at which 30° C. was not measured, linear interpolation between the nearest two data points was used to calculate the time at which LCST reached 30° C. Due to a "salting-out" effect of high concentrations of phosphate ions, the LCST in the buffer used in this study is about 7-10° C. lower than either PBS or serum.

Figure 3B:
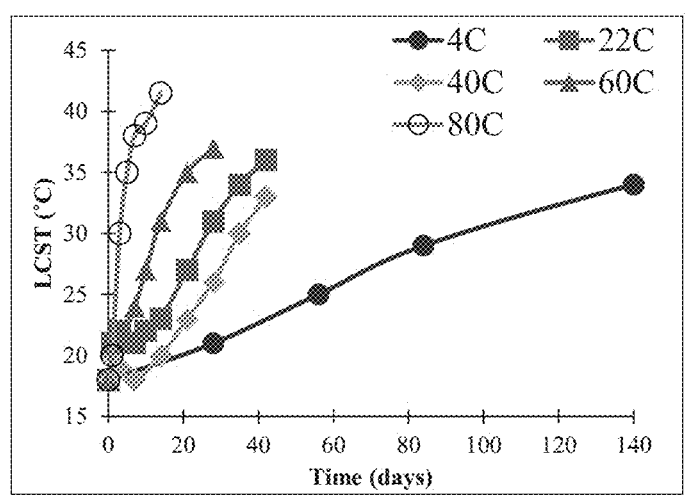
FIG. 3B is a graph of LCST of PNJ18-DBLA versus time at various incubation temperatures in phosphate buffer.

The degradation profile at each incubation temperature is shown in FIG. 3B. The shape of the degradation profiles was similar at all temperatures tested. A comparison of the time required to reach LCST of 30° C. at each incubation temperature is shown in Table 6. Degradation time decreased with increasing temperature, except between 22° C. and 40° C. Slower degradation at 40° C. compared to degradation at 22° C. was attributed to decreased water accessibility of the insoluble polymer at 40° C. (well above the LCST) compared to 22° C., which is only marginally higher than the initial LCST.

TABLE 6

Degradation of PNJ18-DBLA vs. Temperature

| Incubation Temperature | Time to LCST = 30° C. | Fold Increase in Degradation Time vs. 80° C. |
|---|---|---|
| 4° C. | 95.2 days | 31.73 |
| 22° C. | 26.25 days | 8.75 |
| 40° C. | 35 days | 11.67 |
| 60° C. | 13 days | 4.33 |
| 80° C. | 3 days | 1 |

Figure 3C:
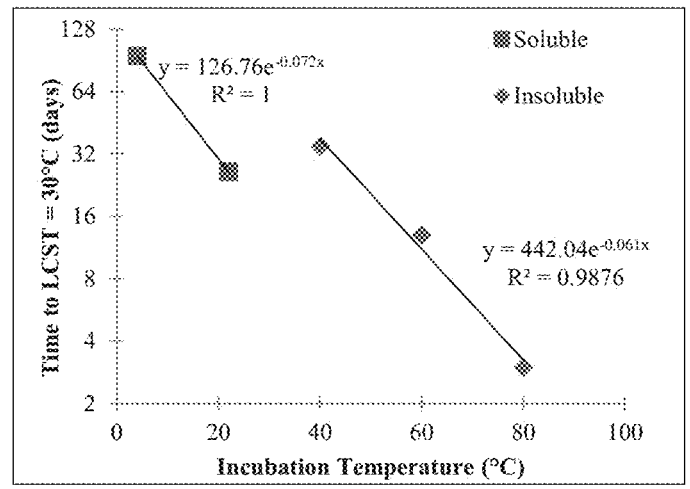
FIG. 3C is a graph of the degradation profile of PNJ18-DBLA at various incubation temperatures in phosphate buffer.

Degradation time to reach 30° C. LCST versus temperature is shown in FIG. 3C. Based on appearance, samples at temperatures of 4° C. and 22° C. were classified as soluble, and samples at higher temperatures were classified as insoluble. Within each temperature range, degradation of DBLA follows Arrhenius kinetics.

A general approximation of Arrhenius kinetics is that reaction rates double for each 10° C. increase in temperature. Degradation at 22° C. was 3.63 times faster than at 4° C., a difference of 2.05-fold per 10° C. interval. Degradation at 80° C. was 11.67 times faster than at 40° C., a difference of 1.85-fold per 10° C. interval. Thus, the data indicate that hydrolysis of lactones bound to temperature-responsive polymers follows Arrhenius kinetics in the range below the LCST and in the range above the LCST, but not between those two ranges. The findings are consistent with the understanding that water accessibility is limited in insoluble temperature-responsive resorbable hydrogels.

Figure 3D:
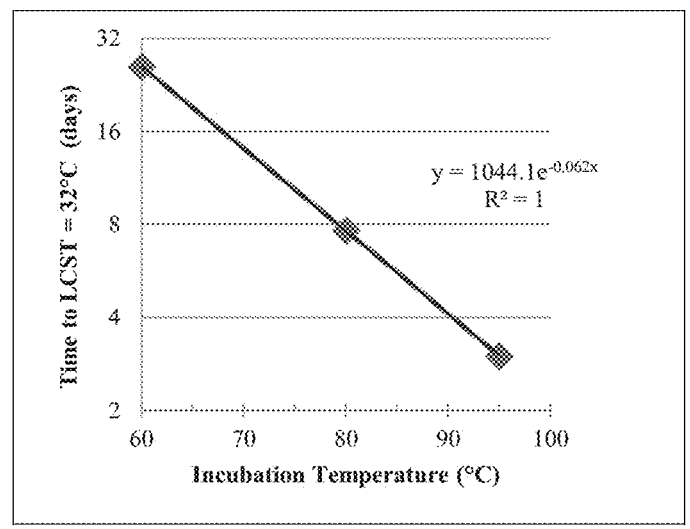
FIG. 3D is a graph of the degradation profile of PNJ18-DBLA at various incubation temperatures in pH 7.0 phosphate buffer.

The same polymer was evaluated at pH 7.0 (where degradation proceeds, but at a slower rate than at pH 7.4). The time to LCST of 32° C. was compared for samples stored at 60, 80, or 95° C. Data indicate that degradation follows Arrhenius kinetics at up to 95° C. as shown in FIG. 3D.

Figure 3E:
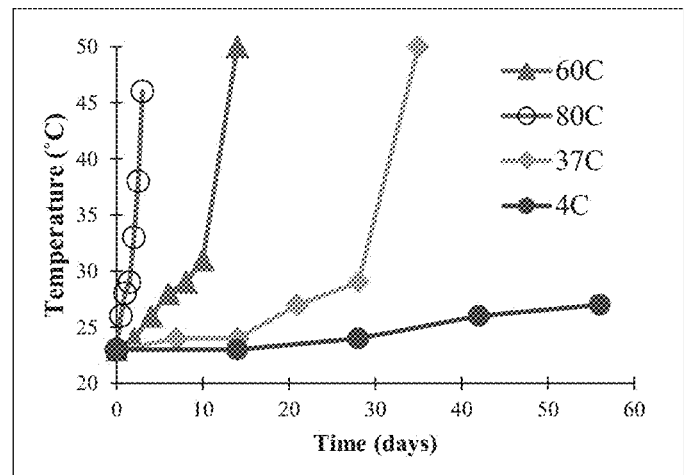
FIG. 3E is a graph of the degradation of PNJ1.3-DB20 at multiple incubation temperatures in 0.2 M phosphate buffer.

A separate study evaluated the polymer PNJ1.3-DB20 using the same methods with incubation at 4, 37, 60, and 80° C. in 0.2 M phosphate buffer (pH 7.4). The content of the polymer was 19.9 mol % DBLAAm, 1.16% JAAm, and the remaining units were NIPAAm. $M_w$ was 32,110 g/mol and Mn was 19,210 g/mol. The LCST of the material was 28° C. in PBS and 19° C. in the 0.2 M phosphate buffer due to salting out from a high concentration of phosphate ions. The same trend was observed as with polymers of NIPAAm, JAAm, and DBLA as shown in FIG. 3E and Table 7.

TABLE 7

Degradation of PNJ1.3-DB20 vs. Temperature

| Incubation Temperature | Time to LCST = 30° C. | Fold Increase in Degradation Time vs. 80° C. |
| --- | --- | --- |
| 4° C. | >56 days | >35 |
| 37° C. | 28.0 days | 17.28 |
| 60° C. | 9.0 days | 5.56 |
| 80° C. | 1.62 days | 1 |

As with polymers containing DBLA, the degradation time decreased with temperature consistent with Arrhenius kinetics for gels incubated above the LCST and relatively faster when soluble than would be predicted by extrapolating the degradation time data for samples above the LCST down to 4° C. The time for the LCST to reach 30° C. in phosphate buffer was used as a metric for degradation kinetics. This time measured about 1.62 days at 80° C., 9.05 days at 60° C., and 28.0 days at 37° C. Extrapolating the data at 4° C. suggests a degradation time of about 87 days, or 54-fold faster than 80° C. Similar to PNJ18-DBLA, degradation follows Arrhenius kinetics at temperatures above the LCST.

Example 4—PNJ-DBLA and PNJ-DBLAAm LCST Versus Time and Temperature at pH 2 Through pH 7.4

In this study, the degradation of PNJ18-DBLA hydrogels at 40° C. was evaluated, which is near the human physiological temperature of 37° C., and over a range of pH values ranging from 3.0 to 7.4. The goal of the study was to ascertain at what pH values the polymer's stability was enhanced compared to the neutral pH buffers conventionally used in the prior art.

PNJ18-DBLA was used for the study. Polymer was dissolved in buffers with pH ranging from 3.5 through 7.0 in increments of 0.5 pH units, and then also at pH 7.4 which is commonly regarded as a general approximation for physiological pH. For all solutions at pH 3.5-5.5, the buffer used was 0.1 M sodium acetate-acetic acid buffer. The lowest pH value of pH 3.5 was obtained by adjusting down the pH of an acetic acid solution with 1 N HCl. For pH 6.0-7.4, 0.1 M phosphate buffered saline was used and titrated to the appropriate pH using 1N HCl. Polymer solutions were prepared at 30 wt %, and about 50 µL of solution was placed into the bottom of 1.5 mL microcentrifuge tubes and warmed, resulting in formation of white, solid hydrogels in all samples. Then buffer (700 µL) was added on top of the samples. The buffer on top of each hydrogel sample was exchanged daily during the first week and weekly thereafter to control the pH to which the samples were exposed for all samples where solid polymer remained in the tube. Samples were collected after 14, 28, 42, 56, or 84 days. After collection, polymer solutions were stored at −20° C. until analysis to prevent additional degradation. Samples were thawed and cooled to obtain a solution, and then each 750 µL sample was diluted with 5.0 mL of phosphate buffered saline (pH 7.4). All samples were diluted using the same buffer to minimize any differences in the salting out effects caused by the buffers used to incubate the samples. The LCST was then measured by cloud point determination. The degradation time of PNJ18-DBLA was separately measured in PBS to be about 23 days.

Figure 4A:
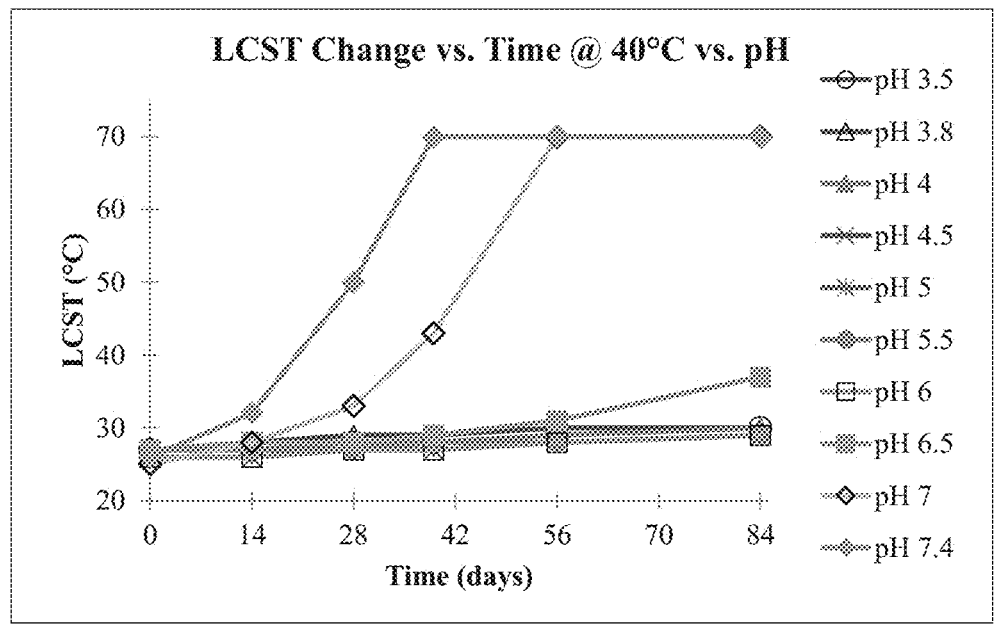
FIG. 4A is a graph of the degradation profile of PNJ18-DBLA at various incubation temperatures in phosphate buffer.

Results are shown in FIG. 4A. For pH values below 7.0, the increase in polymer LCST was dramatically slowed. The degradation time (defined as the time at which the LCST increased to above 37° C.) at pH 7.4 was between 14 and 28 days, consistent with separate studies. At pH 7.0, degradation time was about 32 days. At pH 6.5, degradation time increased to 84 days. The remaining polymers showed no more than 3° C. increase in LCST over the 84-day study, a remarkable finding indicating that the lactone rings of the polymer remained largely intact over a wide range of pH values. This surprising finding demonstrates long-term stability of temperature-responsive degradable polymer solutions over a range of pH values below pH 7.

In another study, stability in pH values as low at pH 2.0 were evaluated. The polymer PNJ15-DBLA was dissolved at 50 mg/mL in 0.2M buffers at pH 2-6 (pH 2: HCl, pH 3: acetic acid, pH 4&5: acetic acid—sodium acetate, pH 6: $Na_2HPO_4$—$NaH_2PO_4$). Samples were incubated in 8 mL glass scintillation vials and maintained at 95° C. in a dry block heater for 0, 2, 6, or 12 days. All runs were completed in triplicate. After the designated time, the samples were dissolved by cooling to 4° C. and stirring, then dialyzed against deionized water (7000 MWCO) at 4° C. overnight and lyophilized to obtain the polymer. The polymer was evaluated by titration for acid content, which was reported as a fraction of the total number of DBLA groups. The study did not discern between acrylic acids (i.e. detached lactone rings) versus hydroxyacids (i.e. open but attached lactone rings). Per the estimates above, a 12 day incubation time at 95° C. is estimated to equate to about 850 days in storage at 4° C. or about 300 days at 40° C., far in excess of the degradation time at physiologic pH.

Figure 4B:
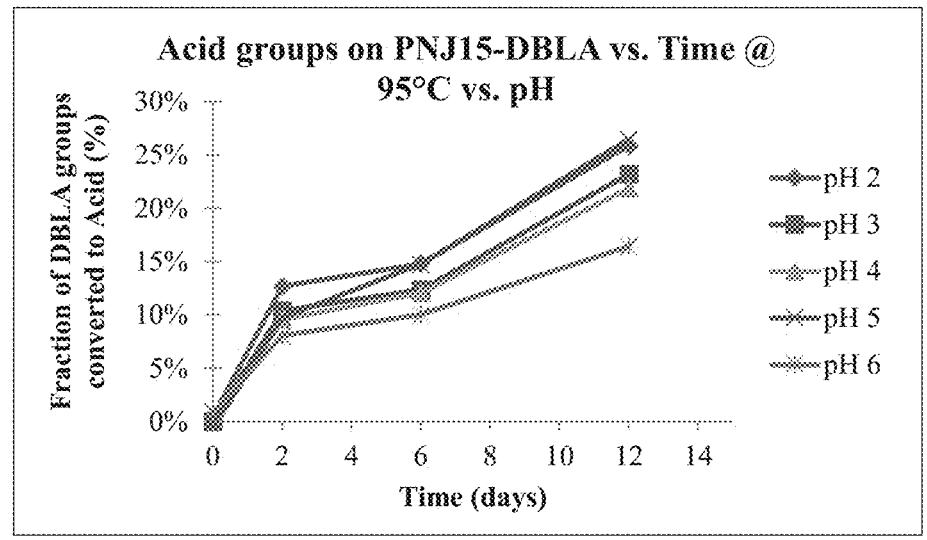
FIG. 4B is a graph of the fraction of acid groups determined by titration after storage in various 0.2M buffers at pH 2-6. Data points are the average of 3 replicates. Lines are intended as a visual guide only.

Results are shown in FIG. 4B. The acid content over time was similar for all groups tested. All groups had an initial increase in acid content during the first 2 days with a slower increase in acid groups thereafter. The initial phase was attributed to an increase in both the reversible formation of hydroxyacids, reaching a low equilibrium proportion, as well as the irreversible formation of acrylic acid groups due to detachment of the DBLA ring by hydrolysis of the ester linkage. These data demonstrate that lactones on temperature-responsive degradable polymers are stabilized over a wide range of acidic pH values in harsh accelerated conditions which simulate over 2 years.

Stability of additional monomers was also evaluated in 95° C. stress conditions as hydrophobic monomers with the function of decreasing the LCST. These are examples of other "fourth units" which can be included in temperature-responsive degradable polymers to introduce predictable control over the hydrogel properties. Briefly, NIPAAm and JAAm were copolymerized with either butyl methacrylate (BMA), butyl acrylate (BA), tert-butyl acrylate (tBA) or tert-butyl acrylamide (tBAm). In each polymer, 1.5 mol % JAAm was included in the feed along with either 6 mol % or 12 mol % of the BMA, BA, tBA, or tBAm, confirming that a wide variety of acrylate and acrylamide monomers and more specifically, alkyl-substituted acrylates and acrylamides, can be copolymerized reliably and conveniently into temperature-responsive polymers. The effects of each monomer on the LCST are negative, as reported in Example 1 Table 5. Polymers were prepared and content was evaluated by $^1$H NMR. NMR indicated that incorporation of each monomer was close to the amount used in the feed. The polymers were dissolved at 50 mg/mL in 0.2 M sodium acetate-acetic acid buffer (pH 4). Separate samples of 5 mL each were incubated at 95° C. for 0, 2, 4, 7, or 14 days to evaluate stability of the hydrophobic monomers, as NIPAAm and JAAm are known to be relatively stable in these conditions. After the designated time, samples were cooled and stirred to re-dissolve the polymer, and the solution was dialyzed to remove salts and any degradants. Then 100 mg of the recovered material for each sample was dissolved in 10 mL deionized water and evaluated for acid content by titration using phenolphthalein as the indicator and 1 mM NaOH as the titrant. The titration data were corrected against a control sample which contained only deionized water, as about 0.9 mL of titrant in 10 mL was required for the indicator to change color.

Figure 4C:
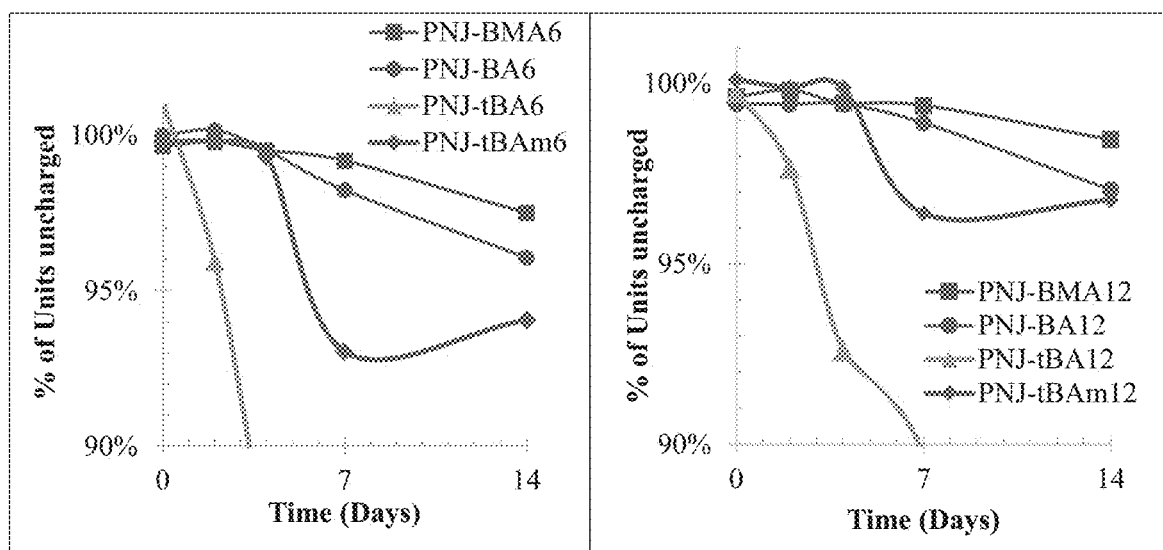
FIG. 4C is a graph of the percent acid groups determined by titration after storage in various 0.2M buffers at pH 2-6. Data points are the average of 3 replicates. Lines are intended as a visual guide only.

Data are shown below in FIG. 4C. In order of stability, BMA, BA, and tBAm were most stable, retaining about 95% or more of their initial structure after up to 14 days in stress conditions. tBA had the poorest stability which was attributed to the size of the tert-butyl leaving group and the susceptibility of the ester linkage to hydrolysis. The relative improvement in stability of tBAm compared to tBA demonstrates the improved hydrolytic stability of an amide linkage, supporting that acrylamides are desirable structures for additional monomers in the polymers described herein. However, (meth)acrylates BA and BMA were also highly stable in acidic conditions.

Example 5—PNJ-DBLA Hydroxyacid and Total Acid Content Versus Time

A pre-filled syringe of temperature-responsive polymer solution is at risk of instability caused by hydrolysis of polymer-bound lactone groups over time in storage. Hydrolysis of butyrolactone is reversible in acidic solutions; the hydroxyacid byproduct condenses to re-form the intact lactone ring. In this study, it was investigated whether storage in acidic solution would result in a low, stable number of intact lactones on the polymer in accelerated conditions.

A single batch of PNJ15-DBLA was used. The polymer was dissolved at 50, 100, or 200 mg/mL in 0.2 M acetic acid—sodium acetate buffers formulated at pH 3.0, 4.0, or 5.0. The solutions were dispensed into 8 mL glass vials and heated to 95° C. in a dry block heater for 0, 1, 2, or 7 days. Per the estimates above, the 7 day incubation time at 95° C. is estimated to equate to about 500 days in storage at 4° C. All samples formed a hard, insoluble mass at the bottom of the vial during heating. Samples were dissolved after recovery by cooling to 4° C. and stirring the solution for 2 hr. Solutions were dialyzed in cassettes (Pierce Slide-α-Lyzer, 7000 MWCO) against deionized water overnight with multiple exchanges to remove buffer salts, and then the samples were frozen and lyophilized.

Polymer samples (100 mg) were evaluated for acid content by titration in deionized water with phenolphthalein as an indicator and 1 mM NaOH as the titrant. The presence of lactone rings was evaluated by $^1$H NMR spectroscopy in methanol-d4, due to the peak attributed to the $CH_2$ protons of the lactone ring (4.1 ppm). Previous studies indicate negligible loss of NIPAAm and JAAm side groups under these conditions, so the NMR peak attributed to the isopropyl proton of NIPAAm ($CH_3CHCH_3$) was treated as an internal standard for calculation of the loss of lactones.

The total number of acid groups was assumed to be equal to the number of hydroxyacids plus the number of acrylic acids (the number of lactones detached). Thus, the number of hydroxyacids was calculated as the total number of acid groups minus the number of lactones lost.

Figure 5A:
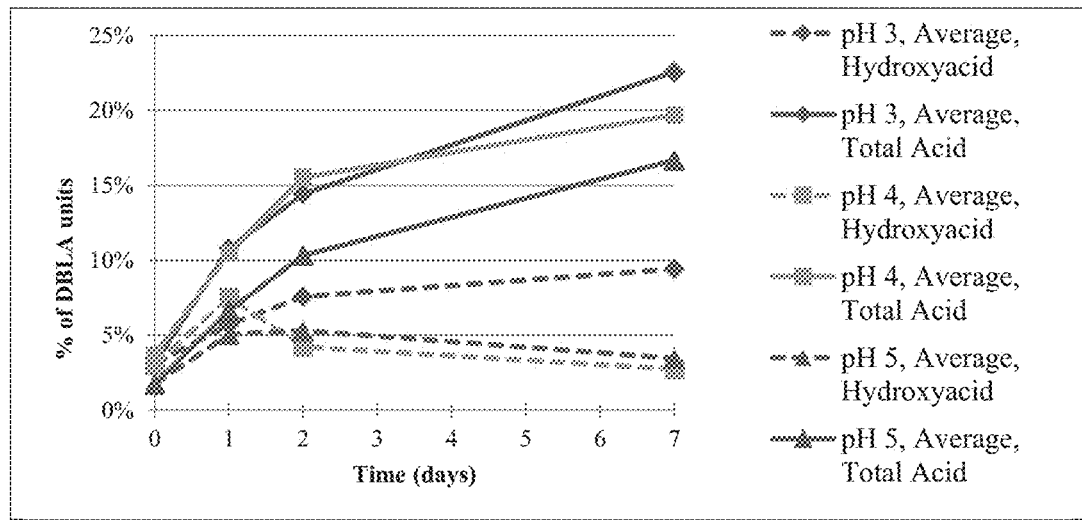
FIG. 5A is a graph of Total acid (solid lines) and hydroxyacid (dashed lines) content of PNJ15-DBLA polymer over time when stored in acidic buffers.

No clear trends were observed as a function of concentration within the range pH 3-5. For the purpose of this summary the data from all concentrations were pooled for each pH. Results are shown in FIG. 5A. The number of hydroxyacids increased from 0 to 2 days and then remained approximately constant between 2 and 7 days, in agreement with the prediction of an equilibrium between lactones and hydroxyacids. Importantly, the equilibrium strongly favors intact lactones over hydroxyacids.

Figure 5B:
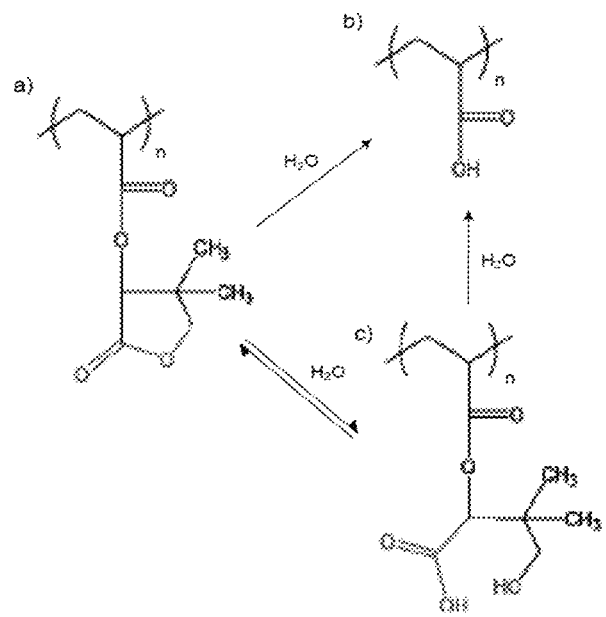
FIG. 5B is a reaction scheme of the Hydrolysis of a) DBLA repeat units produces two species: b) an acrylic acid moiety that is irreversibly formed or c) a ring-opening hydrolysis of the lactone side group. The hydroxyacid may also be converted to acrylic acid.

The number of total acid groups continued to increase throughout the duration of the study, although the increase was slower after the first 2 days. The increase was due to a steady increase in hydrolysis of the ester linkage between the lactone rings and the polymer backbone, resulting in an acrylic acid repeat unit as shown in FIG. 5B. Thus, although acidic solution did stabilize these polymers to an extent superior to storing in conventional buffer solutions as used in prior art, the stability was imperfect due to the slower, yet irreversible hydrolysis reaction. Therefore, suitable structures for the linkage of degradable units are those which are less susceptible to hydrolysis. Specific groups that are susceptible to hydrolysis are ester and anhydride. Examples of linkages that are less susceptible to hydrolysis include: amide, thioamide, $C_1$-$C_6$ alkyl, urea, and thiourea.

Further, these data support the selection of an amide linkage and the use of the specific repeat unit DBLAAm for both improving long-term stability in storage in aqueous solution as well as having greatly reduced generation of low molecular weight byproducts, whereas DBLA has the low molecular weight byproducts of pantolactone and the corresponding hydroxyacid of pantolactone.

More specifically, DBLAAm has an amide linkage between the lactone and polymer backbone whereas DBLA has an ester linkage in the same location. Polymers with DBLAAm are more stable in acidic storage conditions compared to polymers with the analogous previously disclosed structure with DBLA.

Figure 7A:
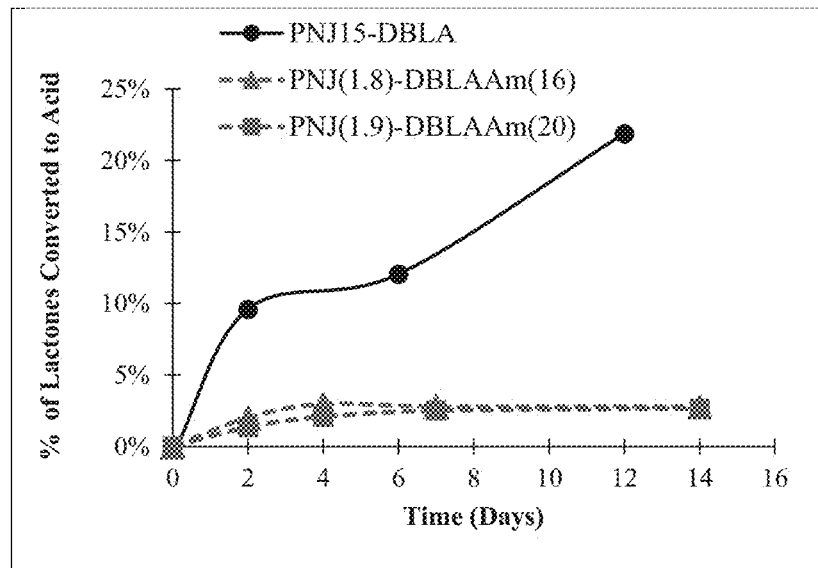
FIG. 7A is a graph of acid content of PNJ-DBLA and PNJ-DBLAAm polymers after accelerated stability testing (pH 4.0, 95° C.).
Figure 7B:
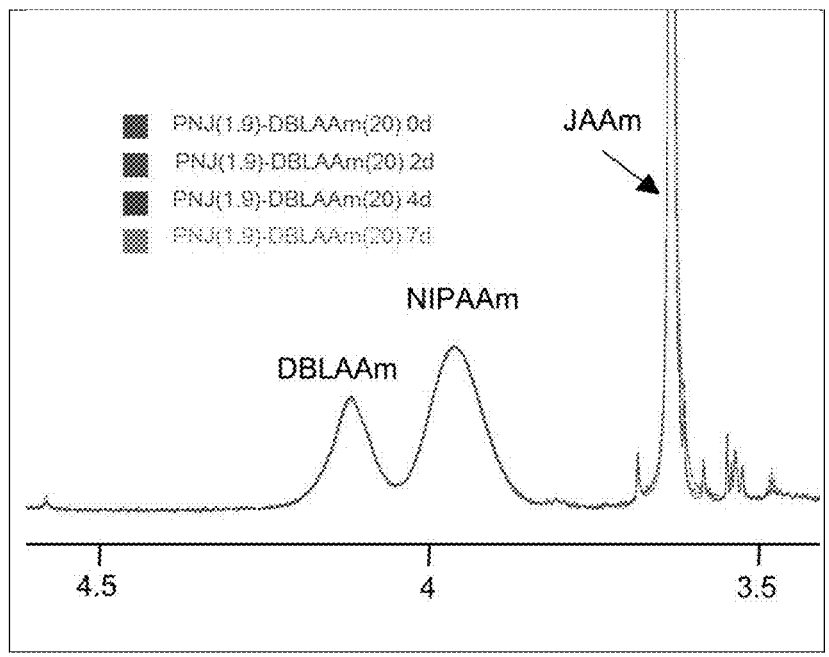
FIG. 7B is a graph of overlaid $^1$H NMR spectra of PNJ(1.9)-DBLAAm(20) polymer, after 0, 2, 4, and 7 day time points. The DBLAAm monomer peak does not decrease, indicating that the lactones did not detach.

For example, polymers with DBLAAm result in fewer low molecular weight byproducts of degradation compared to polymers with DBLA, as shown in FIGS. 5B and 7B (below). This is also support by FIGS. 5A and 7A (below). In particular, about 3 times the amount of DBLAAm can adjust the LCST by the same amount as DBLA despite only a single atom being different.

Moreover, some data show that there is significant overlap between the stability of some amides and esters when either are attached to the polymer backbone. For example, FIG. 4C shows that butyl methacrylate, which has an ester linkage, is more stable than tert-butyl acrylamide which has an amide linkage. The fact that DBLAAm specifically appears to have much lower acrylic acid generation over time in storage compared to DBLA is notable.

Example 6—Reversibility of LCST Change Demonstrating Reversibility of DBLA Hydrolysis As noted above, minimal LCST change and long-term steady (although nonzero) hydroxyacid content in temperature-responsive degradable polymers indicated that an equilibrium between lactones and hydroxyacids favoring a high proportion of lactones was approached in acidic solution. However, the reverse reaction was not explicitly demonstrated. This study was intended to confirm that reversibility could be conclusively demonstrated by first storing a temperature-responsive degradable polymer in neutral conditions, resulting in an increase in LCST due to lactone hydrolysis and then changing the solution to an acidic solution. If the hydrolysis reaction was in fact reversible in acidic conditions, and not just merely slowed, then the LCST would be predicted to decrease after the pH was decreased, whereas if lactone hydrolysis was slowed but not reversible, the LCST would remain constant after the pH was decreased.

PNJ15-DBLA was dissolved at 30 wt % in either pH 3 buffer (0.2 M acetic acid titrated with 1 N HCl) or pH 7.4 buffer (0.2 M phosphate buffer). Four treatment groups were evaluated by storing samples of solution at 80° C. as follows: 1) pH 7.4 only; 2) pH 7.4 for 3 days followed by switch to pH 3.0 thereafter; 3) pH 7.4 for 5 days followed by switch to pH 3.0 thereafter; 4) pH 3.0 only. In the studies where the pH was changed, the polymer was present in sample tubes in a solid polymer-rich gel phase on the bottom of the tubes, so the overlying buffer was decanted and new, fresh, pre-heated buffer was added on top of the solid polymer-rich phase. Samples were frozen at various time points. LCST was analyzed by cloud point determination after diluting the samples 10:1 in 0.2 M phosphate buffer (pH 7.4) to reduce any differences in salt effects between the pH 3 and pH 7.4 buffers.

Figure 6:
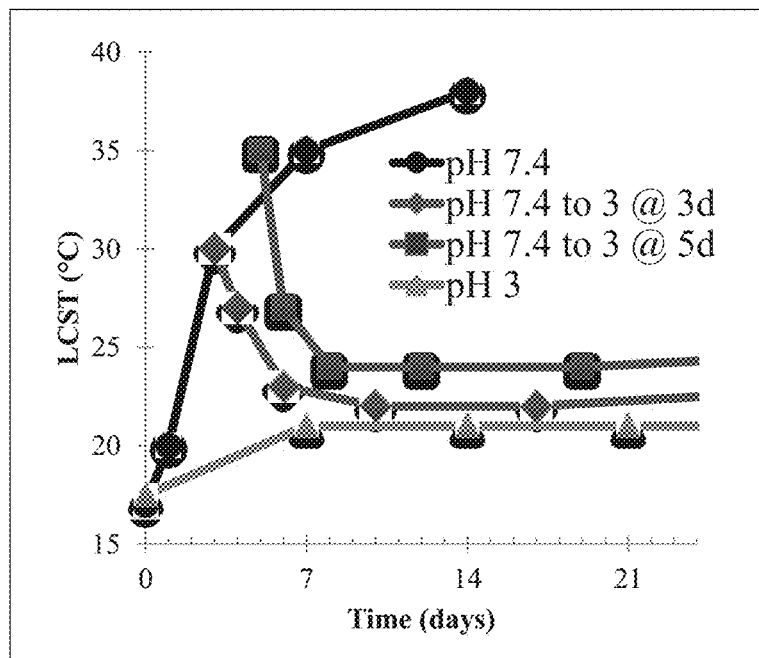
FIG. 6 is a graph of LCST over time with data showing reversibility of lactone hydrolysis in acidic solution. When pH is decreased from 7.4 to 3, the LCST of a temperature-responsive degradable polymer decreased over time and remained reasonably steady thereafter.

As shown in FIG. 6, samples at pH 3 had increasing LCST in the first 7 days, followed by no change between day 7-21. Samples incubated at pH 7.4 had an increasing LCST over time. In samples where the pH was changed from 7.4 to 3.0, the LCST began to decrease, indicating that repeat units in the polymer were becoming more hydrophobic. In samples where the pH was decreased, the LCST did not fully recover to the LCST of samples stored entirely at pH 3. The decrease in LCST is attributable to the "reverse reaction" of hydroxyacids to form lactones. However, at pH 7.4, the ester linkage of DBLA repeat units between the polymer backbone and lactone ring is also hydrolyzable, albeit at a slower rate than hydrolysis of the ester in the lactone ring. Thus the difference in the "plateau" values of LCST for the pH 3 group versus the other groups is attributable to the irreversible generation of acrylic acid repeat units from hydrolysis of the ester linkage.

Example 7—PNJ-DBLAAm Acid Content Versus Time

As noted above, suitable linkage groups in the degradable unit are those that are less susceptible to hydrolysis compared to esters or anhydrides. Dimethyl butyrolactone acrylamide (DBLAAm) contains the same structure as DBLA except that DBLAAm contains a more stable amide linkage between the polymer backbone and lactone ring. Thus, this study was performed to confirm that PNJ-DBLAAm would reach a stable equilibrium in accelerated storage conditions with minimal irreversible detachment of the lactone ring group as shown in FIG. 3A. In this experiment, the stability of PNJ-DBLAAm to PNJ-DBLA in accelerated storage conditions (95° C., pH 4) was compared.

The DBLAAm repeat units of PNJ-DBLAAm are configured to undergo hydrolysis in physiological conditions, opening the lactone ring and forming a hydroxyacid as shown in FIG. 3A. The hydroxyacid species is more hydrophilic than the intact lactone species. As a result, the LCST will increase in proportion to the number of "open rings" or hydroxyacid groups on the polymer. In the similar polymer PNJ-DBLA, the predominant degradation mechanism is also ring-opening hydrolysis of lactones, but a second ester hydrolysis reaction is also possible in which the lactone ring detaches. Three polymers were used as outlined in Table 8.

TABLE 8

Composition of polymers used in Example 7 - Accelerated Stability

| Polymer | Composition (mol %) | | | Mol. Wt. (g/mol) | |
|---|---|---|---|---|---|
| | DBLA | DBLAAm | JAAm | $M_w$ | $M_n$ |
| PNJ(1.8)-DBLAAm(16) | — | 16.26% | 1.83% | 51,550 | 26,400 |
| PNJ(1.9)-DBLAAm(20) | — | 20.36% | 1.95% | 43,900 | 21,470 |
| PNJ15-DBLA | 7.29% | — | 1.35% | 69,580 | 38,180 |

The polymers were dissolved at 40 mg/mL in 0.2 M acetic acid—sodium acetate buffer (pH 4.0). Five mL of each solution was dispensed into multiple 8 mL glass vials and heated to 95° C. in a dry block heater for 0, 2, 4, 7, or 14 days. Per the estimates above, the 14 day incubation time at 95° C. is estimated to equate to about 1,000 days in storage at 4° C. All samples formed a hard, insoluble mass at the bottom of the vial during heating. Samples were dissolved, dialyzed, and lyophilized by the same methods as described in Example 5. Polymer samples were evaluated for acid content by titration and for lactone content by $^1$H NMR spectroscopy in methanol-d4 as described in Example 5.

Total acid content of the polymers is shown in FIG. 7A. The acid content of polymers containing DBLAAm increased during the first 4 days and then remained nearly constant until 14 days (acid content was equal to 2.5% and 2.8% of DBLAAm units of the respective polymers). Thus, in acidic solution, an equilibrium was approached with ~97% lactones. This extent of hydroxyacid formation was not enough to increase the LCST more than 1° C. NMR analysis indicated no detectable detachment of lactones over the duration of the study as shown in FIG. 7B and Table 9. The data demonstrate that DBLAAm repeat units are stable when stored in acidic solution. It is noted that other lactone-bearing repeat unit structures with water-stable linkages can also result in minimal irreversible increase in acid groups and thus LCST over time in acidic solution.

TABLE 9

PNJ(1.9)-DBLAAm(20) stability (95° C., pH 4.0) of DBLAAm side group by $^1$H NMR

| | Mol % | |
|---|---|---|
| Time at 95° C. | NIPAAm | DBLAAm |
| 0 day | 77.4 | 20.6 |
| 2 day | 77.6 | 20.6 |
| 4 day | 77.5 | 20.7 |
| 7 day | 77.4 | 20.6 |
| 14 day | 77.4 | 20.6 |

Example 8—Comparison of Polymers After Pre-Treatment Method and Simulated Shelf Life As noted above, the ratio of lactones to hydroxyacids in temperature-responsive degradable polymers eventually tends toward an equilibrium composition in acidic conditions.

Thus, although the equilibrium composition is not the same as the starting composition of lactone-bearing units, the composition will tend toward the equilibrium composition over time in acidic solution, for example during storage of the solution before being applied. Thus, the lactones on the polymer can be allowed to partially hydrolyze in a preliminary "pre-treatment" step of manufacturing, and then the resulting polymer can be purified and recovered. By allowing the composition of a "pre-treated" polymer to tend toward the equilibrium composition prior to its packaging in solution, for example in a pre-filled syringe or vial, the composition of lactone-bearing repeat units was hypothesized to remain more consistent throughout long-term storage as compared to the polymer as initially prepared, which contains a low proportion (e.g. less than 1%) hydrolyzed lactones and increases toward the equilibrium composition over time in storage.

These studies suggest that the lactone rings of DBLAAm repeat units have an equilibrium composition in 0.2 M acetic acid-sodium acetate buffer (pH 4.0) where less than about 5% of DBLAAm lactone rings are hydroxyacids while the remaining lactones are intact. In this study, 10 wt % polymer solution was heated for 4 days at 95° C. with the intent of bringing the polymer's lactone-bearing DBLAAm units to an equilibrium composition at which about 2-3% of the DBLAAm lactone ring groups are hydrolyzed. The study compared the structures of the polymers over time and certain properties of the polymers relevant to medical device and pharmaceutical applications. Polymers were defined as "initial" or IN, meaning the polymer as made, "pre-treated" or PT, meaning that the polymer was heated for 4 days at 95° C. in pH 4.0 buffer to attempt to obtain an equilibrium composition of lactones versus hydroxyacids, or "shelf life" (SL), denoting a PT polymer which was exposed to 95° C. pH 4 accelerated storage conditions for an additional 10 days which was intended to simulate a shelf life of approximately 2 years in refrigerated storage.

Polymers of NIPAAm, JAAm, and DBLAAm were synthesized with 20% DBLAAm in the feed, 1.1 or 1.5 mol % JAAm in the feed, and the remainder NIPAAm. The solvent blend used in synthesis was held constant at equal parts dioxane and THF in order to yield a suitable molecular weight distribution around the threshold for renal clearance. Polymers are denoted as PNJ(X)-DB(Y) where X is the mol % JAAm used in the feed and Y is the mol % DBLAAm used in the feed, which was held constant at 20 in order to obtain a suitable LCST for pharmaceutical applications. Polymers prepared from ordinary synthesis were termed "IN". Pre-treated polymers (PT) were obtained after initial preparation, dissolved at 10 wt % in 0.2 M sodium acetate—acetic acid buffer (pH 4.0) and stored at 95° C. for 4 days, then dialyzed and lyophilized. Polymers after a simulated shelf life (SL) underwent the PT process followed by an additional step of dissolving once more at 10 wt % in 0.2 M sodium acetate—acetic acid buffer (pH 4.0) and stored at 95° C. for 10 additional days. The hypothesis was that the DBLAAm would partially hydrolyze during the pre-treatment process and approach an equilibrium composition, which would then remain approximately the same after a simulated shelf life. The composition of each polymer after each step was determined by $^1$H NMR and molecular weight distribution was determined by gel permeation chromatography with THF as the mobile and detection by static multi-angle light scattering and refractive index.

TABLE 10

Composition of Polymers in Example 8

| Polymer | Composition (mol %) | | Mol. Wt. (g/mol) | |
| --- | --- | --- | --- | --- |
| | DBLAAm | JAAm | $M_w$ | $M_n$ |
| IN PNJ1.1-DB20 | 20.0% | 0.90% | 43,030 | 23,450 |
| PT PNJ1.1-DB20 | 19.7% | 0.95% | 45,380 | 26,620 |
| SL PNJ1.1-DB20 | 19.6% | 0.79% | 51,230 | 38,580 |
| IN PNJ1.5-DB20 | 19.5% | 1.27% | 49,510 | 24,680 |
| PT PNJ1.5-DB20 | 19.9% | 1.30% | 50,320 | 31,250 |
| SL PNJ1.5-DB20 | 19.5% | 1.10% | 43,030 | 26,890 |

Evaluation of Lactone Hydrolysis and Lactone Loss

The IN and PT polymers were evaluated at various time points over 10 days of storage at 95° C. to simulate storage in refrigerated conditions over approximately 2 years. Polymers were dissolved at 40 mg/mL in 0.2 M acetic acid-sodium acetate (pH 4). Separate 8 mL glass vials were filled with 5 mL of solution and heated to 95° C. in a dry block heater. The time points included 0, 2, 3, 4, 5, 7, and 10 days. After incubation, the polymers formed a hard mass at the bottom of the vial. After the designated time point, the solutions were cooled to 4° C., dissolved using a stir bar, and then dialyzed in a dialysis cassette (3500 MWCO) against deionized water and lyophilized. The samples were then evaluated for acid content by titration and for lactone content by $^1$H NMR spectroscopy in methanol-d4. Taken together, these data can be used to identify the structural changes occurring in the lactone-bearing repeat units. More specifically, titration detects acid groups from either an acrylic acid (resulting from lactone detachment) or a hydroxyacid (open lactone ring remaining bound to the polymer), while NMR detects a peak corresponding to the CH proton of the dimethyl butyrolactone ring, although the amount of hydroxyacid versus intact lactone rings cannot be discerned.

Figure 8A:
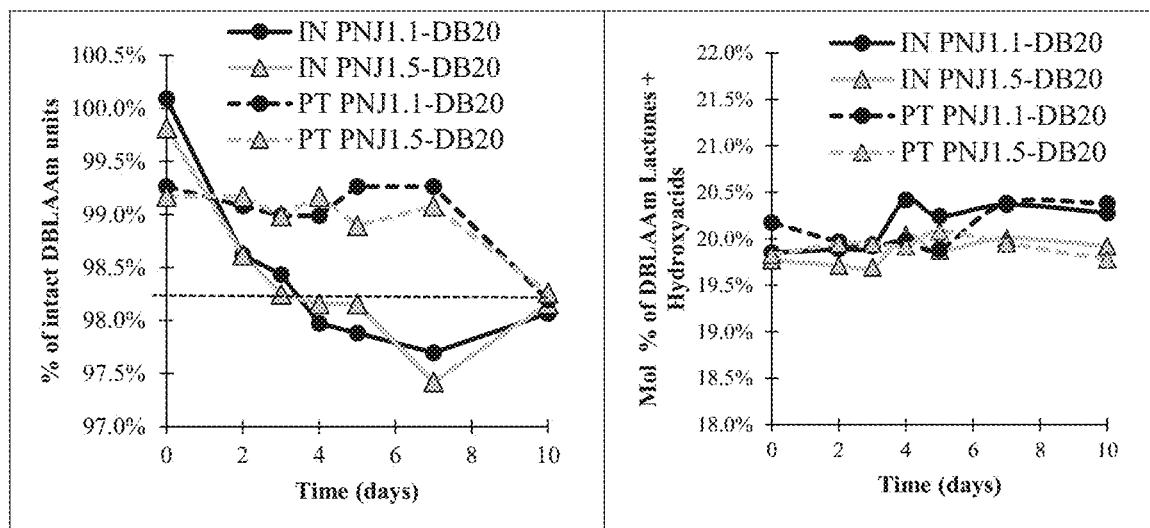
FIG. 8A is a graph of (Left) percentage of DBLAAm units that do not bear an acid group (i.e. intact lactones) in PNJ-DB polymers after accelerated stability testing (pH 4.0, 95° C.) as determined by titration. (Right) The content of DBLAAm rings determined by 1H NMR remaining after accelerated stability testing.

Data are shown in FIG. 8A. All of the polymers showed a slight decrease in intact lactones over the simulated storage time of about 2 years. However, the proportion of lactones remaining intact was high and remained in the range of 97.4-100% for all samples tested. Over the course of the experiment, the proportion of intact lactones varied between 97.7-100% for IN polymers compared to 97.2-98.3% for PT polymers, a narrower range. As shown on the right side of FIG. 8A, the total proportion of lactones plus hydroxyacids remained approximately constant over the duration of the experiment. Differences between samples appear random and are attributed to variability in the NMR analysis. Thus, the data indicate that the lactone rings of DBLAAm do not irreversibly detach to a measurable extent over the time tested, and the proportion of hydroxyacids in the equilibrium composition is low. The "PT" polymers had more consistent acid content over time as compared to the "IN" polymers, indicating an advantage of the pre-treatment method.

Solutions of each polymer at a concentration of 38 wt % were evaluated by rheometry. A temperature sweep method was performed using an Anton Paar Physica MCR-101 rheometer. For each run, 400 mg of solution was placed on the rheometer stage, which was maintained at 5° C. Storage and loss moduli of polymer solutions were measured with a gap height of 0.5 mm and oscillatory strain of 0.1% applied at 1 Hz as the temperature was increased from 5° C. to 45° C. at a rate of 2° C./min. From these data, the temperature range of the sol-gel transition can be estimated. Once the gel thickens/solidifies, comparisons of gel properties above the LCST cannot be definitively made because gel shrinking at higher temperatures causes detachment from the oscillating rheometer head. Nevertheless, it is possible to estimate the properties of the gel within an order of magnitude for temperatures that are only slightly above the sol-gel transition range, for example at 37° C. for the polymers tested. Data were evaluated by first plotting the complex modulus versus temperature to characterize the temperature and breadth of the sol-gel transition, and second to evaluate the phase angle at temperatures both below the LCST (at 5° C.) and above the LCST (37° C.). The phase angle quantifies the relative viscous versus elastic nature of the material, with solid, elastic materials having a phase angle of 0° and fluid, viscous materials having a phase angle of 90°.

Figure 8B:
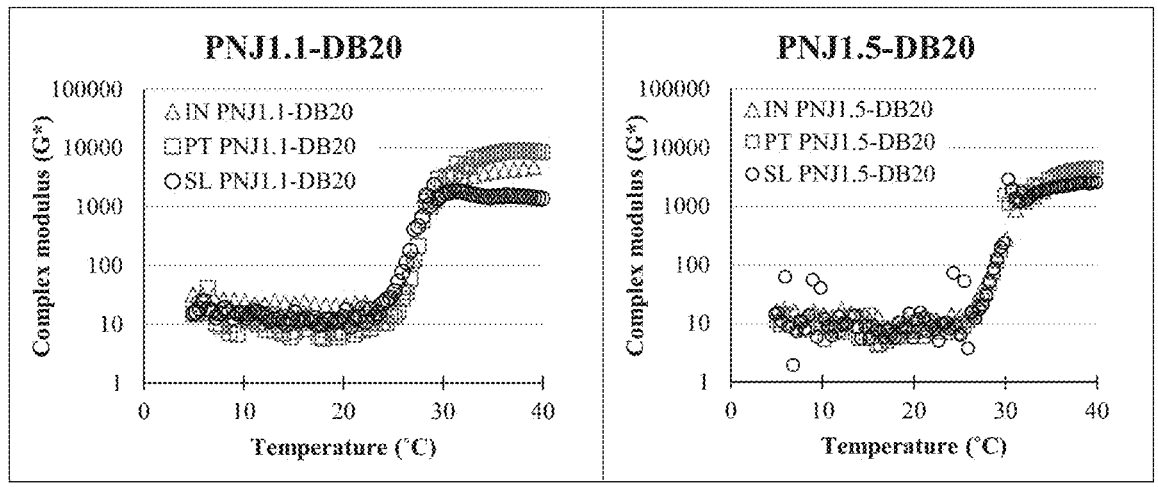
FIG. 8B is a graph of complex moduli of(Left) PNJ(1.1)-DB(20) and (Right)PNJ(1.5)-DB(20) gel formulations at 5-40° C. for IN, PT, and SL polymer. The temperature at which the gel thickens remains consistent between the initial polymer (IN), pre-treated polymer (PT), and polymer exposed to a simulated shelf life (SL).
Figure 8C:
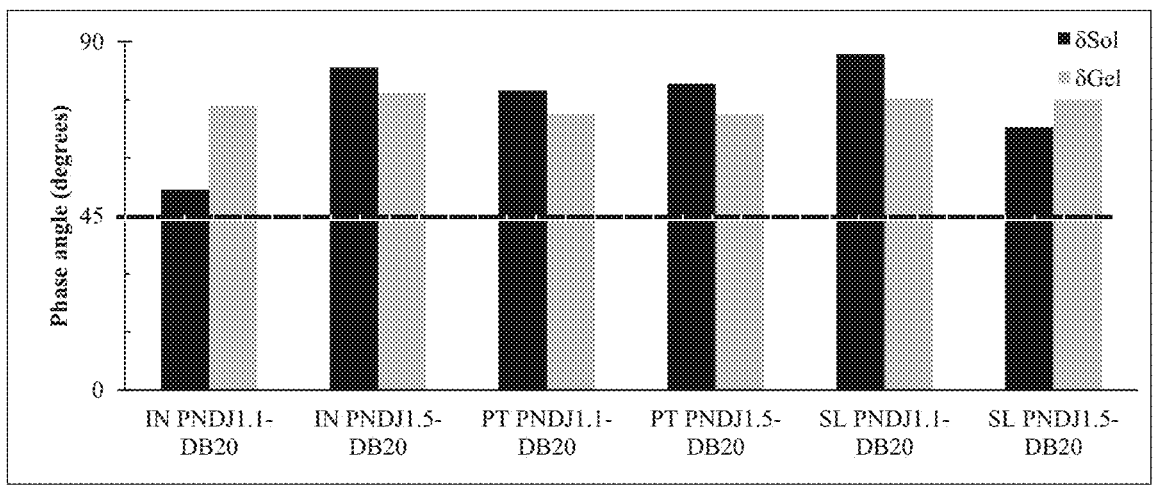
FIG. 8C is a bar chart presenting phase angles of PNJ (1.1)-DB(20) and PNJ(1.5)-DB(20) (IN, PT, and SL) in the solution (S Sol) and gel (S Gel) state. All of the samples tested are predominantly viscous rather than elastic (S>45°). Within each pair of clustered columns, the column on the left denotes measurement as a solution and the column on the right denotes measurement as a gel.

Rheological data are shown in FIGS. 8B-8C. All of the PNJ-DB solutions and hydrogels are technically defined as viscoelastic fluids, with phase angles greater than 450 in both the solution and gel states (i.e., the gels are more viscous than elastic). The complex moduli of PNJ-DB gels are in the 1,000-10,000 Pa range at 37° C. An approximately 100-fold increase in modulus was observed when solutions were heated to form gels. The sol-gel transition occurs over the same temperature range for IN, PT, and SL polymers of the same initial composition, indicating that the temperature-responsive nature of the polymers is preserved following pre-treatment and simulated shelf life in accelerated storage conditions.

Example 9—Dissolution of Temperature-Responsive Degradable Polymers with Antibiotics or Bupivacaine A seemingly appropriate method for dissolving temperature-responsive polymers and active agents would be to dissolve both components at the same time. However, even if the problem of air bubble formation in polymer solutions were avoided, simply introducing active agents to the polymer solution does not solve the problem. Instead, multiple classes of active agents present challenges to such a strategy. Specific limitations of a strategy wherein the polymer and active agent are combined in a single solution are demonstrated below. Uniform, consistent distribution of active agents is desirable in pharmaceutical and medical device products, because inconsistency can lead to lack of control in safety and effectiveness of the product (for example, by giving a poorly controlled dose of active agent or alternatively by giving a composition that contains a poorly controlled or spatially variable concentration of the temperature-responsive polymer throughout the hydrogel).

In the following examples, the polymer PNJ(1.9)-DB-LAAm(20) was dissolved at 30 wt % in either 0.2 M sodium acetate-acetic acid buffer at pH 4.0 (abbreviated NaOAc-HOAc) or phosphate buffered saline at pH 7.4 (abbreviated PBS). The purpose of using these two buffers is that NaOAc-HOAc is within the range that leads to improved polymer stability in storage, whereas PBS is a more conventional buffer. One gram of each polymer solution was added to 8 mL glass vials. Then tobramycin sulfate powder was added to the polymer solutions to result in an overall average tobramycin concentration of 30 mg/g (3 wt %). The vials were photographed, vortexed to distribute the drug, and then allowed to sit at 4° C. and photographed after 1, 3, and 7 hrs. Seven hours was selected as the longest time point—this corresponds to approximately the amount of time over which a dose might be prepared by a single operator (for example a pharmacy technician) in a standard 8 hour work day, and thus would be a maximum (if still inconvenient) time required to prepare a product for a medical procedure.

Figure 9A:
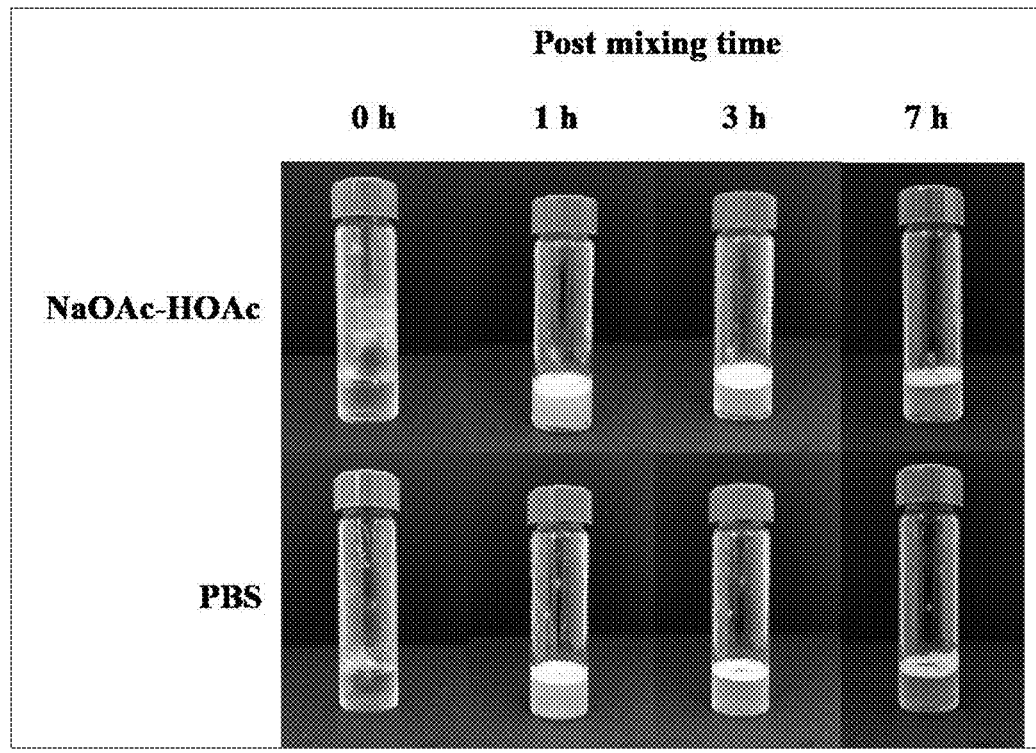
FIG. 9A presents images of samples of poly(NIPAAm-co-DBLAAm-co-JAAm) solution after mixing with tobramycin sulfate powder to result in 3 wt % tobramycin.
Figure 9B:
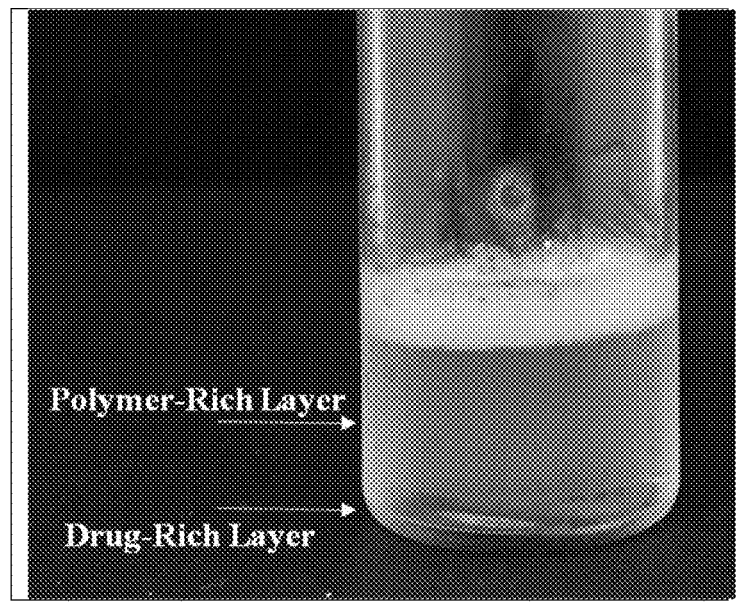
FIG. 9B presents a magnified image of poly(NIPAAm-co-DBLAAm-co-JAAm) solution after mixing with tobramycin sulfate powder to result in 3 wt % tobramycin in NaOAc-HOAc buffer at 7 hours.

Images of the mixed samples are shown in FIG. 9A. Prior to mixing, the solid tobramycin sulfate powder is visible on the walls of the container as well as in a solid mass on top of the polymer solution. Air bubbles remain on the surface of the solution for at least 7 hours after mixing. Additionally, phase separation is evident in each sample, with a translucent white layer separated above a smaller, transparent yellow layer on the bottom. As the air bubbles resolve over time, the phase separation in the samples becomes more apparent. Upon heating the samples, the top layer turned opaque above the LCST whereas the bottom layer did not, indicating that the polymer was present almost entirely in the top layer. A close-up image indicating this phase separation is shown in FIG. 9B. The two layers were tested for tobramycin concentration using a ninhydrin colorometric assay, which indicated that the concentration of tobramycin in the bottom layer (259 mg/mL) was much higher than the concentration in the top layer (7.9 mg/mL). Only the top layer turned opaque upon heating, indicating that essentially no polymer is present in the bottom layer. In summary, the seemingly appropriate method of adding active agent directly to a solution of temperature-responsive degradable polymer was complicated by three drawbacks: slow resolution of air bubbles, non-uniform distribution of the active agent, and non-uniform distribution of the polymer in the mixed composition.

A hydrogel formulation containing tobramycin and vancomycin can have good utility, for example about 3 wt % tobramycin and about 2 wt % tobramycin. The method described above to evaluate mixing with tobramycin was also used to evaluate the feasibility of directly adding the two active agents to polymer solutions. In this study, tobramycin sulfate powder and vancomycin hydrochloride powder were added simultaneously to the polymer solutions to result in an overall average tobramycin concentration of 30 mg/g (3 wt %) and an overall average vancomycin concentration of 20 mg/g (2 wt %). The vials were photographed, either hand-shaken or vortexed to distribute the drug, and then allowed to sit at 4° C. and photographed after 1, 3, and 7 hrs.

Figure 9C:
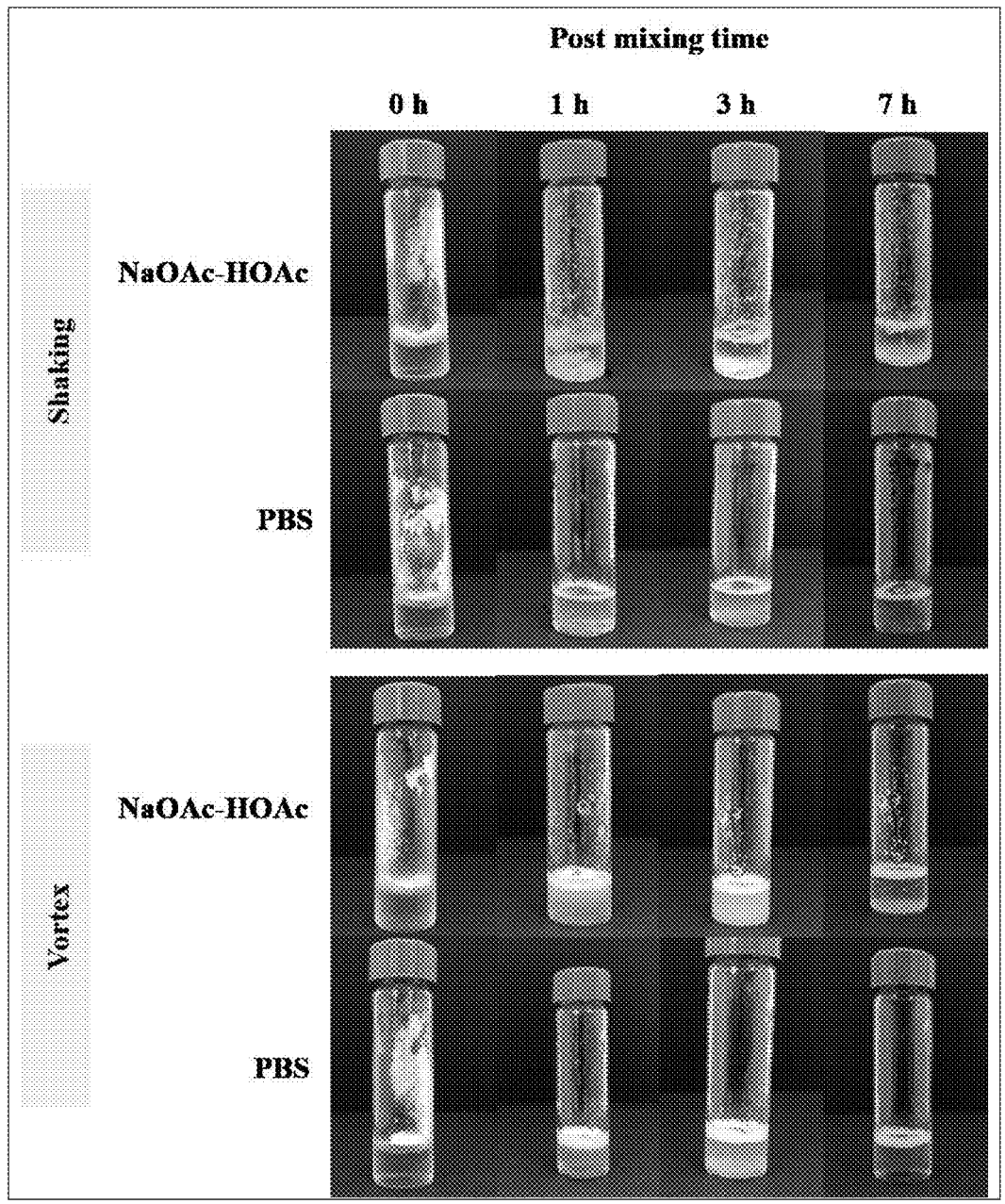
FIG. 9C presents images of samples of poly(NIPAAm-co-DBLAAm-co-JAAm) solution after mixing with tobramycin sulfate powder to result in 3 wt % tobramycin and 2 wt % vancomycin.
Figure 9D:
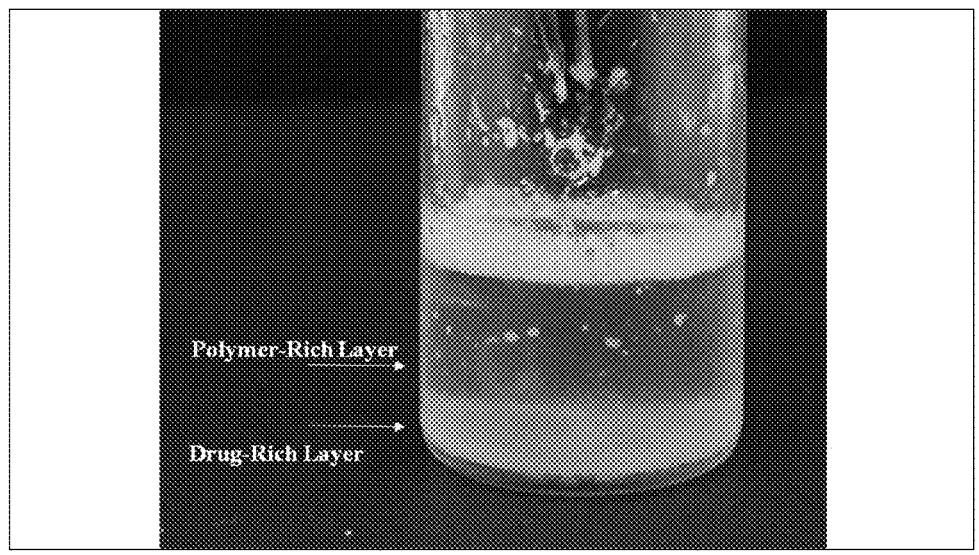
FIG. 9D presents a magnified image of poly(NIPAAm-co-DBLAAm-co-JAAm) solution after mixing with tobramycin sulfate powder to result in 3 wt % tobramycin and 2 wt % vancomycin in NaOAc-HOAc buffer at 7 hours after mixing. Phase separation occurred over time after mixing. A portion of insoluble drug is also visible on the vial walls.

Images of the mixed samples are shown in FIG. 9C. As with tobramycin alone, solid drug powder is visible on the walls of the vials and atop the solution prior to mixing. Neither shaking nor vortex-mixing avoided formation of air bubbles. Phase separation was again evident in all samples, although the drug-rich lower layer had a more turbid appearance in the acidic NaOAc-HOAc buffer. A close-up image indicating this phase separation is shown in FIG. 9D. Once more, the top layer contained a higher concentration of polymer and the bottom layer contained a higher concentration of tobramycin. Additionally, the samples prepared in NaOAc-HOAc buffer had visible residue on the vial walls which could possibly be vancomycin that did not dissolve fully in the polymer solution after mixing. Phase separation also occurred when the antimicrobial gentamicin was used in place of tobramycin, both alone and with vancomycin.

Another aspect of many active agents that limits their usefulness in temperature-responsive degradable hydrogels is insufficient solubility in water to allow uniform mixing or dissolution. As an example of such an active agent is the local anesthetic bupivacaine, which has water solubility of about 2-5 wt % in pH≈6 and less than 0.1 wt % at higher pH above 7.64. The method above was used to evaluate the feasibility of directly adding bupivacaine to polymer solutions. In this study, bupivacaine hydrochloride powder was added to the polymer solutions to result in an overall average bupivacaine concentration of 4 wt % (40 mg/g). The vials were photographed, either hand-shaken or vortexed to distribute the drug, and then allowed to sit at 4° C. and photographed after 1, 3, and 7 hrs.

Figure 9E:
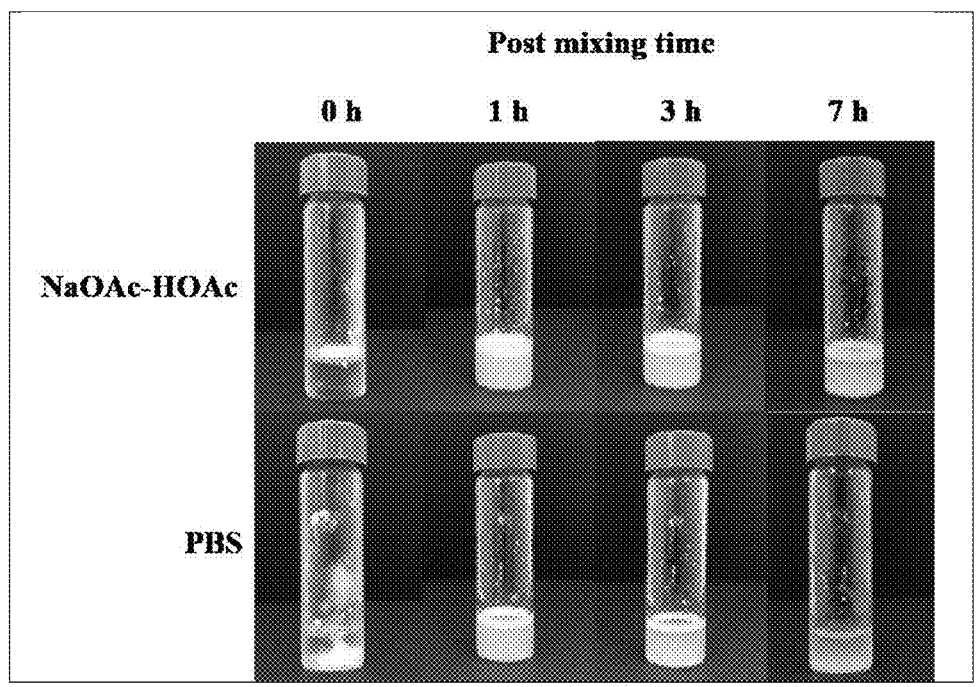
FIG. 9E presents images of samples of poly(NIPAAm-co-DBLAAm-co-JAAm) solution after mixing with bupivacaine hydrochloride powder to result in 4 wt % bupivacaine.

Images are shown in FIG. 9E. Bupivacaine did not fully dissolve in the polymer solution after mixing, and a mixture of solid drug particles were visible suspended within the solutions. By the time that air bubbles began to resolve which was around 7 hours after mixing, the solid bupivacaine particles fell to the bottom of the vial.

In these examples using tobramycin, the combination of tobramycin and vancomycin, or bupivacaine, multiple problems were found, of which any single one would be unacceptable as a process for preparing a pharmaceutical or medical device hydrogel formulation with adequate uniformity. These problems include: 1) slow dissipation of air bubbles following vortex-mixing or shaking of a polymer solution; 2) phase separation of the samples after mixing, as observed with tobramycin and the tobramycin-vancomycin combination; 3) settling of insoluble active agent within the polymer solution, as observed with bupivacaine. Additionally, even if an active agent can be co-dissolved with temperature-responsive degradable polymers, a further concern is the instability of active agents in solution. Appropriate methods for preparation and storage of drugs packaged for reconstitution is commonly provided in labeling for commercially available active agents. For example, tobramycin solution maintained at room temperature is recommended to be used within 24 hours after reconstitution. However, the preparation and storage methods for active agents are unique and optimized for the single agent, usually in deionized water or some widely available solution, and thus the stability of the active agent may be worse when co-dissolved with a temperature-responsive degradable polymer in acidic pH which is required for polymer stability.

Example 10—Preparation of Precursor Therapeutic Composition Using Organic Excipients This study demonstrates combining a polymer solution stored in acidic conditions with a precursor therapeutic composition which includes an active agent. For active agents which are not highly soluble in water, for example those with solubility less than about 5% or especially less than about 1%, an appropriate precursor therapeutic composition may be obtained by a general method wherein the active agent is dispersed uniformly in a solution with a biocompatible organic excipient and then any unsafe solvents are removed, leaving a uniform paste or liquid which can be mixed with the polymer solution in an enclosed volume, for example by end-to-end syringe mixing or through a mixing compartment.

The excipients suitable for the present invention are pharmaceutically acceptable materials. They are liquid at room temperature, and may be uniformly distributed into temperature-responsive polymer solutions. Examples of biocompatible organic excipients include one or more of the following: polyethylene glycol having molecular weight less than 1000 g/mol, polypropylene glycol having molecular weight less than 1000 g/mol, copolymers of ethylene oxide and propylene oxide having molecular weight less than 1000 g/mol, poly(ethylene glycol) ether derivatives having a molecular weight of between 200 and 4,000 g/mol, such as poly(ethylene glycol) mono- or di-alkyl ethers, poly(ethylene glycol)copolymers having a molecular weight of between 200 and 10,000 g/mol such as poly(ethylene glycol-co-polypropylene glycol), propylene glycol mono- or di-esters of a $C_2$-$C_{19}$ aliphatic carboxylic acid or a mixture of such acids, such as propylene glycol dicaprylate or dicaprate, polyvinylpyrrolidone having a molecular weight less than 40,000 g/mol, mono-, di- or tri-glycerides of a $C_2$-$C_{19}$ aliphatic carboxylic acid or a mixture of such acids, such as glyceryl caprylate, glyceryl caprate, glyceryl caprylate/caprate, glyceryl caprylate/caprate/laurate, glycofurol and similar ethoxylated tetrahydrofurfuryl alcohols and their $C_1$-$C_4$ alkyl ethers and $C_2$-$C_{19}$ aliphatic carboxylic acid esters, water-soluble organic solvents (ethanol, propylene glycol, glycerin, N-methyl-2-pyrrolidone, dimethylacetamide, and dimethylsulfoxide), non-ionic surfactants (Cremophor EL, Cremophor RH 40, Cremophor RH 60, d-α-tocopherol, polyethylene glycol 1000 succinate, polysorbate 20, polysorbate 80, Solutol HS 15, sorbitan monooleate, poloxamer 407, Labrafil M-1944CS, Labrafil M-2125CS, Labrasol, Gellucire 44/14, Softigen 767, and mono- and di-fatty acid esters of PEG 300, 400, or 1750), water-insoluble lipids (castor oil, corn oil, cottonseed oil, olive oil, peanut oil, peppermint oil, safflower oil, sesame oil, soybean oil, sunflower oil, other non- or partially hydrogenated vegetable oils, hydrogenated vegetable oils, hydrogenated soybean oil, and medium-chain triglycerides of coconut oil and palm seed oil), organic liquids/semi-solids (beeswax, d-α-tocopherol, oleic acid, medium-chain mono- and diglycerides),various cyclodextrins (α-cyclodextrin, β-cyclodextrin, hydroxypropyl-β-cyclodextrin, and sulfobutylether-β-cyclodextrin), and phospholipids (for example, hydrogenated soy phosphatidylcholine, distearoylphosphatidylglycerol, L-α-dimyristoylphosphatidylcholine, L-α dimyristoylphosphatidylglycerol).

Essentially all water-insoluble active agents are soluble or can be dispersed uniformly in at least one organic solvent. Common examples of organic solvents include ethanol, isopropanol, dimethyl sulfoxide, dimethylformamide, acetone, ethyl acetate, tetrahydrofuran, dichloromethane, 1,4-dioxane, toluene, benzene, and N-methyl-2-pyrrolidone. Generally, solvents can include those that are regarded as safe in medical applications or those which can be evaporated fully. When the solvent itself is not the biocompatible organic excipient, suitable compositions contain no more than a trace amount (1 wt % or less) of organic solvent.

Using bupivacaine as an example of an active agent that is not highly water soluble, precursor therapeutic compositions were successfully prepared using a variety of biocompatible organic excipients.

A general method is as follows: Bupivacaine was combined with the biocompatible organic excipient in a ratio of 1 part bupivacaine to between about 2 and 10 parts excipient by mass in a 20 mL vial. The most common ratio used was about 1 part bupivacaine to 2.75 parts excipient. Then anhydrous acetone was added to co-dissolve the excipient and bupivacaine. A transparent solution was obtained by stirring or sonication. The solution was evaporated at 40° C. under vacuum. When fully evaporated, a white uniform residue formed with a paste-like consistency, which varied depending on the excipient used and the bupivacaine concentration. This was also performed using a variety of biocompatible excipients including d-α-tocopherol, sesame oil, peanut oil, safflower oil, walnut oil, polyethylene glycol methyl ether 550, polyethylene glycol 400, polypropylene glycol 400, polypropylene glycol 725, polypropylene glycol 3500, Jeffamine M-1000, and pentaerythritol ethoxylate combined with bupivacaine at a ratio of 1 part bupivacaine to 2 parts, 5 parts, and 10 parts excipient by mass. The numbers after the polymer names in the previous sentence indicate the number-average molecular weight of the respective polymers. All of the materials resulted in a white to off-white solid paste, except for sesame oil: bupivacaine at 5:1 or 10:1 mass ratios which resulted in a yellow translucent oil with uniformly suspended white particles. One skilled in the art will know that this method is applicable to any active agent which is soluble in organic solvents, and that a variety of organic solvents may be used for this purpose. Acetone was specifically used because of its volatility and safety. Commercially, other solvents may be used. Examples of other suitable organic solvents include ethanol, due to its low toxicity, or dichloromethane, which is highly volatile and immiscible with water.

Additionally, in order to modify the release of bupivacaine, fatty acids including octanoic acid, capric acid, and caprylic acid have been included in the precursor therapeutic composition in a concentration up to about 20 wt % to decrease the pH within the resulting hydrogel, leading to increased bupivacaine release. Antimicrobial preservatives such as parabens, for example methylparaben, may also be included at concentrations up to about 5 wt %.

In one particular example, a precursor phase was prepared using a ratio of 3.94 parts polypropylene glycol 725 to 1 part bupivacaine base to 0.06 parts methylparaben. A rheometer was used with oscillatory shear applied at shear rates of 0.1-10 sec$^1$. Data are reported in Table 11. The material was a white paste at temperatures below 70° C. The paste had reduced viscosity with increasing temperature as well as with shear.

mon (as frequent as 50%) among gram-positive surgical site infections such as prosthetic joint infections. Resistance to aminoglycosides is a concern. On the other hand, resistance to VANC is rare, but VANC is not effective against gram-negative bacteria. Unfortunately, no single antimicrobial agent is likely to have adequate activity against>95% of PJI-causing organisms.

Device-associated infections and surgical site infections are caused by bacteria that form biofim, which is a survival strategy used by bacteria that are attached to surfaces. Biofilm harbors multidrug-tolerant bacterial persister cells invulnerable to killing by host immune cells. Bioflms are treatable only by surgical removal and adjuvant antimicrobial chemotherapy at the extremely high levels capable of complete eradication of the persister cells in the biofilm. Antimicrobial susceptibility of bacterial biofilms may be quantified by the minimum biofilm eradication concentration (MBEC), which is the concentration of an antimicrobial required to sterilize the biofilm.

MBEC of biofilms grown on rabbit muscle specimens in vitro was determined. The goal of the study was to compare the relative spectrum of antimicrobial activity of TOB and VANC either alone or in combination. Muscle specimens were used because they are comparable to the tissue surfaces which would be present in an infected site. This method also allows for controlled culture conditions and quantitative data without confounding phenomena that would be present in an

TABLE 11

Viscosity(in Pa · s) of PPO725/bupivacaine/methylparaben (3.94/1/0.06) versus shear rate at a range of temperatures.

| Shear Rate (sec$^{-1}$) | 5° C. | 10° C. | 20° C. | 30° C. | 40° C. | 50° C. | 60° C. | 70° C. | 80° C. |
|---|---|---|---|---|---|---|---|---|---|
| 0.1 | 2,390,000 | 16,400 | 3,870 | 2,040 | 1,060 | 524 | 29.1 | 0.182 | −0.0357 |
| 0.215 | 13,300 | 3,980 | 2,000 | 1,040 | 543 | 282 | 19.3 | 0.128 | 0.00245 |
| 0.464 | 4,490 | 1,990 | 1,080 | 582 | 312 | 156 | 13.4 | 0.0772 | 0.0121 |
| 1 | 2,230 | 1,050 | 546 | 318 | 201 | 92 | 11.9 | 0.0782 | 0.012 |
| 2.15 | 1,090 | 573 | 302 | 167 | 104 | 54.4 | 10.3 | 0.081 | 0.0177 |
| 4.64 | 552 | 303 | 165 | 91 | 55.3 | 31.8 | 9.07 | 0.0767 | 0.0169 |
| 10 | 241 | 162 | 85.6 | 49.6 | 32.5 | 17.6 | 5.99 | 0.0717 | 0.0168 |

At temperatures above about 70° C., the paste of 3.94 parts polypropylene glycol 725 to 1 part bupivacaine base to 0.06 parts methylparaben became a transparent solution and then reverted to form a white paste after some time when returned to ambient temperature. The liquid composition could be prepared through a simpler process, by combining the components without any additional solvent, heating, and stirring until well-mixed, resulting in the formation of a bupivacaine-laden solution that can be handled as a liquid, including filling into containers such as vials or syringes, and then forms a paste with cooling to ambient temperature.

Example 11—Biofim Susceptibility Data Supporting Tobramycin and Vancomycin Combination Some embodiments of the hydrogels can be for prevention or treatment of device-associated infections or surgical site infections and can include the antimicrobials tobramycin and vancomycin. Gentamicin (GENT), tobramycin (TOB), and vancomycin (VANC) are the most commonly used antimicrobials for local delivery in orthopaedic surgery.

Aminoglycosides have broad spectra of coverage, but resistance to aminoglycosides has been reported to be comanimal model of infection such as variability throughout a single infection, host immune function, and release/transport of antimicrobials.

Ten laboratory standard bacterial strains intended to represent the spectrum of pathogens found in surgical site infections were evaluated: 3 *S. aureus* (2 methicillin-resistant, 1 methicillin-sensitive), 4 *S. epidermidis* (1 methicillin-resistant, 3 methicillin-sensitive), K *Faecalis*, *P. Aeruginosa*, and *E. Coli* (ATCC #BAA-1556, BAA-1680, 49230, 35984, 29886, 700583, 14990, 29212, 27853, and 25922). Both MRSA strains tested (BAA-1556, BAA-1680) are susceptible or intermediately susceptible to both TOB and VANC. *S. epidermidis* (35984), *P. aeruginosa* (27853), and *E. faecalis* (29212) are tobramycin-resistant. None of the gram-positive organisms tested are resistant to vancomycin. Vancomycin is not effective against gram-negative bacteria (*E. coli, P. aeruginosa*).

Aseptically obtained rabbit muscle samples (~40 mg) were incubated in bacterial suspension for 3 days to allow biofilm growth. Tissue specimens were then rinsed and placed in separate wells of a 96-well plate. Medium containing various concentrations of antimicrobials (4000, 2000, 1000, 750, 500, 250, 125, 64, 32, 16, and 0 μg/mL)

were then added to the wells containing the contaminated tissue samples. Plates were then incubated for either 6, 24, or 72 hours at 37° C. Following this "exposure time," the antimicrobial-containing medium was removed and specimens were rinsed with antimicrobial-free growth medium at least 4 times to remove any residual antimicrobials. Then the specimens were subcultured in separate test tubes containing antimicrobial-free medium and incubated at 37° C.

In each series of specimens for a given strain, antimicrobial treatment, and exposure time, the lowest antimicrobial concentration showing no growth after 21 day subculture was measured to be the MBEC. If all subcultures were positive, the MBEC was determined to be >4000 μg/mL. Selected positive subcultures were confirmed by culture identification at a third-party diagnostic laboratory. The MBEC and minimum inhibitory concentration (MIC; the level required to inhibit planktonic, non-biofilm bacteria) were measured using microbiological susceptibility assays against TOB, VANC, or a 1:1 weight combination of each agent (TOB+VANC) for each of three exposure durations (6 hour, 24 hour, 72 hour).

MBEC values are shown in Table 12. MBEC values for the TOB+VANC combination avoided extremely high levels. At 24 and 72 hr exposure, no strains had MBEC>1,000 μg/mL against TOB+VANC, compared to 3 strains with TOB and 6 strains with VANC. Further analysis was focused on 24 hr exposure time based on low MBECs versus the TOB+VANC combination and only a modest decrease in MBEC (2× or less) between 24 and 72 hr exposure.

TABLE 12

Minimum biofilm eradication concentration (MBEC) on rabbit muscle

| Organism | Exposure Time | MBEC (μg/mL) | | |
|---|---|---|---|---|
| | | TOB | VANC | TOB + VANC |
| S. aureus (BAA 1556) | 6 hr | 2000 | 4000 | 500 |
| | 24 hr | 375 | 2000 | 125 |
| | 72 hr | 250 | 1000 | 125 |
| S. aureus (BAA 1680) | 6 hr | >4000 | 4000 | 750 |
| | 24 hr | >4000 | 2000 | 250 |
| | 72 hr | 4000 | 2000 | 250 |
| S. aureus (49230) | 6 hr | 500 | >4000 | 375 |
| | 24 hr | 375 | >4000 | 125 |
| | 72 hr | 250 | 2000 | 250 |
| S. epidermidis (35984) | 6 hr | >4000 | 4000 | 2000 |
| | 24 hr | >4000 | 750 | 750 |
| | 72 hr | >4000 | 375 | 500 |
| S. epidermidis (29886) | 6 hr | 125 | 375 | 125 |
| | 24 hr | 125 | 375 | 125 |
| | 72 hr | 31 | 375 | 31 |
| S. epidermidis (700583) | 6 hr | 125 | 1000 | 250 |
| | 24 hr | 250 | 1000 | 250 |
| | 72 hr | 375 | 1000 | 375 |
| E. faecalis (29212) | 6 hr | >4000 | 1000 | 2000 |
| | 24 hr | >4000 | 375 | 500 |
| | 72 hr | >4000 | 250 | 250 |
| P. aeruginosa (27853) | 6 hr | 2000 | >4000 | 750 |
| | 24 hr | 375 | >4000 | 750 |
| | 72 hr | 62 | >4000 | 375 |
| E. coli (25922) | 6 hr | 250 | >4000 | 375 |
| | 24 hr | 62 | >4000 | 250 |
| | 72 hr | 62 | >4000 | 375 |

| | Exposure Time | TOB | VANC | TOB + VANC |
|---|---|---|---|---|
| # Strains w/ MBEC ≥1000 | 6 hr | 5/10 | 8/10 | 2/10 |
| | 24 hr | 3/10 | 6/10 | 0/10 |
| | 72 hr | 3/10 | 6/10 | 0/10 |
| Median MBEC | 24 hr | 250 | 750 | 250 |
| Max. MBEC | 24 hr | >4000 | >4000 | 750 |

MBEC values for the TOB+VANC combination avoided extremely high levels. At 24 and 72 hr exposure, no strains had MBEC>1,000 μg/mL against TOB+VANC, compared to 3 strains with TOB and 6 strains with VANC. Further analysis was focused on 24 hr exposure time based on low MBECs versus the TOB+VANC combination and only a modest decrease in MBEC (2× or less) between 24 and 72 hr exposure.

The data indicate an advantage of hydrogels containing these two active agents for local delivery in the prevention and treatment of surgical site or device-related infections.

Example 12—Preparation of Solution of Tobramycin and Vancomycin

For highly water-soluble active agents, the precursor therapeutic composition can be prepared by dissolving the active agents in an appropriate aqueous solvent. Some active agents are unstable in long-term storage in solution. Stability information is commonly available for commercially available active agents in the product labeling. In some examples, highly water-soluble active agents can be dissolved to form the precursor therapeutic composition within a short time prior to combining with the polymer solution, for example within less than about 8 hours, or in some examples less than 1 hour.

The combination of tobramycin and vancomycin can be an effective combination of active agents for local sustained delivery in the treatment of infections. The following example describes an example composition of a precursor therapeutic composition for tobramycin and vancomycin. Tobramycin is highly soluble (solubility>30 wt %) in aqueous solutions over a range of pH values. Tobramycin sulfate solution in deionized water results in pH of about 6 due to the alkaline influence of tobramycin (which is itself a base) and the sulfuric acid with which the tobramycin is complexed in the salt form. However, the solubility of vancomycin varies with pH, having maximum solubility at about pH 3 (~19 wt %) with lower solubility in the range pH 4-7.4 (≤2 wt %). When tobramycin sulfate and vancomycin hydrochloride are co-dissolved in deionized water, the pH is approximately 6 and thus the vancomycin hydrochloride does not dissolve. By titrating solutions of tobramycin sulfate at a range of concentrations to pH 3.0 using 1 N HCl, it was determined that the amount of hydrochloric acid that was necessary to decrease the solution of tobramycin sulfate to pH 3.0 was about 0.21 μmol HCl+2.247 μmol HCl per mg tobramycin sulfate. By co-dissolving tobramycin and vancomycin in aqueous solution containing a sufficient concentration of HCl to adjust the pH to 3.0, both agents can be dissolved. Depending upon the ratio of tobramycin and vancomycin, the two agents may alternatively be co-dissolved at up to a total concentration of 22-24 wt % in deionized water. In general, hydrogel compositions having higher polymer concentrations, for example above about 25 wt %, can be beneficial. Thus a high concentration of active agent in the precursor therapeutic composition can allow for relatively minimal dilution of the polymer during mixing while still providing a high concentration of active agent in the therapeutic hydrogel composition. It can also be beneficial for the active agents to dissolve conveniently, for example by shaking in a closed container by hand. However, there can be a tradeoff between active agent concentration and the ease of dissolution. In this example, solutions of equal amounts of tobramycin and vancomycin were evaluated over a range of concentrations.

Drug solutions (2 grams total each) were prepared having one of six total drug concentrations (8, 10, 14, 20, 22, or 24 wt %), and one of two drug ratios (equal parts tobramycin to vancomycin (1T1V), or 3 parts tobramycin to 1 part vancomycin (3TV), for a total of 12 solutions. The drug concentration was defined as the "total" concentration so that 8% of the 1T1V ratio included 4 wt % tobramycin and 4 wt % vancomycin. Tobramycin sulfate (activity 69%) and vancomycin hydrochloride (activity 97%) were added together to 8 mL vials. Then 1 N HCl was added in an amount calculated based on tobramycin content to decrease the pH to 3 along with addition of deionized water to bring the total mass in the vial to 2 grams. In the 24% 3T1V group, 2N HCl was used instead of 1N HCl, as the volume of 1N HCl used would have made the total amount of solution exceed 2 grams. In this study, the density of deionized water and 1N HCl were assumed to be 1 g/mL. The compositions used are shown in Table 13. The masses of tobramycin sulfate and vancomycin hydrochloride are not equal in the samples of the 1T1V drug ratio group because of the difference in the proportion of the drug powder weight that is active drug. Samples were shaken by hand and observed for dissolution and uniformity. Observations are presented in Table 14. Samples described as "dissolved" formed transparent solutions with a light yellow-to-pink color.

TABLE 13

Amounts of Each Component in Preparation of Tobramycin/Vancomycin Solutions

| Sample No. | Batch Size | Total Drug Conc. (wt %) | Drug Ratio (Tob:Vanc) | Tob. Sulfate (g) | Vanc. HCl (g) | H$_2$O (g) | 1N HCl (g) |
|---|---|---|---|---|---|---|---|
| 1 | 2 | 8% | 1T1V | 0.116 | 0.082 | 1.331 | 0.471 |
| 2 | 2 | 8% | 3T1V | 0.174 | 0.041 | 1.184 | 0.601 |
| 3 | 2 | 10% | 1T1V | 0.145 | 0.103 | 1.216 | 0.536 |
| 4 | 2 | 10% | 3T1V | 0.217 | 0.051 | 1.033 | 0.698 |
| 5 | 2 | 14% | 1T1V | 0.203 | 0.144 | 0.987 | 0.666 |
| 6 | 2 | 14% | 3T1V | 0.304 | 0.072 | 0.730 | 0.894 |
| 7 | 2 | 20% | 1T1V | 0.290 | 0.206 | 0.643 | 0.861 |
| 8 | 2 | 20% | 3T1V | 0.435 | 0.103 | 0.275 | 1.187 |
| 9 | 2 | 22% | 1T1V | 0.319 | 0.227 | 0.528 | 0.926 |
| 10 | 2 | 22% | 3T1V | 0.478 | 0.133 | 0.124 | 1.285 |
| 11 | 2 | 24% | 1T1V | 0.348 | 0.247 | 0.413 | 0.992 |
| 12 | 2 | 24% | 3T1V | 0.522 | 0.124 | 0.663 | 0.691 |

TABLE 14

Observations of Tobramycin/Vancomycin Solutions After Addition of Aqueous HCl Solution

| Sample No. | Total Drug Conc. (wt %) | Observation |
|---|---|---|
| 1 | 8% | Dissolved after shaking for 30 s |
| 2 | 8% | Dissolved after shaking for 30 s |
| 3 | 10% | Dissolved after shaking for 45 s |
| 4 | 10% | Dissolved after shaking for 45 s |
| 5 | 14% | Dissolved after shaking for 1 min |
| 6 | 14% | Dissolved after shaking for 1 min |
| 7 | 20% | Dissolved after shaking for 1 min 30 sec, required more vigorous shaking. Trace residue on walls of vial. |
| 8 | 20% | Dissolved after shaking for 1 min |
| 9 | 22% | Dissolved after shaking for 2 min |
| 10 | 22% | Dissolved after shaking for 2 min |
| 11 | 24% | Dissolved after vigorous shaking for 3 min |
| 12* | 24% | Not fully dissolved after 5 min vigorous shaking, turbid suspension with trace residual on vial wall. |

*All solutions except 12 remained transparent and uniform for at least 7 days when stored at 22° C. Sample 12 contained solid substance at the base of the vial.

The observations indicate that tobramycin and vancomycin can be co-dissolved within 2 minutes at a total drug concentration up to about 22 wt %. By selecting a concentration near 22 wt %, tobramycin and vancomycin may be dissolved in a reasonable amount of time while diluting the temperature-responsive degradable polymer in the polymer solution of the present invention to a minimal extent. It is noted that similar approaches can be employed to ascertain an appropriate composition by taking into account the solubility of the active agent of interest in water, which is available for many active agents or can be discerned through simple testing methods for active agents with unknown solubility.

Example 13—Dissolution of Polymer Separately From Drugs

The polymer solution and precursor therapeutic composition can be prepared separately and combined prior to use, thereby avoiding air bubbles, phase separation, settling of insoluble drugs, and drug instability. This example describes a method of mixing the gels and discloses their appearance and texture throughout the hydrogel preparation and mixing process. The example includes mixing with tobramycin, a combination of tobramycin and vancomycin, and bupivacaine. The method for formulation of the precursor therapeutic compositions is described above.

Figure 10:
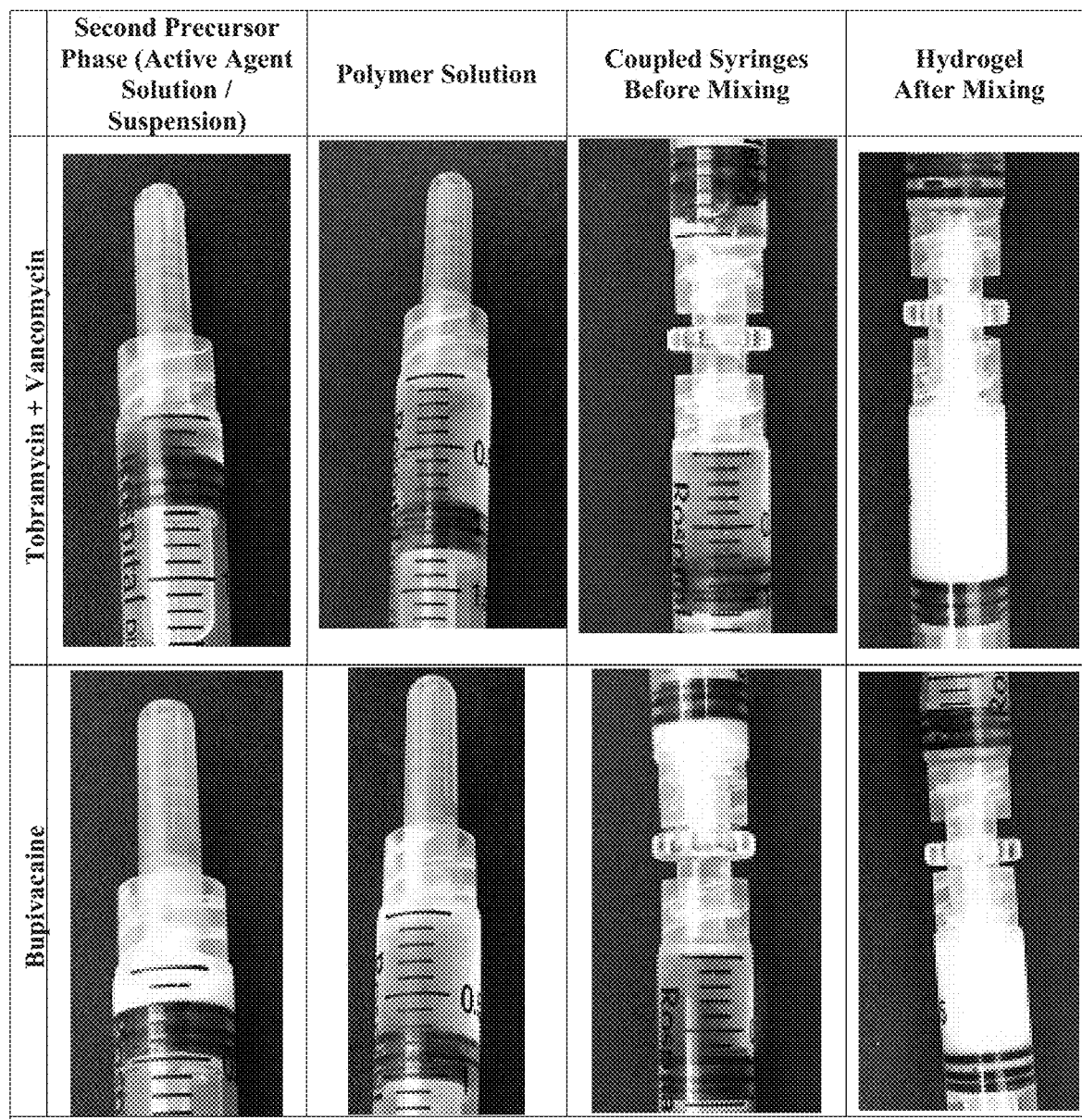
FIG. 10 presents images of various steps in the preparation of drug-containing hydrogels by end-to-end syringe mixing. (Top row) Polymer solution was mixed with tobramycin and vancomycin solution to result in a hydrogel. Each precursor phase is transparent before mixing and the mixed hydrogel is translucent to opaque. (Bottom row) Polymer solution was mixed with bupivacaine suspension in PP0725. The polymer solution was clear, bupivacaine/PP0725 suspension is opaque and white, and the mixed hydrogel is opaque and white.

Hundreds of mixed hydrogels were prepared over a range of hydrogel compositions for the polymers poly(NIPAAm-co-JAAm-co-DBLA) and poly(NIPAAm-co-JAAm-co-DB- LAAm). Most of the polymers tested have had weight-average molecular weight of about 40,000 g/mol to about 70,000 g/mol, spanning a full range of about 20,000 g/mol to 100,000 g/mol. The JAAm content of the polymers has been within the range of about 0.8 mol % to 2 mol %. For polymer containing DBLA, the DBLA content has been within the range of about 5 mol % to 9 mol %, and for polymers containing DBLAAm the DBLAAm content has been within the range of about 6 mol % to 25 mol %. Polymer concentrations in the polymer solution have been within the range of about 20 wt % to 38 wt %. Syringe sizes of 3 mL, 5 mL, 10 mL, and 20 mL each have been used. Syringes of 1 mL volume (for example BD product number 309628) do not allow even mixing, which was attributed to the small difference in diameter between the barrel and tip of the syringe, resulting in less turbulent flow in this area. When 1 mL syringes were used, a gradient would form, as evident by both direct measurements of drug content and visual observation when the precursor therapeutic composition contained bupivacaine in an opaque suspension. The descriptions and pictures provided are representative of the methods used and of the appearance and texture of example hydrogels. Images depicting various steps in the syringe mixing and hydrogel formation process are shown in FIG. 10.

A representative temperature-responsive degradable polymer poly(NIPAAm-co-JAAm-co-DBLAAm) was used, containing 19.73 mol % DBLAAm and 1.34 mol % JAAm and having weight-average molecular weight of 49,510 g/mol. The polymer was dissolved at a concentration of 38 wt % in 0.2 M sodium acetate-acetic acid buffer (pH 4.0), i.e. 38 parts by mass of polymer to 62 parts by mass of buffer. For polymers of comparable molecular weight, it was determined that 38 wt % polymer concentration was about at the maximal concentration that would allow even mixing with drug solution. For polymers having weight-average molecular weight of about 70,000 g/mol, the maximum concentration allowing adequate mixing was about 33 wt % in the polymer solution. The polymer solution was dissolved by vortex mixing to fully wet the polymer powder followed by storage at 4° C. overnight. Then one gram of the polymer solution was drawn into a 3 mL polypropylene syringe via a 14 gauge blunt tip Luer lock tip. Air bubbles on the polymer solution were allowed to resolve within the syringe by storing the syringe at 4° C. with the outlet facing up until all bubbles had resolved, at which time the syringe plunger was set so that the polymer solution filled the entire syringe. A Luer lock syringe cap was attached to the syringe which was stored at 4° C. until mixing. The syringe containing polymer solution was labeled Syringe A.

A precursor therapeutic composition was prepared with tobramycin and vancomycin with a total active drug concentration of 22 wt % (13.2 wt % tobramycin+8.8 wt % vancomycin). The solution was prepared by adding tobramycin sulfate and vancomycin hydrochloride powders to a vial and then adding an appropriate amount of 745 mM HCl (aq.) and shaking to dissolve, resulting in a light yellow to pink solution. The solution was then transferred by mass to a 3 mL polypropylene syringe using a micropipette, drawing in the syringe plunger to allow the drug solution in. Any bubbles formed on the syringe plunger were resolved by holding the syringe with the opening facing up, bringing the syringe plunger down, and flicking with a finger to dislodge air bubbles. The plunger was then adjusted to bring the level of the solution to the top of the syringe, and a Luer lock syringe cap was attached to the syringe which was stored at 4° C. until mixing. The syringe containing drug solution is referred to as Syringe B. For each 1 gram of polymer solution in Syringe A, 292 mg of drug solution was added to Syringe B, resulting in overall concentrations in the mixed gel of about 29.4 wt % polymer, 3 wt % tobramycin, and 2 wt % vancomycin.

After tightening the syringes to each end of the coupler, the syringe contents were mixed by alternately pushing the contents from one end to the other for 10-12 times each, until the content within the syringes appeared uniform. Syringe mixing was done at a rate of about 160-180 strokes per minute. Much slower rates, for example 60 strokes per minute, did not produce adequate mixing using this method. Mixing can be done while the syringe contents are at a temperature below the LCST of the contents. In this specific case, the LCST was about 25° C.

Following mixing, the mixed contents were pushed as much as possible into one syringe. The other syringe and coupler were twisted off, and the mixed hydrogel was applied by pushing the hydrogel out of the syringe. A variety of applicator tips can be used, including 22-gauge needles, 20-gauge needles, 18-gauge needles, 16-gauge needles, 14-gauge needles, and 14-gauge Luer-lock intravenous catheters. The resulting hydrogel was flowable, syringeable, and uniform in texture and appearance with a translucent light yellow to pink color. No air bubbles were evident within the hydrogel.

For preparation of a gel containing 4 wt % bupivacaine in the final gel, the precursor therapeutic composition was instead prepared by combining 71.66 wt % polypropylene glycol 725, 26.67 wt % bupivacaine, and 1.66 wt % methylparaben (a preservative), and then either adding 2-fold excess acetone and vacuum drying or by heating the mixture without any additional solvent to 70° C. Syringes were then loaded with the resulting material, which was a white solid spreadable paste at ambient temperature and a clear viscous solution at 70° C. For each 1 gram of polymer solution in Syringe A, 176 mg of drug solution was added to Syringe B, resulting in overall concentrations in the mixed gel of about 32.3 wt % polymer, 4 wt % bupivacaine, and 0.25% methylparaben. The resulting hydrogel was flowable, syringeable, and uniform in texture and appearance with an opaque white color. No air bubbles were evident within the hydrogel.

Pharmaceutical formulations, such as the hydrogels described in this example, are often required to be provided as sterile (i.e. free of micro-organisms such as bacteria). Methods of sterilization used in medicine include autoclaving (high-pressure steam), ethylene oxide gas sterilization, gamma irradiation, or electron beam irradiation.

Polymer solution were prepared in a sterile fashion in two different ways. In the first method, lyophilized temperature-responsive degradable polymer was sterilized by ethylene oxide gas and then dissolved and loaded into syringes aseptically using a laminar flow cabinet. In the second method, non-sterile polymer was dissolved, loaded into an appropriate syringe, and then irradiated by gamma irradiation, for example in the range of 12-50 kGy, or about 20-35 kGy. Syringes that are compatible with gamma irradiation are known to those skilled in the art and can be looked up in compatibility tables. Polycarbonate syringes or copolyester syringes (NuGen brand, DMC Medical Limited, Shannon, Co. Clare, Ireland) were used. Neither sterilization method has been found to have a deleterious effect on the LCST of the resulting hydrogel.

The precursor therapeutic compositions may be sterilized by filtration, for example using a 0.2 μm pore size filter. The bupivacaine solution may either be filter sterilized while heated as a solution or when dissolved in acetone using a compatible filter (for example, a syringe filter with 0.2 μm pore size and a compatible housing and membrane). The precursor therapeutic compositions may be prepared aseptically prior to the time of use, for example by dissolving sterile lyophilized active agents with sterile aqueous solvents such as sterile water.

The syringe coupler may be sterilized separately and attached immediately prior to mixing. The syringe couplers were sterilized by autoclave in commercially available adhesive-seal sterilization packs. Syringes, needles, and other accessories are commonly commercially available pre-sterilized.

Example 14—Viscosity of Polymer Solutions and Homogeneity Data on Drug Distribution After Syringe Mixing Using end-to-end mixing between two coupled syringes per the method described above, it was found that the uniformity of mixing depends upon the viscosity of the polymer solution and the time for which mixing is done. It is noted that the viscosity of the polymer solution itself depends upon the initial polymer concentration and the molecular weight of the polymer in the polymer solution. A number of studies have been completed with the goal of ascertaining suitable polymer solution compositions for conveniently and reliably obtaining a uniform composition of active agents throughout the hydrogel after mixing. The scope of these studies has primarily focused on polymers having weight-average molecular weight of about 40,000 g/mol (LMW; low molecular weight) or about 70,000 g/mol (HMW; high molecular weight). The lower molecular weight polymers were prepared using equal volumes THF and dioxane as the solvent during synthesis whereas the higher molecular weight polymers were prepared using an 80:20 ratio of dioxane to THF. This range of molecular weight is on the high end of the range of molecular weights that are expected to be cleared safely by renal excretion after degradation and dissolution of the polymer into individual soluble polymer molecules over time in physiological conditions.

Viscosity under shear was evaluated using an Anton Paar Physica MCR-101 rheometer using 400 μL of polymer solution on a temperature-controlled stage. Homogeneity of drug distribution was evaluated by first mixing Syringes A and B as described above (approximately 160-180 strokes/minute for 10-12 strokes)unless otherwise noted and then dispensing fractions of the mixed gel sequentially out of the syringe into separate containers which were then analyzed for concentration of the drug of interest. The compositions of the polymers used are described in Table 14. Polymer solution was in 0.2 M sodium acetate-acetic acid buffer (pH 4.0). When applicable tobramycin or gentamicin was quantified by a colorometric ninhydrin assay, and vancomycin or bupivacaine was quantified by UV absorbance at 280 nm in a UV-transparent 96-well plate using a spectrophotometer. Briefly, the ninhydrin assay consisted of combining 250 μL of unknown sample with 75 μL of 1.25 wt % ninhydrin solution in water, followed by heating at 95° C. for 15 minutes, cooling on ice, and measuring absorbance of the samples at 400 nm in a 96-well plate using a spectrophotometer.

In addition to the specific studies reported under this example, many more studies were also conducted to characterize drug release, degradation time, and other properties of mixed hydrogels. Although thorough mixing is used to consistently perform these studies, mixing is typically not evaluated directly. For example, replicates within a hydrogel group for drug release kinetics studies have been performed using hydrogel from different fractions of a hydrogel batch after mixing in the fashion described. The examples in this specification that describe in vitro release studies therefore reflect conditions under which thorough gel mixing was achieved, unless the study was performed using single replicates.

TABLE 14

Composition of polymers used in Example 14

| Polymer | Composition (mol %) | | | Mol. Wt. (g/mol) | |
| --- | --- | --- | --- | --- | --- |
| | DBLA | DBLAAm | JAAm | $M_w$ | $M_n$ |
| LMW1 | 5.41% | — | 1.03% | No Data | No Data |
| LMW2 | 7.40% | — | 1.30% | 34,040 | 19,810 |
| HMW1 | 7.29% | — | 1.35% | 69,580 | 38,180 |
| LMW3 | — | 20.0% | 0.90% | 43,030 | 23,450 |
| LMW4 | — | 19.89% | 1.18% | 45,410 | 19,730 |
| LMW5 | — | 19.5% | 1.27% | 49,510 | 24,680 |
| LMW6 | — | 19.10% | 1.57% | 47,310 | 25,490 |
| HMW2 | 6.83% | — | 1.47% | No Data | No Data |
| HMW3 | 6.35% | — | 1.93% | No Data | No Data |
| HMW4 | 6.71% | — | 1.97% | No Data | No Data |
| HMW5 | 6.28% | — | 1.94% | No Data | No Data |
| HMW6 | 6.87% | — | 1.22% | No Data | No Data |
| HMW7 | 9.02% | — | 1.97% | No Data | No Data |
| LMW7 | 6.93% | — | 1.28% | No Data | No Data |

*Samples for which no molecular weight data was collected were classified as low or high molecular weight based on the solvent blend used during polymer synthesis.

Three polymers (LMW 1, LMW 2, HMW 1) were each dissolved at 30, 33, 36, and 40 wt % and viscosity vs. shear rate was measured at 5° C. and 20° C. At a shear rate above 10/sec, the viscosity was approximately constant. Viscosity as measured at 100/sec shear rate was used as a metric to compare between the solutions. Separately, samples were mixed with tobramycin/vancomycin solution according to the method described previously to evaluate feasibility of end-to-end syringe mixing preparing 3 g of hydrogel in coupled 5 mL syringes. The maximum concentration which appeared visually well-mixed was recorded. Solutions of HMW 1 had higher viscosity at comparable molecular weight. Data are shown in Table 15. Subsequent testing indicated that 38 wt % LMW polymer solutions with viscosity up to 1.68 Pa*s were also able to be mixed. The data suggest that the maximum polymer solution viscosity at 100/sec shear rate that can be mixed is greater than about 1.5 Pa*s but less than about 3 Pa*s.

TABLE 15

Viscosity (Pa*s) of polymer solutions at 30-40 wt %, 100/sec

| Polymer | 30 wt % | 33 wt % | 36 wt % | 40 wt % | Max Conc. To Mix |
| --- | --- | --- | --- | --- | --- |
| LMW1 | 0.321 | 0.484 | 0.744 | 0.634 | 40 wt % |
| LMW2 | 0.355 | 0.953 | 1.25 | 3.11 | 36 wt % |
| HMW1 | 0.663 | 1.19 | 5.66 | 14.8 | 33 wt % |

Four additional LMW polymers (LMW 3-6) with a range of JAAm content were evaluated by viscometry at 38 wt %. Results are shown in Table 16. Each polymer was separately used in drug release studies and mixed successfully when present at 38 wt % in the polymer solution. All of the polymers were less viscous at 20° C. than at 5° C., in agreement with temperature sweep rheometry data on similar polymers. Generally, the viscosity of the polymer solutions decrease with increasing temperature until the temperature approaches the LCST. Based on this study LMW polymers within the range of compositions tested can be mixed at concentrations up to 38 wt % in the polymer solution having viscosity up to 1.68 Pa*s at 100/sec shear rate at 20° C.

TABLE 16

Viscosity of polymer solutions at 38 wt %

| Polymer | Viscosity at 100/sec, 5° C. (Pa*s) | Viscosity at 100/sec, 20° C. (Pa*s) |
|---|---|---|
| LMW3 | 2.40 | 1.51 |
| LMW4 | 1.95 | 1.27 |
| LMW5 | 2.78 | 1.68 |
| LMW6 | 2.16 | 1.55 |

Polymer HMW 2 was evaluated for mixing at concentrations of 20, 25, 26.25, 27.5, 28.75, and 30 wt %. Each of the solutions was mixed with a precursor therapeutic composition containing tobramycin sulfate. Approximately 3 grams of gel was prepared using coupled 5 mL syringes. The hydrogels were dispensed in 3 or 4 sequential fractions. The tobramycin concentration in each fraction was measured and is reported in Table 17 as the percentage of the average tobramycin concentration.

Each fraction in a perfectly mixed gel would contain 100% of the average tobramycin concentration. The drug content in each fraction was within 12% of the average concentration for all fractions except for the 30 wt % group, where the first fraction contained 230% of the average tobramycin concentration and the 4th fraction contained only 2.65% of the average tobramycin concentration.

TABLE 17

Tobramycin concentration as a fraction of average concentration in fractions of hydrogel after syringe mixing

| | 20 wt % | 25 wt % | 26.25 wt % | 27.5 wt % | 28.75 wt % | 30 wt % |
|---|---|---|---|---|---|---|
| Fraction 1 | 97.63% | 103.09% | 91.74% | 104.41% | 95.99% | 230.06% |
| Fraction 2 | 100.44% | 96.57% | 104.41% | 106.87% | 99.02% | 138.70% |
| Fraction 3 | 100.37% | 102.19% | 103.85% | 88.72% | 104.99% | 28.59% |
| Fraction 4 | 101.56% | 98.15% | N/A | N/A | N/A | 2.65% |

Figure 11:
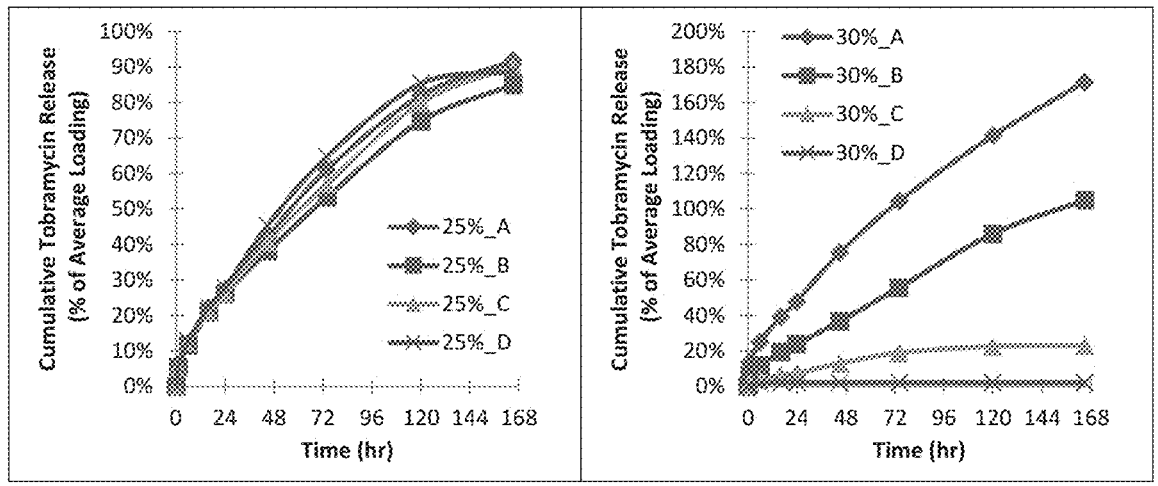
FIG. 11 is a graph of cumulative release of tobramycin vs. time for hydrogel fractions after mixing of Polymer HMW2 with an initial polymer concentration of 25 wt % (left) and 30 wt % (right) in the polymer solution. The average tobramycin content in the gels was 3 wt %.

Hydrogels prepared at 20, 25 and 30 wt % of Polymer HMW2 were evaluated for tobramycin release over time. Each of the solutions was mixed with a precursor therapeutic composition containing tobramycin sulfate. Approximately 3 grams of each hydrogel was prepared using coupled 5 mL syringes. Four fractions of hydrogel (three of approximately 1 g each and a 4th fraction of about 300 mg each) were dispensed into separate 20 mL vials which were placed in a 37° C. water bath for 10-15 seconds, causing the hydrogel to form a white and opaque semi solid material. Then 20 mL PBS (pH 7.4) pre-warmed to 37° C. was gently added on top of the hydrogel samples. At various time points, aliquots of the PBS were removed and the entire volume of PBS was replaced. The cumulative amount of tobramycin released versus time was then determined by measuring the tobramycin concentration in the aliquots. All of the samples remained as white, opaque, stable gels during the course of the study. Data are shown in FIG. 11. The well-mixed gel at 25 wt % initial polymer concentration provides consistent sustained tobramycin release from each fraction. The gel with 30 wt % initial polymer concentration was poorly mixed and thus the amount of drug released is the greatest for the first fraction (A) and then decreases for subsequent fractions. All of the fractions show sustained release over about the same period of time, but the total amount of drug contained in the gels varied, indicating poor mixing. The data indicate that polymers with molecular weight in the HMW range may be mixed adequately at initial concentrations up to 28.75 wt %.

Another study used Polymer HMW2 at an initial concentration of 27.5 wt % and mixing with either tobramycin only (T), vancomycin only (V), half each tobramycin and vancomycin (1T1V), or tobramycin and vancomycin in 3:1 ratio (3T1V). Approximately 3 grams of each hydrogel was prepared using coupled 5 mL syringes. The final polymer concentration in the gel was 23 wt % and the final average active agent concentration in the gel after mixing was 3.14 wt %. Fractions were dispensed from the syringe and evaluated for drug release over time. The release profiles were comparable across replicates (i.e., fractions of the syringe) for all groups. Total drug recovered from each fraction are shown in Table 18 as a percentage of the average across all fractions. The data indicate that both active agents distribute uniformly when mixed into the hydrogel either as single agents in the precursor therapeutic composition or as part of a combination of active agents in the precursor therapeutic composition.

TABLE 18

Fraction of Tobramycin (Left) or Vancomycin (Right) average concentration for fractions of mixed hydrogel dispensed

| | Tobramycin | | | Vancomycin | | |
|---|---|---|---|---|---|---|
| | Tob Only | 1T1V | 3T1V | Vanc Only | 1T1V | 3T1V |
| Fraction 1 | 97.6% | 99.0% | 94.3% | 102.6% | 96.1% | 93.4% |
| Fraction 2 | 101.0% | 100.4% | 98.7% | 99.4% | 101.6% | 94.9% |
| Fraction 3 | 98.4% | 99.3% | 97.5% | 97.2% | 97.4% | 105.1% |
| Fraction 4 | 103.1% | 101.2% | 109.5% | 100.8% | 104.9% | 106.6% |

Another study used Polymers HM4W 3-5 at an initial concentration of 27.5 wt/% and mixing with gentamicin only. The final polymer concentration in the gel was 23 wt/% and the final average active agent concentration in the gel after mixing was 3.14 wt/%. Fractions were dispensed from the syringe and evaluated for drug release over time in 0.15 M phosphate buffer. Release profiles were consistent, within 10%/cumulative release at all time points. Release was incomplete within 7 days, but the total amount released within the first 7 days is reported as a percentage of the total mass of drug expected in the samples assuming perfect mixing. Release was consistent across all samples, indicating good mixing.

TABLE 19

Fraction of Gentamicin released within 7 days in vitro from fractions of mixed hydrogel

| | HMW3 | HMW4 | HMW5 |
|---|---|---|---|
| Fraction 1 | 60.14% | 81.21% | 70.06% |
| Fraction 2 | 62.74% | 81.66% | 74.77% |
| Fraction 3 | 81.56% | 77.77% | 85.13% |
| Fraction 4 | 83.12% | 61.74% | 58.21% |

Another study used Polymers HMW 6-7 at an initial concentration of 25 wt % and mixing with tobramycin only.

Approximately 3 grams of each hydrogel was prepared using coupled 5 mL syringes. The final polymer concentration in the gel was 22.7 wt % and the final average active agent concentration in the gel after mixing was 3.14 wt %. Polymer HMW 6 was mixed for either 5, 10, 15, or 30 seconds. Polymer HMW 7 was mixed for 15 seconds. Polymer HMW 2 was evaluated by the same method at an initial concentration of 29.5 wt %, final concentration of 25 wt %, and mixing for 8 seconds. Each gel fraction (approx. 500 mg each) was distributed into a 20 mL scintillation vial and a release study was started in PBS (pH 7.4). After 1 hour, an aliquot of the release medium was sampled and assayed for tobramycin concentration as an estimate of "initial burst" release. Then the PBS was fully replaced and the samples were cooled on ice to dissolve the samples, liberating the remaining tobramycin which was also measured. The total drug content in each fraction as a percentage of the average drug content across all fractions is shown in Table 20, and the percentage of tobramycin released from each fraction during the 1 hour time frame is shown in Table 21. All of the gels mixed adequately, with between 91 and 107% of the average concentration in each fraction of each sample. However, hydrogels which were mixed for 10 seconds or longer showed increased burst release in the last fractions, which was attributed to gelation of the hydrogel before it was transferred out of the syringe, resulting in compression of the hydrogel in its insoluble, gelled state. Thus, it can be advantageous to mix by end-to-end syringe mixing for less than 10 seconds to maintain consistent drug release properties throughout the mixed hydrogel.

TABLE 20

Percentage of average Tobramycin concentration in each gel fraction

| | Polymer | | | | | |
|---|---|---|---|---|---|---|
| | HMW6 | HMW6 | HMW6 | HMW6 | HMW7 | HMW2 |
| | | Mix Time | | | | |
| | 5 sec mix | 10 sec mix | 15 sec mix | 30 sec mix | 15 sec mix | 8 sec mix |
| Fraction 1 | 93.39% | 115.78% | 98.36% | 101.23% | 102.15% | 101.34% |
| Fraction 2 | 93.90% | 92.08% | 94.83% | 105.68% | 99.99% | 104.93% |
| Fraction 3 | 100.74% | 92.87% | 97.15% | 104.55% | 99.09% | 91.82% |
| Fraction 4 | 105.58% | 97.30% | 117.31% | 94.78% | 95.44% | 106.06% |
| Fraction 5 | 99.78% | 95.74% | 97.06% | 90.30% | 93.95% | 105.75% |
| Fraction 6 | 106.60% | 106.23% | 95.29% | 103.46% | 101.31% | 90.09% |
| Fraction 7 | N/A | N/A | N/A | N/A | 101.42% | N/A |
| Fraction 8 | N/A | N/A | N/A | N/A | 106.65% | N/A |

TABLE 21

Percentage of Tobramycin content released during the first hour in vitro

| | Polymer | | | | | |
|---|---|---|---|---|---|---|
| | HMW6 | HMW6 | HMW6 | HMW6 | HMW7 | HMW2 |
| | | Mix Time | | | | |
| | 5 sec mix | 10 sec mix | 15 sec mix | 30 sec mix | 15 sec mix | 8 sec mix |
| Fraction 1 | 11.14% | 12.88% | 11.79% | 14.45% | 18.39% | 5.14% |
| Fraction 2 | 10.84% | 12.77% | 12.17% | 17.61% | 15.84% | 4.20% |
| Fraction 3 | 13.38% | 13.27% | 10.77% | 14.91% | 16.14% | 4.65% |
| Fraction 4 | 15.66% | 12.97% | 14.31% | 16.05% | 20.46% | 4.44% |
| Fraction 5 | 14.47% | 18.23% | 28.33% | 32.31% | 39.41% | 4.90% |
| Fraction 6 | 13.32% | 47.67% | 53.35% | 54.37% | 51.11% | 3.89% |
| Fraction 7 | N/A | N/A | N/A | N/A | 68.23% | N/A |
| Fraction 8 | N/A | N/A | N/A | N/A | 84.29% | N/A |

Another study used Polymer LMW 7 at an initial concentration of 38 wt %/and mixing with tobramycin only, using either no mixing (pre-weighing all components into a vial and vortex mixing) or mixing by syringe for 3, 5, 7, or 11 seconds. The gels were mixed in approximately 3.3 gram total batches in 5 mL syringes and the fractions were approximately 1 gram each. Burst release and total drug content from each fraction were weighed. Results are shown in Table 22 and Table 23. The data indicate that adequate mixing was achieved in all groups using mixing time as low as 3 seconds, the lowest tested. However, with the 11 second mix time, burst release increased especially for the last fraction, in agreement with studies above. A notable result was that the gels that were prepared by syringe mixing for 3-7 seconds showed on average lower burst release than gels mixed by vortex. This may be attributable to reduced air entrapment in the gels and thus greater stability during the 1 hour allowed for drug release.

TABLE 22

Percentage of average Tobramycin concentration in each gel fraction

| Mix Time | No mix | 3 sec mix | 5 sec mix | 7 sec mix | 11 sec mix |
|---|---|---|---|---|---|
| Fraction 1 | 97.0% | 105.1% | 105.7% | 103.5% | 90.8% |
| Fraction 2 | 100.0% | 101.2% | 100.8% | 110.8% | 107.2% |
| Fraction 3 | 102.9% | 93.6% | 93.4% | 85.6% | 102.0% |

TABLE 23

Percentage of Tobramycin content released during the first hour in vitro

| Mix Time | No mix | 3 sec mix | 5 sec mix | 7 sec mix | 11 sec mix |
|---|---|---|---|---|---|
| Fraction 1 | 11.2% | 8.7% | 4.7% | 7.4% | 10.2% |
| Fraction 2 | 11.5% | 11.0% | 5.3% | 5.6% | 17.5% |
| Fraction 3 | 12.8% | 13.1% | 9.0% | 14.0% | 35.4% |

A polymer HMW 8 was identified as a suitable formulation for local anesthetic delivery, and was evaluated for mixing with a bupivacaine-laden paste. The initial polymer concentration was 27.5 wt % or 26.25 wt %. The precursor therapeutic composition contained 71.66 wt % polypropylene glycol 725, 26.67 wt % bupivacaine, and 1.66 wt % methylparaben, and the final bupivacaine concentration in the mixed gel was 4 wt %. Approximately 2 grams of gel was mixed in coupled 3 mL syringes by rapid mixing for 5 seconds, and 10 fractions of each were dispensed. The results are shown in Table 24. Both gels visibly mixed, but the gel containing a higher polymer concentration had poorer uniformity, with a difference of about 2-fold between the fractions with the greatest and least bupivacaine concentration. The data suggest that mixing with bupivacaine-laden paste is adequate when the concentration of the polymer solution is less than 27.5 wt % for polymers in the HMW range. Subsequent studies with at least 14 other polymers in the LMW range (containing 5-9 mol % DBLA, 1.3-2.0 mol % JAAm, and 89-94 mol % NIPAAm) suggest that an initial concentration of up to 38 wt % allows mixing with the same bupivacaine paste, with improved uniformity using an initial polymer concentration of 35 wt %. Although formulations with uniform mixing can be more suitable than those that do not, avoidance of air bubbles following mixing and improved stability of the active agent by not requiring co-dissolution with the polymer is also beneficial.

TABLE 24

Percentage of average Bupivacaine concentration in each gel fraction

|  | 27.5 wt % | 26.25 wt % |
| --- | --- | --- |
| Fraction 1 | 107.5% | 106.4% |
| Fraction 2 | 130.7% | 110.6% |
| Fraction 3 | 125.3% | 123.4% |
| Fraction 4 | 127.9% | 106.6% |
| Fraction 5 | 120.4% | 93.5% |
| Fraction 6 | 109.0% | 99.0% |
| Fraction 7 | 83.8% | 91.9% |
| Fraction 8 | 67.8% | 90.3% |
| Fraction 9 | 64.5% | 88.5% |
| Fraction 10 | 63.1% | 89.8% |

Example 15—Appropriate MW range vs. concentration for mixing and gelation

The concentration of a temperature-responsive polymer solution that is adequate for formation of a semi-solid hydrogel is known to vary depending on the molecular weight of the polymer. Below this minimum concentration, the polymer molecules precipitate to form a suspension. Additionally, in embodiments which include mixing with a precursor therapeutic composition, the polymer concentration in the polymer solution must have low enough viscosity to allow for mixing. Based on the preceding example, the maximum permissible viscosity for mixing is between 1.68 and 3 Pa*s, or about 2 Pa*s. The goal of this experiment was to determine, over a range of polymer molecular weights, what range of polymer concentrations meet each of these requirements.

Six polymers of N-isopropylacrylamide were prepared using either benzene, dioxane, 80:20 dioxane:THF, 50:50 dioxane:THF, or THF only as the polymerization solvent. Two batches were made using THF only, one of which included 2 mol % mercaptoethanol as a chain transfer agent to further decrease the molecular weight. These processes yielded weight-average molecular weights of 1510, 183, 70, 43, 18 kDa, and 10 kDa, respectively. Each polymer was dissolved at a range of concentrations in 0.2 M sodium acetate-acetic acid buffer at pH 4.0. Hydrogel formation was evaluated by a gel inversion test. Briefly, the polymer solutions (800 mg each) were prepared in 4 mL glass vials and heated to 37° C. for 5 minutes. Then the vials were inverted. Hydrogels were identified as solid white materials that did not visibly flow within 5 seconds upon inversion of the vial. The minimum concentration which did not flow was recorded as the minimum gelation concentration. At least one concentration below the minimum gelation concentration was tested (0.5, 1, 2, 2, 12, and 20 wt %, respectively for the 6 polymers tested). The viscosity of polymer solutions was measured under shear in the shear rate range of 0.1-100 sec−1 at 20° C. The maximum concentration which had a viscosity of less than 2 Pa*s at a shear rate of 100 sec$^{-1}$ was determined to be the maximum mixing concentration. Viscosity data are shown in Table 25. The maximum mixing concentration at 70 kDa was identified as 33 wt % based on mixing studies in Example 14 (visual mixing of polymer HMW1 at 33 wt %) and a release study in Example 17 Study 7 which was performed with an initial polymer concentration of 32 wt %. The maximum mixing concentration at 43 kDa was based on mixing studies in Example 14 using Polymers LMW 3-6 and release studies including those described in Example 16.

TABLE 25

Viscosity of selected temperature-responsive polymer solutions

| Polymer $M_w$ | Concentration | Viscosity at 100/sec, 20° C. (Pa * s) |
| --- | --- | --- |
| 1,510 kDa | 20 wt % | Did not flow |
| 1,510 kDa | 15 wt % | 0.86 |
| 183 kDa | 30 wt % | 1.99 |
| 183 kDa | 25 wt % | 0.67 |
| 18 kDa | 42 wt % | 1.05 |
| 18 kDa | 45 wt % | 1.70 |
| 10 kDa | 50 wt % | 1.98 |
| 10 kDa | 45 wt % | 1.19 |

TABLE 26

Minimum gelation concentration and maximum mixing concentration for temperature-responsive polymers of various molecular weights

| Polymer $M_w$ | Minimum Gelation Concentration | Maximum Mixing Concentration |
| --- | --- | --- |
| 1,510 kDa | 1 wt % | 15 wt % |
| 183 kDa | 2 wt % | 30 wt % |
| 70 kDa | 3 wt % | 33 wt % |
| 43 kDa | 3 wt % | 38 wt % |
| 18 kDa | 12 wt % | 45 wt % |
| 10 kDa | 20 wt % | 50 wt % |

Figure 12:
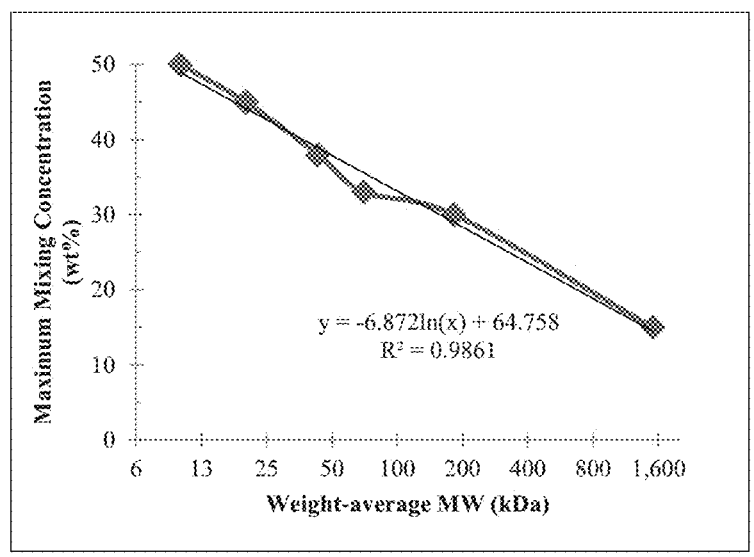
FIG. 12 is a graph of maximum mixing concentration in the polymer solution versus polymer molecular weight. Data points are shown as diamonds with a best-fit logarithmic function indicated on a line.

The maximum mixing concentration versus weight-average molecular weight is shown in FIG. 12. The data fit well with a logarithmic fit y=−6.872*ln(x)+64.76, where y is the maximum mixing concentration in wt/% and x is the weight-average molecular weight in kDa.

Due to uncertainty in the data, the polymer solution may have a concentration slightly higher (for example, up to 2 wt % higher) than what is predicted by the best-fit curve. Therefore, the polymer solution is expected to have a concentration (in wt %) that is no greater than about (~6.872*ln(x)+66.76), where x is the weight-average molecular weight in kDa of the temperature-responsive degradable polymer.

Figure 13:
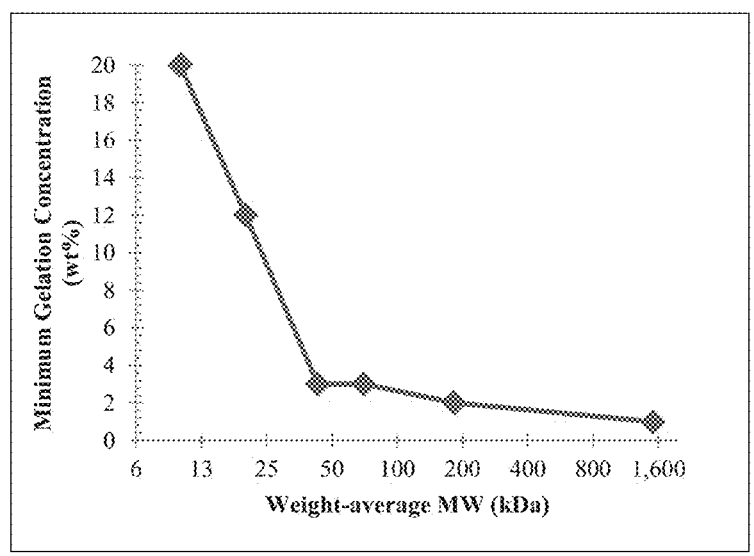
FIG. 13 is a graph of minimum gelation concentration versus polymer molecular weight. Data points are shown as diamonds. The line connecting the data points is a visual guide only.

The minimum gelation concentration data did not fit well as a logarithmic or polynomial function of molecular weight as shown in FIG. 13. The minimum concentration of temperature-responsive polymer required to form a hydrogel may be estimated by the line on FIG. 13.

Based on the data, the minimum gelation concentration may be predicted using a linear fit for the data for $M_w$≤43 kDa because the minimum gelation concentration closely fits the line y=−0.494*Mw+23.68, where y is the minimum gelation concentration in wt % and Mw is the weight-average molecular weight in kDa ($R_2$=0.964). Thus, the minimum gelation concentration (in wt %) can be estimated as −0.494*Mw+23.68 where $M_w$ is in kDa for Mw<43 kDa, 3 wt % for 183 kDa≥Mw>43 kDa, 2 wt % for 1,510 kDa≥Mw>183 kDa, and about 1 wt % for $M_w$ >1,510 kDa.

An alternative method to estimate the minimum gelation concentration would be to assume that regions between the data points are reflected by the measurement at the next highest molecular weight, such that the minimum concentration of temperature-responsive degradable polymer in the hydrogel would be: about 1 wt % for $M_w$ >1,510 kDa, 2 wt % for 1,510 kDa≥Mw>183 kDa, 3 wt % for 183 kDa≥Mw>43 kDa, 12 wt % for 43 kDa≥Mw>18 kDa, 20 wt % for 18 kDa≥Mw>10 kDa, and [−0.494*Mw+23.68] wt % for Mw<10 kDa where $M_w$ is in kDa.

Example 16—In Vitro Release of Tobramycin and Vancomycin

Using end-to-end mixing between two coupled syringes per the methods described above, the sustained release of various active agents was evaluated, including the antimicrobials tobramycin and vancomycin, which are highly water-soluble, and also the local anesthetic bupivacaine, which is not highly water soluble (see Example 17). Sustained release of these active agents is improved by preparing the hydrogel as two separate precursor phases prior to mixing. Whereas conventional methods of incorporating active agents cause the formation of bubbles, inconsistency between samples, and instability of the hydrogel itself, the methods of the proposed invention lead to hydrogels with more consistent content throughout the hydrogel without the instability caused by air bubbles. It is noted that the exact parameters, for example content of the water-soluble polymer-bearing repeat unit and the lactone-bearing repeat unit in the temperature-responsive degradable polymer, will depend upon the application and the properties of the active agent.

Methods: A general method for studies to evaluate the release of active agents over time is as follows: Unless otherwise noted, all hydrogels were prepared by end-to-end syringe mixing of a separately prepared polymer solution and precursor therapeutic composition as described previously, where the polymer solution was a 38 wt % solution of a temperature-responsive degradable polymer having a weight-average molecular weight of about 40,000 g/mol.

Polymers were dissolved in 0.2 M acetic acid-sodium acetate buffer (pH 4.0) at a concentration of 33-38 wt % and stored at 4° C. for at least overnight to allow complete dissolution. Then the polymer solution is transferred into a tared 3 mL syringe and the polymer solution measured by weight. For experiments with single replicates, 400 mg solution was used. For experiments with three replicates, 1.2 grams of polymer solution was used. Syringes were allowed to sit upright overnight during storage at 4° C. for bubbles to resolve.

Viscosity of the polymer solution increases with polymer molecular weight and polymer concentration in the initial solution. It was determined that a viscosity for the polymer solution of less than about 2 Pa*s at 5° C. can allow for the drug to be evenly distributed throughout the dose after mixing. For temperature-responsive degradable polymers with Mw of 35,000-45,000 g/mol, the maximum feasible polymer concentration is about 38 wt %.

For gels releasing tobramycin and vancomycin, the precursor therapeutic composition was a solution of tobramycin and vancomycin containing 22 wt % active drug in aqueous HCl solution. For gels releasing bupivacaine and prepared by syringe mixing, the precursor therapeutic composition contained 26.7 wt % bupivacaine, 73.3 wt % polypropylene glycol 725. The mass of the precursor therapeutic composition was selected to result in the desired drug concentration in the mixed gel.

Following preparation of each syringe, the syringe containing polymer solution was removed from storage at 4° C. and a Luer-lock female-to-female coupler was attached to the syringe containing polymer solution, the polymer solution was pushed to fill the coupler (to minimize air bubbles in the mixed hydrogel), and then the syringe containing the drug solution was secured to the other end of the coupler. The contents were mixed rapidly end to—end between the syringes for 10-12 strokes, resulting in a translucent mixture with a uniform distribution of the active agent(s).

After mixing of the dose, the full dose was pushed into one syringe, and the other syringe and coupler were removed. Then a 20-gauge Luer-lock needle was affixed to the syringe containing the gel, and the gel was dispensed into a tared glass 8 mL scintillation vial.

The mass of gel added to the vial was recorded. Then the vial is transferred to a 37° C. water bath to allow for gelation. The dose is allowed to form a gel for at least 1 minute and then 8 mL of pre-warmed PBS (37° C., pH 7.4) is added on top of the gel. The gels or the overlying solution were typically not agitated except before each aliquot collection (3 gentle inversions and pipette mixing of the media). Aliquots of the buffer are collected at various time points, including at least 1, 6, 24, 48, 72, 120, and 168 hr, and the buffer was replaced at each time point. The timing of buffer replacement does not affect results in these experiments, indicating that infinite sink conditions are maintained. Vancomycin was measured by UV spectrophotometry (280 nm). Tobramycin was measured for some samples by a colorometric ninhydrin assay. Tobramycin and vancomycin were found to be released proportionally from the gels; vancomycin release alone is reported. Bupivacaine was measured by UV absorbance at 280 nm.

Study 1.

Pharmaceutical formulations are often prepared by reconstitution of solid components into a solution or suspension, for example by adding an aqueous solution into a septum-capped vial. Thus, selected hydrogels were also prepared in a fashion that resembles this method to ascertain differences in gel texture and the timing of drug release as compared to an end-to-end syringe mixing method, as described herein. To evaluate the release of tobramycin and vancomycin, the drug powders tobramycin sulfate and vancomycin hydrochloride were added to a pre-dissolved polymer solution in individual 8 mL vials, stirred, and allowed to sit for at least 48 hours to dissolve as much as possible. Then the samples were either shaken by hand until uniform in appearance or mixed using a vortex mixer. Although vortex mixers are not typically used to mix pharmaceutical formulations in practice, they provide a consistent and thorough shaking motion.

In one study, hydrogels prepared by each technique (shake, vortex-mix, or end-to-end syringe mix) were evaluated for drug release over time per the methods above and also were photographed immediately after gel formation and then at 1, 3, and 21 hours after PBS was added. All of the hydrogels were prepared from the same polymer containing 8.34% DBLA, 1.25% JAAm, and the balance NIPAAm, having a weight-average molecular weight of 37,280 g/mol.

Figure 14:
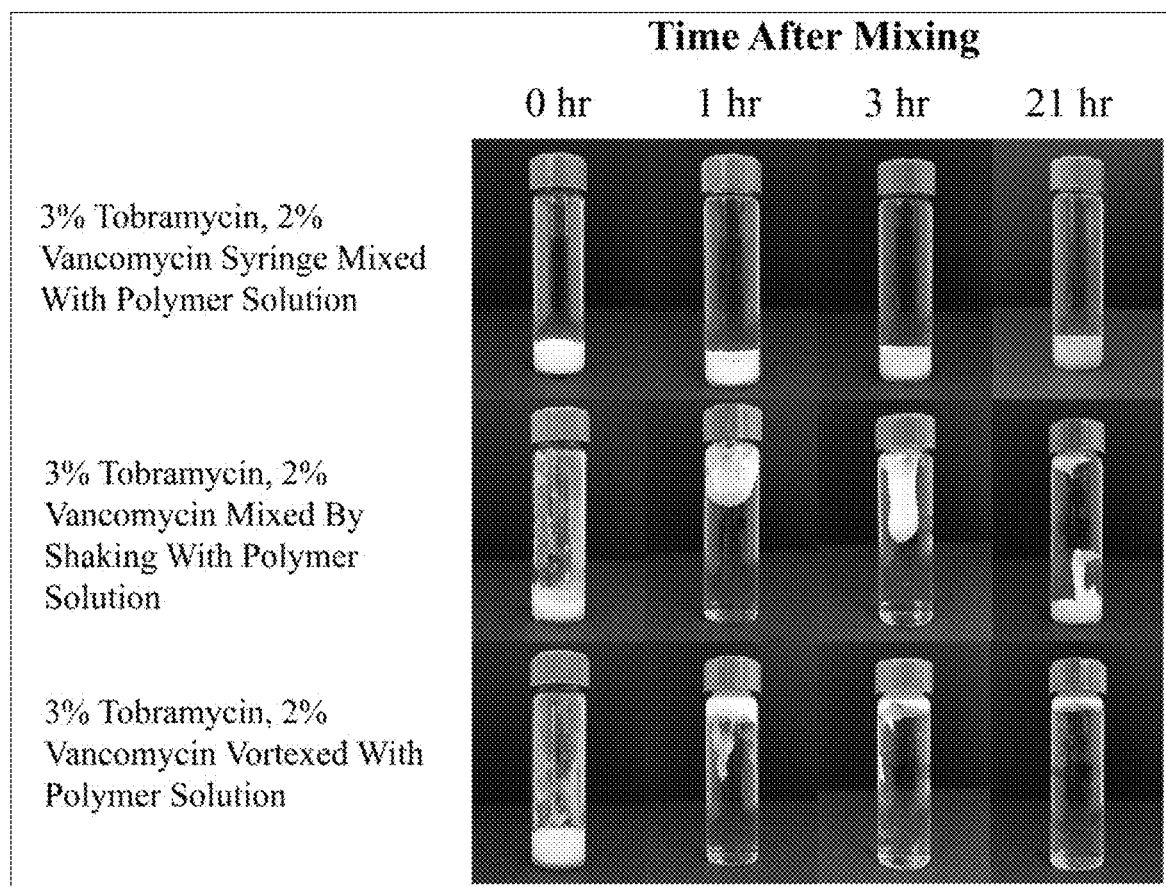
FIG. 14 presents images of temperature-responsive degradable hydrogels over time at 37° C. after loading with 3% tobramycin and 2% vancomycin by either end-to-end syringe mixing (top), hand-shaking (middle), or vortex-mixing (bottom) of two precursor phases. Pre-warmed (37° C.) PBS was added to the vials after the initial picture at 0 hr and the vials were maintained at 37° C.

The appearance of the hydrogels over time after mixing by each of three methods is shown in FIG. 14. The syringe-mixed gels formed a solid cohesive and stable material that remained at the bottom of the vial throughout the study. However, both of the gels that were hand-shaken or vortex-mixed de-adhered from the bottom of the glass vial, floating to the top within 1 hour. After 21 hours, part of the hand-mixed gel returned to the bottom of the vial while part remained at the top around the rim. The instability of the hand-shaken and vortex-mixed hydrogels was attributed to air bubbles within the gel arising during mixing, causing it to float toward the top. As the viscous gel allows air bubbles to rise through it over time, a part of the hand-mixed gel became dense enough to sink to the bottom of the vial again.

Figure 15:
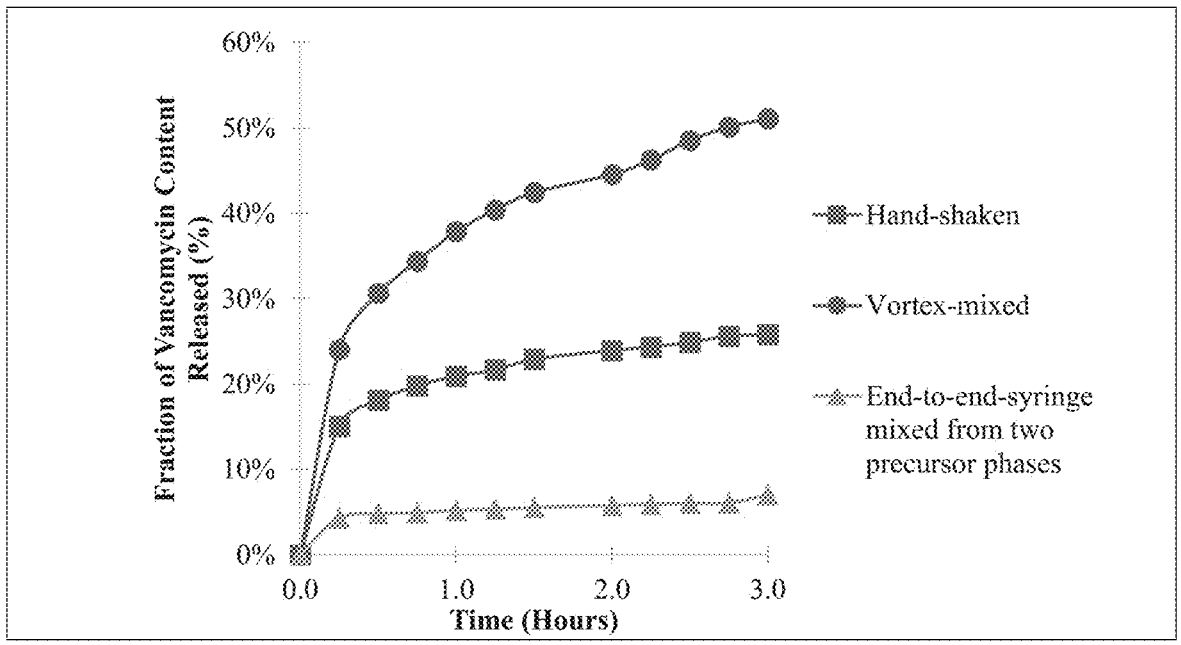
FIG. 15 is a graph of vancomycin release over time from hydrogels prepared by three hydrogel preparation methods. Hydrogels were prepared from the same polymer and contained 3% tobramycin and 2% vancomycin.

Data showing drug release over the first 3 hours from the same gels are shown in FIG. 15. Vancomycin release from the hand-shaken and vortex-mixed gels was rapid. Whereas the syringe-mixed gel released only 5.2% of its vancomycin content in the first hour, the shaken gel and vortex-mixed gel released 20.9% and 37.9% of their vancomycin content, respectively. The gel images and antimicrobial release data indicate the superiority of a syringe mixing method utilizing a closed volume without entrapped air for providing hydrogels with uniform composition, lack of air bubbles, and reliable gel properties compared to existing methods.

Drug release studies using gentamicin, tobramycin, or the combination of tobramycin and vancomycin were conducted using a range of polymer compositions. These studies have largely focused on formulations with a suitable LCST in the range of about 20-30° C. and other suitable polymer properties (for example drug release duration) for useful delivery of the particular active agents for particular applications. Notably the content of DBLA as the degradable unit was selected to be in the range of about 4-9 mol %, while the content of DBLAAm as the degradable unit was higher, in the range of about 15-25 mol % in most batches.

Study 2.

Release kinetics of tobramycin (TOB) and vancomycin (VANC) were measured using the method described above from each permutation of 4 polymers and 9 TOB/VANC ratios. The 4 polymers were identified by numbers 1, 2, 3, and 4. These followed preliminary studies (not shown) that evaluated TOB content between 0 and about 3.75 wt % and VANC content between 0 and about 3.14 wt %. The drug combinations were described with letters A through I as shown in Tables 27 and 28 below:

TABLE 27

Polymers used in Example 16 release Study 2

| Polymer | Composition (mol %) | | Molecular Weight | |
|---|---|---|---|---|
| | DBLA | JAAm | $M_w$ | $M_n$ |
| Polymer 1 | 6.78% | 1.02% | 35,870 | 19,330 |
| Polymer 2 | 7.40% | 1.30% | 34,040 | 19,810 |
| Polymer 3 | 5.48% | 1.45% | 36,320 | 17,400 |
| Polymer 4 | 7.02% | 1.19% | 39,450 | 23,850 |

TABLE 28

Drug ratios used in Study 2

| Drug Conc. (wt %) | 0.78% VANC | 1.57% VANC | 2.35% VANC |
|---|---|---|---|
| 2.35% TOB | A | B | C |
| 2.75% TOB | D | E | F |
| 3.14% TOB | G | H | I |

Figure 16A:
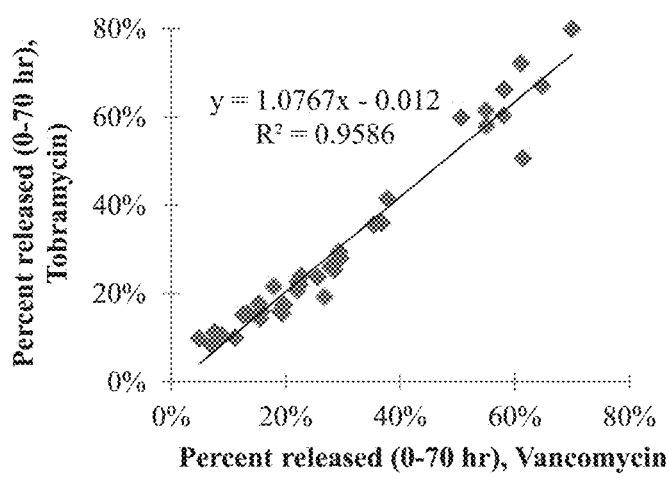
FIG. 16A is a graph of cumulative fraction of TOB vs. VANC released through 70 hr for 36 gels.

Single samples of each polymer/dose combination were evaluated (36 samples total). Release was found to be approximately linear for most samples tested, although some samples showed an increased rate of release during the first 6 hours. Data were plotted as the percentage of the payload released between 0-6 hr and between 6-70 hr as shown in FIG. 16A. Across all samples, the fraction of VANC and TOB released from the same gel were approximately equal as shown in FIG. 16A. For simplicity, only the release of VANC is shown in following figures. The fraction of each drug released is approximately equal.

Figure 16B:
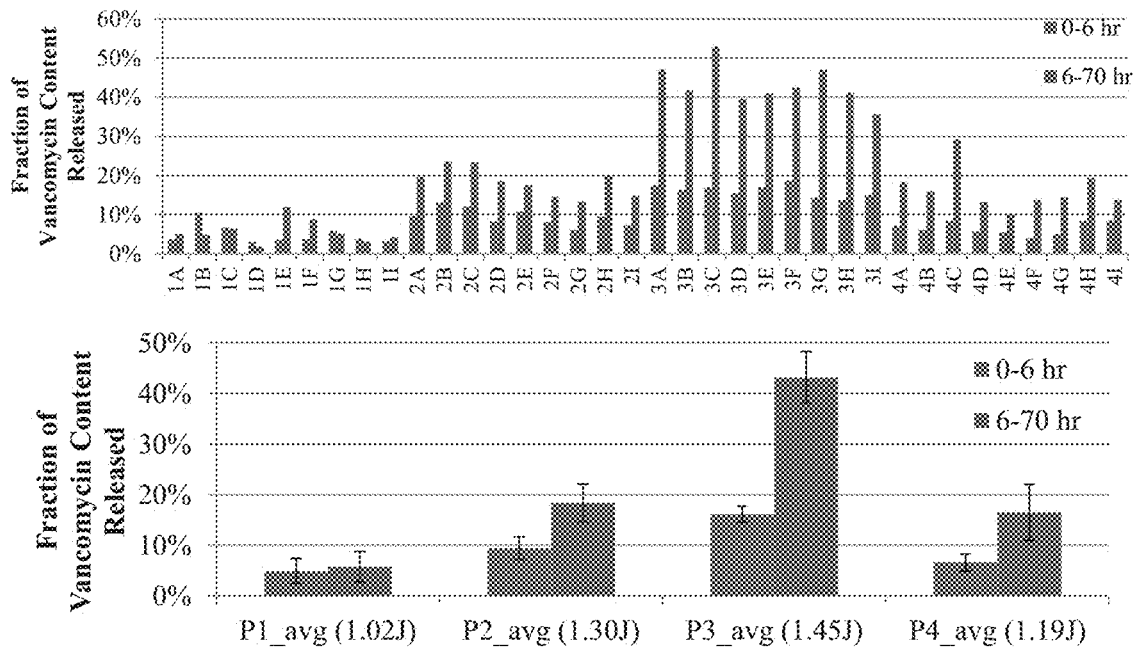
FIG. 16B is a bar chart presenting (Top) fraction of VANC released from PNJ-DBLA gels containing 4 different polymers and 9 drug ratios. (Bottom) Average release of VANC during the 0-6 hr interval and 6-70 hr interval for each polymer, averaging the release data with all drug ratios. The content of JAAm in each polymer is listed next to each polymer in the bottom axis label. Within each sample or group, the release during 0-6 hr is shown on the left and the release from 6-70 hr is shown on the right.

Release data for all samples are shown in FIG. 16B. Within the range of drug ratios tested, the amount of drug release was not affected. Across all polymers and TOB concentrations, gels with 2.35% VANC released 1.4% more of their payload (standard deviation 5.7%) between 6-70 hr compared to gels with 0.78% VANC. Across all polymers and VANC concentrations, gels with 3.14% TOB released on average 4.7% less of their payload (standard deviation 6.3%) between 6-70 hr compared to gels with 2.35% TOB. JAAm content in the polymer was determined to affect release, with increasing JAAm content resulting in increased release. Pooled data for all 9 drug combinations for each polymer is shown in FIG. 16B (bottom). Release increased with JAAm content in the polymer.

Figure 16C:
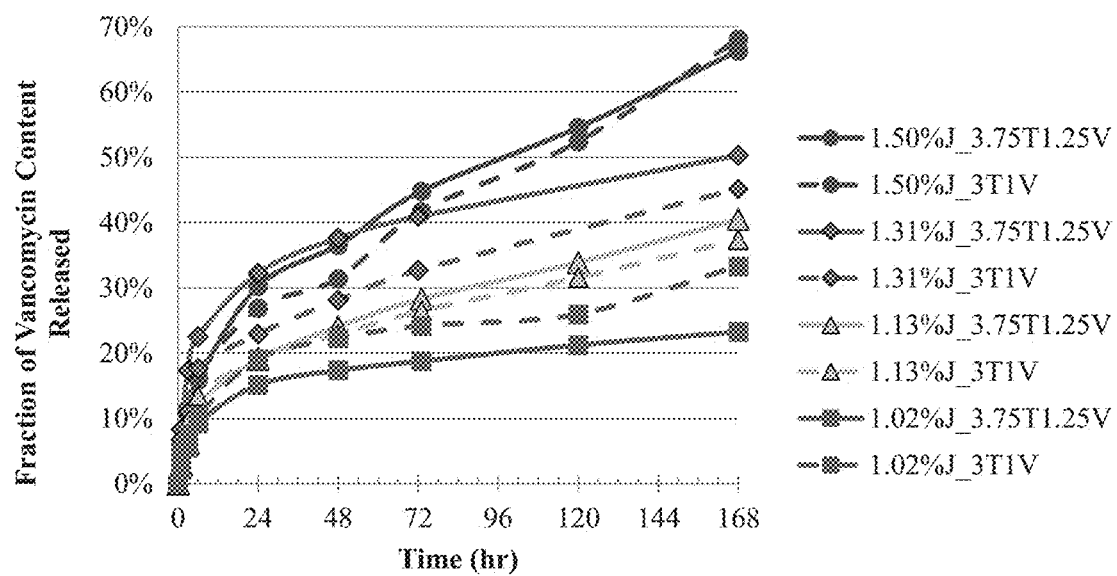
FIG. 16C is a graph of VANC release from PNJ-DBLA gels containing 4 different JAAm contents (JAAm mol % is shown in the legend) and two different drug loadings, either 3.75% TOB+1.25% VANC (solid lines), or 3% TOB+1% VANC (dashed lines). Data shown are average of 3 samples. Standard deviation for all samples was less than 8.5% except for 1.50% J_3.75T1.25V at 72-168 hr, which had standard deviations of 10-13.1%.

Study 3:

PNJ-DBLA [poly(NIPAAm-co-JAAm-co-DBLA] polymers with 4 JAAm contents (1.02-1.50 mol %) were evaluated with drug ratios of 3.75% TOB+1.25% VANC (abbreviated as 3.75T1.25V) or 3% TOB+1% VANC (3TV). All polymer solutions were prepared at 38 wt %. The final polymer concentration in the mixed gels was 31.1 wt % for the 3T1V group and 29.4 wt % for the 3.75T1.25V group. Mw of all batches was 35-45 kDa and DBLA content was 6.42-7.40 mol %. Results are shown in FIG. 16C. Consistent with prior art, higher content of the water-soluble polymer-containing repeat unit JAAm was associated with increased release. There was no clear effect of drug loading on release kinetics. The use of multiple replicates in this study with low variability in the release data indicate uniform content and properties in different fractions of a hydrogel mixed according to the present invention.

Figure 16D:
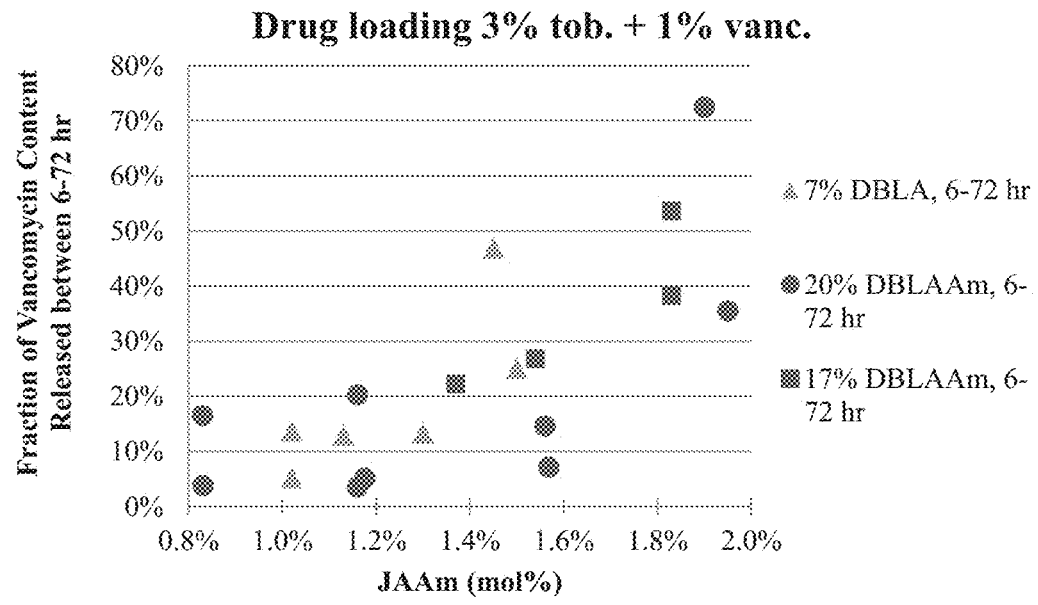
FIG. 16D is a graph of VANC released during 6-72 hr in vitro from gels containing 3% TOB, 1% VANC. Data shown were collected across multiple studies. Most points represent single experimental samples.
Figure 16E:
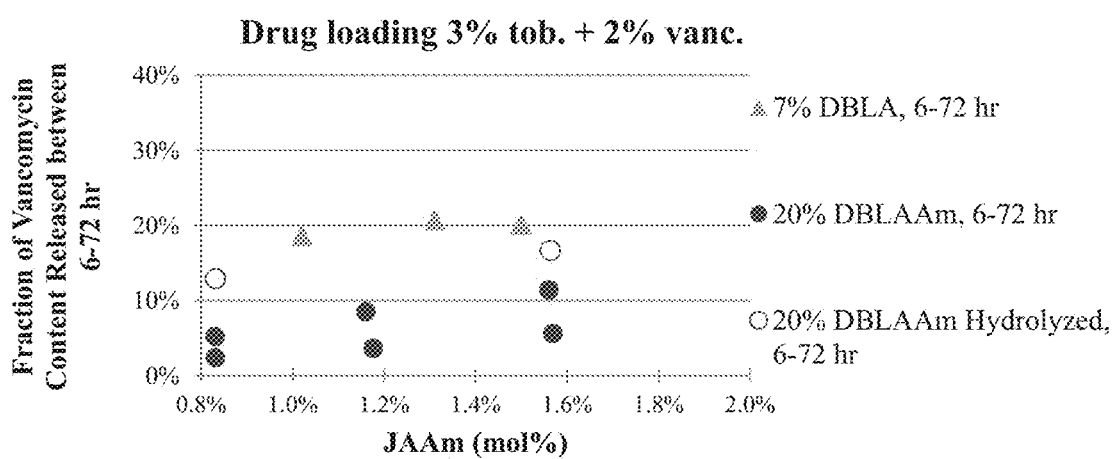
FIG. 16E is a graph of VANC released during 6-72 hr in vitro from gels containing 3% TOB+2% VANC. Data shown were collected across multiple studies and represent averages of 3 replicates.

Study 4:

The figures below report in vitro release of vancomycin during the 6-72 hr window. In all groups tested, the release in the first 6 hours after gelation was low (≤20%) The release during 6-72 hr is reported because the drugs are expected to release in vivo over this time (see Example 20) and the in vitro release profiles are generally linear during this period. In FIGS. 16D-16E, release during the 6-72 hr window (as a fraction of the drug payload) is reported for batches with a range of JAAm content. Various polymer batches containing about 7% DBLA, 20% DBLAAm, or 17% DBLAAm as the degradable repeat unit in the temperature-responsive degradable polymer were used. Release is comparable across these gels. Within the range of 1.0-1.4 mol % JAAm, release rates were comparable regardless of the degradable unit used. Above this content, release rates increased with JAAm content.

Studies using gels containing 3% TOB+2% VANC (FIG. 16E) indicates slower release from gels containing DBLAAm. After partial hydrolysis of DBLAAm units in pH 4.0 buffer for 4 days at 95° C., comparable release to PNJ-DBLA gel was obtained. The data show that release of active agents is tunable in these gels by adjusting the amount of incorporation of water-soluble polymer-bearing macromers in the temperature-responsive degradable polymer. Multiple lactone-bearing degradable units are compatible with sustained release of active agents from the hydrogel.

Figure 16F:
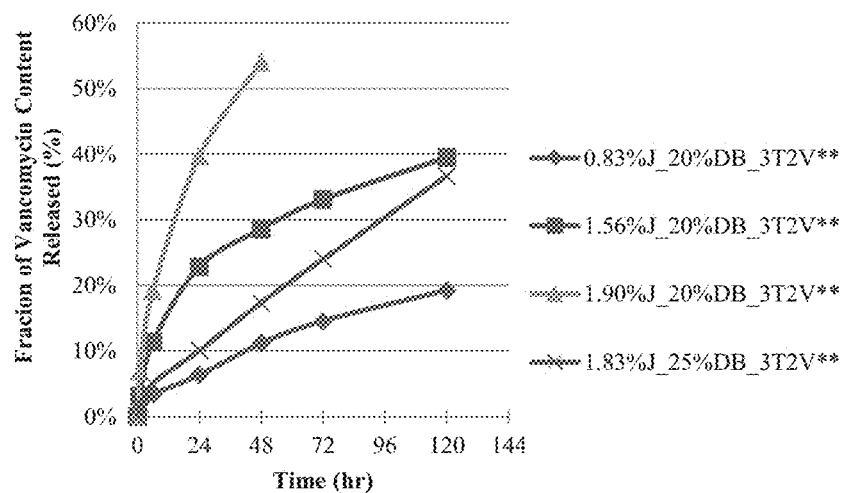
FIG. 16F is a graph of vancomycin release over time from hydrogels prepared by end-to-end syringe mixing from 4 different polymers of poly(NIPAAm-co-JAAm-co-DBLAAm).

Study 5:

Four polymers of poly(NIPAAm-co-JAAm-co-DBLAAm) were used, having content listed in the figure legend of FIG. 16F, where J denotes JAAm and DB denotes DBLAAm. All of the polymers were hydrolyzed to approach equilibrium composition by dissolving at 10 wt % in pH 4.0 buffer and storing for 4 days at 95° C., and then polymers were dialyzed and lyophilized prior to dissolution in the polymer solution. All hydrogels were mixed by the end-to-end syringe mixing method described previously using 38 wt % polymer solution in the polymer solution and 22 wt % total active agent concentration in the precursor therapeutic composition, with the mixed hydrogel containing 3% tobramycin and 2% vancomycin (3T2V).

Release data are shown in FIG. 16F. Release increased with JAAm content across the 3 polymers tested with the same DBLAAm content of 20 mol %. Slower release was measured for the gel with 1.83% JAAm and 25% DBLAAm compared to 1.90% JAAm and 20% DBLAAm, suggesting that increasing DBLAAm content resulted in decreased sustained release.

Study 6.

Figure 16G:
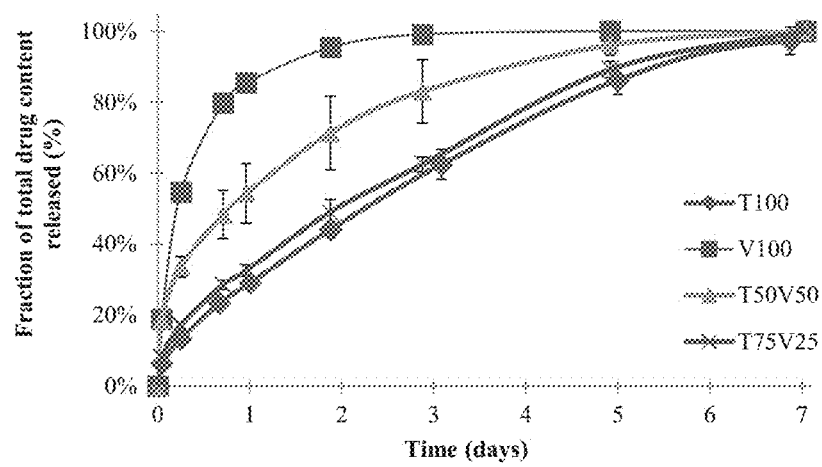
FIG. 16G is a graph of tobramycin and vancomycin release over time from hydrogels prepared by end-to-end syringe mixing using poly(NIPAAm-co-JAAm-co-DBLA) and four different drug ratios in the precursor therapeutic composition. Error bars denote the standard deviation among 3 samples per group.

PNJ-DBLA [poly(NIPAAm-co-JAAm-co-DBLA] containing 6.83 mol % DBLA and 1.47% JAAm and having weight-average molecular weight of 69,580 g/mol was dissolved in 0.2 M sodium acetate buffer (pH 4.0) at 27.5 wt % concentration and loaded into 5 mL syringes as the polymer solution. Into a separate syringe was either tobramycin (T100), vancomycin (V100), or tobramycin/vancomycin combination at 50/50 ratio (T50V50) or 75/25 ratio (T75/25) by active mass. The total active agent concentration in the precursor therapeutic composition was about 19 wt %. The total drug concentration in the mixed hydrogels was 3.14 wt % and the polymer concentration was 23 wt %. For each hydrogel, approximately 3 grams was prepared using coupled 5 mL syringes. One gram fractions were placed in 20 mL vials with 20 mL of PBS used. Otherwise the release study method described previously was followed. The results are shown in FIG. 16G. All hydrogels released their entire payload of drug throughout the 7 day study. Release from gels with vancomycin only (V100) was complete within 3 days. Gels with tobramycin only provided release over about 7 days. In the gels loaded with both antimicrobials, the antimicrobials eluted over approximately the same duration (5 days for 50T50V or 7 days for 75T25V). The release of each individual agent occurred in approximately the same ratio as present in the initial gel and over the same amount of time; in other words, vancomycin eluted more slowly from the hydrogels containing T50V50 than from hydrogels containing V100. The low standard deviations within each group demonstrate that the hydrogels were adequately mixed.

Study 7.

A study was done to evaluate the effect of buffer strength in the polymer solution, polymer content, and a "pre-treatment" hydrolysis method on the release profile of vancomycin from hydrogels containing both tobramycin and vancomycin. Six PNJ-DBLA polymers with compositions as shown in Table 29 and all having weight-average molecular weight of approximately 70,000 g/mol were prepared at 32 wt % in sodium-acetate-acetic acid buffer (pH 4.0) with either 20 mM or 200 mM ionic strength. Polymer 3 was "pre-treated" by hydrolyzing Polymer 2 toward an equilibrium composition of acid groups. DBLA content was measured to decrease during pre-treatment from 8.20% to 7.07%, suggesting partial hydrolysis of the ester linkage between the polymer backbone and lactone ring. Pre-treatment involved preparing 10 wt % solutions of Polymer 2 in 0.2 M acetic acid buffer (pH 3.0), heating to 80° C. for 7 days, and then obtaining the polymer by dialysis and lyophilization. Three fractions of each mixed hydrogel batch were dispensed and treated as replicates within the same group. All of the gels contained 1.57% tobramycin and 1.57% vancomycin in the mixed hydrogels.

TABLE 29

Composition of polymers used in Example 16 Study 7

| Polymer | Composition (mol %) | | Pre-Treated? |
| --- | --- | --- | --- |
| | DBLA | JAAm | |
| Polymer 1 | 6.69% | 1.52% | No |
| Polymer 2 | 8.20% | 1.27% | No |
| Polymer 3 | 7.07% | 1.26% | Yes |
| Polymer 4 | 7.93% | 1.23% | No |
| Polymer 5 | 6.38% | 1.21% | No |
| Polymer 6 | 6.51% | 0.76% | No |

Figure 16H:
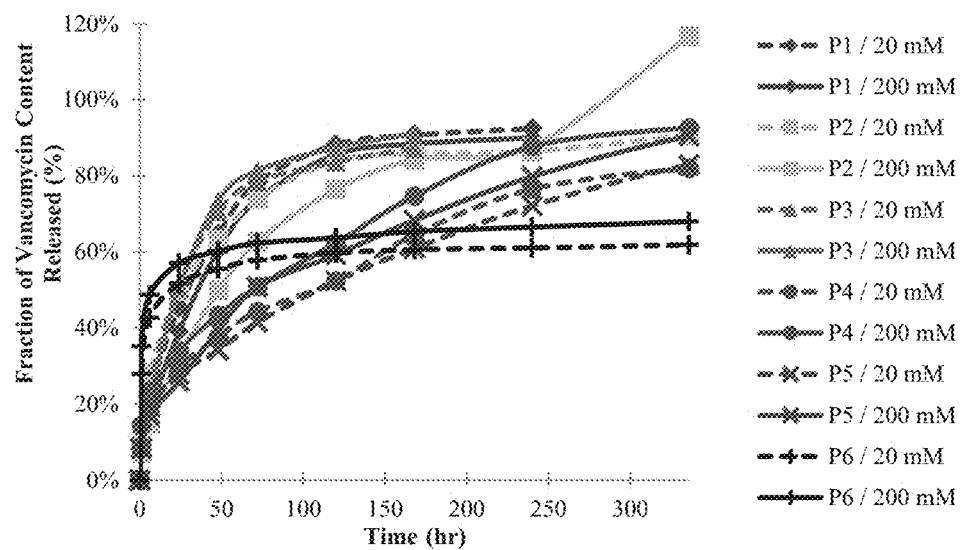
FIG. 16H is a graph of vancomycin release over time from hydrogels prepared by end-to-end syringe mixing using poly(NIPAAm-co-JAAm-co-DBLA) of six compositions. All data points are the average of 3 replicates.

Data are shown in FIG. 16H. Buffer strength did not have a notable effect on drug release rates in the hydrogels tested. The pre-treated polymer, Polymer 3, released vancomycin in a similar fashion to Polymer 2, which was the same material before pre-treatment. Polymer 6, which contained the least JAAm, provided the greatest "burst release" during the first 1-6 hours, with the slowest release thereafter (less than 4% per day after the first day), whereas Polymer 1 provided among the lowest burst release, with faster release thereafter (about 20% per day between 6-72 hr).

Example 17—In Vitro Release of Bupivacaine and Observations of Hydrogel Preparation with Bupivacaine Sustained release of bupivacaine was evaluated from temperature-responsive hydrogels using the methods as described in Example 16, except where exceptions are noted for each study below.

Study 1.

This study sought to evaluate the preparation of hydrogels with bupivacaine as a model drug with low water solubility. In all groups, the polymer solution contained 35 wt % of a polymer containing 90.40 mol % NIPAAm, 8.34 mol % DBLA, and 1.25 mol % JAAm and having a weight-average molecular weight of about 45,000 g/mol. The polymer was dissolved in PBS (pH 7.4). Bupivacaine is prepared clinically by reconstitution of the hydrochloride salt with water at a concentration of about 0.5%. However, in a sustained release formulation, a higher concentration would be desirable so that an effective concentration may be provided near the application site for a longer time, for example 3 to 5 days rather than 8 hours for unencapsulated drug. The gel texture after loading with bupivacaine and the release of bupivacaine over time were evaluated for the following groups: 1) Bupivacaine paste (20 wt % bupivacaine; 80% polypropylene glycol 725) syringe-mixed with polymer solution in a 1:4 ratio; 2) Bupivacaine hydrochloride solid powder was added to the polymer solution to result in 4 wt % bupivacaine concentration and vortex-mixed to distribute the drug; 3) Bupivacaine base solid powder was added to the polymer solution to result in 4 wt % bupivacaine concentration and vortex-mixed to distribute the drug; 4) Bupivacaine hydrochloride was suspended in water at 5 wt % and syringe-mixed with polymer solution in a 1:4 ratio (resulting in 1 wt % bupivacaine in the mixed gel); 5) Bupivacaine hydrochloride was suspended in water at 20 wt % and syringe-mixed with polymer solution in a 1:4 ratio (resulting in 4 wt % bupivacaine in the mixed gel). Bupivacaine was not uniformly distributed in the aqueous suspensions used in group 4 and 5 due to settling of the drug powder which occurred rapidly even after vigorous mixing.

Figure 17A:
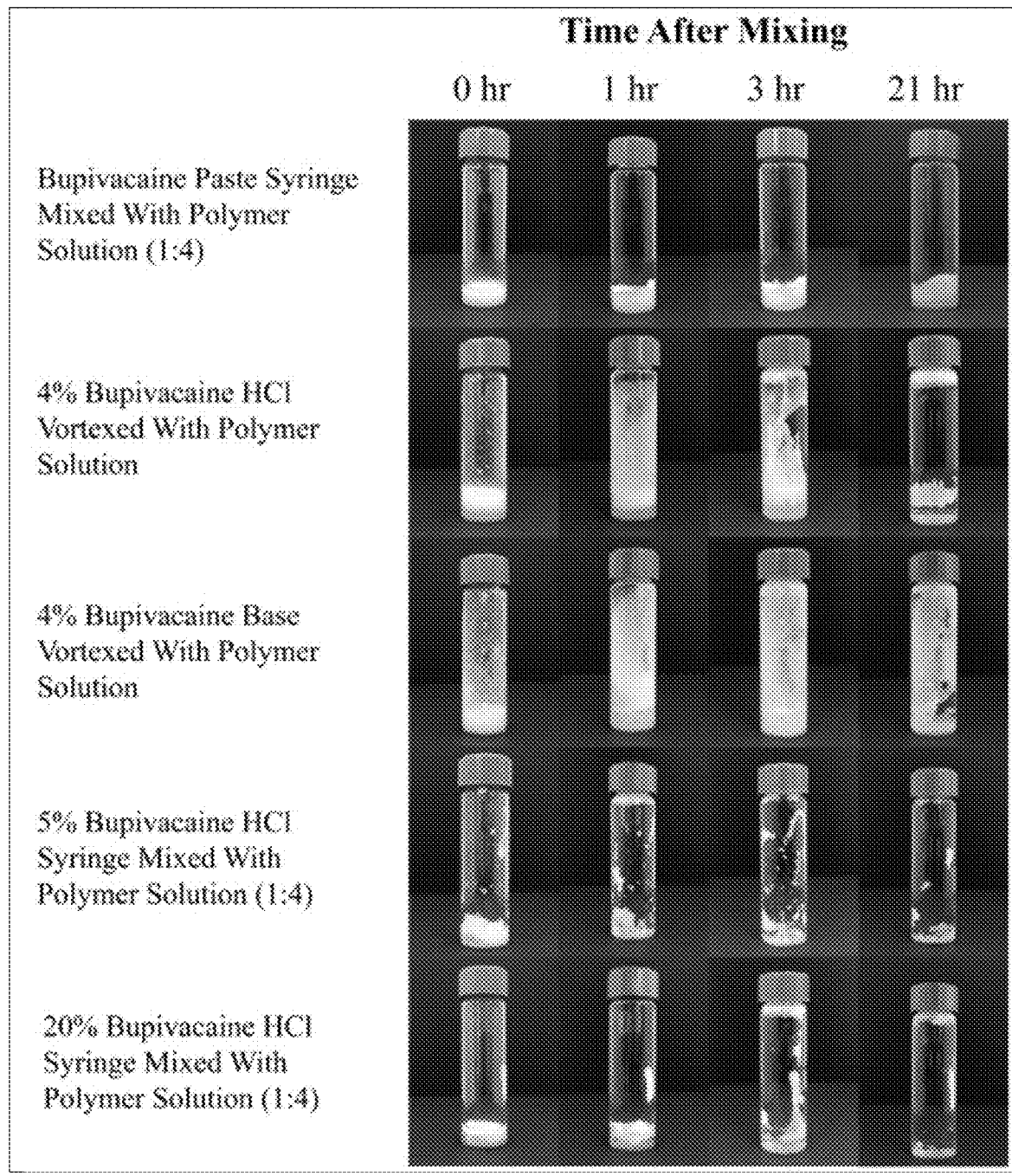
FIG. 17A presents images of temperature-responsive degradable hydrogels over time at 37° C. after loading with bupivacaine by either end-to-end syringe mixing polymer solution with bupivacaine/PP0725 paste (top row), vortex-mixing with bupivacaine hydrochloride (second row), vortex-mixing with bupivacaine base (third row), syringe-mixing with 5% bupivacaine HCl solution (fourth row), or syringe-mixing with 20% bupivacaine HCl solution (bottom row). PBS was added to the vials after the initial picture at 0 hr.

The appearance of the hydrogels over time after mixing by each of five methods is shown in FIG. 17A. The syringe-mixed gels using bupivacaine/polypropylene glycol 725 paste formed a solid cohesive and stable material which remained at the bottom of the vial throughout the study. Hydrogels which were mixed with drug powder failed to fully entrap the white drug powder, and the bupivacaine powder was suspended in the vial after 1 hour. Additionally, the hydrogels de-adhered from the bottom of the vial by 21 hours after buffer was added. The hydrogel prepared by mixing with 5% bupivacaine aqueous solution disintegrated within the first hour, with many pieces of gel evident on the vial walls and at the top of the solution. The hydrogel prepared by mixing with 20% bupivacaine aqueous suspension de-adhered from the glass vial within about 3 hours. The hydrogel appearance indicates that the presence of large insoluble drug particles within the hydrogel result in an unstable gel, whereas insoluble drug contained within a liquid or semi-solid organic excipient layer does not destabilize the gel. In this experiment, the liquid or semi-solid excipient was polypropylene glycol 725.

Figure 17B:
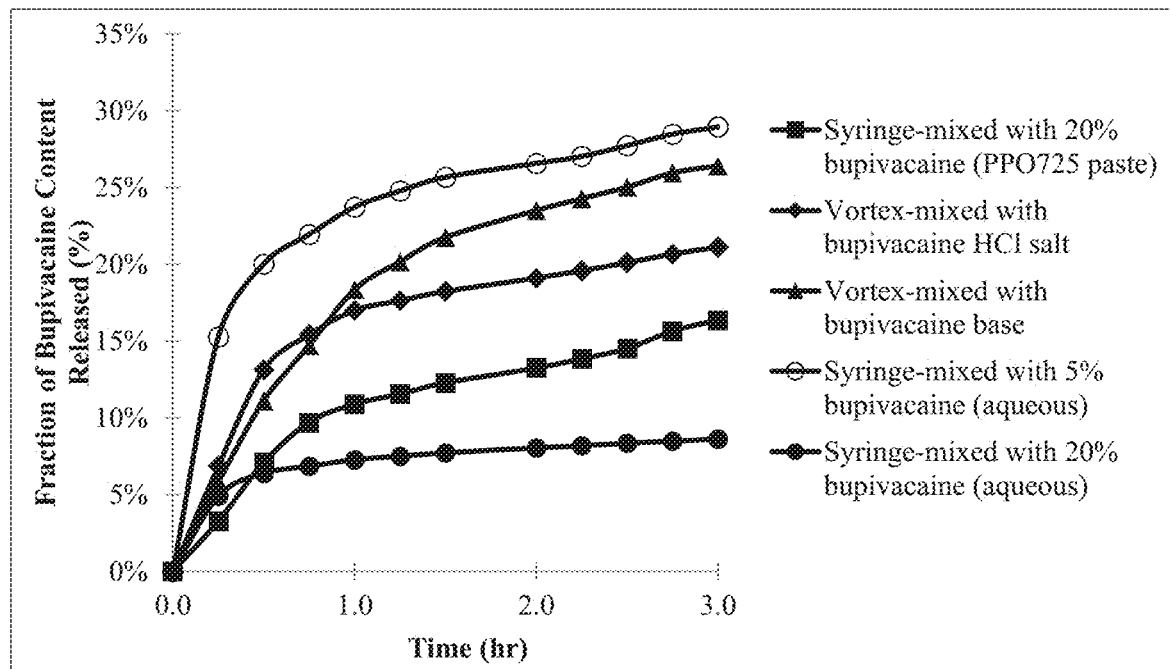
FIG. 17B is a graph of bupivacaine release over time from hydrogels prepared by five hydrogel preparation methods. Hydrogels were prepared from the same polymer.

Data showing drug release over the first 3 hours from the same gels are shown in FIG. 17B. Despite poor gel stability, less than 30% cumulative release was observed from all of the gels within the first 3 hours, which was attributed to the low solubility of bupivacaine within the hydrogel, limiting the transport of the vast majority of the bupivacaine content. However, the gel images support the superiority of using a mixing method utilizing a closed volume without entrapped air and uniformly suspended bupivacaine in a biocompatible organic excipient, for leading to a hydrogel with a stable and cohesive texture. Alternatively, mixing of polymer solution with drug powder or a non-uniformly distributed drug suspension led to hydrogels which did not form stable, cohesive gels.

Study 2.

Bupivacaine release was evaluated from six temperature-responsive degradable polymer hydrogels. The six polymers used had the compositions listed in Table 30 and weight-average molecular weight of about 70,000 g/mol. Polymers 3-6 have similar DBLA content with varying JAAm content and thus water content in the hydrogel. Polymers 1 and 2 were also evaluated as polymers with lower LCSTs due to higher content of DBLA, a hydrophobic comonomer. Hydrogels were prepared in a single vial by combining 27 wt % polymer, 5 wt % bupivacaine base, and 51 wt % phosphate buffer (75 mM, titrated to pH 4.0), storing overnight, and then adding 17 wt % 1 N HCl to improve dissolution of the bupivacaine. The white opaque suspension was vortex-mixed on moderate speed and then 300-350 mg samples of the mixed hydrogel were dispensed into the bottom of 20 mL scintillation vials using a micropipette. The vials were tilted to the side to allow the gels to form a reproducible shape in the corner of the vial. The mass of gel added to each vial was recorded. The gels were formed and the release study proceeded as described previously, with exchange of the release medium (PBS, pH 7.4) at selected time points throughout the study. Three samples were evaluated from each polymer.

TABLE 30

Composition of polymers used in Example 17 Study 2

| Polymer | Composition (mol %) | |
|---|---|---|
| | DBLA | JAAm |
| Polymer 1 | 8.71% | 1.50% |
| Polymer 2 | 10.78% | 1.20% |
| Polymer 3 | 6.78% | — |
| Polymer 4 | 6.51% | 0.76% |
| Polymer 5 | 6.87% | 1.22% |
| Polymer 6 | 6.35% | 1.93% |

Figure 17C:
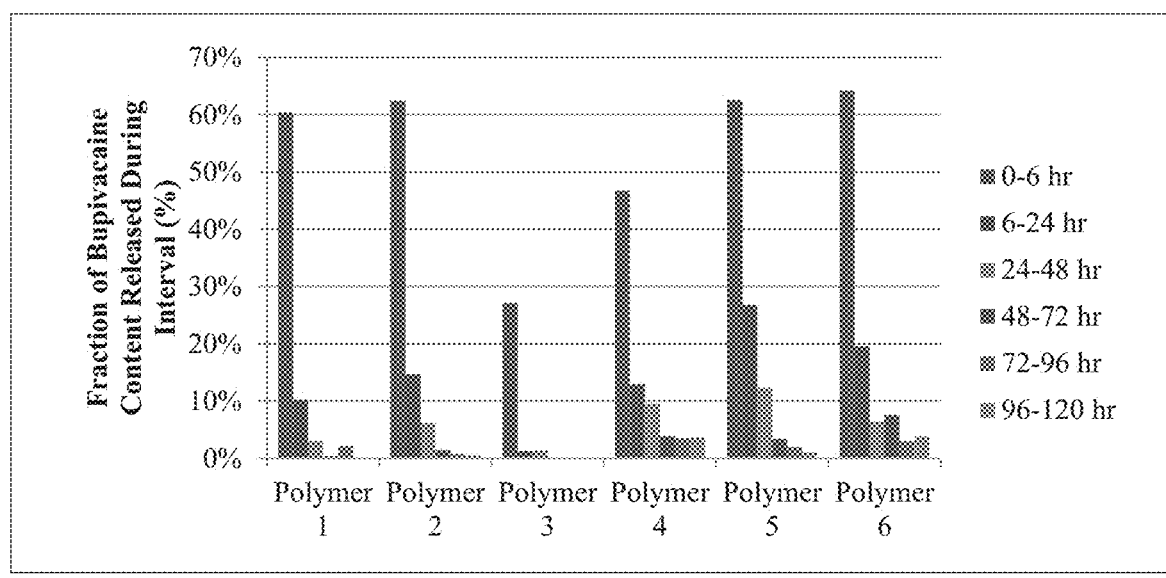
FIG. 17C is a bar chart presenting bupivacaine release for temperature-responsive degradable hydrogels prepared by vortex-mixing of the hydrogel components.

Results are shown in FIG. 17C. The burst release observed in this study was high, which is generally undesirable for sustained release applications. All of the hydrogels released bupivacaine primarily within the first 6 hours with less release thereafter. Polymer 3, which contained no JAAm and thus formed a hydrophobic gel, released about 27% of its payload within the first 6 hours and then retained nearly all of the remaining content for longer than 5 days. Thus, while a portion of the bupivacaine was lost during an initial "burst" release period during which the hydrogel phase-separates from a fraction of its initial solvent (syneresis), the remaining drug moved (diffused) through the gel very slowly. JAAm content in the polymer leads to increased water content in the resulting hydrogel. With increasing JAAm content as seen in Polymers 4, 5, and 6, the initial burst release increased, and some sustained release was also observed for up to 2 days after the start of the study. This indicates that transport of bupivacaine is increased within hydrogels containing a pendent water-soluble polymer, despite its low solubility in neutral pH conditions. This finding is consistent with the findings for highly water-soluble drugs (Example 16 Study 7).

Study 3.

Bupivacaine release was evaluated from hydrogels which were prepared using the same temperature-responsive degradable polymer combined by end-to-end syringe mixing with 4 different bupivacaine/PP0725 suspensions. The polymer contained 92.53 mol % NIPAAm, 5.95 mol % DBLA, and 1.53 mol % JAAm and had a weight-average molecular weight of about 70,000 g/mol. The polymer was dissolved at 25 wt % in PBS titrated to pH 4. PP0725 and bupivacaine suspensions were prepared separately by combining with acetone and then evaporating to yield a white paste. Gels (about 400 mg each) were mixed individually in coupled 1 cc syringes. The mixed hydrogels contained either 30 or 40 wt % of the PP0725/bupivacaine mixture. The final bupivacaine concentration in the mixed hydrogel was either 3% or 6% (for 40 wt % paste) or 4% or 7% (for 30 wt % paste). Four replicates were mixed in each group. The mixed hydrogels were dispensed into the bottom of 20 mL scintillation vials after syringe mixing. The vials were tilted to the side to allow the gels to form a reproducible shape in the corner of the vial and release was evaluated over time by the methods above with 20 mL PBS as the release medium.

Figure 17D:
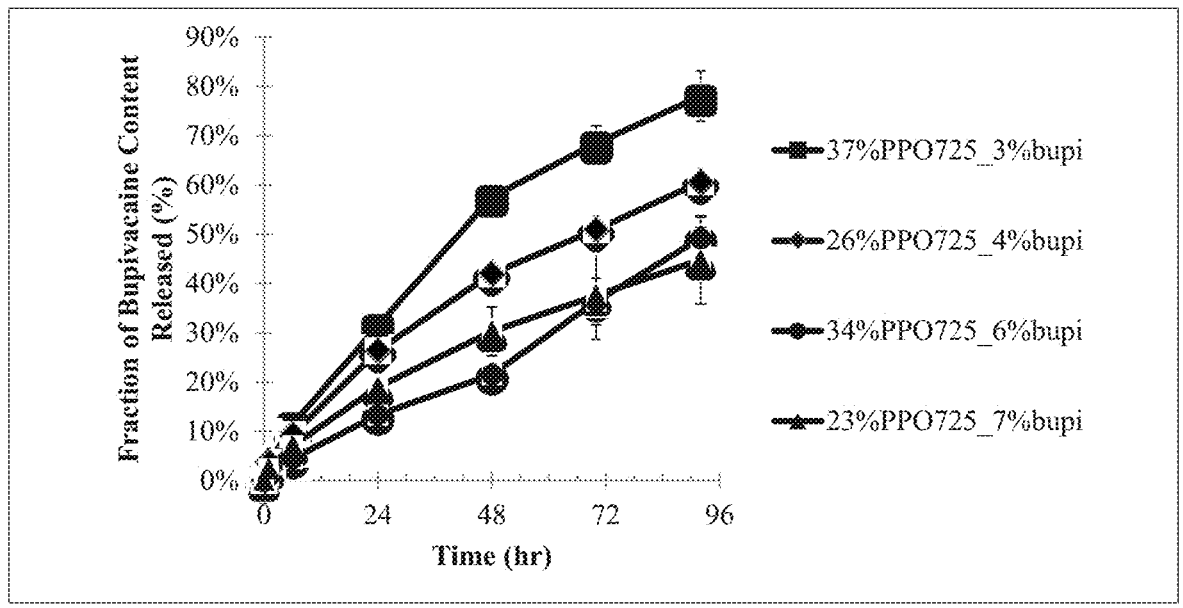
FIG. 17D is a graph of bupivacaine release for temperature-responsive degradable hydrogels prepared by end-to-end syringe mixing with PP0725/bupivacaine paste with various amounts of PP0725 and bupivacaine in the mixed hydrogel. Data points and error bars represent mean+s.d. of 4 samples per group.

Results are shown in FIG. 17D. Sustained release from all gels was observed with low burst release. Content of up to 40 wt % PP0725/bupivacaine (resulting in an overall polymer concentration of 15 wt %) formed stable gels. Minimal initial burst release was observed from all gels (no sample showed greater than 12% release in the first 6 hours). A trend was observed indicating faster release for gels containing less bupivacaine. The hydrogels in this study showed desirable in vitro release characteristics for application in the treatment or prevention of postoperative pain. Specifically, the rate of bupivacaine release over the first 4 days was controlled and relatively steady over time as compared to the hydrogels in Study 2, which showed minimal release after the first 24 hours.

Study 4.

An aqueous acidic solvent can be used to stabilize temperature-responsive degradable polymers. Bupivacaine has increased solubility in water in acidic pH. Thus, it was hypothesized that increasing the concentration of the aqueous acidic solvent may affect the release of bupivacaine by improving its solubility within the mixed hydrogel. A single polymer was used containing 92.53 mol % NIPAAm, 5.95 mol % DBLA, and 1.53 mol % JAAm and had a weight-average molecular weight of about 70,000 g/mol. The entire study included 12 hydrogels (all combinations of 4 buffers and 3 bupivacaine concentrations). The polymer was dissolved at 25 wt % in sodium acetate-acetic acid buffer having a total ionic strength of 200, 20, or 2 mM. In a comparator group, the polymer was dissolved in PBS (pH 7.4). Hydrogels were prepared from each polymer solution to result in 1.5, 3, or 6 wt % bupivacaine in the mixed hydrogel. In each case the bupivacaine was incorporated into the hydrogel by end-to-end syringe mixing of the polymer solution with a uniform paste containing 16.7 wt % bupivacaine and 83.3 wt % PP0725. Each hydrogel was prepared from about 600 mg of material in coupled 1 mL syringes, and 400-450 mg of each hydrogel was dispensed into the corner of a 20 mL vial for evaluation of drug release with 20 mL of PBS (pH 7.4) as the release medium.

Figure 17E:
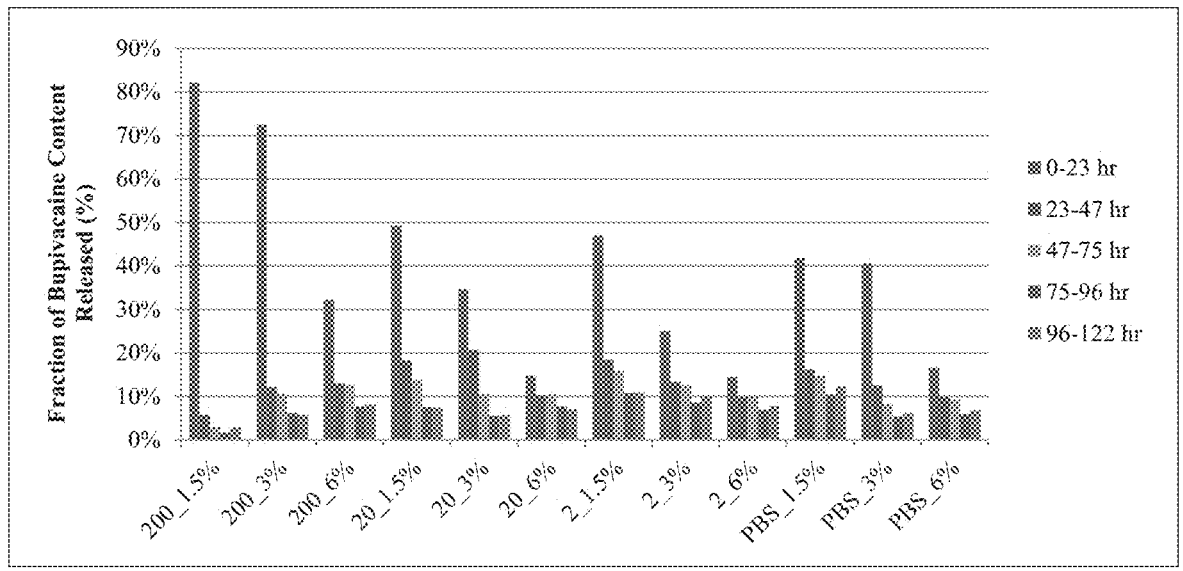
FIG. 17E is a bar chart presenting bupivacaine release for temperature-responsive degradable hydrogels prepared by end-to-end syringe mixing with PP0725/bupivacaine paste. The polymer solution was prepared in either 200 mM, 20 mM, or 2 mM sodium acetate-acetic acid buffer (pH 4.0) or PBS (pH 7.4). The treatment group denotes the concentration of the buffer used to dissolve the polymer solution (in mM) and then the concentration of bupivacaine in the mixed hydrogel (in wt %). Within each group (clustered set of columns), the columns are ordered sequentially in time from left to right. The leftmost column indicates release during 0-23 hr, the next from 23-47 hr, and so on as indicated by the figure legend.

Results are shown in FIG. 17E. All of the gels provided sustained release over multiple days. Stronger acidic buffer, especially the 200 mM buffer, led to increased release during the first day of the study. However, after the first day, the effect of buffer strength on drug release was marginal, less than 4% per day compared to hydrogels prepared with lower strength buffers. This was especially evident when comparing the gels containing 6% bupivacaine, as shown in Table 31.

TABLE 31

Fraction of bupivacaine content released for 4 hydrogels containing 6 wt % bupivacaine with different aqueous acidic solvents in the initial polymer solution

|  | 200 mM, pH 4.0 | 20 mM, pH 4.0 | 2 mM, pH 4.0 | PBS, pH 7.4 |
| --- | --- | --- | --- | --- |
| 0-23 hr | 32.18% | 14.76% | 14.36% | 16.62% |
| 23-47 hr | 13.07% | 10.21% | 9.82% | 9.81% |
| 47-75 hr | 12.62% | 10.41% | 9.89% | 9.19% |
| 75-96 hr | 7.67% | 7.70% | 6.89% | 5.97% |
| 96-122 hr | 8.13% | 7.07% | 7.76% | 6.71% |

Example 18—In Vitro Release of Antimicrobials After Storage or After Hydrolysis Toward an Equilibrium Composition Example compositions described herein can include a counter-intuitive property; namely, they can allow for a temperature-responsive degradable polymer that degrades by hydrolysis, yet that can maintain their properties after they are stored in aqueous solution. The sustained release of water-soluble antimicrobials from temperature-responsive degradable polymers was evaluated after long-term storage in acidic solution (Studies 1 and 2) and after a pre-treatment hydrolysis step in manufacturing in which pendent lactones are partially hydrolyzed (Study 3).

The goal of these studies was to evaluate whether hydrogels prepared from long-term stored polymer solutions or partially hydrolyzed polymer are capable of providing sustained drug release.

Study 1.

In a preliminary study, gentamicin release was evaluated from hydrogels when prepared immediately or using a polymer stored for 9 months in acidic conditions. A polymer containing 91.81 mol % NIPAAm, 6.35 mol % DBLA, and 1.84 mol % JAAm with a weight-average molecular weight of about 70,000 g/mol was dissolved at 35 wt % in 75 mM phosphate buffer which was titrated to pH 4.0 using 1N HCl. The polymer solution was stored at 4° C. until use. Either immediately or after 9 months (274 days), polymer solution was dispensed in approximately 1 gram amounts into three separate 20 mL vials, and then aqueous gentamicin sulfate solution was added to each vial. The contents were stirred with a spatula to incorporate the gentamicin into the polymer solution to result in a polymer concentration of 30 wt % and a gentamicin concentration of 3.14 wt % in the mixed hydrogel. The total mass of gel remaining in the vial was weighed, as some material was lost on the spatula. Then the material was allowed to gel by placing the vials in a 37° C. water bath. After at least 1 minute, 20 mL of pre-warmed 37° C. phosphate buffer (pH 7.4) was added to each vial. The gels or the overlying solution were not agitated except before each aliquot collection (3 gentle inversions and pipette mixing of the media). Aliquots of the buffer were collected at about 1, 6, 24, 48, 72, 120, and 168 hr after the gels were dispensed, and the buffer was replaced at each time point. Gentamicin concentration was measured by colorometric ninhydrin assay and release was evaluated as a fraction of the initial gentamicin content of the hydrogel.

Figure 18A:
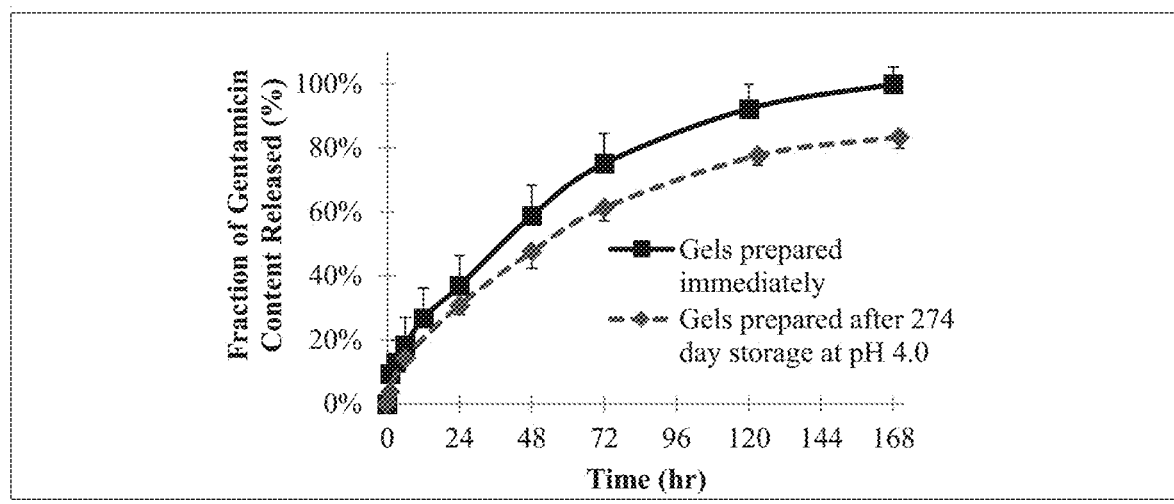
FIG. 18A is a graph of gentamicin release in vitro from hydrogels prepared from the same temperature-responsive degradable polymer hydrogel either immediately or after 9 months of storage in solution.

Gentamicin release data are shown in FIG. 18A. Release was relatively unaffected by 9-month storage at pH 4.0, indicating that the polymer did not undergo substantial irreversible degradation over 9 months in storage, which would have resulted in much faster release, including possibly immediate release if the DBLA groups had hydrolyzed to a sufficient extent to cause the LCST to increase to above 37° C. Additional studies utilized a new release medium, phosphate buffered saline, which contains more sodium chloride and less phosphate ions.

Phosphate ions "salt out" temperature-responsive polymers, in this case causing a lower LCST by about 7-10° C. than in serum or phosphate buffered saline (PBS). The spatula mixing method to prepare the hydrogels was also abandoned eventually due to inconvenience. Nevertheless, the results of this study clearly demonstrate consistent sustained release properties for temperature-responsive degradable hydrogels stored for 9 months in aqueous solution. The degradation time of the polymer used (i.e., the time required for the LCST to increase to 37° C.) is only about 28 days in the same buffer at pH 7.4.

Study 2.

A temperature-responsive degradable polymer containing 92.00 mol % NIPAAm, 6.49% DBLA, and 1.51% JAAm and having weight-average molecular weight of about 70,000 g/mol was dissolved at a concentration of 27.5 wt % in 0.2 M sodium acetate-acetic acid buffer at four pH values: 3.7, 4.0, 4.5, and 5.0. These values represent a large portion of the pH range possible using this buffering system (3.7-5.6). Two days were allowed to allow the solutions to dissolve and load them into syringes. One 5 mL syringe containing 3 grams of polymer solution was stored at each pH for either 0, 8, 16, or 26 weeks at 4° C. After the designated storage time, hydrogels were prepared by mixing the polymer solutions by end-to-end syringe mixing with tobramycin sulfate solution to result in hydrogels containing 23 wt % polymer and 3.14 wt % tobramycin. Syringe mixing was done for 7 seconds at a rate of 160 strokes per minute. After mixing of the dose, the full dose was pushed into one syringe, and the other syringe and coupler were removed. Three one-gram fractions of hydrogel were then dispensed into tared 20 mL scintillation vials and the mass of gel added to each vial was recorded. All of the hydrogels tested were able to be manipulated by syringe and had apparently similar viscosity and gelation temperature. Each vial was transferred to a 37° C. water bath to allow for gelation immediately after the gel was weighed. After at least 1 minute, 20 mL of pre-warmed 37° C. phosphate buffered saline (PBS, pH 7.4) was added to each vial. Aliquots of the release medium were then collected as described previously with full replacement of the buffer at each sampling time point. Tobramycin concentration in the aliquots was measured by a colorometric ninhydrin assay.

Figure 18B:
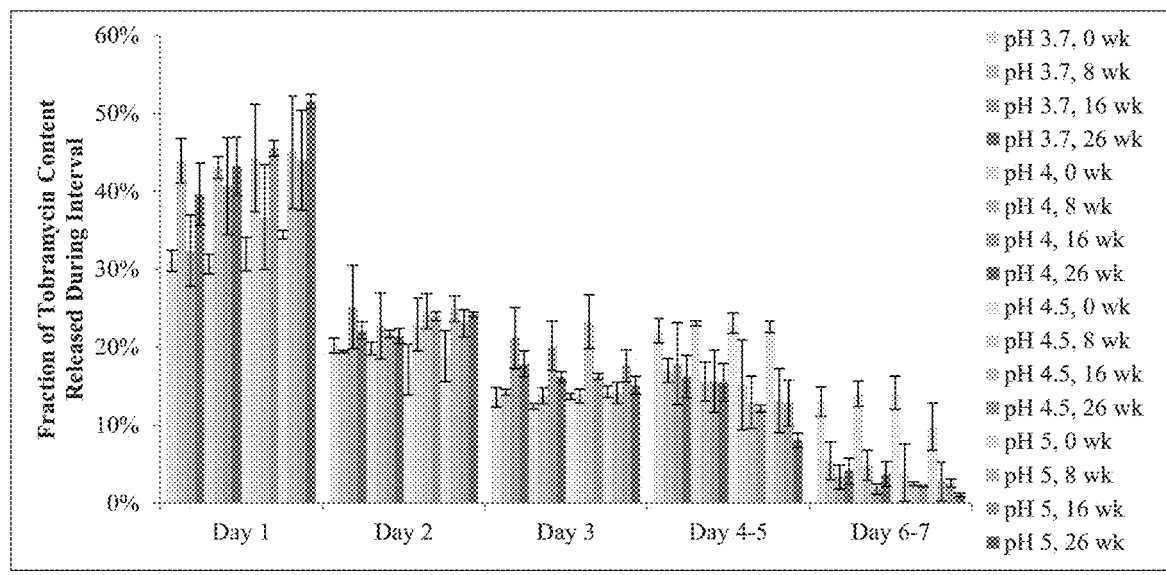
FIG. 18B is a bar chart presenting tobramycin release in vitro during various intervals versus the pH of storage solution and the time for which the polymer solutions were stored at 4° C. Bars and error bars denote the mean +/− standard deviation of 3 samples each. Within each group (clustered set of columns), the columns are ordered sequentially in time from left to right in the same order as from the top to the bottom of the figure legend. The leftmost column for release within each day denotes pH 3.7, 0 wk while the rightmost column denotes pH 5, 26 wk.

Results are shown in FIG. 18B. Sustained release was achieved after storage in all pH values tested, with release persisting for at least 5 days. The data show a trend indicating faster release after storage, which could be attributable to partial irreversible hydrolysis of the linkage ester of DBLA over time in storage. Whereas the samples that were not stored provided sustained release for about 6-7 days as indicated by greater than 10% of the tobramycin content being released during Days 6-7 of the study, the samples that were stored for 8-26 weeks showed increased release on Day 1, similar release on Day 2 and Day 3, slightly less release in the period of Days 4-5, and greatly decreased release during the period of Days 6-7. There was also a slight trend toward faster release at higher pH values within the range of the study, with the greatest release on Day 1 and the least release on Days 4-5 observed for hydrogels prepared from polymer solution stored at pH 5.0. Although the release of tobramycin was affected by storage time, the hydrogels were fully capable of providing sustained release over multiple days in vitro. This is a remarkable result because in physiological conditions (pH 7.4, 37° C.), the polymer used in this study undergoes an increase in LCST such that its LCST increases to 37° C. in 23 days. Thus, the polymer was incorporated in a hydrogel which provided sustained release of tobramycin after being stored in solution for nearly 8 times longer than its degradation time in physiological conditions.

Study 3.

Release of tobramycin and vancomycin was evaluated from hydrogels prepared from each of 4 polymers both before and after a pre-treatment process to cause partial hydrolysis of the polymer lactones. A portion of each polymer was partially hydrolyzed by dissolving at 10 wt % in 0.2 M acetic acid buffer (pH 3.0) and storing at 80° C. for 7 days, followed by dialysis and lyophilization to recover the material. The composition of each polymer before and after pre-treatment is listed in Table 32. Each pre-treated material is denoted by an asterisk. Each pre-treated polymer had lower DBLA content (by 0.24-0.82 mol %) and slightly lower JAAm content (by 0.01-0.07 mol %) compared to the initial polymer. All polymers were prepared with 80:20 dioxane:THF as the polymerization solvent and had weight-average molecular weight of about 70,000 g/mol.

Hydrogels were prepared by the end-to-end syringe mixing method as described in the methods of Study 2 except that each of the mixed hydrogels contained 1.57 wt % tobramycin and 1.57 wt % vancomycin. Drug release over time was measured by the same method as described for Study 2.

TABLE 32

Composition of polymers used in Example 18 Study 3

| | Composition (mol %) | | |
|---|---|---|---|
| Polymer | DBLA | JAAm | Pre-Treated |
| Polymer 1 | 6.38% | 1.21% | No |
| Polymer 1 | 5.93% | 1.18% | Yes |
| Polymer 2 | 6.21% | 1.46% | No |
| Polymer 2 | 5.59% | 1.39% | Yes |
| Polymer 3 | 8.60% | 1.54% | No |
| Polymer 3 | 7.78% | 1.53% | Yes |
| Polymer 4 | 7.93% | 1.23% | No |
| Polymer 4 | 7.69% | 1.21% | Yes |

Figure 18C:
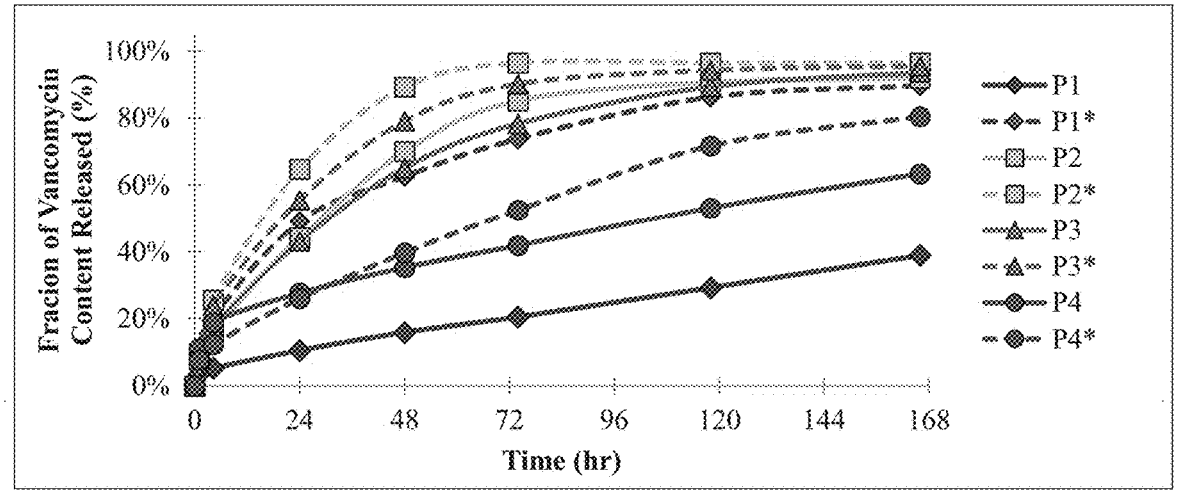
FIG. 18C is a graph of vancomycin release in vitro from hydrogels of 4 polymers of poly(NIPAAm-co-JAAm-co-DBLA) before and after pre-treatment. P1 in the legend denotes "Polymer 1", and asterisks denote that pre-treated polymers were used. Data points are the mean value from 3 samples. Data points from pre-treated batches are connected with dashed lines.

Results for vancomycin release over time from the hydrogels are shown in FIG. 18C. Tobramycin release was similar to vancomycin release for all samples tested (not shown). The majority of the release data points had a standard deviation under 8%, indicating good gel mixing. All of the formulations provided sustained release over multiple days after the pre-treatment process. Faster drug release was observed from gels prepared with pre-treated polymer for all polymers tested. This was attributed to the increase in the number of hydrophilicity of the polymer (hydroxyacid groups and a small number of acrylic acid repeat units formed on the polymer backbone), reducing the hydrophobic interactions that contribute to polymer chain entanglement and gelation.

Study 4.

Sustained release of antimicrobials over time was evaluated from hydrogels prepared with selected poly(NIPAAm-co-JAAm-co-DBLAAm) copolymers from Example 8. The polymers used were "pre-treated" or PT, meaning that the polymer was heated for 4 days at 95° C. in pH 4.0 buffer after initial synthesis to attempt to obtain an equilibrium composition of lactones versus hydroxyacids, or "shelf life" (SL), denoting a PT polymer which was exposed to 95° C. pH 4 accelerated storage conditions for an additional 10 days which was intended to simulate a shelf life of approximately 2 years in refrigerated storage.

Figure 18D:
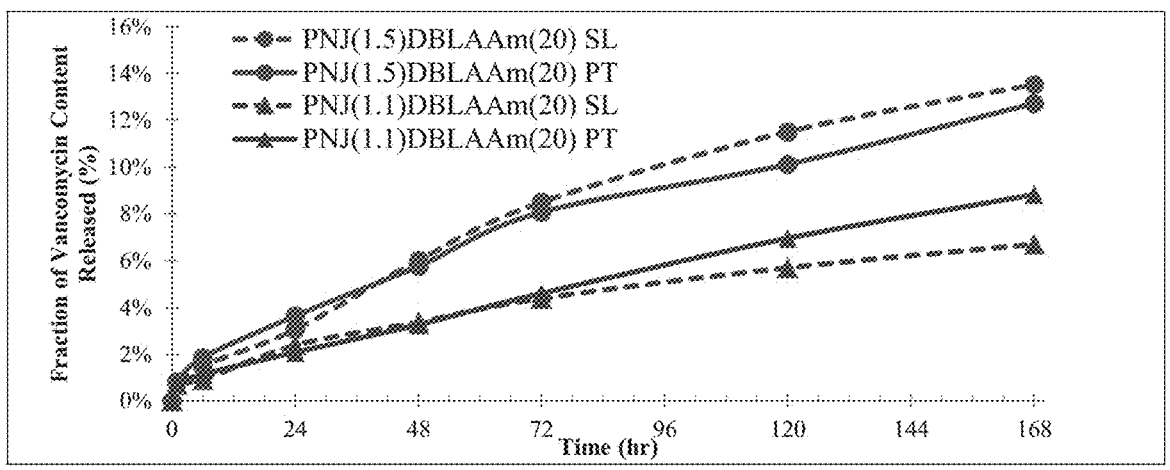
FIG. 18D is a graph of vancomycin release in vitro from hydrogels of 2 polymers of poly(NIPAAm-co-JAAm-co-DBLAAm) after pre-treatment (PT) and additional exposure to stress conditions simulating shelf life (SL). The polymers used are described in Example 8. Data points are the mean value from 3 samples. Data points from SL batches are connected with dashed lines.

Results are shown in FIG. 18D. Consistent, sustained release in vitro was observed for all hydrogels. Slower release was observed from gels with lower JAAm content, consistent with other studies. Importantly, over 4 days (PT) or 14 days (SL) in 95° C. stress conditions, the polymers did not lose their capacity to provide sustained release in physiological conditions. This is a remarkable finding because the LCST would rapidly increase in 95° C. stress conditions in physiological pH. Additionally, the minimal difference between release from PT and SL polymers in this study indicates that the sustained release capability of the polymer was not meaningfully affected over a simulated 2 year shelf life after the "pre-treatment" process of partially hydrolyzing the lactones on the polymer toward an equilibrium composition. Taken together with the characterization from Example 8, this study demonstrates the long-term stability of temperature-responsive degradable polymers for sustained drug release applications when stored in an aqueous acidic solution. One skilled in the art will know that the consistency observed in this experiment applies to the stability and properties of the polymers themselves (and specifically the stability of the lactone-bearing repeat units)

and thus is applicable to formulations prepared with other active agents and is also applicable to polymers in which JAAm or some other water-soluble polymer-bearing unit is present in other amounts or not present at all.

Example 19—In Vitro Release of Bupivacaine with Various Excipients in the Precursor Therapeutic Composition In embodiments of the present invention in which the precursor therapeutic composition contains an active agent that is not highly water soluble, the precursor therapeutic composition may further contain a biocompatible organic excipient in which the active agent is uniformly distributed. Put another way, the role of the biocompatible organic excipient is analogous to the role of an aqueous solvent in a precursor therapeutic composition containing a highly water-soluble active agent. Specific examples of suitable biocompatible organic excipients are listed and explained in Example 10.

The capability of a hydrogel to provide sustained drug release is a valuable attribute that must be preserved when mixing with a precursor therapeutic composition. The release of bupivacaine as a model drug was evaluated with low water solubility (approximately 200 µg/mL) using three different organic excipients: polypropylene glycol 725 (PP0725), polyethylene glycol 400 (PEG400), and α-tocopherol (vitamin E). These three excipients have a range of solubility in water. Vitamin E is water-insoluble, whereas PEG400 and PP0725 are miscible with water, and PP0725 is more hydrophobic whereas PEG400 is more hydrophilic. Thus the three excipients tested represent a wide spectrum of possible compatible excipients in the precursor therapeutic composition. Additional studies using PP0725 as the biocompatible organic excipient are provided in Example 17. A combination of PP0725 with an organic-soluble fatty acid, octanoic acid (OA), was further evaluated for its potential effects on bupivacaine release. Bupivacaine has increased solubility at acidic pH, 64 and thus it was hypothesized that incorporation of a fatty acid in the precursor therapeutic composition might increase the solubility of bupivacaine within the hydrogel, accelerating its release over time. All studies utilized temperature-responsive degradable polymers containing about 92.0 mol % NIPAAm, 6.5 mol % DBLA, and 1.50 mol % JAAm with molecular weight of about 70,000 g/mol. The polymer solution was prepared by dissolving the temperature-responsive degradable polymer at 25 wt % in PBS which was adjusted to pH 4.0 by addition of 1 N HCl.

Study 1. (PP0725, PEG400, Vitamin E)

The precursor therapeutic compositions were prepared by dissolving the biocompatible organic excipient (PP0725, PEG, or Vitamin E) along with bupivacaine in acetone and then drying under vacuum at 40° C. while stirring until a white material with a liquid or paste-like texture was obtained. The PP0725/bupivacaine or PEG400/bupivacaine phases were prepared to result in 30 wt % of the precursor therapeutic composition overall and either 1.5, 3, 4.5, or 6 wt % bupivacaine in the mixed hydrogel. Thus the concentrations of bupivacaine in the precursor therapeutic compositions were about 1.5/30 (5%), 3/30 (10%), 4.5/30 (15%), or 6/30 (20%) respectively. Three replicates were prepared using PP0725/bupivacaine and one replicate of each was prepared using PEG400/bupivacaine.

The precursor therapeutic composition with vitamin E was prepared such that the mixed hydrogels would contain 10 wt % vitamin E and either 1, 3, 5, or 7 wt % bupivacaine. Thus the concentrations of bupivacaine in the bupivacaine/vitamin E precursor therapeutic compositions were about 1/11 (9.09%), 3/13 (23.08%), 5/15 (33.33%), or 7/17 (41.18%) respectively.

Hydrogels were mixed by end-to-end syringe mixing as described previously, with mixing being done at 160-180 strokes/minute for 10 seconds. All hydrogels appeared to be well mixed. Hydrogels weighing approximately 300-500 mg were dispensed into the bottom of a 20 mL scintillation vial tilted to the side to allow the gels to form a reproducible shape in the corner of the vial. The mass of gel added to each vial was recorded. The gels were formed and the release study proceeded as described previously, with exchange of the release medium (PBS, pH 7.4) at selected time points throughout the study. Due to the low volume of the samples relative to the release medium volume and the frequency of medium exchange, the measured concentrations did not approach solubility of bupivacaine and thus it was concluded that infinite sink conditions were reasonably maintained. Concentration of bupivacaine in each aliquot was measured by UV absorbance (280 nm) and the cumulative release of bupivacaine as a fraction of the initial amount in the hydrogel was determined.

Figure 19A:
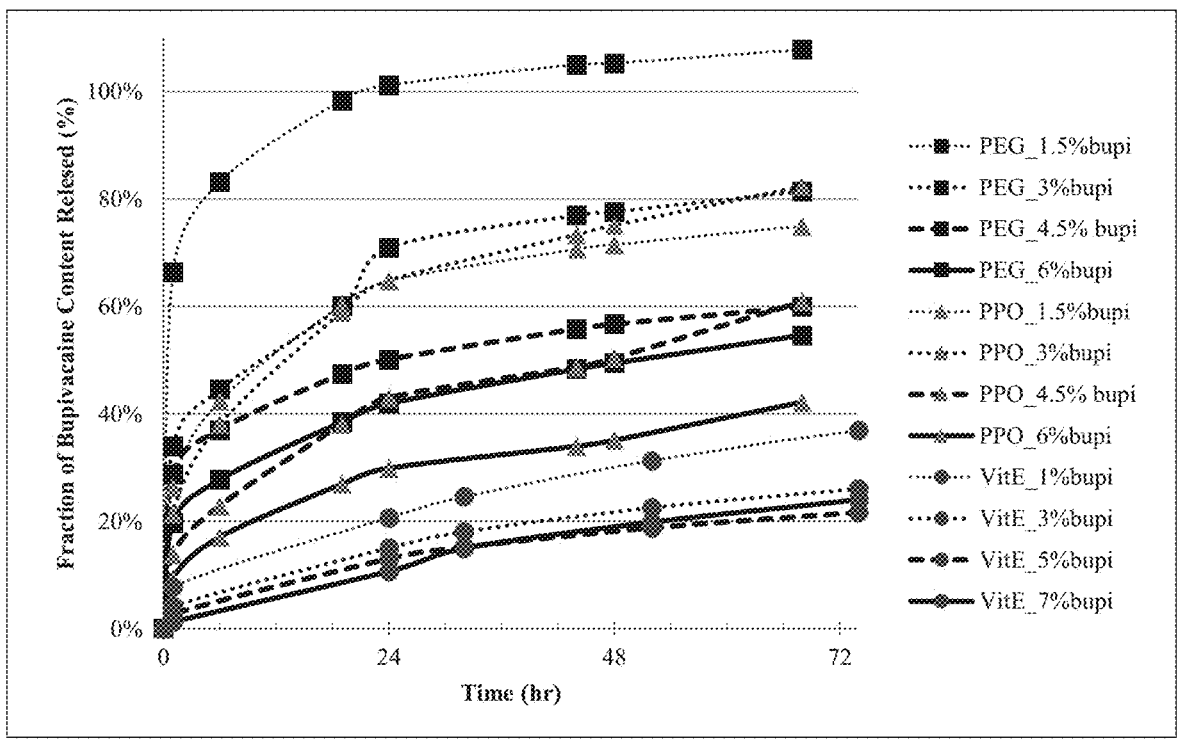
FIG. 19A is a graph of bupivacaine release in vitro from hydrogels of poly(NIPAAm-co-JAAm-co-DBLA) using 3 biocompatible organic excipients in the precursor therapeutic composition over a range of bupivacaine concentrations. Each excipient is represented by a different shape of the data points and increasing concentration is indicated by a more bold or solid line connecting the points. Data for PPO are an average of 3 samples; others are individual data points.

Bupivacaine release data are shown in FIG. 19A. Sustained release was observed from hydrogels prepared with all three excipients. Bupivacaine release was fastest for gels containing PEG400 compared to PP0725, and Vitamin E led to the slowest release. This may be explained by differences in water solubility between the excipients; namely Vitamin E which is not water soluble may remain as a separate phase, possibly emulsified, within the hydrogel, retaining the bupivacaine, whereas PEG400 or PP0725 may distribute throughout the hydrogel, allowing the bupivacaine to diffuse from the gel over time. Release was faster for hydrogels containing less bupivacaine. A single group measured slightly over 100% cumulative release; this was attributed to propagation of measurement error.

Study 2.

The precursor therapeutic compositions were prepared as described above except that OA was added along with PP0725 and bupivacaine prior to drying. The PP0725/bupivacaine/OA phases were prepared to result in 30% (by weight) of the precursor therapeutic composition overall, including 6% bupivacaine, and either 0.5, 1, 3, or 6% OA in the mixed hydrogel (i.e. 20% bupivacaine and either 1.67, 3.33, 10, or 20% OA in the precursor therapeutic composition). Gels were mixed for about 10 seconds by end-to-end syringe mixing of the polymer solution and precursor therapeutic composition, and the same gel size and release study method was used as described above in Study 1.

Figure 19B:
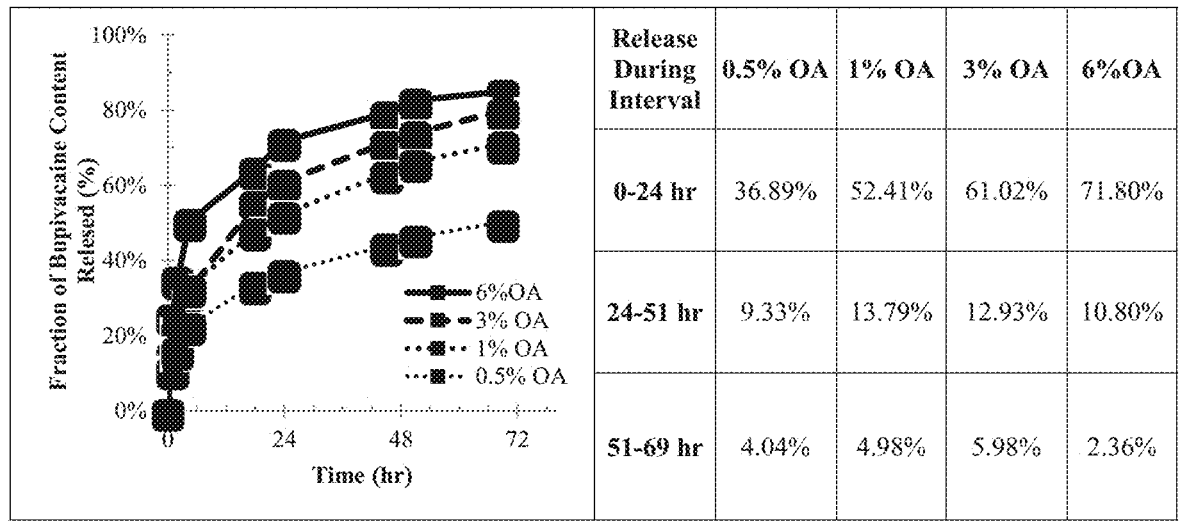
FIG. 19B is a graph and table of bupivacaine release in vitro from hydrogels of poly(NIPAAm-co-JAAm-co-DBLA)using various concentrations of octanoic acid (OA) in the hydrogel by including OA in the precursor therapeutic composition with PP0725 and bupivacaine. The concentration noted in the table reflects the concentration of OA in the mixed hydrogel.

Data are shown in FIG. 19B. Gels with greater OA content provided greater release of bupivacaine. However, the effect was limited to the first 24 hours of the study. Following the first 24 hours, the fraction of bupivacaine released from the hydrogels was comparable. Similar results were observed when instead including 1, 3, 6, or 10 wt % palmitic acid (PA) in the mixed hydrogel as shown in Table 33. A smaller effect on release was observed, which was attributed to PA having a lower number of acid groups per mass and much lower solubility in water compared to OA.

TABLE 33

Fraction of bupivacaine released with various concentrations of palmitic acid (PA) in the mixed hydrogel

| Release During Interval | 1% PA | 3% PA | 6% PA | 10% PA |
|---|---|---|---|---|
| 0-25 hr | 31.75% | 40.61% | 39.93% | 49.23% |
| 25-47.5 hr | 9.93% | 15.23% | 8.97% | 9.22% |
| 47.5-71 hr | 8.16% | 8.70% | 8.84% | 4.64% |
| 71-93 hr | 6.44% | 5.74% | 5.17% | 2.36% |
| 93-124 hr | 6.80% | 6.12% | 5.66% | 3.05% |
| 124-168 hr (2 days) | 6.82% | 4.78% | 5.01% | 3.25% |

Example 20—In Vivo Release and Tissue Levels of Tobramycin and Vancomycin Delivered from Temperature-Responsive Degradable Hydrogels One advantage of using a temperature-responsive degradable hydrogel as opposed to administering the drug alone is that the hydrogel can affect the timing of release of the active agent. As described previously, the antimicrobials tobramycin and vancomycin can provide a promising combination of antimicrobials for the treatment or prevention of biofilm infections. Temperature-responsive degradable hydrogels are soft and viscous, conforming to the sites in which they are placed, whereas other drug release-modifying materials either provide faster drug release (e.g., collagen sponge, PEG hydrogels) or are firm solids which do not conform to a dosing site as well [e.g. microspheres, copolymers of lactic and glycolic acid, and polyanhydrides such as erucic acid dimer—sebacic acid copolymers].

Depending on the site in which a hydrogel is placed, the hydrogel may be exposed to different stresses or assume variable complex shapes, which could affect the rates of drug release. Therefore, the goal of this study was to measure the antimicrobial concentrations within the gel and in tissues immediately next to the gel versus time in orthopaedic surgical sites. Multiple dosing sites in the hindlimbs of New Zealand White rabbits were used. The dosing sites are smaller than what is present in a human, and thus the applied gels have greater surface area to volume ratios compared to what would be expected in humans.

Multiple dosing sites were evaluated to represent sites in which a hydrogel might be applied-a soft tissue surgical wound, a debrided knee, in the intramedullary canal of the femur, and an intact muscle.

New Zealand White rabbits (female, ~3 kg) were used. Gel was given in 7 sites on all animals: 3 sites per hindlimb plus one site on the left hindlimb only. Both hindlimbs received gel in a soft tissue wound, intramuscular injection, and in the knee following synovectomy.

The right hindlimb only received gel in the femoral canal (in a pilot study, the tibia was used instead of the femur). A partial thickness soft tissue wound was created in the midthigh region of the quadriceps by an anterolateral incision and resection of approximately 1 gram of muscle. In the thigh wound, a 14-gauge 2" length IV catheter was inserted into the wound percutaneously and the surgical incision was sutured closed. Then, following end-to-end syringe mixing of polymer and drug solutions as described previously, a syringe containing the mixed gel was secured onto the end of the catheter and injected into the site. Syringe mixing was done independently for each dose in coupled 3 mL syringes. The knees were accessed by an incision anterior to the joint, and debridement (including removal of the joint capsule) will be performed to mimic the soft tissue environment in the clinical situation of a knee prosthetic joint infection. The structures of the joint were left intact. The left femoral canal was accessed through the distal end of the femur using a drill, and then the marrow removed by irrigation with saline. Approximately 1.5 grams of gel was injected to fill the femoral canal, and the drill hole was sealed with bone wax. The incision at the knee was then closed and 1 g of gel was injected in the site in the same fashion as described for the thigh. An intramuscular injection of 1 gram of gel was also given in each biceps femoris using an 18-gauge needle.

All rabbits returned to ambulation postoperatively. Rabbits were euthanized at 24 hr postoperatively in two preliminary studies. In a third study, rabbits were euthanized at either 8, 24, or 72 hr. Necropsies were performed under a heat lamp to maintain the tissue temperature near 37° C. to avoid dissolution of the gel. All remaining gel and 2-3 pieces of tissue (1-2 mm thick) apposed to each gel were collected from each site in tared vials and weighed. All specimens were weighed, suspended in sterile water, and sonicated to liberate any antimicrobials contained in the specimens. The solution from each specimen was evaluated for TOB content by agar diffusion microbiological assay against *P. aeruginosa* (ATCC #27853), which is not sensitive to VANC. Total antimicrobial concentration was calculated assuming proportional release of VANC as observed in in vitro studies. When multiple samples of gel were obtained from a single site, the average antimicrobial concentration remaining in the gel was calculated using a weighted average formula where each sample was weighted according to its proportion of the total gel mass recovered. For the purposes of calculating concentrations, the density of all gel and tissue samples was assumed to be 1 g/mL.

The polymers used in each study are shown in Table 34 below. In a pilot study in 2 rabbits, 25 wt % PNJ18-DBLA was used. Gels contained 1.57% tobramycin and 1.57% vancomycin. At 24 hr after dosing, clear, viscous fluid was observed in all dosing sites except one tibia and one thigh wound, suggesting poor durability of PNJ18-DBLA gels. This was attributed to high JAAm content (1.67 mol %) and low polymer concentration which results in soft/weak gels. Low concentrations of antimicrobials in gel and tissue were present.

In a second study, the formulations were adjusted with the goal of resulting in more durable, cohesive gels and providing slower release in vivo. The polymer concentration was increased and JAAm content was decreased. Molecular weight of the polymers was also decreased to reduce the risk of poor clearance. Gels contained 3% TOB+1% VANC (drug ratio A) or 3.75% TOB+1.25% VANC (drug ratio B). Molecular weight is controlled by the ratio of THF/dioxane used in polymer synthesis. Four rabbits were used. Each rabbit received doses prepared with a single polymer. Formulations with drug ratio A were given in the right leg and formulations with drug ratio B were given in the left leg.

In a third study, two polymer formulations were selected at the low and high ranges determined to provide high tissue levels at 24 hr. The polymer concentration and molecular weights were the same or similar as the second study above. Gels contained 3% TOB+1% VANC (3T1V) or 3% TOB+2% VANC (3T2V). A total of 12 rabbits were used. Six each received Polymer 1 or Polymer 2. Drug ratio 3T2V was given in the right leg and 3T1V was given in the left leg. Rabbits survived either 8 hr, 24 hr, or 72 hr prior to euthanasia and necropsy (n=2 per polymer).

In a fourth study, two polymer formulations were selected using polymers containing DBLAAm instead of DBLA as in the previous studies. Polymers were "pre-treated" by dissolving at 10 wt/% in 0.2 M sodium acetate—acetic acid buffer (pH 4.0) and storing at 95° C. for 4 days, then dialyzed and lyophilized prior to dissolution for the study. Gels contained 3% TOB+2% VANC (3T2V). A total of 4 rabbits were used. Two each received Polymer 1 or Polymer 2 in each site. Rabbits survived 24 hr prior to euthanasia and necropsy (n=2 per polymer).

TABLE 34

Composition of polymers used in Example 20

| Polymer | Study#/ Polymer# | Composition (mol %) | | Molecular Weight (g/mol) | |
|---|---|---|---|---|---|
| | | DBLA(Am) | JAAm | $M_w$ | $M_n$ |
| PNJ18-DBLA | Study 1 | 7.07% | 1.67% | 57,200 | 29,090 |
| PNJ(1.02)-DBLA | Study 2 Polymer 1 | 6.78% | 1.02% | 35,870 | 19,330 |
| PNJ(1.13)-DBLA | Study 2 Polymer 2 | 6.42% | 1.13% | 39,450 | 23,850 |
| PNJ(1.31)-DBLA | Study 2 Polymer 3 | 7.40% | 1.31% | 36,870 | 23,150 |
| PNJ(1.50)-DBLA | Study 2 Polymer 4 | 6.63% | 1.50% | 36,320 | 17,400 |
| PNJ(1.09)-DBLA | Study 3 Polymer 1 | 6.62% | 1.09% | 35,110 | 16,290 |
| PNJ(1.36)-DBLA | Study 3 Polymer 2 | 6.69% | 1.36% | 34,040 | 19,810 |
| PNJ(0.91)-DBLAAm | Study 4 Polymer 1 | 19.38% | 0.91% | 45,350 | 19,570 |
| PNJ(1.29)-DBLAAm | Study 4 Polymer 2 | 19.25% | 1.29% | 43,630 | 23,820 |

Results—Study 1.

Figure 20A:
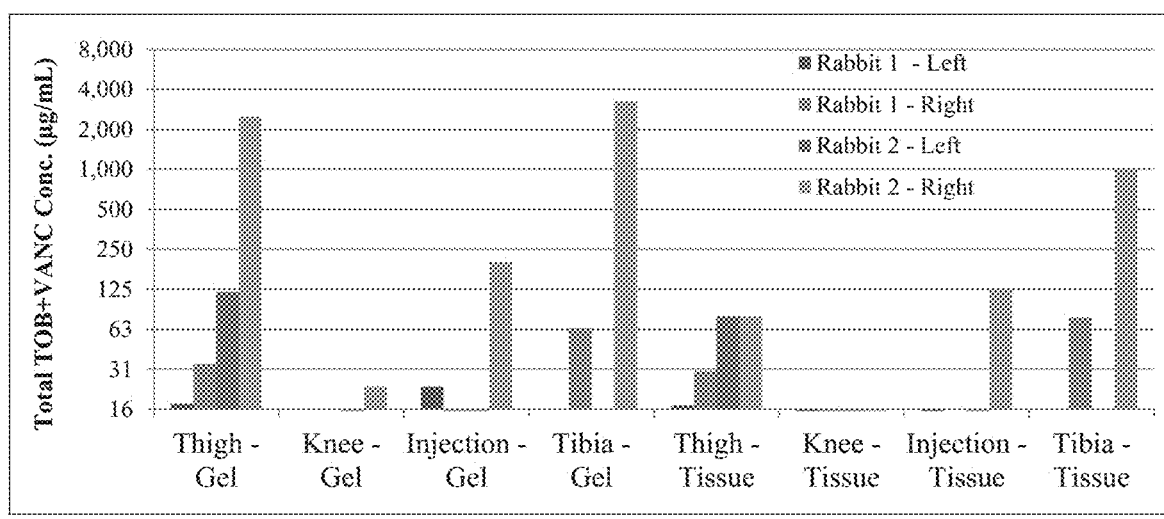
FIG. 20A is a bar chart presenting total antimicrobial concentration within each gel and tissue specimen from pilot study using 25 wt % PNJ18-DBLA (1.67% JAAm) in Example 19 Study 1. Missing bars in the "Knee" and "Injection" groups indicate concentrations below 16 µg/mL. "Tibia" samples were available for the right leg only. Tissues from all sites except Rabbit 2 right tibia contained average concentrations less than 125 µg/mL. Within each group (clustered set of columns), the columns are ordered sequentially from left to right in the same order as from the top to the bottom of the figure legend.

Total antimicrobial concentrations (TOB+VANC) are shown below in FIG. 20A for each site on each rabbit limb. As noted above, most sites had clear, viscous fluid in the wound upon dissection at necropsy. Intact white gel was recovered from the two sites with the highest measured antimicrobial concentrations (Rabbit 2 right tibia and Rabbit 2 right thigh wound). Drug levels in tissue were below 125 µg/mL for all sites except for the tibia of Rabbit 2 (1,012 µg/mL). The initial concentration of antimicrobials in the gel was approximately 31,400 µg/mL. Release over 24 hr was determined to be complete or nearly complete in all sites. Only the two sites from which intact gel was recovered (Rabbit 2 right tibia and Rabbit 2 right thigh wound) contained gel with greater than 300 µg/mL, meaning that all but 2 gel samples contained less than 1% of the injected dose after 24 hr.

Results—Study 2.

Gel was recovered from all dosing sites. Gels with lower JAAm content had a white, opaque, desiccated appearance. Gels with higher JAAm content were translucent and had a more gelatinous texture, especially in the knee. Total antimicrobial concentrations are shown below in FIG. 20B for each site on each rabbit limb. "A" denotes gels with initial drug content 3% TOB+1% VANC (all given in the left leg) and "B" denotes gels with initial drug content 3.75% TOB+1.25% VANC (all given in the right leg).

Figure 20B:
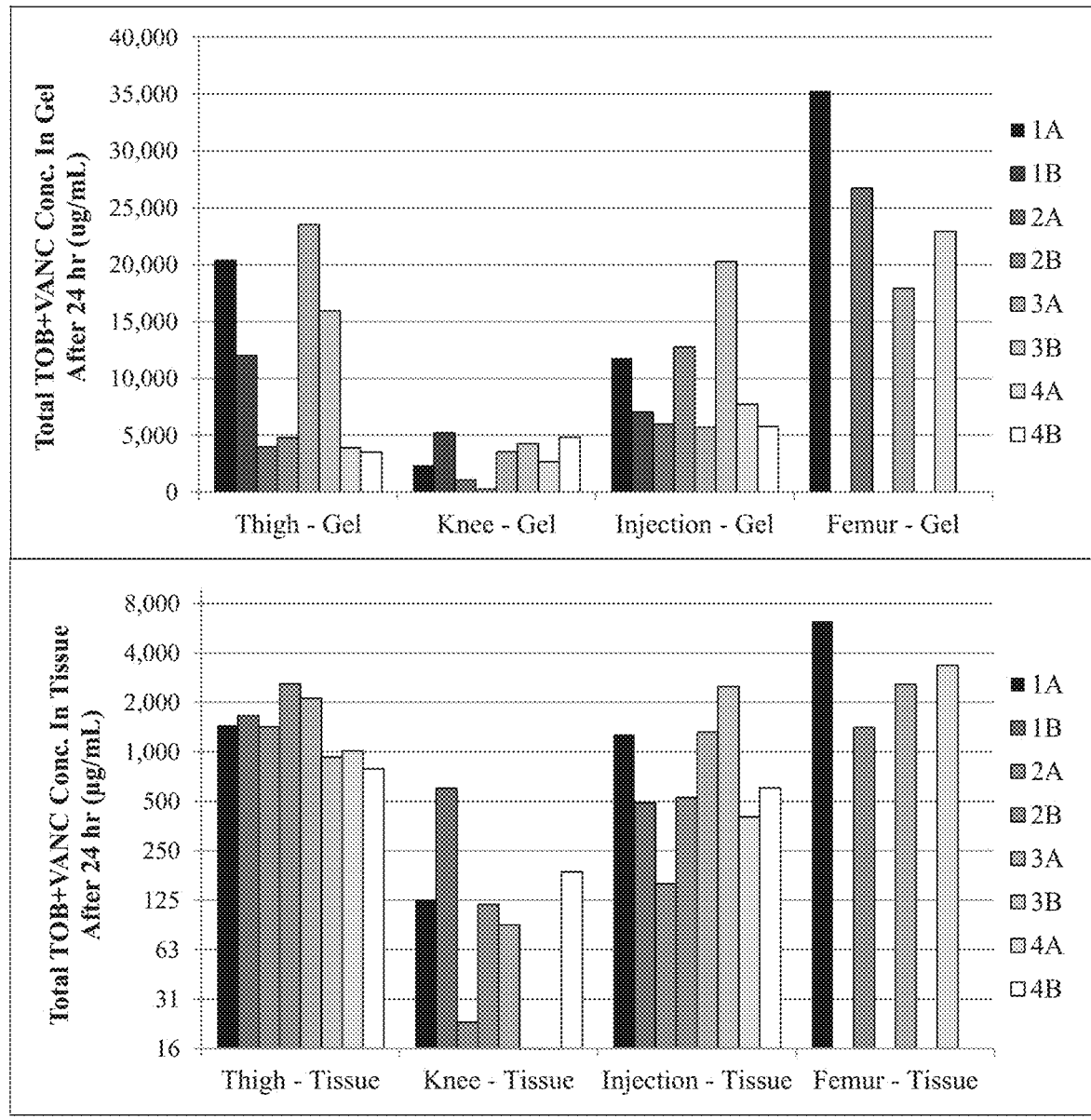
FIG. 20B is a bar chart presenting total antimicrobial concentration within gel specimens (top) and tissue specimens (bottom) obtained 24 hr after dosing in rabbit surgical sites in Example 19 Study 2. In the legend, the number refers to the polymer number on Table 9 and the letter refers to the initial TOB+VANC content in the gel (A=3% TOB+1% VANC; B=3.75% TOB+1.25% VANC). Missing bars on the right indicate the gel was not tested in with drug ratio "B" in the femur. Initial concentration of TOB+VANC in the gels was 40,000-50,000 µg/mL. Within each group (clustered set of columns), the columns are ordered sequentially from left to right in the same order as from the top to the bottom of the figure legend (1A on the left, 4B on the right).

Data are shown in FIG. 20B. Analysis of antimicrobial concentration in the gels suggested faster release in vivo compared to in vitro. Release was fastest in the injection (71-86% release) and knee (90-99% released in 24 hr) which was attributed to stresses on the gel and high gel surface area in these sites. For the soft tissue surgical wound sites, the measured concentration of tobramycin was found to be consistently high, with tobramycin levels in the range of 788-2,596 µg/mL across all groups (mean 1,497 µg/mL). Levels in bone were also high (1,408-6,245 µg/mL; mean 3,399 µg/mL). More variability in concentration was found in tobramycin levels in the tissue recovered from the knee (3-600 µg/mL; mean 144 µg/mL) and IM injection (157-2,499 µg/mL; mean 910 µg/mL). Low levels in the knee tissues were attributed to the lower ability of the antimicrobial agents to diffuse into surrounding tissues (tendon, cartilage, periosteum, synovium). Gels apposed to these tissues contained 1,000-5,000 µg/mL. No clear trend was found in local levels as a function of JAAm content or initial drug content in the gel.

Concentrations in the thigh surgical wound site compare favorably with the concentrations and exposure time necessary to eradicate biofilm on tissues, which are reported in Example 11.

Results—Study 3.

Figure 20C:
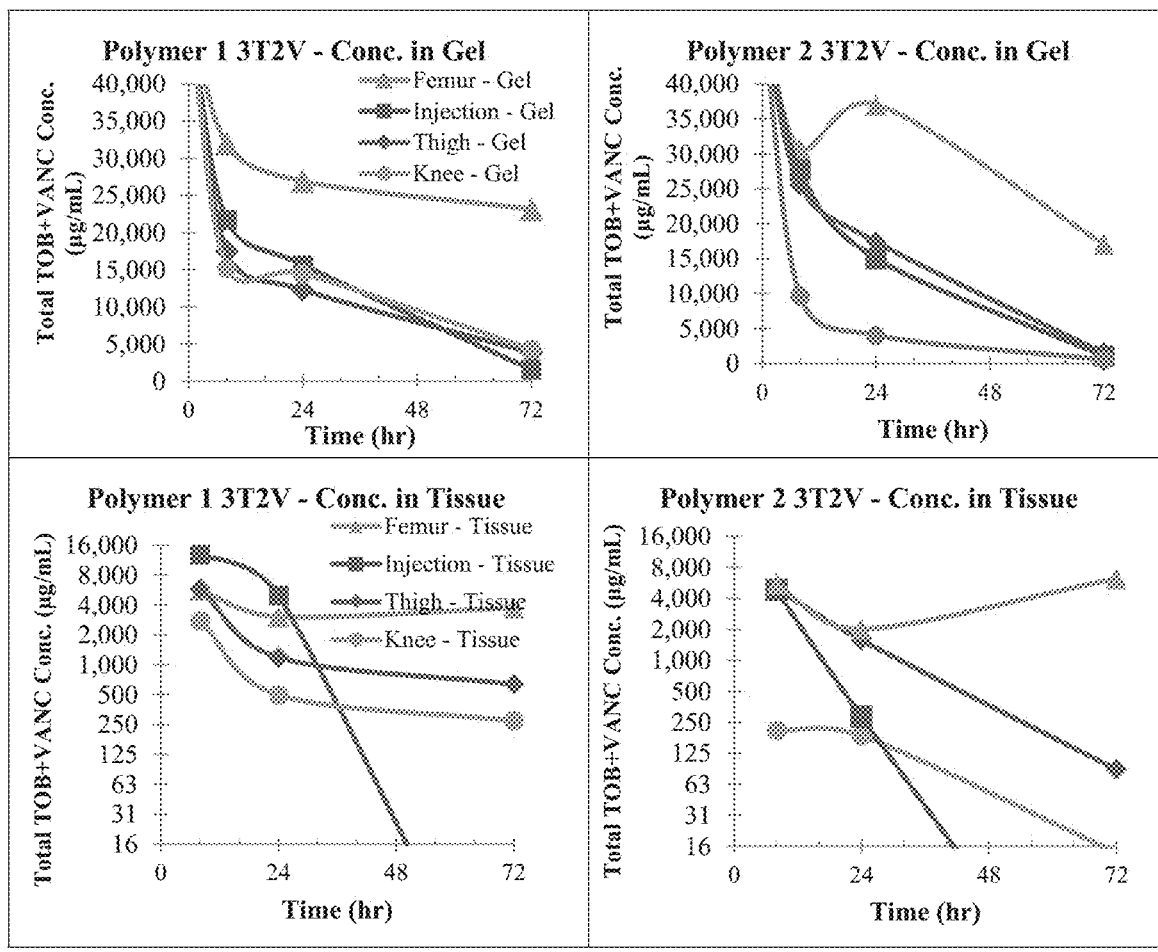
FIG. 20C is a graph of total antimicrobial concentration within gel specimens (top) and tissue specimens (bottom) obtained at 8, 24, or 72 after dosing in rabbit surgical sites in Example 19 Study 3. Plots on the left show results for Study 3 Polymer 1 (1.09% JAAm), and plots on the left show results for Polymer 2 (1.36% JAAm). Gels contained 3% TOB+2% VANC, total 50,000 µg/mL. Data points are the average of 4 sites, except for the levels in the femur which are the average of 2 sites. Lines connecting the data points are only intended as a visual guide. The legends on the figures on the left also apply to the figures to the right.
Figure 20D:
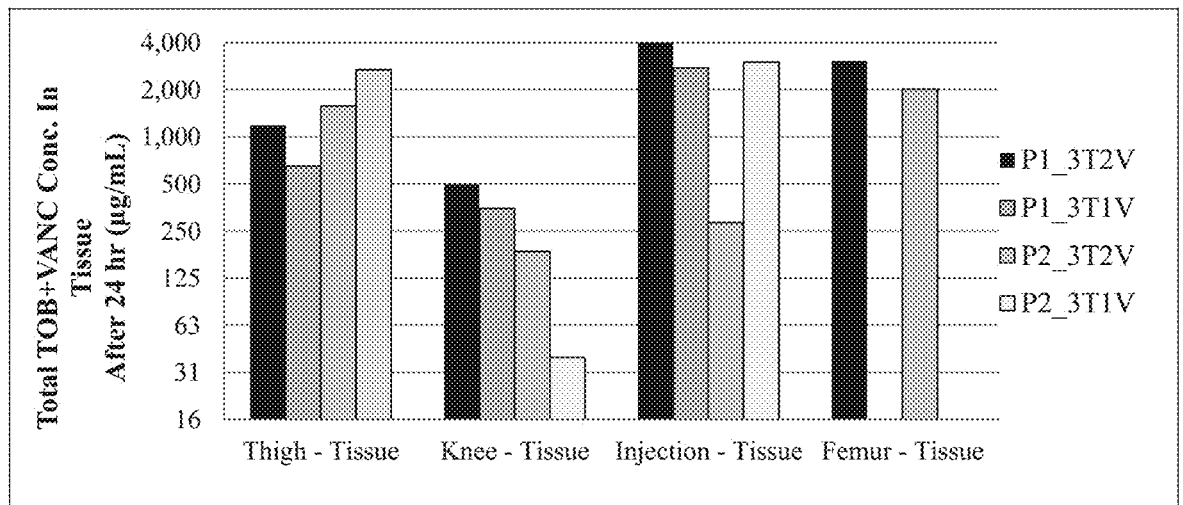
FIG. 20D is a bar chart presenting total antimicrobial concentration within tissue specimens obtained 24 hr after dosing in rabbit surgical sites in Example 19 Study 3. In the legend, the number after "P" refers to the polymer number on Table 9 and the other information refers to initial drug content in the gel (3T2V=3% TOB+2% VANC). Missing bars on the right indicate the gel was not tested in with drug ratio 3T1V in the femur. Reported values are averages from 2 sites in separate rabbits. Initial concentration of TOB+VANC in the gels was 40,000-50,000 µg/mL. Within each group (clustered set of columns), the columns are ordered sequentially from left to right in the same order as from the top to the bottom of the figure legend.

Gel was recovered from all sites. Gel appearance was the same as described above for study 2. Total antimicrobial concentrations versus time in gel and tissue specimens are shown below in FIG. 20C for the 3T2V drug loading. Results for 3T1V are not shown, but are similar. Average total antimicrobial concentrations across all groups in tissues at 24 hr are shown in FIG. 20D.

Concentration data collected over time indicates that antimicrobial release occurs at a high rate within the first 8 hours after dosing followed by a period of more steady release between 8-72 hr. The rate of drug release was slower for gels applied in the femur compared to the other sites tested, which was consistent with preliminary studies. For both polymers tested, release in the injection, thigh wound, and knee sites were similar, with about 70% release (equating to about 15,000 µg/mL remaining in the gel) through 24 hr and near-complete release by 72 hr, except that Polymer 2 (which contained more JAAm) showed greater release in the knee, with approximately 92% release in the first 24 hr. Polymer 2 is softer and less durable than Polymer 1 which could explain this difference in the knee. However, even for Polymer 1, most tissue specimens at 72 hr measured zero. The high average for Polymer 1 at 72 hr was due to a single sample which showed an anomalously high antimicrobial concentration (1,088 µg/mL), despite other samples not containing measurable levels.

Including both drug ratios, all 14 sites dosed with Polymer 1 collected at 72 hr contained measurable levels of antimicrobials in local tissue. The lowest levels were in the knee (17-8,259 µg/mL; mean 2,162 µg/mL). Gel samples of Polymer 2 had measurable levels in 4/4 thigh sites (693-4,728 µg/mL, mean 2,083 µg/mL), both femur sites, 1/4 knee sites, and 2/4 injection sites.

Antimicrobial concentration in local tissue at 24 hr was similar to preliminary studies. Polymer 1 provided more sustained antimicrobial concentration, with minimal decrease in tissue concentrations between 24 and 72 hr, whereas levels with Polymer 2 decreased more rapidly after 24 hr. As in preliminary studies, low levels in the knee tissues were attributed to the lower ability of the antimicrobial agents to diffuse into surrounding tissues (tendon, cartilage, periosteum, synovium).

Notably, a hematoma occurred in a single rabbit receiving Polymer 1 3T2V which was recovered at 24 hr, allowing measurement of a hydrated mass of material in the knee site. The apposed tissue specimens (fat pad, synovium, and superpatellar pouch) measured 30-69 µg/mL, whereas the hematoma in the same site contained 1,384 µg/mL.

Excluding the knee, local concentrations at 8 hr in all sites exceeded 4,000 µg/mL (range 4,812-12,960 µg/mL) for the 3T2V drug loading and 3,000 µg/mL (range 3,012-8,177 µg/mL) for 3T1V. Local concentrations at 24 hr were generally high. For the thigh wound and injection sites, the average tissue level at 24 hr for Polymer 1 was 2,378 µg/mL and for Polymer 2 was 1,887 µg/mL.

Based on the levels in gel and tissues at 72 hr, the data indicate that the drug release from Polymer 2 was faster than that from Polymer 1, in agreement with in vitro studies showing increased drug release rates with higher water content in the hydrogel caused by higher JAAm content in the temperature-responsive degradable polymer. As shown in Example 11, biofilm susceptibility studies support a target of about 125-750 µg/mL sustained for 24 hr, which was met by the gels in this study.

Results—Study 4.

Figure 20E:
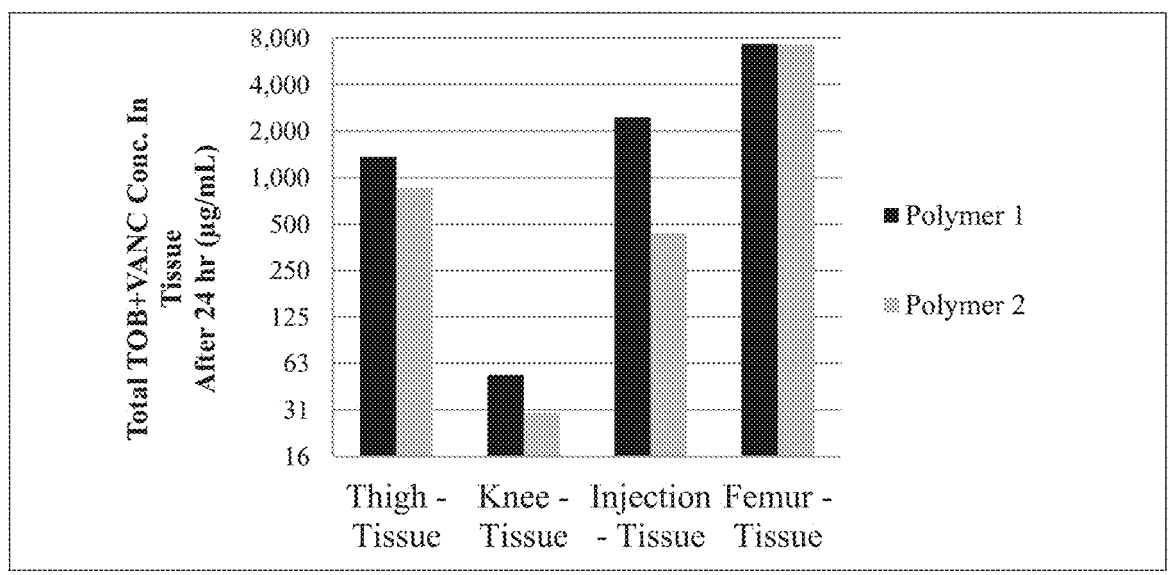
FIG. 20E is a bar chart presenting total antimicrobial concentration within tissue specimens obtained 24 hr after dosing in rabbit surgical sites in Example 19 Study 4. Reported values are averages from 2 sites in separate rabbits. Initial concentration of TOB+VANC in the gels was 50,000 µg/mL. Within each group (clustered set of columns), levels for Polymer 1 are indicated on the left and Polymer 2 on the right.

Gel was recovered from all sites. Hydrogels made with Polymer 1 was more opaque and solid whereas hydrogels made with Polymer 2 were softer. Data are shown in FIG. 20E. Excluding the knee, local concentrations at 24 hr in all sites were generally high, exceeding 750 µg/mL. Levels within the gel specimens are not shown, but were high. Gel in the knee contained an average of 2,080 µg/mL for Polymer 2 or 8,640 µg/mL for Polymer 1. All other sites had average concentrations in the gel of at least 14,000 µg/mL (range 14,620-49,230 µg/mL), indicating that release in all sites from both polymers was sustained for longer than 24 hr. The data demonstrate that polymers containing DBLAAm and undergoing a hydrolysis step in manufacturing prior to dissolution to form the polymer solution provide sustained antimicrobial release and tissue levels in vivo.

For the application of delivery of tobramycin and vancomycin in treatment or prevention of device-related or surgical site infections the compositions of the polymers used in the second, third, and fourth studies (less than about 1.50 mol % JAAm or less than about 12 wt % JAAm in the polymer) showed some advantages over the composition used in the first study based on the data indicating sustained tissue concentrations in these sites.

Example 21—In Vivo Data on Effectiveness Against Infection Using Antibiotic-Loaded Hydrogels The present studies utilized the same rabbit infection treatment model initially adapted from Nelson and colleagues delivering tobramycin mixed into the hydrogel by the methods described herein. Twenty rabbits were infected with S. aureus ATCC 49230 and six rabbits were infected with MRSA ATCC BAA-1556. The polymer used in the hydrogels was PNJ18-DBLA with the composition reported in Table 34, and the hydrogel contained 3.14 wt % tobramycin as an active agent which was dissolved separately at the time of use and mixed with polymer solution by end-to-end syringe mixing.

All 12 rabbits treated with the hydrogel, including six rabbits infected with S. aureus ATCC 49230 and six infected with MRSA, were successfully treated as determined by negative culture of surgical site tissues 4 weeks after debridement and local application of hydrogel. The results obtained with temperature-responsive degradable hydrogel compared favorably to outcomes of rabbits treated with daily subcutaneous injections of 10 mg tobramycin (4/7 remained infected with ATCC 49230) or commercially available tobramycin-loaded bone cement (2/7 remained infected with ATCC 49230).

Example 22—In Vivo Data on Sustained Release and Effectiveness of Bupivacaine-Loaded Hydrogels The local anesthetic active agent bupivacaine is known to be effective in the reduction of pain at a painful site, for example after a surgical procedure. In this example, temperature-responsive degradable hydrogels containing bupivacaine were evaluated for and effectiveness in reducing sensation at the dosing site and for evidence of sustained release by monitoring the concentration of bupivacaine in the blood over time after dosing.

Study 1.

The effectiveness of bupivacaine-loaded temperature-responsive degradable hydrogels was evaluated using a pig model of incisional postoperative pain. A Yucatan micro minipig (20 kg) was used. Pig skin is morphologically similar to human skin. Unlike in rodents, pigs and humans both have skin that is tightly attached to underlying subcutaneous and muscle tissues.

Under anesthesia and using proper aseptic technique, skin incisions were made on each animal. The incisions were 3-5 cm in length at 3-5 cm lateral to and parallel to the spine on each shoulder and flank. Each incision was carried through the skin. Then the treatments were applied by making 6 small subcutaneous injections in a circle around the incision site. The anterior dosing sites received either hydrogel with 4 wt % bupivacaine or 0.5% bupivacaine HCl solution as a control which is currently commercially available and widely used. The posterior sites received hydrogel with either 3 wt % bupivacaine or 2 wt % bupivacaine. The polymer used contained 8.60% DBLA, 1.54% JAAm, and the balance NIPAAm, and the weight-average molecular weight was approximately 70,000 g/mol. The polymer concentration in the polymer solution was 25 wt % (in 20 mM acetic acid) and after dissolution was 20-22.2 wt %. The precursor therapeutic composition contained 20 wt % bupivacaine, 78.75 wt % polypropylene glycol 725, and 1.25 wt % methylparaben. The bupivacaine dose was adjusted by adjusting the volume ratio of the precursor therapeutic composition to the polymer solution. The hydrogels contained 0.12-0.25% methylparaben as an antiseptic. The polymer was sterilized by ethylene oxide gas, dissolved aseptically to form the polymer solution, and then stored in pre-filled syringes. Immediately prior to dosing, the hydrogel was prepared by end-to-end syringe mixing with pre-filled syringes containing the precursor therapeutic composition and then injected via an 18-gauge needle.

Pain was assessed by mechanical sensitivity of each site starting on the day of surgery (1 hr and 6 hr) and continuing once per day for up to 7 days. von Frey filaments of forces ranging from 1 gram to 60 grams were used to apply a small controlled force onto the skin near the incision. The tests were performed by the same technician at each time point and conducted in the pig's home pen. The filaments were applied at a 5 mm distance away from the incision, applied three times at 5-10 second intervals in a parallel line to the incision, once near the center and once near each end of the incision line. If withdrawal is observed then a thinner (lower force) filament was applied. If withdrawal is not observed, then a thicker (higher force) filament was applied. By alternating filaments, the minimum force required to achieve a withdrawal reaction was determined.

Figure 21:
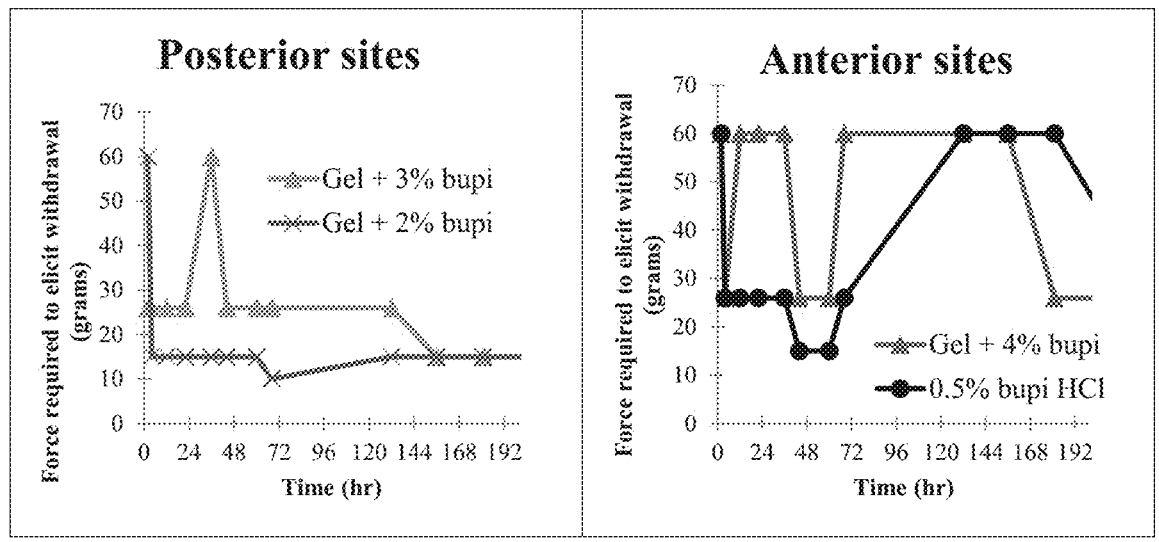
FIG. 21 is a graph of force required to elicit withdrawal versus time after dosing with various treatments in a pig model of incisional pain. Points are individual measurements from a single pig on contralateral sites.

The data are shown in FIG. 21. Contralateral sites were compared within the same pig. Among the two posterior incision sites near the hip, a site dosed with gel with 3% drug showed decreased sensitivity compared to a site dosed with 2% drug for up to 5 days after dosing. For two incision sites near the shoulder on the same pig, a gel with 4% drug provided improved pain reduction over drug alone for all time points between 12-72 hours. After 132 hours, no withdrawal was observed from either site, precluding a comparison between treatment groups. In general, the posterior sites were less sensitive than the anterior sites. The data indicate that reduced sensation occurs from bupivacaine-loaded hydrogel compared to unencapsulated bupivacaine, and reduced pain may be provided for as much as about 5 days.

Study 2.

In this study, the pharmacokinetics (systemic plasma concentrations over time) of bupivacaine were measured following a single subcutaneous injection in dogs for either temperature-responsive degradable hydrogel or liposomal bupivacaine. Non-naive adult female beagle dogs (~8 kg, n=4 per group) received 160 mg bupivacaine either in temperature-responsive hydrogel (4.3 wt % bupivacaine) or liposomal bupivacaine (1.3 wt % bupivacaine), a commercially available sustained release formulation. The volume of the dose was adjusted in each group so that the total dose of bupivacaine was held constant at 160 mg/animal. In the temperature-responsive hydrogel group, the polymer used contained 8.60% DBLA, 1.54% JAAm, and the balance NIPAAm, and the weight-average molecular weight was approximately 70,000 g/mol. The polymer concentration in the polymer solution was 25 wt % (in 20 mM acetic acid) and after dissolution was 21.25 wt %. The precursor therapeutic composition contained 26.7 wt % bupivacaine, 73.3 wt % polypropylene glycol 725. The polymer was sterilized by ethylene oxide gas, dissolved aseptically to form the polymer solution, and then stored in pre-filled syringes. Immediately prior to dosing, the hydrogel was prepared by end-to-end syringe mixing with pre-filled syringes containing the precursor therapeutic composition and then injected via an 18-gauge needle.

Figure 22:
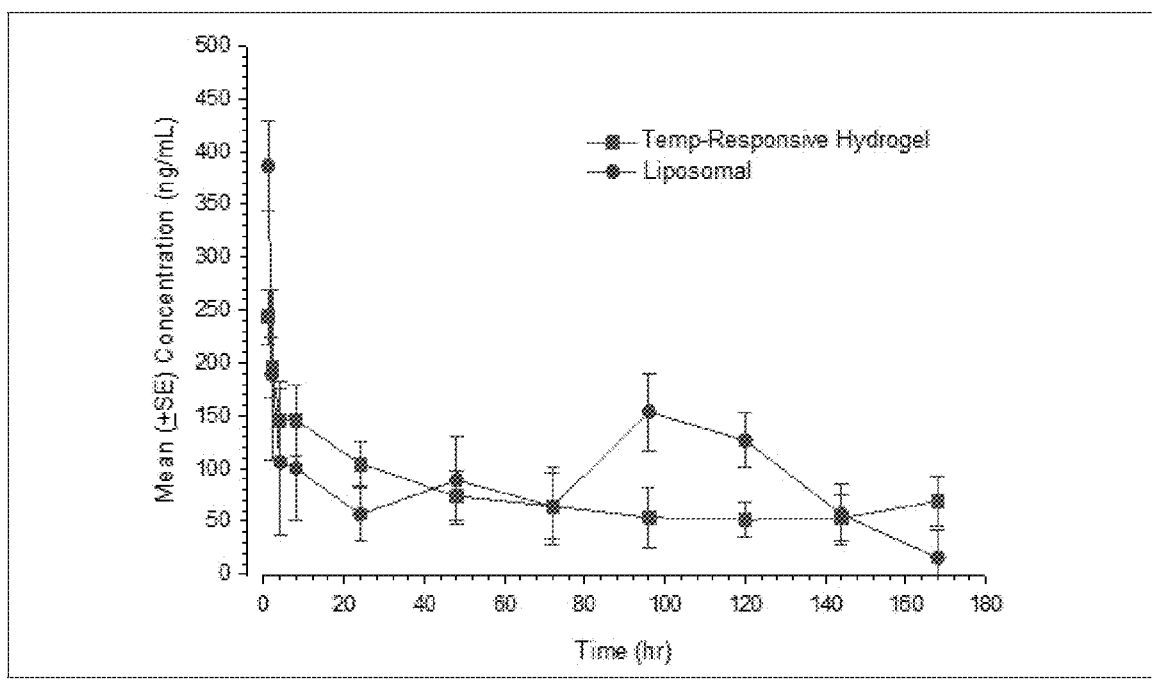
FIG. 22 is a graph of bupivacaine concentration in plasma versus time after subcutaneous injection for temperature-responsive hydrogel containing bupivacaine versus commercially available liposomal bupivacaine. Each data point represents the mean level among 4 dogs.

The doses were given in the scruff of the neck. After dosing, plasma samples were obtained at 1, 2, 4, 8, 24, 48, 72, 96, 120, 144, and 168 hours post-dose. Bupivacaine concentration was assayed using LCMS-MS. Data are shown in FIG. 22. Liposomal bupivacaine showed biphasic release with an increase in plasma concentration at 4-5 days post-dose. The temperature-responsive degradable hydrogel group had a lower Cmax (indicative of lower initial burst release), and slow release thereafter. Toxic systemic levels of bupivacaine are about 1,000-2,000 ng/mL. According to pharmacokinetic modeling, approximately 40% of the bupivacaine dose remained after 1 week. The standard error in the hydrogel group is low throughout the study, indicating consistency in sustained release properties between individual animals and supporting the reproducibility of the dose preparation and mixing method used in the study. The data demonstrate that bupivacaine is released from temperature-responsive hydrogels in a safe, sustained, and consistent fashion when prepared according to the methods described herein.

Example 23—Decreased Generation of Low Molecular Weight Byproducts from Degradation of Temperature-Responsive Degradable Polymers Containing Amide Linkages One embodiment of the present invention is a temperature-responsive degradable polymer that contains lactone-bearing repeat units with amide linkages between the lactone and the polymer backbone. One potential advantage of polymers with amide linkages compared to those with ester linkages is decreased generation of low molecular weight byproducts following hydrogel degradation at physiological pH. Generating fewer low molecular weight byproducts is desirable because these byproducts are associated with an increased risk of toxicity to be characterized and monitored in products for biomedical applications.

In this study, loss of lactones was monitored by $^1$H NMR spectroscopy following exposure of various temperature-responsive degradable polymers at physiological pH. A total of 12 polymers (6 polymers containing amide linkages between the lactone and polymer backbone and 6 polymers containing ester linkages) were prepared at 30 wt % and dissolved in phosphate buffered saline (PBS, pH 7.4). The polymer solutions were formed into hydrogels by heating to 37° C., and then warm PBS was added on top of the gels to maintain pH and hydration. Each gel in PBS was contained in a sealed container that was heated to 60° C. and incubated for 14 days to cause polymer degradation. Following the 14-day incubation period, the samples were cooled to 21° C. All samples were confirmed to have an LCST greater than 37° C. The samples were then dialyzed (3500 MWCO) against deionized water overnight to remove any salts and degradation byproducts, and then the samples were lyophilized. The resulting lyophilized polymers were evaluated by $^1$H NMR. The relative amounts of each side group, in mol %, were determined and compared to the amounts of lactones present in the same polymer batch prior to degradation. $^1$H NMR was run in methanol-d4 using at least 32 scans per sample (Varian Inova, 400 MHz).

NIPAAm units were quantified by the peak at 3.95 ppm (1H). JAAm units were quantified by the peak at 3.63 ppm (76H). Lactones or hydroxyacids of DBLAAm units were quantified using the peak at 4.12 ppm (2H). Lactones or hydroxyacids of DBLA units were quantified using the peak at 5.58 ppm (1H).

Results are shown in Table 35. Polymers containing DBLAAm units had a relative decrease in lactones of 4.57%±2.37% (mean f s.d.), whereas polymers containing DBLA units had a relative decrease in lactones of 13.94%±7.61%. The results indicate that a greater proportion of lactones was retained on the polymer backbone for temperature-responsive degradable polymers containing amide linkages between the lactone and the polymer backbone.

TABLE 35

Content of Polymers in Example 23 and Loss of Polymer-Bound Lactones

| | Initial Composition (mol %) | | | Lactones After Degradation (mol %) | Relative Change in Lactones (mol %) |
|---|---|---|---|---|---|
| | DBLA | DBLAAm | JAAm | | |
| Polymer 1 | — | 20.14% | 0.83% | 19.57% | −2.83% |
| Polymer 2 | — | 16.21% | 0.94% | 15.22% | −6.13% |
| Polymer 3 | — | 19.08% | 1.07% | 18.75% | −1.68% |
| Polymer 4 | — | 19.32% | 1.22% | 18.68% | −3.32% |
| Polymer 5 | — | 19.29% | 1.65% | 17.75% | −8.01% |
| Polymer 6 | — | 24.38% | 1.60% | 23.05% | −5.47% |
| Polymer 7 | 6.62% | — | 1.09% | 5.51% | −16.77% |
| Polymer 8 | 7.02% | — | 1.19% | 5.03% | −28.29% |
| Polymer 9 | 7.40% | — | 1.30% | 6.67% | −9.84% |
| Polymer 10 | 5.48% | — | 1.45% | 4.89% | −10.68% |
| Polymer 11 | 4.12% | — | 1.45% | 3.75% | −9.04% |
| Polymer 12 | 8.03% | — | 1.58% | 7.31% | −9.03% |

Example 24—Decreased Degradation in Dissolution Conditions Including Alkaline pH for Temperature Responsive Degradable Copolymers Containing Amide Linkages One potential advantage of polymers including amide linkages between the polymer backbone and lactone is improved stability during dissolution in a range of aqueous solutions. The temperature-responsive polymers based on N-isopropylacrylamide repeat units can require about 24-48 hours to form a solution suitable for use in a pharmaceutical formulation. Although longer-term stability as a liquid solution over several months or years can be desirable, a minimum threshold can be that the polymer remain stable during the time it takes for the polymer to dissolve.

In this study, three polymers of poly(NIPAAm-co-DBLA-co-JAAm) and three polymers of poly(NIPAAm-co-DBLAAm-co-JAAm) were dissolved at 30 wt % in phosphate buffer at pH values of 7.0 and 8.0, and also in sodium bicarbonate buffer at pH values of 9.0, 10.0, and 11.0. Each polymer was combined with each buffer and stored at 4° C. for either 24 or 48 hours. After the designated time for each sample, the samples were diluted to 10 wt %, pH-adjusted to pH 7.0 using 1 N NaOH, and the polymer was recovered by dialysis against deionized water and lyophilization. The resulting polymers were then characterized for stability by cloud point determination and titration. For cloud point determination, the lyophilized polymer samples were dissolved at 0.1 wt % in PBS (pH 7.4) and absorbance was measured in 1° C. increments until a maximum value was reached, indicating polymer globule aggregation. The breadth of LCST transition (expressed as the change in temperature between 10% and 90% of the max absorbance value) and the percentage of the absorbance increase below 37° C. were also recorded as indicators of stability. A more stable polymer would be expected to have a narrower breadth of LCST transition and a more complete transition below 37° C. In addition, a more stable polymer would also be expected to generate fewer acid groups due to hydrolysis than a less stable formulation.

Figure 23:
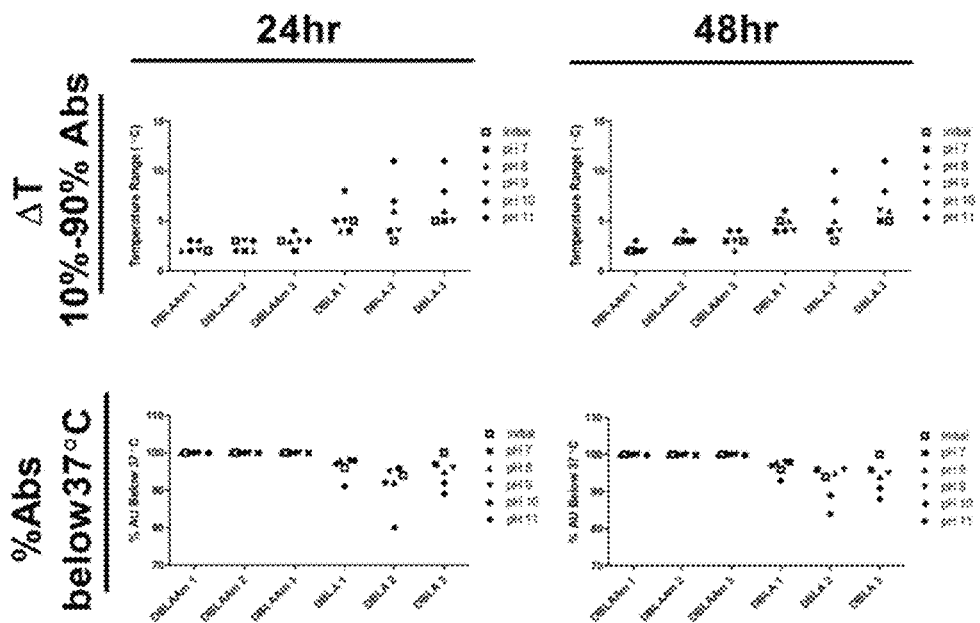
FIG. 23 is a graph of the breadth of LCST transition and percentage of absorbance increase below 37° C. for temperature responsive polymers containing DBLAAm versus DBLA. Polymers with amide linkages have more complete LCST transitions below 37° C. and a narrower LCST transition across a range of pH values between 7-11. Temperature-responsive degradable polymers with ester linkages between the polymer backbone and lactones have broader LCST transitions following dissolution especially in high pH buffers (pH 10 and 11).
Figure 24:
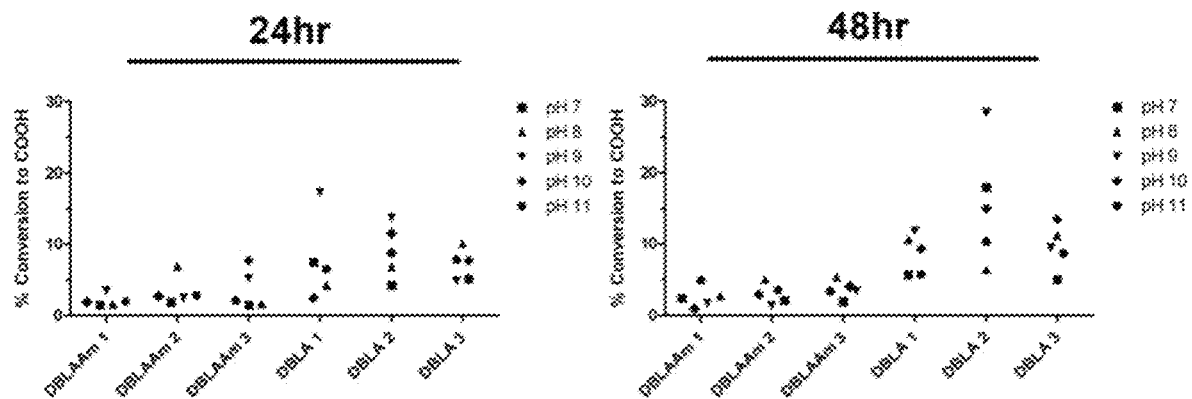
FIG. 24 is a graph of acid groups as a fraction of lactones in poly(NIPAAm-co-DBLAAm-co-JAAm) versus poly(NIPAAm-co-DBLA-co-JAAm) following 24 or 48 hour dissolution time. Temperature-responsive degradable polymers with ester linkages between the polymer backbone and lactones have greater acid content after 24-48 hr dissolution time in neutral to alkaline buffers (pH 7 and higher).

Results are shown in FIGS. 23 and 24. As indicated in FIG. 23, polymers containing DBLA units have a broader LCST transition and incomplete sol-gel transition before heating to 37° C., whereas polymers containing DBLAAm have narrower LCST transitions and complete (100%) transitions below 37° C. FIG. 24 shows increased acid content on polymer containing ester linkages, indicating inferior stability of these polymers in dissolution conditions.

The results indicate that temperature-responsive degradable polymers with amide linkages between the polymer backbone and lactones have improved stability in solution during a timeframe relevant to dissolution in a range of buffers having pH values up to at least 11, including the pH range 7-11. Alkaline hydrolysis of ester linkages introduces unwanted heterogeneity in structure and properties within a single polymer solution, negatively impacting its gelling properties, including at 37° C. The results support the superiority of temperature-responsive degradable polymers with amide linkages over those with ester linkages due to compatibility with a wide range of dissolution buffers, including in the range of neutral to alkaline pH (greater than 7, or as specifically shown, from 7 to 11). These data suggest that the maximum feasible pH for dissolution of DBLAAm-containing polymers is at least 11, based on there being minimal breadth of the LCST transition and complete absorbance at or below 37° C. after up to 48 hr dissolution time.

Combined with the above examples it has been demonstrated that temperature-responsive degradable polymers with amide linkages between the backbone and pendent lactones are feasible for preparation in solution and have useful properties for hydrogel formation and drug delivery when formulated in buffers having a pH between about 2 and about 11, which represents the full range of pH values tested. The pH of a polymer solution can be controlled independently of other attributes of the examples presented herein (e.g., choice of active agent, solution viscosity, polymer concentration or molecular weight, etc.) with minimal impact on the convenient use and properties of the temperature-responsive polymer solution, including mixing of a polymer solution with a second precursor phase to form a hydrogel.

It should be understood that the above-described methods are only illustrative of some embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, may be made without departing from the principles and concepts set forth herein.

What is claimed is:

1. A therapeutic system, comprising:
   a polymer composition that comprises an un-crosslinked temperature-responsive degradable polymer having a lower critical solution temperature (LCST) of about 37° C. or below and comprising:
   an LCST-imparting unit having the structure:

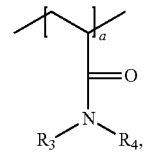

a lactone-bearing unit having the structure:

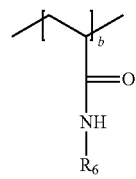

wherein:
   $R_3$ is isopropyl and $R_4$ is H or $R_3$ is ethyl and $R_4$ is ethyl;
   $R_6$ is a butyrolactone or a valerolactone;
   the LCST-imparting unit is present in the polymer in an amount of from about 50 mol % to about 99 mol %;
   the lactone-bearing unit is present in the polymer in an amount of from about 1 mol % to about 50 mol %;
   the LCST-imparting unit and the lactone bearing unit are present in the polymer in a combined amount of at least 80 mol %; and the temperature-responsive degradable polymer has a $M_w$ of from about 3,000 g/mol to about 74,092,000,000 g/mol; and an aqueous vehicle, wherein:

the polymer composition has a pH of from about 2 to about 7; and the temperature-responsive degradable polymer is present in the composition in an amount of from about 1 wt % to about 50 wt %; and a precursor therapeutic composition, comprising:

a therapeutic agent and a liquid or semi-solid carrier, wherein:

the therapeutic agent comprises an antimicrobial agent, an anesthetic agent, an opioid, an anti-inflammatory agent, a polysaccharide, a polynucleotide, an antigen, an antibody, a vaccine, a vitamin, an enzyme, a protein, or a combination thereof;

the therapeutic agent is present in the precursor therapeutic composition in an amount of from about 5 wt % to about 40 wt %; and the polymer composition is contained in a first container and the precursor therapeutic composition is contained in a second container.

2. The therapeutic system of claim 1, wherein the therapeutic agent comprises an anesthetic agent and the carrier comprises one or more of the following: polyethylene glycol having a weight average molecular weight less than 1000 g/mol, polypropylene glycol having a weight average molecular weight less than 1000 g/mol, copolymers of ethylene oxide and propylene oxide having a weight average molecular weight less than 1000 g/mol, poly(ethylene glycol) ether derivatives having a weight average molecular weight of between 200 g/mol and 4,000 g/mol, poly(ethylene glycol) copolymers having a weight average molecular weight of between 200 g/mol and 10,000 g/mol; propylene glycol mono- or di-esters of a $C_2$-$C_{19}$ aliphatic carboxylic acid or a mixture of such acids; mono-, di- or tri-glycerides of a $C_2$-$C_{19}$ aliphatic carboxylic acid or a mixture of such acids, water-soluble organic solvents, non-ionic surfactants, water-insoluble lipids, organic liquids/semi-solids, cyclodextrins, or phospholipids.

3. The therapeutic system of claim 2, wherein the therapeutic agent comprises bupivacaine, levobupivacaine, dibucaine, mepivacaine, procaine, lidocaine, tetracaine, or ropivacaine.

4. The therapeutic system of claim 2, wherein the therapeutic agent is present in the precursor therapeutic composition in an amount of from about 10 wt % and about 25 wt %.

5. The therapeutic system of claim 4, wherein the carrier comprises polyethylene glycol having a weight average molecular weight less than 1000 g/mol.

6. The therapeutic system of claim 5, wherein the therapeutic agent comprises bupivacaine.

7. The therapeutic system of claim 1, wherein the therapeutic agent comprises an antimicrobial agent.

8. The therapeutic system of claim 7, wherein the carrier comprises water.

9. The therapeutic system of claim 7, wherein the therapeutic agent comprises one or more of the following: tobramycin, vancomycin, gentamicin, cefazolin, penicillin, amoxicillin, doxycycline, cephalexin, ciprofloxacin, metronidazole, azithromycin, sulfamethoxazole/trimethoprim, bacitracin, levofloxacin, ceftaroline, dalbavancin, oritavancin, amikacin, rifampin, or teixobactin.

10. The therapeutic system of claim 7, wherein the therapeutic agent is present in the precursor therapeutic composition in an amount of from about 10 wt % and about 25 wt %.

11. The therapeutic system of claim 8, wherein the therapeutic agent comprises tobramycin and vancomycin.

12. The therapeutic system of claim 11, wherein the therapeutic agents are present in the precursor therapeutic composition in an amount of from about 18 wt % and about 24 wt %.

13. A method of making a therapeutic hydrogel composition, comprising:

providing system according to claim 1 having a polymer composition and precursor therapeutic composition, said precursor therapeutic composition, comprising a therapeutic agent and a liquid or semisolid carrier; and mixing the polymer composition and the precursor therapeutic composition to prepare the therapeutic hydrogel composition, wherein:

the therapeutic agent comprises an antimicrobial agent, an anesthetic agent, an opioid, an anti-inflammatory agent, a polysaccharide, a polynucleotide, an antigen, an antibody, a vaccine, a vitamin, an enzyme, a protein, or a combination thereof; and the therapeutic agent is present in the precursor therapeutic composition in an amount of from about 5 wt % to about 40 wt %.

14. The method of claim 13, wherein mixing is performed using end-to-end mixing or a metered mixing dispenser.

15. The method of claim 6, wherein:

the therapeutic agent comprises one or more of the following: bupivacaine, levobupivacaine, dibucaine, mepivacaine, procaine, lidocaine, tetracaine, or ropivacaine; and the carrier comprises one or more of the following: polyethylene glycol having a weight average molecular weight less than 1000 g/mol, polypropylene glycol having a weight average molecular weight less than 1000 g/mol, copolymers of ethylene oxide and propylene oxide having a weight average molecular weight less than 1000 g/mol, poly(ethylene glycol) ether derivatives having a weight average molecular weight of between 200 g/mol and 4,000 g/mol, poly(ethylene glycol) copolymers having a weight average molecular weight of between 200 g/mol and 10,000 g/mol; propylene glycol mono- or di-esters of a $C_2$-$C_{19}$ aliphatic carboxylic acid or a mixture of such acids; mono-, di- or tri-glycerides of a $C_2$-$C_{19}$ aliphatic carboxylic acid or a mixture of such acids, water-soluble organic solvents, non-ionic surfactants, water-insoluble lipids, organic liquids/semi-solids, cyclodextrins, or phospholipids.

16. The method of claim 15, wherein the therapeutic agent is present in the precursor therapeutic composition in an amount of from about 10 wt % and about 25 wt %, and the carrier comprises polyethylene glycol having a weight average molecular weight less than 1000 g/mol.

17. The method of claim 16, wherein the therapeutic agent comprises bupivacaine.

18. The therapeutic system of claim 1, wherein the first container and the second container are syringes.

19. The therapeutic system of claim 1, wherein the first container and the second container are coupled and form a third container comprising a first compartment and a second compartment that are substantially isolated from one another.

20. The therapeutic system of claim 19, wherein the third container is a double a double-barrel syringe which comprises a metered mixing dispenser configured to mix the polymer composition and the precursor therapeutic composition during dispensing.

* * * * *